(12) United States Patent
Lee et al.

(10) Patent No.: US 7,879,848 B2
(45) Date of Patent: Feb. 1, 2011

(54) DIPEPTIDYL PEPTIDASE-IV INHIBITING COMPOUNDS, METHOD OF PREPARING THE SAME, AND PHARMACEUTICAL COMPOSITIONS CONTAINING THE SAME AS AN ACTIVE AGENT

(75) Inventors: Chang-Seok Lee, Daejeon (KR); Jong Sung Koh, Daejeon (KR); Ki Dong Koo, Daejeon (KR); Geun Tae Kim, Daejeon (KR); Kyoung-Hee Kim, Daejeon (KR); Sang Yong Hong, Daejeon (KR); Sungsub Kim, Daejeon (KR); Min-Jung Kim, Daejeon (KR); Hyeon Joo Yim, Daejeon (KR); Dongchul Lim, Daejeon (KR); Hye Jin Kim, Daejeon (KR); Hee Oon Han, Daejeon (KR); Seong Cheol Bu, Daejeon (KR); Oh Hwan Kwon, Daejeon (KR); Sung Ho Kim, Daejeon (KR); Gwong-Cheung Hur, Daejeon (KR); Ji Young Kim, Daejeon (KR); Zi-Ho Yeom, Daejeon (KR); Dong-Jun Yeo, Daejeon (KR)

(73) Assignee: LG Life Sciences, Ltd. (KR)

( * ) Notice: Subject to any disclaimer, the term of this patent is extended or adjusted under 35 U.S.C. 154(b) by 372 days.

(21) Appl. No.: 11/910,370

(22) PCT Filed: Mar. 30, 2006

(86) PCT No.: PCT/KR2006/001169

§ 371 (c)(1),
(2), (4) Date: Oct. 1, 2007

(87) PCT Pub. No.: WO2006/104356

PCT Pub. Date: Oct. 5, 2006

(65) Prior Publication Data

US 2008/0188471 A1   Aug. 7, 2008

(30) Foreign Application Priority Data

| Apr. 1, 2005 | (KR) | 10-2005-0027756 |
| Jun. 22, 2005 | (KR) | 10-2005-0053761 |
| Sep. 15, 2005 | (KR) | 10-2005-0085980 |
| Dec. 13, 2005 | (KR) | 10-2005-0122361 |

(51) Int. Cl.
C07D 471/04 (2006.01)
C07D 413/14 (2006.01)
A61K 31/519 (2006.01)
A61K 31/5355 (2006.01)
A61K 31/4355 (2006.01)
A61P 3/10 (2006.01)
A61K 31/437 (2006.01)
A61K 31/5025 (2006.01)
C07D 487/04 (2006.01)
C07D 217/14 (2006.01)
C07D 498/04 (2006.01)

(52) U.S. Cl. .................. 514/230.8; 514/264.1; 514/302; 514/249; 544/279; 544/117; 544/350; 544/303; 546/146; 546/115; 546/119

(58) Field of Classification Search ................ 544/58.2, 544/117, 279, 350; 514/264.1, 230.8, 302
See application file for complete search history.

(56) References Cited

U.S. PATENT DOCUMENTS

| 2009/0012117 A1* | 1/2009 | Kawatkar et al. ........... 514/307 |
| 2009/0076001 A1* | 3/2009 | Sundermann et al. .... 514/234.2 |
| 2009/0176811 A1* | 7/2009 | Oberborsch et al. .... 514/264.11 |
| 2009/0176825 A1* | 7/2009 | Fitch et al. .................. 514/301 |
| 2009/0186899 A1* | 7/2009 | Merla et al. ................. 514/249 |

FOREIGN PATENT DOCUMENTS

| WO | 0034241 A1 | 6/2000 |
| WO | 03004498 A1 | 1/2003 |
| WO | 03037327 A1 | 5/2003 |

(Continued)

OTHER PUBLICATIONS

Zimmet, P., et al.; "Global and societal implications of the diabetes epidemic"; Nature; vol. 414; pp. 782-787; Dec. 13, 2001.

(Continued)

*Primary Examiner*—James O Wilson
*Assistant Examiner*—Cecilia M Jaisle
(74) *Attorney, Agent, or Firm*—Cantor Colburn LLP

(57) ABSTRACT

Novel compounds exhibiting good inhibitory activity versus Dipeptidyl Peptidase-IV(DPP-IV) include those of the following formula (1) or pharmaceutically acceptable salt thereof:

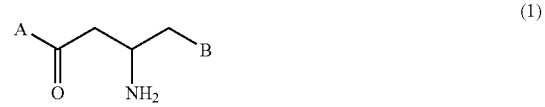

(1)

wherein A is a substituted or unsubstituted 1,4,5,7-tetrahydro-pyrazolo[3,4-c]pyridine, 5,6-dihydro-8H-[1,2,4]triazolo[4,3-a]pyrazine, 4,5-dihydro-7H-isooxazolo[3,4-c]pyridine, 3,4-dihydroisoquinoline, 5,8-dihydropyrido[3,4-d]pyrimidine, or 6,7-dihydro[1,3]thiazolo[4,5,c]pyridine, and B is a substituted or unsubstituted piperidin-2-one, morpholin-3-one, oxazolidin-2-one, pyrrolidin-2-one, or 1,5-dihydro-pyrrol-2-one. Methods of preparing the novel inhibitory compounds of formula (1) and pharmaceutical compositions containing the same as an active agent are disclosed.

22 Claims, No Drawings

FOREIGN PATENT DOCUMENTS

| | | |
|---|---|---|
| WO | 03057144 A2 | 7/2003 |
| WO | 03082817 A2 | 10/2003 |
| WO | 03093231 A2 | 11/2003 |
| WO | 2004007468 A1 | 1/2004 |
| WO | 2004064778 A2 | 8/2004 |
| WO | 2004069162 A2 | 8/2004 |
| WO | 2005082849 A1 | 9/2005 |

OTHER PUBLICATIONS

Moller, D. E.; "New drug targets for type 2 diabetes and the metabolic syndrome"; Nature; vol. 414; pp. 821-827; Dec. 13, 2001.

Marguet, D., et al.; "Enhanced insulin secretion and improved glucose tolerance in mice lacking CD26"; PNAS; vol. 97, No. 12; pp. 6874-6879; Jun. 6, 2000.

Pospisilik, J. A., et al.; "Long-Term Treatment With the Dipeptidyl Peptidase IV Inhibitor P32/98 Causes Sustained Improvements in Glucose Tolerance, Insulin Sensitivity, Hyperinsulinemia, and B-Cell Glucose Responsiveness in VDF (fa/fa) Zucker Rats"; Diabetes; vol. 51; pp. 943-950; Apr. 2002.

Ewing, W. R., et al.; "Design and Structure-Activity Relationships of Potent and Selective Inhibitors of Blood Coagulation Factor Xa"; J. Med. Chem.; vol. 42; pp. 3557-3571; 1999.

Chizhov, D. L., et al.; "2,4-Bridged 1,5-bis(fluoroalkyl)-1,3,5-triketones: synthesis and properties"; Journal of Fluorine Chemistry; vol. 123; pp. 267-272; 2003.

Abd-Elfattah, A. M., et al.; Reactions With a-Substituted Cinnamontriles; Tetrahedron; vol. 39, No. 19; pp. 3197-3199; 1983.

Kim, D., et al.; "(2R)-4-Oxo-4-[3-(Trifluoromethyl)-5,6-dihydro[1,2,4]triazolo[4,3-1]pyrazin-7(8H)-yl]-1-(2,4,5-trifluorophenyl)butan-2-amine: A Potent, Orally Active Dipeptidyl Peptidase IV Inhibitor for the Treatment of Type 2 Diabetes"; J. Med. Chem.; vol. 48; pp. 141-151; 2005.

Tanaka, T., et al; "Enhancement of antigen-induced T-cell proliferation by soluble CD26/dipeptidyl peptidase IV"; Proc. Natl. Acad. Sci. USA; vol. 91; pp. 3082-3086; Apr. 1994.

International Preliminary Report on Patentability dated Jul. 10, 2006 for Application No. PCT/KR2006/001169.

Written Opinion dated Jul. 10, 2006 for Application No. PCT/KR2006/001169.

International Search Report dated Jul. 10, 2006 for Application No. PCT/KR2006/001169.

Noula, C., et al.; "An Efficient Method for the Synthesis of Enantiopure w-Amino Acids with Proteinogenic Side Chains"; Synthesis; No. 12; pp. 1735-1739; 2002.

* cited by examiner

DIPEPTIDYL PEPTIDASE-IV INHIBITING COMPOUNDS, METHOD OF PREPARING THE SAME, AND PHARMACEUTICAL COMPOSITIONS CONTAINING THE SAME AS AN ACTIVE AGENT

TECHNICAL FIELD

The present invention relates to compounds of novel structure, having good inhibition activity versus Dipeptidyl Peptidase-IV (DPP-IV), methods of preparing the same and pharmaceutical compositions containing the same as an active agent.

BACKGROUND ART

Diabetes mellitus has serious effects on people's health and accompanies various complications. There are two major types of diabetes mellitus: type I diabetes mellitus characterized by little or no insulin secretory capacity due to the destruction of pancreatic cells, and type II diabetes mellitus characterized by insulin deficiency and insulin resistance due to other causes. The prevalence of type II diabetes mellitus is 90% or more of total patients with diabetes mellitus. Representative examples of complications accompanying diabetes include hyperlipidemia, hypertension, retinopathy and renal insufficiency (Paul Zimmer, et al., Nature, 2001, 414, 782). Sulfonylureas (stimulating insulin secretion in pancreatic cells), biguanides (inhibiting glucose production in the liver), α-glucosidase inhibitors (inhibiting glucose absorption in the intestines), etc. have been used as agents to treat diabetes. Recently, peroxisome proliferator-activated receptor gamma (PPARγ) accelerators (Thiazolidinediones, increasing insulin sensitivity) have drawn attention as therapeutic agents for diabetes. However, these drugs have side effects such as hypoglycemia, weight gain and the like (David E. Moller, Nature, 2001, 414, 821). Accordingly, there is a strong need to developed diabetes therapeutic agents with decreased side effects, in particular without inducing hypoglycemia and weight gain.

Recently, it has been found that dipeptidyl peptidase-IV (DPP-IV) deficient mice maintained glucagon-like protein 1 (GLP-1) activity and high insulin levels, resulting in decreased blood glucose levels, which suggested the possibility of it being used as a therapeutic agent for diabetes (Marguet D. et al, Natl. Acad. Sci. USA, (2000) 97, 6874-6879). GLP-1 induces differentiation and growth of pancreatic β-cells in vivo and plays an important role in the production and secretion of insulin. GLP-1 is inactivated by DPP-IV, and DPP-IV inhibitors have been reported to increase insulin secretion by means of inhibiting said inactivation mechanism. DPP-IV inhibitors are also being developed as a treatment for obesity because they lead to satiety in rats and slow down digestion of foods in the intestines, resulting in weight loss. Further, many investigators have also shown that DPP-IV inhibitors control blood glucose and lipid levels in animal experiments (Pospislik J. A., et al, Diabetes, (2002) 51, 943-950). In this regard, DPP-IV inhibitors can be considered as potentially useful agents for treatment of diabetes.

To date, much research for developing DPP-IV inhibitors has focused on materials in which cyano group is bonded to pyrrolidine ring. For example, WO 00/34241 discloses DPP-IV inhibitors represented by the below formula.

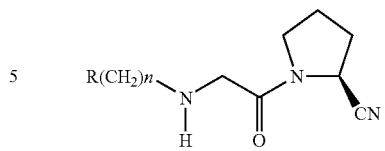

wherein R is an adamantyl group, and n is 0 to 3.

Another inhibitors are disclosed in WO 04/064778, WO 03/004498, WO 03/082817, etc., and among them, WO 04/064778 discloses DPP-IV inhibitors represented by the below formula.

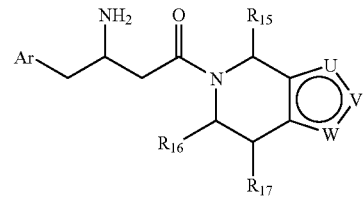

wherein Ar is unsubstituted or substituted phenyl group; $R_{15}$, $R_{16}$ and $R_{17}$ are hydrogen or alkyl group; and U, V and W are nitrogen, oxygen, or substituted nitrogen or carbon.

WO 03/004498 discloses DPP-IV inhibitors represented by the below formula.

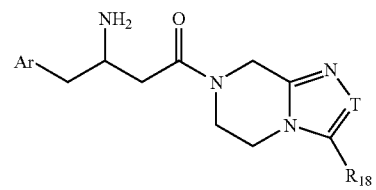

wherein Ar is unsubstituted or substituted phenyl group; $R_{18}$ is hydrogen or alkyl group; and T is nitrogen or substituted carbon.

WO 03/082817 discloses DPP-IV inhibitors represented by the below formula.

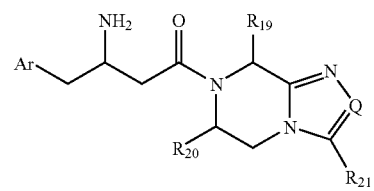

wherein Ar is unsubstituted or substituted phenyl group; $R_{19}$, $R_{20}$ and $R_{21}$ are hydrogen or alkyl group; and Q is nitrogen or substituted carbon.

These DPP-IV inhibitors has the amide bond in their molecular structures likewise the present invention; however, the unsubstituted or substituted phenyl groups which is represented as Ar in the above formulas of these inhibitors are entirely different from the saturated or unsaturated, 5-membered or 6-membered heterocyclic substituents of the present invention. Moreover, DPP-IV inhibitors of the present invention having the lactam ring at the phenyl group position of the above inhibitors have not been disclosed in the prior art.

DISCLOSURE OF INVENTION

Technical Problem

The inventors of the present invention, while carrying out extensive research and many experiments to develop compounds exhibiting DPP-IV inhibitor effects, found that compounds having an optionally substituted lactam ring structure exhibit excellent inhibitory activity versus DPP-IV. The present invention was accomplished on the basis of such finding.

It is therefore an object of the invention to provide novel compounds of an optionally substituted lactam ring structure having good inhibitory activity versus DPP-IV.

It is a further object of the present invention to provide processes for preparation of such compounds.

It is another object of the present invention to provide pharmaceutical compositions for inhibiting DPP-IV activity comprising a pharmaceutically effective amount of these compounds as an active agent, and also provide methods for treating or preventing diseases caused by inappropriate activity of DPP-IV by the use of the compounds of the present invention.

Other objects and advantages of the present invention will become apparent to those skilled in the art from the following detailed description.

Technical Solution

According to the present invention, there are provided the compound of Formula 1 below.

(1)

wherein (A) A is selected from the group consisting of substituents of Formulas 2 to 7 below:

(2)

wherein $R_1$ is hydrogen, or substituted or unsubstituted $C_1$-$C_4$ alkyl; and X is carbon or nitrogen;

(3)

wherein $R_2$ is hydrogen, or substituted or unsubstituted $C_1$-$C_4$ alkyl;

(4)

(5)

wherein $R_3$ is hydrogen, or substituted or unsubstituted alkyl, cycloalkyl, aryl or heteroaryl; and $R'_3$ is hydrogen, $CF_3$;

(6)

wherein $R_4$ is hydrogen, halogen, or substituted or unsubstituted $C_1$-$C_4$ alkyl, or selected from the substituents of Formulas 6a and 6b below:

(6a)

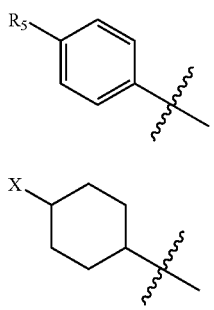

(6b)

wherein R$_5$ is hydrogen, halogen, or substituted or unsubstituted C$_1$-C$_4$alkyl; and X is oxygen, sulfur, or sulfone;

(7)

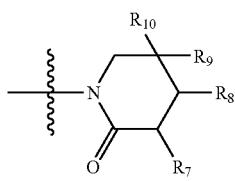

wherein R$_6$ is halogen, or substituted or unsubstituted C$_1$-C$_4$alkyl;

(B) B is selected from the group consisting of substituents of Formulas 8 to 11 below:

(8)

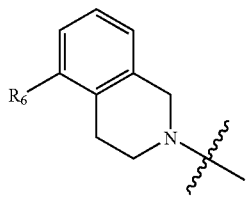

wherein R$_7$, R$_8$, R$_9$ and R$_{10}$ are each independently hydrogen, halogen, or substituted or unsubstituted C$_1$-C$_4$ alkyl;

(9)

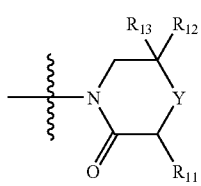

wherein R$_{11}$, R$_{12}$ and R$_{13}$ are each independently hydrogen, halogen, or substituted or unsubstituted C$_1$-C$_4$ alkyl; and Y is oxygen, sulfur or SO$_2$;

(10)

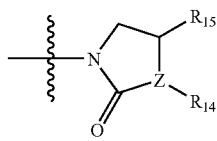

wherein R$_{14}$ and R$_{15}$ are each independently hydrogen, halogen, or substituted or unsubstituted C$_1$-C$_4$ alkyl; and Z is —CH— or oxygen, where Z is oxygen, R$_{14}$ is nothing;

(11)

wherein R$_{17}$ is substituted or unsubstituted C$_1$-C$_4$ alkyl.

Where C$_1$-C$_4$ alkyl is substituted, as defined in the above formula, it is preferably the alkyl substituted with halogen, and more preferably the alkyl substituted with fluoride.

In a preferable embodiment, R$_3$ in Formula 5 is selected from the group consisting of the below substituents:

(i) hydrogen;
(ii) substituted or unsubstituted C$_1$-C$_4$ alkyl;
(iii) formula $$-\underset{2}{CH} - R_{18},$$

wherein R$_{18}$ is C$_1$-C$_4$ alkoxyalkyl, or C$_3$-C$_7$ cycloalkyl unsubstituted or substituted with halogen or hydroxy, or phenyl unsubstituted or substituted with halogen or hydroxy;

(iv) substituted or unsubstituted $$\underset{3}{C} - C_7$$

cycloalkyl;
(v) formula formula wherein R$_{19}$ and R$_{20}$ are each independently hydrogen, halogen, or substituted or unsubstituted C$_1$-C$_4$ alkyl; and (vi) 5-membered or 6-membered heteroaryl unsubstituted or substituted with halogen or hydroxy.

In the above embodiment, where $C_3$-$C_7$ cycloalkyl and $C_1$-$C_4$ alkyl are of a substituted form, they are preferably the cycloalkyl and alkyl substituted with halogen or hydroxy.

The preferable examples of the heteroaryl as defined above include, but not limited to 2-furane, 3-furane, 2-thiophene, 3-thiophene, 2-pyridine, 3-pyridine, 4-pyridine, 2-pyrrole, 3-pyrrole, etc.

The compounds according to the present invention include isomers thereof, and a preferable isomer is the compound of Formula 1a below in which the carbon adjacent to $NH_2$ is a chiral center:

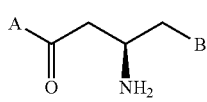

(1a)

wherein, A and B are the same as in Formula 1.

The compound of the present invention may form an acid adduct with a pharmaceutically acceptable acid. As used herein, the pharmaceutically acceptable salt includes inorganic salts, organic salts, amino acid salts, etc., and more specifically, salts with inorganic acids such as hydrochloric acid, hydrobromic acid, phosphoric acid or sulfuric acid; salts with organic carboxylic acids such as acetic acid, citric acid, trifluoroacetic acid, formic acid, maleic acid, oxalic acid, succinic acid, benzoic acid, tartaric acid, fumaric acid, mandelic acid, ascorbic acid, malic acid and the like; salts with methanesulfonic acid, p-toluenesulfonic acid and the like.

The compound of the present invention or the pharmaceutically acceptable salts thereof can be present in a form of hydrate or solvate.

In a particularly preferred embodiment, the compounds of Formula 1 according to the present invention are compounds as defined below:

3-[2S-amino-4-oxo-4-(3-trifluoromethyl-5,6-dihydro-8H-[1,2,4]triazolo[4,3-a]pyrazin-7-yl)-butyl]-oxazolidin-2-one;

3-[2S-amino-4-oxo-4-(3-trifluoromethyl-5,6-dihydro-8H-[1,2,4]triazolo[4,3-a]pyrazin-7-yl)-butyl]-5-methyl-oxazolidin-2-one;

1-[2S-amino-4-oxo-4-(3-trifluoromethyl-5,6-dihydro-8H-[1,2,4]triazolo[4,3-a]pyrazin-7-yl)-butyl]-piperidin-2-one;

1-[2S-amino-4-oxo-4-(3-trifluoromethyl-5,6-dihydro-8H-[1,2,4]triazolo[4,3-a]pyrazin-7-yl)-butyl]-4-methyl-pyrrolidin-2-one;

1-[2S-amino-4-oxo-4-(3-trifluoromethyl-5,6-dihydro-8H-[1,2,4]triazolo[4,3-a]pyrazin-7-yl)-butyl]-4,4-dimethyl-pyrrolidin-2-one;

1-[2S-amino-4-oxo-4-(3-trifluoromethyl-5,6-dihydro-8H-[1,2,4]triazolo[4,3-a]pyrazin-7-yl)-butyl]-3-fluoro-pyrrolidin-2-one;

1-[2S-amino-4-oxo-4-(3-trifluoromethyl-5,6-dihydro-8H-[1,2,4]triazolo[4,3-a]pyrazin-7-yl)-butyl]-pyrrolidin-2-one;

1-[2S-amino-4-oxo-4-(3-trifluoromethyl-5,6-dihydro-8H-[1,2,4]triazolo[4,3-a]pyrazin-7-yl)-butyl]-3-fluoro-piperidin-2-one;

1-[2S-amino-4-oxo-4-(3-trifluoromethyl-5,6-dihydro-8H-[1,2,4]triazolo[4,3-a]pyrazin-7-yl)-butyl]-3-methyl-pyrrolidin-2-one;

1-[2S-amino-4-oxo-4-(3-trifluoromethyl-5,6-dihydro-8H-[1,2,4]triazolo[4,3-a]pyrazin-7-yl)-butyl]-4-methyl-1,5-dihydro-pyrrol-2-one;

1-[2S-amino-4-oxo-4-(3-trifluoromethyl-5,6-dihydro-8H-[1,2,4]triazolo[4,3-a]pyrazin-7-yl)-butyl]-4-methyl-piperidin-2-one;

1-[2S-amino-4-oxo-4-(3-trifluoromethyl-5,6-dihydro-8H-[1,2,4]triazolo[4,3-a]pyrazin-7-yl)-butyl]-5,5-difluoro-piperidin-2-one;

1-[2S-amino-4-oxo-4-(3-trifluoromethyl-5,6-dihydro-8H-[1,2,4]triazolo[4,3-a]pyrazin-7-yl)-butyl]-5R-methyl-piperidin-2-one;

3-[2S-amino-4-oxo-4-(3-trifluoromethyl-5,6-dihydro-8H-[1,2,4]triazolo[4,3-a]pyrazin-7-yl)-butyl]-3-aza-bicyclo[3.1.0]hexane-2-one;

1-[2S-amino-4-oxo-4-(3-trifluoromethyl-5,6-dihydro-8H-[1,2,4]triazolo[4,3-a]pyrazin-7-yl)-butyl]-4-trifluoromethyl-pyrrolidin-2-one;

1-[2S-amino-4-oxo-4-(3-trifluoromethyl-5,6-dihydro-8H-[1,2,4]triazolo[4,3-a]pyrazin-7-yl)-butyl]-4-trifluoromethyl-piperidin-2-one;

1-[2S-amino-4-oxo-4-(3-trifluoromethyl-5,6-dihydro-8H-[1,2,4]triazolo[4,3-a]pyrazin-7-yl)-butyl]-5-trifluoromethyl-piperidin-2-one;

4-[2S-amino-4-oxo-4-(3-trifluoromethyl-5,6-dihydro-8H-[1,2,4]triazolo[4,3-a]pyrazin-7-yl)-butyl]-6-methyl-morpholin-3-one;

1-[2S-amino-4-(3,4-dihydro-1H-isoquinolin-2-yl)-4-oxobutyl]-piperidin-2-one;

1-[2S-amino-4-(3,4-dihydro-1H-isoquinolin-2-yl)-4-oxobutyl]-4-methyl-pyrrolidin-2-one;

1-[2S-amino-4-oxo-4-(3-trifluoromethyl-4,5-dihydro-7H-isooxazolo[3,4-c]pyridin-6-yl)butyl]-piperidin-2-one;

1-[2S-amino-4-oxo-4-(3-trifluoromethyl-1,4,5,7-tetrahydro-pyrazolo[3,4-c]pyridin-6-yl)-butyl]-piperidin-2-one;

1-[2S-amino-4-oxo-4-(4-trifluoromethyl-5,8-dihydro-6H-pyrido[3,4-d]pyrimidin-7-yl)-butyl]-5R-methyl-1-piperidin-2-one;

(5R)-1-{(2S)-2-amino-4-oxo-4-[2-phenyl-4-(trifluoromethyl)-5,8-dihydropyrido[3,4-d]pyrimidin-7(6H)-yl]butyl}-5-methylpiperidin-2-one;

(6S)-4-{(2S)-2-amino-4-oxo-4-[2-phenyl-4-(trifluoromethyl)-5,8-dihydropyrido[3,4-d]pyrimidin-7(6H)-yl]butyl}-6-methylmorpholine-3-one;

1-{(2S)-2-amino-4-oxo-4-[2-phenyl-4-(trifluoromethyl)-5,8-dihydropyrido[3,4-d]pyrimidin-7(6H)-yl]butyl}-5,5-difluoropiperidin-2-one;

1-{(2S)-2-amino-4-[2-cyclopropyl-4-(trifluoromethyl)-5,8-dihydropyrido[3,4-d]pyrimidin-7(6H)-yl]-4-oxobutyl}-5,5-difluoropiperidin-2-one;

1-{(2S)-2-amino-4-[2-cyclopropyl-4-(trifluoromethyl)-5,8-dihydropyrido[3,4-d]pyrimidin-7(6H)-yl]-4-oxobutyl}-5-methylpiperidin-2-one;

(6S)-4-{(2S)-2-amino-4-[2-cyclopropyl-4-(trifluoromethyl)-5,8-dihydropyrido[3,4-d]pyrimidin-7(6H)-yl]-4-oxobutyl}-6-methylmorpholine-3-one;

1-{(2S)-2-amino-4-oxo-4-[5-(trifluoromethyl)-3,4-dihydroisoquinolin-2(1H)-yl]but yl}-5,5-difluoropiperidin-2-one;

(6S)-4-{(2S)-2-amino-4-oxo-4-[5-(trifluoromethyl)-3,4-dihydroisoquinolin-2(1H)-yl]butyl}-6-methylmorpholine-3-one;

1-{(2S)-2-amino-4-[2-(4-fluorophenyl)-4-(trifluoromethyl)-5,8-dihydropyrido[3,4-d ]pyrimidin-7(6H)-yl]-4-oxobutyl}-5,5-difluoropiperidin-2-one;

(6S)-4-{(2S)-2-amino-4-[2-(4-fluorophenyl)-4-(trifluoromethyl)-5,8-dihydropyrido[3,4-d]pyrimidin-7(6H)-yl]-4-oxobutyl}-6-methylmorpholine-2-one;

1-{(2S)-2-amino-4-[2-(3-fluorophenyl)-4-(trifluoromethyl)-5,8-dihydropyrido[3,4-d]pyrimidin-7(6H)-yl]-4-oxobutyl}-5,5-difluoropiperidin-2-one;

(6S)-4-{(2S)-2-amino-4-[2-(3-fluorophenyl)-4-(trifluoromethyl)-5,8-dihydropyrido[3,4-d]pyrimidin-7(6H)-yl]-4-oxobutyl}-6-methylmorpholine-3-one;

(5R)-1-{(2S)-2-amino-4-[2-(4-fluorophenyl)-4-(trifluoromethyl)-5,8-dihydropyrido[3,4-d]pyrimidin-7(6H)-yl]-4-oxobutyl}-5-methylpiperidin-2-one;

1-{(2S)-2-amino-4-[2-(3,4-difluorophenyl)-4-(trifluoromethyl)-5,8-dihydropyrido[3,4-d]pyrimidin-7(6H)-yl]-4-oxobutyl}-5,5-difluoropiperidin-2-one;

(6S)-4-{(2S)-2-amino-4-[2-(3,4-difluorophenyl)-4-(trifluoromethyl)-5,8-dihydropyrido[3,4-d]pyrimidin-7(6H)-yl]-4-oxobutyl}-6-methylmorpholine-3-one;

(5R)-1-{(2S)-2-amino-4-[2-(3,4-difluorophenyl)-4-(trifluoromethyl)-5,8-dihydropyrido[3,4-d]pyrimidin-7(6H)-yl]-4-oxobutyl}-5-methylpiperidin-2-one;

(5R)-1-{(2S)-2-amino-4-[2-cyclopentyl-4-(trifluoromethyl)-5,8-dihydropyrido[3,4-d]pyrimidin-7(6H)-yl]-4-oxobutyl}-5-methylpiperidin-2-one;

(6S)-4-{(2S)-2-amino-4-[2-cyclopentyl-4-(trifluoromethyl)-5,8-dihydropyrido[3,4-d]pyrimidin-7(6H)-yl]-4-oxobutyl}-6-methylmorpholine-3-one;

1-{(2S)-2-amino-4-[2-cyclopentyl-4-(trifluoromethyl)-5,8-dihydropyrido[3,4-d]pyrimidin-7(6H)-yl]-4-oxobutyl}-5,5-difluoropiperidin-2-one;

(5R)-1-[(2S)-2-amino-4-oxo-4-{2-[4-(trifluoromethyl)phenyl]-6,7-dihydro[1,3]thiazolo[4,5-c]pyridin-5(4H)-yl}butyl]-5-methylpiperidin-2-one;

(6S)-4-[(2S)-2-amino-4-oxo-4-{2-[4-(trifluoromethyl)phenyl]-6,7-dihydro[1,3]thiazolo[4,5-c]pyridin-5(4H)-yl}butyl]-6-methylmorpholine-3-one;

1-[(2S)-2-amino-4-oxo-4-{2-[4-(trifluoromethyl)phenyl]-6,7-dihydro[1,3]thiazolo[4,5-c]pyridin-5(4H)-yl}butyl]-5,5-difluoropiperidin-2-one;

(5R)-1-{(2S)-2-amino-4-[2-(4-fluorophenyl)-6,7-dihydro[1,3]thiazolo[4,5-c]pyridin-5(4H)-yl]-4-oxobutyl}-5-methylpiperidin-2-one;

(6S)-4-{(2S)-2-amino-4-oxo-4-[2-(4-fluorophenyl)-6,7-dihydro[1,3]thiazolo[4,5-c]pyridin-5(4H)-yl]butyl}-6-methylmorpholine-3-one;

1-{(2S)-2-amino-4-[2-(4-fluorophenyl)-6,7-dihydro[1,3]thiazolo[4,5-c]pyridin-5(4H)-yl]-4-oxobutyl}-5,5-difluoropiperidin-2-one;

(5R)-1-{(2S)-2-amino-4-oxo-4-[2-(tetrahydro-2H-pyran-4-yl)-6,7-dihydro[1,3]thiazolo[4,5-c]pyridin-5(4H)-yl]butyl}-5-methylpiperidin-2-one;

(6S)-4-{(2R)-2-amino-4-oxo-4-[2-(tetrahydro-2H-pyran-4-yl)-6,7-dihydro[1,3]thiazolo[4,5-c]pyridin-5(4H)-yl]butyl}-6-methylmorpholine-3-one;

1-{(2S)-2-amino-4-oxo-4-[2-(tetrahydro-2H-pyran-4-yl)-6,7-dihydro[1,3]thiazolo[4,5-c]pyridin-5(4H)-yl]butyl}-5,5-difluoropiperidin-2-one;

(6S)-4-{(2S)-2-amino-4-oxo-4-[2-(trifluoromethyl)-6,7-dihydro[1,3]thiazolo[4,5-c]pyridin-5(4H)-yl]butyl}-6-methylmorpholine-3-one;

1-{(2S)-2-amino-4-oxo-4-[2-(trifluoromethyl)-6,7-dihydro[1,3]thiazolo[4,5-c]pyridin-5(4H)-yl]butyl}-5,5-difluoropiperidin-2-one;

(5R)-1-{(2S)-2-amino-4-[2-(2-methoxyethyl)-4-(trifluoromethyl)-5,8-dihydropyrido[3,4-d]pyrimidin-7(6H)-yl]-4-oxobutyl}-5-methylpiperidin-2-one;

1-{(2S)-2-amino-4-[2-(2-methoxyethyl)-4-(trifluoromethyl)-5,8-dihydropyrido[3,4-d]pyrimidin-7(6H)-yl]-4-oxobutyl}-5,5-difluoropiperidin-2-one;

(5R)-1-{(2S)-2-amino-4-[2-(cyclopropylmethyl)-4-(trifluoromethyl)-5,8-dihydropyrido[3,4-d]pyrimidin-7(6H)-yl]-4-oxobutyl}-5-methylpiperidin-2-one;

1-{(2S)-2-amino-4-[2-(cyclopropylmethyl)-4-(trifluoromethyl)-5,8-dihydropyrido[3,4-d]pyrimidin-7(6H)-yl]-4-oxobutyl}-5,5-difluoropiperidin-2-one;

(5R)-1-{(2S)-2-amino-4-oxo-4-[2-pyridin-4-yl-4-(trifluoromethyl)-5,8-dihydropyrido[3,4-d]pyrimidin-7(6H)-yl]butyl}-5-methylpiperidin-2-one;

1-{(2S)-2-amino-4-oxo-4-[2-pyridin-4-yl-4-(trifluoromethyl)-5,8-dihydropyrido[3,4-d]pyrimidin-7(6H)-yl]butyl}-5,5-difluoropiperidin-2-one;

(5R)-1-{(2S)-2-amino-4-[2-(4-fluorobenzyl)-4-(trifluoromethyl)-5,8-dihydropyrido[3,4-d]pyrimidin-7(6H)-yl]-4-oxobutyl}-5-methylpiperidin-2-one;

1-{(2S)-2-amino-4-[2-(4-Fluorobenzyl)-4-(trifluoromethyl)-5,8-dihydropyrido[3,4-d]pyrimidin-7(6H)-yl]-4-oxobutyl}-5,5-difluoropiperidin-2-one;

(5R)-1-{(2S)-2-amino-4-oxo-4-[2-(3-thienyl)-4-(trifluoromethyl)-5,8-dihydropyrido[3,4-d]pyrimidin-7(6H)-yl]butyl}-5-methylpiperidin-2-one;

1-{(2S)-2-amino-4-oxo-4-[2-(3-thienyl)-4-(trifluoromethyl)-5,8-dihydropyrido[3,4-d]pyrimidin-7(6H)-yl]butyl}-5,5-difluoropiperidin-2-one;

(5R)-1-{(2S)-2-amino-4-oxo-4-[2-(2-thienyl)-4-(trifluoromethyl)-5,8-dihydropyrido[3,4-d]pyrimidin-7(6H)-yl]butyl}-5-methylpiperidin-2-one;

1-{(2S)-2-amino-4-oxo-4-[2-(2-thienyl)-4-(trifluoromethyl)-5,8-dihydropyrido[3,4-d]pyrimidin-7(6H)-yl]butyl}-5,5-difluoropiperidin-2-one;

(5R)-1-{(2S)-2-amino-4-[2-(2-furyl)-4-(trifluoromethyl)-5,8-dihydropyrido[3,4-d]pyrimidin-7(6H)-yl]-4-oxobutyl}-5-methylpiperidin-2-one;

1-{(2S)-2-amino-4-[2-(2-furyl)-4-(trifluoromethyl)-5,8-dihydropyrido[3,4-d]pyrimidin-7(6H)-yl]-4-oxobutyl}-5,5-difluoropiperidin-2-one;

(5R)-1-{(2S)-2-amino-4-[2-(3-furyl)-4-(trifluoromethyl)-5,8-dihydropyrido[3,4-d]pyrimidin-7(6H)-yl]-4-oxobutyl}-5-methylpiperidin-2-one;

1-{(2S)-2-amino-4-[2-(3-furyl)-4-(trifluoromethyl)-5,8-dihydropyrido[3,4-d]pyrimidin-7(6H)-yl]-4-oxobutyl}-5,5-difluoropiperidin-2-one;

(5R)-1-{(2S)-2-amino-4-oxo-4-[2-(1H-pyrrol-2-yl)-4-(trifluoromethyl)-5,8-dihydro pyrido[3,4-d]pyrimidin-7(6H)-yl]butyl}-5-methylpiperidin-2-one;

1-{(2S)-2-amino-4-oxo-4-[2-(1H-pyrrol-2-yl)-4-(trifluoromethyl)-5,8-dihydropyrido[3,4-d]pyrimidin-7(6H)-yl]butyl}-5,5-difluoropiperidin-2-one;

(5R)-1-{(2S)-2-amino-4-oxo-4-[2-pyridin-3-yl-4-(trifluoromethyl)-5,8-dihydropyrido[3,4-d]pyrimidin-7(6H)-yl]butyl}-5-methylpiperidin-2-one;

1-{(2S)-2-amino-4-oxo-4-[2-pyridin-3-yl-4-(trifluoromethyl)-5,8-dihydropyrido[3,4-d]pyrimidin-7(6H)-yl]butyl}-5,5-difluoropiperidin-2-one;

1-{(2S)-2-amino-4-[2-ethyl-4-(trifluoromethyl)-5,8-dihydropyrido[3,4-d]pyrimidin-7(6H)-yl]-4-oxobutyl}-5,5-difluoropiperidin-2-one;

(6S)-4-{(2S)-2-amino-4-[2-ethyl-4-(trifluoromethyl)-5,8-dihydropyrido[3,4-d]pyrimidin-7(6H)-yl]-4-oxobutyl}-6-methylmorpholine-3-one;

1-{(2S)-2-amino-4-[2-isopropyl-4-(trifluoromethyl)-5,8-dihydropyrido[3,4-d]pyrimidin-7(6H)-yl]-4-oxobutyl}-5,5-difluoropiperidin-2-one;

1-{(2S)-2-amino-4-[2-isopropyl-4-(trifluoromethyl)-5,8-dihydropyrido[3,4-d]pyrimidin-7(6H)-yl]-4-oxobutyl}-5-methylpiperidin-2-one;

(6S)-4-{(2S)-2-amino-4-[2-isopropyl-4-(trifluoromethyl)-5,8-dihydropyrido[3,4-d]pyrimidin-7(6H)-yl]-4-oxobutyl}-6-methylmorpholine-3-one;

(6R)-4-{(2S)-2-amino-4-oxo-4-[3-(trifluoromethyl)-5,6-dihydro[1,2,4]triazolo[4,3-a]pyrazin-7(8H)-yl]butyl}-6-methylmorpholine-3-one;

(6S)-4-{(2S)-2-amino-4-oxo-4-[3-(trifluoromethyl)-5,6-dihydro[1,2,4]triazolo[4,3-a]pyrazin-7(8H)-yl]butyl}-6-methylmorpholine-3-one;

(5S)-1-{(2S)-2-amino-4-oxo-4-[3-(trifluoromethyl)-5,6-dihydro[1,2,4]triazolo[4,3-a]pyrazin-7(8H)-yl]butyl}-5-methylpiperidin-2-one;

(5S)-1-{(2S)-2-amino-4-[2,4-bis(trifluoromethyl)-5,8-dihydropyrido[3,4-d]pyrimidin-7(6H)-yl]-4-oxobutyl}-5-methylpiperidin-2-one;

(5R)-1-{(2S)-2-amino-4-[2-methyl-4-(trifluoromethyl)-5,8-dihydropyrido[3,4-d]pyrimidin-7(6H)-yl]-4-oxobutyl}-5-methylpiperidin-2-one;

(5R)-1-{(2S)-2-amino-4-[2,4-bis(trifluoromethyl)-5,8-dihydropyrido[3,4-d]pyrimidin-7(6H)-yl]-4-oxobutyl}-5-methylpiperidin-2-one;

1-{(2S)-2-amino-4-[2,4-bis(trifluoromethyl)-5,8-dihydropyrido[3,4-d]pyrimidin-7(6H)-yl]-4-oxobutyl}-5,5-difluoropiperidin-2-one;

(5R)-4-{(2S)-2-amino-4-[2,4-bis(trifluoromethyl)-5,8-dihydropyrido[3,4-d]pyrimidin-7(6H)-yl]-4-oxobutyl}-6-methylmorpholine-3-one;

1-{(2S)-2-amino-4-[2-methyl-4-(trifluoromethyl)-5,8-dihydropyrido[3,4-d]pyrimidin-7(6H)-yl]-4-oxobutyl}-5,5-difluoropiperidin-2-one;

(6S)-4-{(2S)-2-amino-4-[2-methyl-4-(trifluoromethyl)-5,8-dihydropyrido[3,4-d]pyrimidin-7(6H)-yl]-4-oxobutyl}-6-methylmorpholine-3-one;

1-{(2S)-2-amino-4-oxo-4-[4-(trifluoromethyl)-5,8-dihydropyrido[3,4-d]pyrimidin-7(6H)-yl]butyl}-5,5-difluoropiperidin-2-one;

(6S)-4-{(2S)-2-amino-4-oxo-4-[4-(trifluoromethyl)-5,8-dihydropyrido[3,4-d]pyrimidin-7(6H)-yl]butyl}-6-methylmorpholine-3-one;

1-{(2S)-2-amino-4-oxo-4-[3-(pentafluoroethyl)-5,6-dihydro[1,2,4]triazolo[4,3-a]pyrazin-7(8H)-yl]butyl}-5,5-difluoropiperidin-2-one;

(6S)-4-{(2S)-2-amino-4-oxo-4-[3-(pentafluoroethyl)-5,6-dihydro[1,2,4]triazolo[4,3-a]pyrazin-7(8H)-yl]butyl}-6-methylmorpholine-3-one;

4-{(2S)-2-amino-4-[2,4-bis(trifluoromethyl)-5,8-dihydropyrido[3,4-d]pyrimidin-7(6H)-yl]-4-oxobutyl}-6-methylthiomorpholin-3-one;

1-{(2S)-2-amino-4-[2-t-butyl-4-(trifluoromethyl)-5,8-dihydropyrido[3,4-d]pyrimidin-7(6H)-yl]-4-oxobutyl}-5,5-difluoropiperidin-2-one;

(6S)-4-{(2S)-2-amino-4-[2-t-butyl-4-(trifluoromethyl)-5,8-dihydropyrido[3,4-d]pyrimidin-7(6H)-yl]-4-oxobutyl}-6-methylmorpholine-3-one;

4-{(2S)-2-amino-4-oxo-4-[3-(trifluoromethyl)-5,6-dihydro[1,2,4]triazolo[4,3-a]pyrazin-7(8H)-yl]butyl}-6-methylthiomorpholin-3-one;

(5R)-1-{(2S)-2-amino-4-[2-ethyl-4-(trifluoromethyl)-5,8-dihydropyrido[3,4-d]pyrimidin-7(6H)-yl]-4-oxobutyl}-5-methylpiperidin-2-one;

(5R)-1-{(2S)-2-amino-4-oxo-4-[2-(pentafluoroethyl)-4-(trifluoromethyl)-5,8-dihydropyrido[3,4-d]pyrimidin-7(6H)-yl]butyl}-5-methylpiperidin-2-one;

(6S)-4-{(2S)-2-amino-4-oxo-4-[2-(pentafluoroethyl)-4-(trifluoromethyl)-5,8-dihydropyrido[3,4-d]pyrimidin-7(6H)-yl]butyl}-6-methylmorpholine-3-one;

1-{(2S)-2-amino-4-oxo-4-[2-(pentafluoroethyl)-4-(trifluoromethyl)-5,8-dihydropyrido[3,4-d]pyrimidin-7(6H)-yl]butyl}-5,5-difluoropiperidin-2-one;

(5R)-1-{(2S)-2-amino-4-oxo-4-[2-propyl-4-(trifluoromethyl)-5,8-dihydropyrido[3,4-d]pyrimidin-7(6H)-yl]butyl}-5-methylpiperidin-2-one;

1-{(2S)-2-amino-4-oxo-4-[2-propyl-4-(trifluoromethyl)-5,8-dihydropyrido[3,4-d]pyrimidin-7(6H)-yl]butyl}-5,5-difluoropiperidin-2-one;

(5R)-1-{(2S)-2-amino-4-[2-(fluoromethyl)-4-(trifluoromethyl)-5,8-dihydropyrido[3,4-d]pyrimidin-7(6H)-yl]-4-oxobutyl}-5-methylpiperidin-2-one;

1-{(2S)-2-amino-4-[2-(fluoromethyl)-4-(trifluoromethyl)-5,8-dihydropyrido[3,4-d]pyrimidin-7(6H)-yl]-4-oxobutyl}-5,5-difluoropiperidin-2-one;

1-{(2S)-2-amino-4-[2,4-bis(trifluoromethyl)-5,8-dihydropyrido[3,4-d]pyrimidin-7(6H)-yl]-4-oxobutyl}-4-methyl-1,5-dihydro-2H-pyrrol-2-one;

1-{(2S)-2-amino-4-[2-(3-furyl)-4-(trifluoromethyl)-5,8-dihydropyrido[3,4-d]pyrimidin-7(6H)-yl]-4-oxobutyl}-4-methyl-1,5-dihydro-2H-pyrrol-2-one;

1-{(2S)-2-amino-4-[2,4-bis(trifluoromethyl)-5,8-dihydropyrido[3,4-d]pyrimidin-7(6H)-yl]-4-oxobutyl}-4-methyloxopyrrolidin-2-one;

1-{(2S)-2-amino-4-[2-(3-furyl)-4-(trifluoromethyl)-5,8-dihydropyrido[3,4-d]pyrimidin-7(6H)-yl]-4-oxobutyl}-4-methylpyrrolidin-2-one;

1-{(2S)-2-amino-4-[2,4-bis(trifluoromethyl)-5,8-dihydropyrido[3,4-d]pyrimidin-7(6H)-yl]-4-oxobutyl}-5-(trifluoromethyl)piperidin-2-one;

1-{(2S)-2-amino-4-[2,4-bis(trifluoromethyl)-5,8-dihydropyrido[3,4-d]pyrimidin-7(6H)-yl]-4-oxobutyl}-4-(trifluoromethyl)pyrrolidin-2-one;

1-{(2S)-2-amino-4-[2-(3-furyl)-4-(trifluoromethyl)-5,8-dihydropyrido[3,4-d]pyrimidin-7(6H)-yl]-4-oxobutyl}-4-(trifluoromethyl)pyrrolidin-2-one;

1-{(2S)-2-amino-4-[2,4-bis(trifluoromethyl)-5,8-dihydropyrido[3,4-d]pyrimidin-7(6H)-yl]-4-oxobutyl}-4-methyloxopiperidin-2-one;

1-{(2S)-2-amino-4-[2-(3-furyl)-4-(trifluoromethyl)-5,8-dihydropyrido[3,4-d]pyrimidin-7(6H)-yl]-4-oxobutyl}-4-methylpiperidin-2-one;

(5R)-1-{(2S)-2-amino-4-[2-cyclobutyl-4-(trifluoromethyl)-5,8-dihydropyrido[3,4-d]pyrimidin-7(6H)-yl]-4-oxobutyl}-5-methylpiperidin-2-one;

1-{(2S)-2-amino-4-[2-cyclobutyl-4-(trifluoromethyl)-5,8-dihydropyrido[3,4-d]pyrimidin-7(6H)-yl]-4-oxobutyl}-5,5-difluoropiperidin-2-one.

The present invention also relates to processes for preparation of the compound of Formula 1.

As the first illustrative process for such preparation, the compound of Formula 1 can be prepared by a process comprising a step of reacting the compound of Formula 12 below with the compound of Formula 13 and a step of removing an amine-protecting group $P_1$:

(12)

(13)

wherein, $R_{21}$ is selected from the group consisting of the substituents of Formulas 13a to 13d:

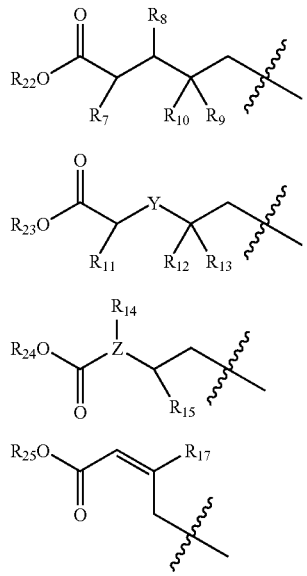

wherein,

A, B, Y, Z, $R_7$, $R_8$, $R_9$, $R_{10}$, $R_{11}$, $R_{12}$, $R_{13}$, $R_{14}$, $R_{15}$ and $R_{17}$ are the same as defined above;

$R_{22}$, $R_{23}$, $R_{24}$ and $R_{25}$ are each independently $C_1$-$C_3$ alkyl;

$P_1$ is amine-protecting group; and $G_1$ is nothing, or hydrochloric acid, sulfuric acid or trifluoroacetic acid.

The above reaction can be conducted in the presence of an organic solvent such as dichloroethane or cyclic ether (e.g., tetrahydrofuran (THF)) at a temperature of −10 to 40° C. The reaction product can be isolated and purified from the reactants by means of conventional methods such as chromatography.

The compound of Formula 12 above can be desirably prepared by Reaction Scheme 1 below:

[Reaction Scheme 1]

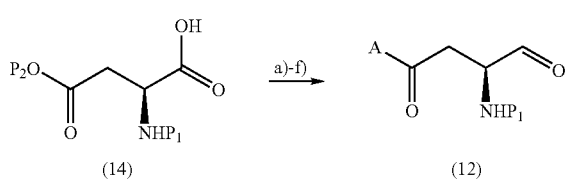

wherein, a is $ClCO_2Et$, $Et_3N$, THF; $NaBH_4$, MeOH;

b is TBSCl, imidazole, DMF;

c is Pd/C, $H_2$ (benzyl ester) or LiOH—$H_2O$, MeOH—$H_2O$ (methyl or ethyl ester);

d is EDC, HOBT, AH;

e is TBAF, THF;

f is Swern [O] or Dess Martin [O];

A and $P_1$ are the same as defined above; and $P_2$ is benzyl, methyl or ethyl.

More specifically, the carboxylic acid of Formula 14 above is converted into an ester anhydride which is then reduced using $NaBH_4$ in a presence of methanol solvent to product a primary alcohol. The resulting primary alcohol is protected with t-butyl dimethyl silyl group, then in the case of a benzyl ester form, a hydrolysis reaction is carried out using platinum complex and hydrogen, and in the case of methyl or ethyl form, a hydrolysis reaction is carried out using lithium hydroxide, thereby obtaining a carboxylic acid. Herein, a desired amine group can be converted into by a coupling reaction using EDC and HOBT, then TBS group is removed, followed by oxidation with Swern or Dess-Martin to obtain an aldehyde of Formula 12. Where the amine-protecting group is Boc, it can be removed using TFA or HCl, and where the amine-protecting group is Cbz, it can be removed using $H_2$/Pd/C or TMSI, and where the amine-protecting group is Fmoc, it can be removed using $Et_2NH$.

An amine 'A' in Formula 12 can be prepared by methods set forth in WO 04/064778, WO 03/004498, WO 03/082817, etc., or commercially available amines can be used.

Alternatively, the compound of Formula 12 can be synthesized from the compound of Formula 14 with reference to a known process (e.g., J. Med. Chem. 1999, 42(18), 3557-3571; WO 04/069162 etc.).

As the second illustrative process for such preparation, the compound of Formula 1 can be prepared by a process comprising a step of reacting the compound of Formula 13 above with the compound of Formula 15 below, a step of removing an acid-protecting group $P_3$: and a step of reacting the resulting product with a compound of Formula AH (wherein A is the same as in Formula 1), followed by removing an amine-protecting group:

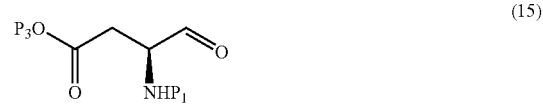

wherein, $P_1$ is the same as defined above; and $P_3$ is benzyl or t-butyl.

For example, the above process can be conducted by Reaction Scheme 2 below:

[Reaction Scheme 2]

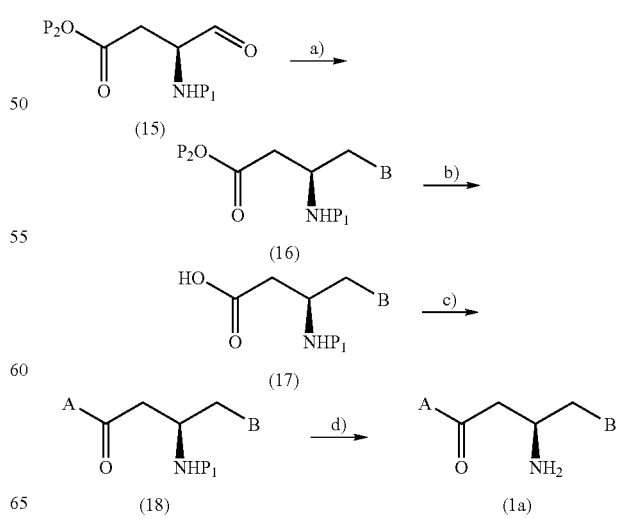

wherein, a) is Na(OAc)$_3$BH, R$_{21}$NH$_2$G$_1$, and ClCH$_2$CH$_2$Cl;

b) is Pd/C, H$_2$ (benzyl ester) or TFA/CH$_2$Cl$_2$ (t-Butyl ester, P$_1$=Boc) and then Boc$_2$O;

c) is EDC, HOBT, AH;

d) is HCl/Dioxane;

A and B are the same as defined above;

P$_1$ is an amine-protecting group such as Boc, Cbz or Fmoc;

P$_2$ is benzyl or t-butyl;

G$_1$ is nothing, or hydrochloric acid, sulfuric acid or trifluoroacetic acid.

A method for preparation of a compound of Formula 16 is known (e.g., J. Med. Chem. 1999, 42(18), 3557-3571).

Reaction a) is conducted in the presence of an organic solvent such as dichloroethane or cyclic ether (e.g., tetrahydrofuran (THF)) at a temperature of −10 to 40° C. by reacting a compound of Formula 15 with preferably 0.7 to 1.5 equivalent of a primary amine (a compound of Formula 13). Herein, a cyclization reaction is further procedured at the same condition as above to synthesize a compound of Formula 16, and the compound of Formula 16 is converted a carboxylic acid of Formula 17 via Reaction b).

Herein, where a protection group P$_2$ is benzyl, P$_2$ is removed by the condition of H$_2$/Pd/C to synthesize a carboxylic acid. Where P$_2$ is t-butyl and P$_1$ is Boc, these protection groups are together removed using dichloromethane/TFA, an amine group is again protected with Boc to synthesize a carboxylic acid. Using the thus prepared carboxylic acid and amine AH, a compound of Formula 18 is obtained by the known Reaction c).

Where an amine-protecting group P$_1$ is Boc, a compound of Formula 1a is obtained by Reaction d). Where P$_1$ is Cbz, P$_1$ is removed using H$_2$/Pd/C or TMSI, and where P$_1$ is Fmoc, P$_1$ is removed using Et$_2$NH, thereby obtaining a compound of Formula 1a.

An amine AH in Reaction c) can be prepared by methods set forth in WO 04/064778, WO 04/007468, etc., or commercially available amines can be used.

Among amines in Reaction c), the amine as defined below can be synthesized, for example, by Reaction Scheme 3 below:

[Reaction Scheme 3]

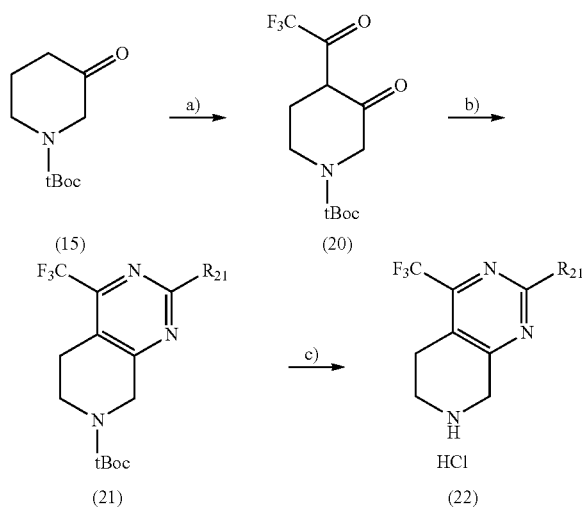

wherein, a is LHMDS, CF$_3$CO$_2$Et, DME;

b is (1) R$_{21}$C=NH(NH$_2$), EtOH or iPrOH, reflux,
(2) R$_{21}$C=NH(NH$_2$)HCl, NaOEt, EtOH or iPrOH, reflux,
(3) R$_{21}$C=NH(NH$_2$), cat. BF$_3$OEt$_2$, iPrOH, reflux, or
(4) R$_{21}$C=NH(NH$_2$), pyridine, reflux;

c is HCl/Dioxane or HCl/Ethyl Acetate;

R$_{21}$ is hydrogen, alkyl or aryl.

More specifically, a compound of Formula 20 can be prepared by making an enolate from a compound of Formula 19 using LHMDS and then adding trifluoroacetate thereto (reference: J. Fluorine Chem. 2003, 123(2), 267-272). There are various methods of preparing a compound 21 having a pyrimidine ring from a compound of Formula 20, and among them, a method of using BF$_3$OEt$_2$ as a catalyst (Synthesis 2000, 12, 1738-1748) and a method of using pyridine as a solvent (Tetrahedron 1983, 39(19), 3197-3199) are preferable to obtain the good yield. Using the thus prepared compound of Formula 21, a desired compound of Formula 22 can be obtained.

As the third illustrative process for such preparation, the compound of Formula 1 can be prepared by a process comprising a step of reacting the compound of Formula 15 above with the compound of Formula 23 below:

(23)

wherein,

G$_2$ is nothing or acid, preferably hydrochloric acid, sulfuric acid or trifluoroacetic acid;

R$_{26}$ is hydrogen, substituted or unsubstituted C$_1$-C$_4$ alkyl.

Where a compound of Formula 15 reacts with a compound of Formula 23, a cyclization reaction occurs at the compound, which is prepared in the same manner as a compound of Formula 13 in the second illustrative process, using COCl$_2$ to form the moiety B, and the following reaction is conducted in the same manner as in the second illustrative process to synthesize a compound of Formula 1. From this reaction of a compound of Formula 15 and a compound of Formula 12, a compound of Formula 1 in which Z is O in Formula 10 can be prepared.

Compounds as starting materials are know compounds, except the case where the methods for preparation of them are particularly described in the present invention, or they can be synthesized from known compounds by known methods or methods similar thereto.

A compound of Formula 1 can be isolated and purified from the reaction product by means of conventional methods such as recrystallization, ion electrophoresis, silica gel column chromatography, ion exchange resin chromatography and the like.

As described above, the compounds according to the present invention, starting materials for preparation thereof and intermediates can be synthesized by various methods, which should be interpreted to be included within the scope of the present invention in connection with the preparation of the compound of Formula 1.

Also, the present invention provides a pharmaceutical composition for inhibiting DPP-IV comprising the compound of Formula 1 or a pharmaceutically acceptable salt thereof and a pharmaceutically acceptable carrier.

The compound of Formula 1 can be administered in various pharmaceutical dosage forms in accordance with intended use. In the preparation of pharmaceutical compositions in accordance with the present invention, an active agent, more specifically a compound of Formula 1 may be mixed with one or more pharmaceutically acceptable carriers which can be selected depending on the dosage form to be prepared. For example, the pharmaceutical composition according to the present invention can be formulated into dosage forms suitable for injection or oral administration.

The compound of Formula 1 may be formulated in a conventional manner using known pharmaceutically acceptable carriers and excipients and presented in unit dosage form or in multidose containers. The formulations may take such forms as solutions, suspensions or emulsions in oily or aqueous vehicles, and may contain conventional dispersing, suspending or stabilizing agents. Alternatively, the active ingredient may be in powder form for reconstitution with sterile pyrogen-free water, before use. The compound of Formula 1 may also be formulated into suppositories containing conventional suppository bases such as cocoa butter or other glycerides. Solid dosage forms for oral administration include capsule, tablet, pill, powder and granule. Preferable dosage forms are capsule and tablet. It is preferable that tablets and pills be coated. The solid dosage forms for oral administration may be obtained by mixing the compound of Formula 1 as an active agent with inactive diluents such as sucrose, lactose, starch and the like and carriers such as lubricant, for example magnesium stearate, including disintegrator, binder and the like.

If necessary, the compound of Formula 1 and compositions comprising the same according to the present invention may be administered in combination with other pharmaceutical agents, for example, other diabetes treating agents.

When the formulation is presented in unit dosage form, the compound of Formula 1 as an active agent can be preferably contained in an amount of about 0.1~1,500 mg unit dosage. The dosage amount of the compound of Formula 1 will be dependent on the subject's weight and age, the nature and severity of the affliction and the judgment of the prescribing physician. For adult administration, the dosage amount required will be about in the range of 1 to 500 mg a day depending on the frequency and strength of the dosage. For intramuscular or intravenous administration to adults, a total dosage amount of about 5~300 mg a day will be sufficient. In some patients, the dosage amount in a day will be higher than that.

Further, the present invention provides the use of the compound of Formula 1 as defined in claim 1 for manufacture of a medicament for the treatment or prevention of diseases involving inappropriate activity of DPP-IV.

Representative examples of the diseases caused by inappropriate levels of DPP-IV include, but are in no way limited to, diabetes mellitus, obesity and the like as described above. Among diabetes mellitus, the present invention is preferred to treat and prevent type II diabetes mellitus.

MODE FOR THE INVENTION

The present invention will now be illustrated in more detail by the following preparations and examples. However, it will be understood that the present invention is not limited to these specific preparations and examples, but is subject to various modifications that will be recognized by one skilled in the art to which the present invention pertains.

PREPARATION 1

Synthesis of 3-aminomethyl-4,4,4-trifluoro-butanoic acid ethyl ester hydrochloric acid salt (1) Synthesis of 4,4,4-trifluoro-3-nitromethyl-butyric acid ethyl ester 1.0 g (5.94 mmol) of 4,4,4-trifluoro-2-butenoic acid ethyl ester and 0.15 mL (1.19 mmol) of 1,1,3,3-tetramethyl guanidine and 1.6 mL (29.8 mmol) of nitromethane were mixed. The resulting mixture was cooled to 0° C. and then stirred for 3 hours at room temperature, followed by addition of 100 mL of ethylacetoacetate. The reaction mixture was washed with water, and then an organic layer was dried over anhydrous magnesium sulfate. The solvent was distilled off under reduced pressure to give 1.1 g (4.80 mmol) of the title compound in a yield of 81%.

NMR: $^1$H-NMR (CDCl$_3$) δ 5.21~4.59 (2H, m), 4.22 (2H, q, J=8 Hz), 3.67~3.64 (1H, m), 2.82~2.72 (1H, m), 2.63~2.57 (1H, m), 1.28 (3H, t, J=8 Hz)

Mass (EI) 176 (M$^+$+1)

(2) Synthesis of N-hydroxy-3-(t-butoxycarbonylamino-methyl)-4,4,4-trifluoro-butyric acid ethyl ester 1.1 g (4.80 mmol) of 4,4,4-trifluoro-3-nitromethyl-butyric acid ethyl ester obtained in the above step (1) was dissolved in 20 mL of methanol, and then 1.85 g (8.47 mmol) of di-t-butyl dicarbonate was added thereto. A reaction was conducted with 180 mg of 10% palladium/carbon under atmospheric pressure for 15 hours. The reaction solution was filtered by Cellite and distilled off under reduced pressure, then without further purification to give 1.5 g (4.80 mmol) of the title compound in a yield of 100%.

NMR: $^1$H-NMR (CDCl$_3$) δ 6.48 (1H, s), 4.20 (2H, q, J=8 Hz), 3.89~3.83 (1H, m), 3.66~3.62 (1H, m), 3.24~3.17 (1H, m), 2.76~2.68 (1H, m), 2.53 (1H, dd, J=8 Hz, 16 Hz), 1.48 (9H, s), 1.25 (3H, t, J=8 Hz)

Mass (EI) 262 (M$^+$+1)

(3) Synthesis of 3-(t-butoxycarbonylamino-methyl)-4,4,4-trifluoro-butyric acid ethyl ester 760 mg (2.41 mmol) of N-hydroxy-3-(t-butoxycarbonylamino-methyl)-4,4,4-trifluoro-butyric acid ethyl ester obtained in the above step (2) was dissolved in 80 mL of methanol and 40 mL of water, then 2.4 g (28.9 mmol) of sodium acetate was added thereto, followed by dropwise addition of 4 mL (4.81 mmol) of aqueous 20% titanium trichloride at room temperature. After 20 minutes, 300 mL of ethylacetoacetate and was added to the solution and the reaction solution was washed with water, then an organic layer was dried over anhydrous magnesium sulfate. The solvent was distilled off under reduced pressure and then, the residue was purified by column chromatography to give 550 mg (2.24 mmol) of the title compound in a yield of 92%.

NMR: $^1$H-NMR (CDCl$_3$) δ 4.70 (1H, s), 4.18 (2H, q, J=6.8 Hz), 3.64~3.53 (1H, m), 3.35~3.34 (1H, m), 3.05~2.90 (1H, m), 2.60 (1H, dd, J=5.2 Hz, 16.4 Hz), 2.48 (1H, dd, J=8 Hz, 16.4 Hz), 1.43 (9H, s), 1.27 (3H, t, J=6.8 Hz)

Mass (EI) 246 (M$^+$+1)

(4) Synthesis of 3-aminomethyl-4,4,4-trifluoro-butanoic acid ethyl ester hydrochloric acid salt 170 mg (0.69 mmol) of 3-(t-butoxycarbonylamino-methyl)-4,4,4-trifluoro-butyric acid ethyl ester obtained in the above step (3) was dissolved in 6 mL of ethyl acetate saturated with hydrochloric acid gas, followed by stirring at room temperature for 3 hours. The solvent was distilled off under reduced pressure and then, the residue was purified by column chromatography to give 110 mg (0.69 mmol) of the title compound in a yield of 86%.

NMR: $^1$H-NMR (CDCl$_3$) δ 8.50 (2H, brs), 4.18 (2H, q, J=4 Hz), 3.50~3.20 (3H, m), 2.97~2.64 (2H, m), 1.24 (3H, t, J=4 Hz)

Mass (EI) 182 (M$^+$+1)

PREPARATION 2

Synthesis of 4-amino-3-methyl-butyric acid methyl ester hydrochloric acid salt

(1) Synthesis of 3-methyl-4-nitro-butyric acid methyl ester 3 g (29.9 mmol) of trans-2-butenoic acid methyl ester and 0.69 g (5.99 mmol) of tetramethylguanidine and 9.14 g (149 mmol) of nitromethane were mixed. The resulting mixture was stirred at room temperature for 24 days. 100 mL of ethylacetoacetate was added to the solution and the reaction solution was washed with water, then an organic layer was dried over anhydrous magnesium sulfate. The solvent was distilled off under reduced pressure, then the residue was purified by column chromatography to give 5.7 g (23.6 mmol) of the title compound in a yield of 100%.

NMR: $^1$H-NMR (CDCl$_3$) δ 4.48 (1H, dd, J=4 Hz, 12 Hz), 4.35 (1H, dd, J=4 Hz, 12 Hz), 3.71 (3H, s), 2.84~2.74 (1H, m), 2.47 (1H, dd, J=4 Hz, 16 Hz), 2.37 (1H, dd, J=8 Hz, 16 Hz), 1.11 (3H, d, J=8 Hz)

Mass (EI) 162 (M$^+$+1)

(2) Synthesis of N-t-butyloxycarbonylhydroxy-4-t-butoxycarbonylamino-3,3-dimethyl-butyric acid methylester 4 g (24.8 mmol) of 3-methyl-4-nitro-butyric acid methyl ester obtained in the above step (1) was dissolved in 50 mL of methanol and then 10.4 g (47.6 mmol) of di-t-butyldicarbonate was added thereto. A reaction was conducted with 500 mg of 10% palladium/carbon under a pressure of 50 psi for 9 hours. The reaction solution was filtered by Cellite and distilled off under reduced pressure, then the residue was purified by column chromatography to give 3.6 g (10.3 mmol) of the title compound and 1.1 g (4.45 mmol) of N-hydroxy-4-t-butoxycarbonylamino-3,3-dimethyl-butyric acid methylester in a yield of 62%.

Mass (EI) 348 (M$^+$+1)

(3) Synthesis of N-hydroxy-4-t-butoxycarbonylamino-3,3-dimethyl-butyric acid methylester 600 mg (1.72 mmol) of N-t-butyloxycarbonylhydroxy-4-t-butoxycarbonylamino-3,3-dimethyl-butyric acid methylester obtained in the above step (2) was dissolved in 80 mL of methanol, followed by addition of sodium bicarbonate 250 and stirring at 80° C. for 9 hours. 200 ml of ethyl acetate was added to the solution and the reaction solution was washed with water, and then an organic layer was dried over anhydrous magnesium sulfate. The solvent was distilled off under reduced pressure, and then the residue was purified by column chromatography to give 332 mg (1.34 mmol) of the title compound in a yield of 77%

NMR: $^1$H-NMR (CDCl$_3$) δ 7.27 (1H, brs), 3.49 (3H, s), 3.46 (1H, dd, J=4 Hz, 12 Hz), 3.33 (1H, dd, J=5.6 Hz, 14.4 Hz), 2.51~2.42 (1H, m), 2.39 (1H, dd, J=4 Hz, 16 Hz), 2.22 (1H, dd, J=4 Hz, 16 Hz), 1.48 (9H, s), 0.98 (3H, d, J=8 Hz)

Mass (EI) 248 (M$^+$+1)

(4) Synthesis of 4-t-butoxycarbonylamino-3-methyl-butyric acid methylester 213 mg (0.92 mmol) of the title compound was obtained in a yield of 47% in the same manner as in PREPARATION 1(3), except that 330 mg (1.33 mmol) of N-hydroxy-4-t-butoxycarbonylamino-3,3-dimethyl-butyric acid methylester obtained in the above step (3) was used.

NMR: $^1$H-NMR (CDCl$_3$) δ 4.65 (1H, brs), 3.68 (3H, s), 3.10~3.00 (2H, m), 2.38~2.33 (1H, m), 2.20~2.05 (2H, m), 1.44 (9H, s), 0.96 (3H, d, J=8 Hz)

Mass (EI) 232 (M$^+$+1)

(5) Synthesis of 4-amino-3-methyl-butyric acid methyl ester hydrochloric acid salt 62 mg (0.36 mmol) of the title compound was obtained in a yield of 83% in the same manner as in PREPARATION 1(4), except that 100 mg (0.43 mmol) of 4-t-butoxycarbonylamino-3-methyl-butyric acid methylester obtained in the above step (4) was used.

NMR: $^1$H-NMR (CDCl$_3$) δ 8.26 (2H, brs), 3.68 (3H, s), 3.10~2.99 (2H, m), 2.77~2.35 (3H, m), 1.13 (3H, d, J=8 Hz)

Mass (EI) 168 (M$^+$+1)

PREPARATION 3

Synthesis of 4-amino-2-fluoro-butyric acid methyl ester hydrochloric acid salt

(1) Synthesis of 2-oxo-pyrrolidin-1-carboxylic acid t-butyl ester 1 g (11.7 mmol) of 2-pyrrolidinone was dissolved in 15 mL of dichloromethane, and then 2.5 mL (17.8 mmol) of triethylamine and 107 mg (0.87 mmol) of dimethylaminopyridine and 2.7 g (12.3 mmol) of di-t-butyl dicarbonate were added thereto. The reaction solution was stirred at room temperature for 8 hours. 100 mL of ethylacetate was added to the solution, and the reaction solution was washed with water, and then an organic layer was dried over anhydrous magnesium sulfate. The solvent was distilled off under reduced pressure, and then the residue was purified by column chromatography to give 1.2 g (6.47 mmol) of the title compound in a yield of 55%.

NMR: $^1$H-NMR (CDCl$_3$) δ 3.76~3.73 (2H, m), 2.53~2.49 (2H, m), 2.04~1.88 (2H, m), 1.53 (9H, s)

Mass (EI) 186 (M$^+$+1)

(2) Synthesis of 3-fluoro-2-oxo-pyrrolidin-1-carboxylic acid t-butyl ester 300 mg (1.61 mmol) of 2-oxo-pyrrolidin-1-carboxylic acid t-butyl ester obtained in the above step (1) was dissolved in tetrahydrofuran and cooled to −78° C. To the resulting solution, was dropwise added 1.7 mL (1.7 mmol) of 1.0 M lithium bis(trimethylsilyl)amide in tetrahydrofuran, followed by stirring for 1 hours. 561 mg (1.78 mmol) of N-fluorobenzene sulfonimide was added to the resulting solution, and then the temperature was gradually raised to −30° C. for 2 hours. 100 mL of ethylacetoacetate was added to the solution, and the reaction solution was washed with aqueous ammonium chloride, and then an organic layer was dried over anhydrous magnesium sulfate. The solvent was distilled off under reduced pressure, then the residue was purified by column chromatography to give 60 mg (0.29 mmol) of the title compound in a yield of 18%.

NMR: $^1$H-NMR (CDCl$_3$) δ 5.16~5.12 (0.5H, m), 5.01~4.94 (0.5H, m), 3.91~3.85 (1H, m), 3.64~3.57 (1H, m), 2.50~2.45 (1H, m), 2.25~2.13 (1H, m), 1.54 (9H, s)

Mass (EI) 204 (M$^+$+1)

(3) Synthesis of 4-t-butoxycarbonylamino-2-fluoro-butyric acid methyl ester 60 mg (0.29 mmol) of 3-fluoro-2-oxo-pyrrolidin-1-carboxylic acid t-butyl ester obtained in the above step (2) was dissolved in 3 mL of methanol, and then 32 mg (0.59 mmol) of sodium methoxide was added thereto at 0° C. After 1 hour, 10 mL of ethylacetate was added to the solution, and the reaction solution was washed with aqueous ammonium chloride, and an organic layer was dried over anhydrous magnesium sulfate. The solvent was distilled off under reduced pressure, then the residue was purified by column chromatography to give 49 mg (0.29 mmol) of the title compound in a yield of 18%.

Mass (EI) 236 (M$^+$+1)

(4) Synthesis of 4-amino-2-fluoro-butyric acid methyl ester hydrochloric acid salt 17 mg (0.099 mmol) of the title compound was obtained in a yield of 47% in the same manner as in PREPARATION 1(4), except that 50 mg (0.21 mmol) of 4-t-butoxycarbonylamino-2-fluoro-butyric acid methyl ester obtained in the above step (3) was used.

NMR: $^1$H-NMR (CD$_3$OD) δ 5.24~5.20 (0.5H, m), 5.15~4.95 (0.5H, m), 3.81 (3H, s), 3.21~3.08 (2H, m), 2.40~2.10 (2H, m)

Mass (EI) 172 (M$^+$+1)

PREPARATION 4

Synthesis of 5-amino-2-fluoro-pentanoic acid methyl ester hydrochloric acid salt (1) Synthesis of 2-oxo-piperidin-1-carboxylic acid t-butyl ester 1.17 g (8.88 mmol) of the title compound was obtained in a yield of 88% in the same manner as in PREPARATION 3(1), except that 1 g (10.08 mmol) of 2-piperidinone was used.

NMR: $^1$H-NMR (CDCl$_3$) δ 3.67~3.64 (2H, m), 2.52~2.49 (2H, m), 1.86~1.78 (4H, m), 1.53 (9H, s)

Mass (EI) 200 (M$^+$+1)

(2) Synthesis of 3-fluoro-2-oxo-piperidin-1-carboxylic acid t-butyl ester 160 mg (0.73 mmol) of the title compound was obtained in a yield of 48% in the same manner as in PREPARATION 3(2), except that 300 mg (1.5 mmol) of 2-oxo-piperidin-1-carboxylic acid t-butyl ester obtained in the above step (1) was used.

NMR: $^1$H-NMR (CDCl$_3$) δ 5.03~4.75 (1H, m), 3.75~3.55 (2H, m), 2.35~2.22 (1H, m), 2.05~1.78 (3H, m), 1.54 (9H, s)

Mass (EI) 218 (M$^+$+1)

(3) Synthesis of 5-t-butoxycarbonylamino-2-fluoro-pentanoic acid methyl ester 56 mg (0.22 mmol) of the title compound was obtained in a yield of 30% in the same manner as in PREPARATION 3(3), except that 160 mg (0.73 mmol) of 3-fluoro-2-oxo-piperidin-1-carboxylic acid t-butyl ester in the above step (2) was used.

NMR: $^1$H-NMR (CDCl$_3$) δ 5.02~4.87 (1H, m), 4.63 (1H, brs), 3.80 (3H, s), 3.25~3.05 (2H, m), 1.99~1.88 (2H, m), 1.72~1.64 (2H, m), 1.44 (9H, s)

Mass (EI) 250 (M$^+$+1)

(4) Synthesis of 5-amino-2-fluoro-pentanoic acid methyl ester hydrochloric acid salt 40 mg (0.21 mmol) of the title compound was obtained in a yield of 95% in the same manner as in PREPARATION 1(4), except that 56 mg (0.224 mmol) of 5-t-butoxycarbonylamino-2-fluoro-pentanoic acid methyl ester in the above step (3) was used.

NMR: $^1$H-NMR (CDCl$_3$) δ 5.15~4.95 (1H, m), 3.81 (3H, s), 3.00~2.90 (2H, m), 2.10~1.73 (4H, m)

Mass (EI) 186 (M$^+$+1)

PREPARATION 5

Synthesis of 4-amino-2-methyl-butanoic acid methyl ester hydrochloric acid salt (1) Synthesis of 3-methyl-2-oxo-pyrrolidin-1-carboxylic acid t-butyl ester 300 mg (1.61 mmol) of 2-oxo-pyrrolidin-1-carboxylic acid t-butyl ester was dissolved in tetrahydrofuran and then cooled to −78° C. To the resulting solution, was dropwise added a solution of 1.7 mL (1.7 mmol) of 1.0 M lithium bis(trimethylsilyl)amide tetrahydrofuran, followed by stirring for 1 hour. 0.19 mL (3.05 mmol) of iodomethane was dropwise added thereto. Thereafter, the temperature was gradually raised to −30° C. for 2 hours. 50 mL of ethyl acetate was added to the solution, and the reaction solution was washed with aqueous ammonium chloride, and an organic layer was dried over anhydrous magnesium sulfate. The solvent was distilled off under reduced pressure, then the residue was purified by column chromatography to give 130 mg (0.65 mmol) of the title compound in a yield of 40%.

NMR: $^1$H-NMR (CDCl$_3$) δ 3.79~3.74 (1H, m), 3.61~3.54 (1H, m), 2.59~2.53 (1H, m), 2.25~2.17 (1H, m), 1.67~1.59 (1H, m), 1.53 (9H, s), 1.20 (3H, d, J=12 Hz)

Mass (EI) 200 (M$^+$+1)

(2) Synthesis of 4-t-butoxycarbonylamino-2-methyl-butanoic acid methyl ester 120 mg (0.51 mmol) of the title compound was obtained in a yield of 78% in the same manner as in PREPARATION 3(3), except that 130 mg (0.65 mmol) of 3-methyl-2-oxo-pyrrolidin-1-carboxylic acid t-butyl ester obtained in the above step (1) was used.

NMR: $^1$H-NMR (CDCl$_3$) δ 4.58 (1H, brs), 3.68 (3H, s), 3.17~3.14 (2H, m), 2.55~2.47 (1H, m), 1.89~1.80 (1H, m), 1.67~1.60 (1H, m), 1.44 (9H, s), 1.19 (3H, d, J=4 Hz)

Mass (EI) 232 (M$^+$+1)

(3) Synthesis of 4-amino-2-methyl-butanoic acid methyl ester hydrochloric acid salt 80 mg (0.47 mmol) of the title compound was obtained in a yield of 92% in the same manner as in PREPARATION 1(4), except that 120 mg (0.51 mmol) of 4-t-butoxycarbony-lamino-2-methyl-butyric acid methyl ester obtained in the above step (2) was used.

NMR: $^1$H-NMR (CD$_3$OD) δ 3.70 (3H, s), 3.05~2.90 (2H, m), 2.65~2.55 (1H, m), 2.05~1.70 (2H, m), 1.23 (3H, d, J=6 Hz)

Mass (EI) 168 (M$^+$+1)

PREPARATION 6

Synthesis of 4-amino-3-methyl-2-butenoic acid methyl ester hydrochloric acid salt (1) Synthesis of (2-hydroxy-propyl)-carbamic acid t-butyl ester 1 g (13.3 mmol) of 1-amino-propane-2-ol was dissolved in 40 mL of methanol and 10 mL of water and then, 3.7 g (16.9 mmol) of di-t-butyl dicarbonate added thereto, followed by stirring for 3 hours at room temperature. To the solution, were added 200 mL of ethyl acetate and the reaction solution was washed with water, and then an organic layer was dried over anhydrous magnesium sulfate. The solvent was distilled off under reduced pressure, then the residue was purified by column chromatography to give 2.24 g (12.8 mmol) of the title compound in a yield of 96%.

NMR: $^1$H-NMR (CDCl$_3$) δ 4.91 (1H, brs), 3.95~3.85 (1H, m), 3.30~3.22 (1H, m), 3.05~2.95 (1H, m), 1.43 (9H, s), 1.16 (3H, d, J=4 Hz)

Mass (EI) 176 (M$^+$+1)

(2) Synthesis of (2-oxo-propyl)-carbamic acid t-butyl ester 2.24 g (12.7 mmol) of (2-hydroxy-propyl)-carbamic acid t-butyl ester obtained in the above step (1) was dissolved in 30 mL of dichloromethane, and then 3.6 mL (25.7 mmol) of triethylamine was dropwise added. To the resulting solution, was added a solution of 6.05 g (19 mmol) of 50% pyridine sulfur trioxide which was dissolved in 15 mL of dimethylsul-foxide. After 6 hours, 200 mL of ethyl acetate was added thereto and the reaction solution was washed with water, then an organic layer was dried over anhydrous magnesium sulfate. The solvent was distilled off under reduced pressure, then the residue was purified by column chromatography to give 1.15 g (6.64 mmol) of the title compound in a yield of 52%.

NMR: $^1$H-NMR (CDCl$_3$) δ 5.20 (1H, brs), 4.05~4.00 (2H, m), 2.17 (3H, s), 1.43 (9H, s)

Mass (EI) 174 (M$^+$+1)

(3) Synthesis of cis-4-t-butoxycarbonylamino-3-methyl-2-butenoic acid methylester 500 mg (2.88 mmol) of (2-oxo-propyl)-carbamic acid t-butyl ester obtained in the above step (2) was dissolved in 8 mL of benzene, and then 1.45 g (4.33 mmol) of methyl (triphenyl phosphoranylidene) acetate and 35 mg (0.28 mmol) of benzoic acid was added thereto. The reaction solution was heated to 80° C. for 3 hours. The solvent was distilled off under reduced pressure, then the residue was purified by column chromatography to give 54 mg (6.64 mmol) of the title compound in a yield of 23% and 301 mg (1.31 mmol) of the trans compound in a yield of 45%.

NMR: $^1$H-NMR (CDCl$_3$) δ 5.77 (1H, s), 5.17 (1H, brs), 4.16 (2H, d, J=6.4 Hz), 3.69 (3H, s), 2.05 (3H, s), 1.44 (9H, s)

Mass (EI) 230 (M$^+$+1)

(4) Synthesis of 4-amino-3-methyl-2-butenoic acid methyl ester hydrochloric acid salt 30 mg (0.23 mmol) of the title compound was obtained in a yield of 97% in the same manner as in PREPARATION 1(4), except 54 mg (0.235 mmol) of cis-4-t-butoxycarbony-lamino-3-methyl-2-butenoic acid methylester obtained in the above step (3) was used.

NMR: $^1$H-NMR (CD$_3$OD) δ 6.05 (1H, s), 4.00 (2H, s), 3.72 (3H, s), 3.29~3.28 (2H, m), 2.05 (3H, s)

Mass (EI) 130 (M$^+$+1)

PREPARATION 7

Synthesis of (R)-5-amino-4-methyl-pentanoic acid methyl ester hydrochloric acid salt (1) Synthesis of (S)-3-methanesulfonyloxy-2-methyl-propionic acid methyl ester 3 g (25.3 mmol) of (S)-3-hydroxy-2-methyl-propionic acid methyl ester was dissolved in dichloromethane 50 mL, then 5.3 mL (37.9 mmol) of triethylamine was dropwise added thereto. Thereafter, 2.16 mL (27.9 mmol) of methanesulfonyl chloride was added to the solution at 0° C. After 1 hour, 200 mL of ethylacetoacetate was added to the solution and then the reaction solution was washed with water and then an organic layer was dried over anhydrous magnesium sulfate. The solvent was distilled off under reduced pressure, then the residue was purified by column chromatography to give 4.97 g (25.3 mmol) of the title compound in a yield of 100%.

Mass (EI) 197 (M$^+$+1)

(2) Synthesis of (S)-3-azido-2-methyl-propionic acid methyl ester 4.97 g (25.3 mmol) of (S)-3-methanesulfonyloxy-2-methyl-propionic acid methyl ester obtained in the above step (2) was dissolved in 40 mL of dimethylformamide, and then 5 g (76.8 mmol) of sodium azide was added thereto, followed by stirring at 60° C. for 24 hours. 200 mL of ethylacetoacetate was added to the solution, and the reaction solution was washed with water, then an organic layer was dried over anhydrous magnesium sulfate. The solvent was distilled off under reduced pressure, then the residue was purified by column chromatography to give 3.5 g (24.4 mmol) of the title compound in a yield of 96%.

NMR: $^1$H-NMR (CDCl$_3$) δ 3.71 (3H, s), 3.54~3.52 (1H, m), 3.40~3.30 (1H, m), 2.80~2.65 (1H, m), 1.20 (3H, d, J=7.2 Hz)

Mass (EI) 144 (M$^+$+1)

(3) Synthesis of (S)-3-t-butoxycarbonylamino-2-methyl-propionic acid methyl ester 3.9 g (26.8 mmol) of (S)-3-azido-2-methyl-propionic acid methyl ester obtained in the above step (2) was dissolved in 50 mL of methanol, followed by addition 8.8 g (40.3 mmol) of di-t-butyl dicarbonate. A reaction was conducted with 40 mg of 20% palladium/carbon under hydrogen atmosphere for 9 hours. The reaction solution was filtered by Celite and distilled off under reduced pressure, then the residue was purified by column chromatography to give 2.6 g (11.9 mmol) of the title compound in a yield of 44%.

NMR: $^1$H-NMR (CDCl$_3$) δ 4.92 (1H, brs), 3.70 (3H, s), 3.31~3.20 (2H, m), 2.70~2.55 (1H, m), 1.43 (9H, s), 1.15 (3H, d, J=12 Hz)

Mass (EI) 218 (M$^+$+1)

(4) Synthesis of (S)-(3-hydroxy-2-methyl-propyl)-carbamic acid t-butylester 500 mg (2.30 mmol) of (S)-3-t-butoxycarbonylamino-2-methyl-propionic acid methyl ester obtained in the above step (3) was dissolved in 30 mL of tetrahydrofuran, and then 262 mg (6.9 mmol) of lithium aluminum hydride was slowly added thereto at 0° C. After warming-up to room temperature, a reaction was conducted for 4 hours. The reaction solution was cooled to 0° C., and then 0.26 mL of water and 0.26 mL of sodium hydroxide solution and 0.78 mL of water were slowly added thereto. The reaction solution was filtered by Celite and distilled off under reduced pressure, then the residue was purified by column chromatography to give 430 mg (2.27 mmol) of the title compound in a yield of 98%.

NMR: $^1$H-NMR (CDCl$_3$) δ 4.78 (1H, brs), 3.55~3.50 (1H, m), 3.33~3.20 (2H, m), 3.05~2.98 (1H, m), 1.75~1.65 (1H, m), 1.46 (9H, s), 0.87 (3H, d, J=12 Hz)

Mass (EI) 190 (M$^+$+1)

(5) Synthesis of (S)-(2-methyl-3-oxo-propyl)-carbamic acid t-butylester 423 mg (2.26 mmol) of the title compound was obtained in a yield of 99% in the same manner as in PREPARATION 6-(2), except that 430 mg (2.27 mmol) of (S)-(3-hydroxy-2-methyl-propyl)-carbamic acid t-butylester obtained in the above step (4) was used.

Mass (EI) 188 (M$^+$+1)

(6) Synthesis of (R)-5-t-butoxycarbonylamino-4-methyl-2-pentenoic acid methylester 380 mg (2.26 mmol) of the title compound was obtained in a yield of 99% in the same manner as in PREPARATION 6-(3), except that 423 mg (2.26 mmol) of (S)-(2-methyl-3-oxo-propyl)-carbamic acid t-butylester obtained in the above step (5) was used.

NMR: $^1$H-NMR (CDCl$_3$) δ 6.84 (1H, dd, J=15 Hz, 10 Hz), 5.84 (1H, d, J=15 Hz), 4.55 (1H, brs), 3.72 (3H, s), 3.25~3.15 (1H, m), 3.06~3.00 (1H, m), 2.54~2.47 (1H, m), 1.42 (9H, s), 1.03 (3H, d, J=15 Hz)

Mass (EI) 244 (M$^+$+1)

(7) Synthesis of (R)-5-t-butoxycarbonylamino-4-methyl-pentanoic acid methylester 370 mg (2.26 mmol) of (R)-5-t-butoxycarbonylamino-4-methyl-2-pentenoic acid methylester obtained in the above step (6) was dissolved in 50 mL of methanol. A reaction was conducted with 40 mg of 20% palladium hydroxide under hydrogen atmosphere for 9 hours and the reaction solution was filtered by Celite. The filtrated solution was distilled off under reduced pressure, then the residue was purified by column chromatography to give 310 mg (1.26 mmol) of the title compound in a yield of 55%.

NMR: $^1$H-NMR (CDCl$_3$) δ 4.87 (1H, brs), 3.67 (3H, s), 3.05~2.96 (2H, m), 2.39~2.27 (2H, m), 1.75~1.40 (3H, m), 1.44 (9H, s), 0.87 (3H, d, J=12 Hz)

Mass (EI) 246 (M$^+$+1)

(8) Synthesis of (R)-5-amino-4-methyl-pentanoic acid methyl ester hydrochloric acid salt 220 mg (1.21 mmol) of the title compound was obtained in a yield of 96% in the same manner as in PREPARATION 1-(4), except that 310 mg (1.26 mmol) of (R)-5-t-butoxycarbonylamino-4-methyl-pentanoic acid methylester obtained in the above step (7) was used.

NMR: $^1$H-NMR (CD$_3$OD) δ 3.87(3H, s), 2.96~2.91 (1H, m), 2.81~2.76 (1H, m), 2.47~2.40 (2H, m), 1.88~1.76 (2H, m), 1.56~1.50 (1H, m), 1.04 (3H, d, J=6.4 Hz)

Mass (EI) 182 (M$^+$+1)

PREPARATION 8

Synthesis of 5-amino-3-methyl-pentanoic acid methyl ester hydrochloric acid salt (1) Synthesis of 4-methyl-piperidin-1-carboxylic acid t-butylester 3.5 g (17.5 mmol) of the title compound was obtained in a yield of 87% in the same manner as in PREPARATION 6-(1), except that 2 g (20.1 mmol) of 4-methylpiperidine was used.

Mass (EI) 200 (M$^+$+1)

(2) Synthesis of 4-methyl-2-oxo-piperidin-1-carboxylic acid t-butylester 1 g (5.02 mmol) of 4-methyl-piperidin-1-carboxylic acid t-butylester obtained in the above step (1) was dissolved in 70 mL of ethylacetate. To the resulting solution, was dropwise added a solution in which 5.4 g (25.2 mmol) of sodium periodate and 247 mg (1.85 mmol) of ruthenium dioxide were dissolved in 40 mL of water. After 3 hours, 5% sodium thiosulfate was added thereto, and the resulting solution was extracted with ethylacetate, then an organic layer was dried over anhydrous magnesium sulfate. The solvent was distilled off under reduced pressure, then the residue was purified by column chromatography to give 750 mg (3.52 mmol) of the title compound in a yield of 70%.

NMR: $^1$H-NMR (CDCl$_3$) δ 4.11~3.77 (1H, m), 3.53~3.49 (1H, m), 2.62~2.56 (1H, m), 2.15~1.90 (3H, m), 1.49 (9H, s), 1.48~1.26 (1H, m), 1.02 (3H, d J=4 Hz)

Mass (EI) 214 (M$^+$+1)

(3) Synthesis of 5-t-butoxycarbonylamino-3-methyl-pentanoic acid methyl ester 410 mg (1.67 mmol) of the title compound was obtained in a yield of 97% in the same manner as in PREPARATION 3-(3), except that 368 mg (1.72 mmol) of 4-methyl-2-oxo-piperidin-1-carboxylic acid t-butylester obtained in the above step (2) was used.

$^1$H NMR (CDCl$_3$) δ 4.5-4.6 (1H, br s), 3.65 (3H, s), 3.0-3.2 (2H, m), 2.3 (1H, m), 2.15 (1H, m), 2.0 (1H, m), 1.4-1.5 (2H, m), 1.45 (9H, s)

Mass (m/e) 268 (M+Na)

(4) Synthesis of 5-amino-3-methyl-pentanoic acid methyl ester hydrochloric acid salt 226 mg (1.24 mmol) of the title compound was obtained in a yield of 74% in the same manner as in PREPARATION 1-(4), except that 410 mg (1.24 mmol) of 5-t-butoxycarbonylamino-3-methyl-pentanoic acid methyl ester obtained in the above step (3) was used.

$^1$H NMR (CD$_3$OD) δ 3.65 (3H, s), 2.9-3.0 (2H, m), 2.34 (1H, dd, J=15, 7 Hz), 2.27 (1H, dd, J=15, 7 Hz), 2.0 (1H, m), 1.7 (1H, m), 1.54 (1H, m), 0.98 (3H, d, J=7 Hz)

Mass (m/e) 146 (M+1)

PREPARATION 9

Synthesis of 4-aminomethyl-5,5,5-trifluoro-pentanoic acid methyl ester hydrochloric acid salt

(1) Synthesis of 5-trifluoromethyl-piperidin-2-one 1 g (6.13 mmol) of 5-trifluoromethyl-2-pridinol was dissolved in 20 mL of acetic acid. A reaction was conducted with 300 mg of platinum oxide under a pressure of 50 psi of hydrogen (g) for 9 hours. The reaction solution was filtered by Celite and distilled off under reduced pressure, then the residue was purified by column chromatography to give 920 mg (5.50 mmol) of the title compound in a yield of 89%.

NMR: $^1$H-NMR (CDCl$_3$) δ 3.56~3.51 (1H, m), 3.42~3.36 (1H, m), 2.59~2.53 (2H, m), 2.45~2.41 (1H, m), 2.19~2.13 (1H, m), 1.95~1.87 (1H, m)

Mass (EI) 168 (M$^+$+1)

(2) Synthesis of 2-oxo-5-trifluoromethyl-piperidin-1-carboxylic acid t-butylester 1.3 g (7.7 mmol) of 5-trifluoromethyl-piperidin-2-one obtained in the above step (1) was dissolved in 10 mL of acetonitrile. To the solution was added 2.0 g (14.3 mmol) of triethylamine and 48 mg (0.39 mmol) of dimethylaminopyridine and 1.8 g (8.2 mmol) of di-t-butyl dicarbonate. After stirring at 80° C. for 4 hours, 100 mL of ethyl acetate was added to the solution previously formed and the reaction solution was washed with water. An organic layer was dried over anhydrous magnesium sulfate. The solvent was distilled off under reduced pressure, and then the residue was purified by column chromatography to give 669 mg (2.5 mmol) of the title compound in a yield of 32% by column chromatography.

NMR: $^1$H-NMR (CDCl$_3$) δ 4.09~3.97 (1H, m), 3.77~3.71 (1H, m), 2.70~2.47 (3H, m), 2.15~2.10 (1H, m), 1.97~1.89 (1H, m), 1.50 (9H, s)

Mass (EI) 268 (M$^+$+1)

(3) Synthesis of 4-(t-butoxycarbonylamino-methyl)-5,5,5-trifluoro-pentanoic acid methylester 500 mg (1.67 mmol) of the title compound was obtained in a yield of 66% in the same manner as in PREPARATION 3-(3), except that 669 mg (2.5 mmol) of 2-oxo-5-trifluoromethyl-piperidin-1-carboxylic acid t-butylester obtained in the above step (2) was used.

NMR: $^1$H-NMR (CDCl$_3$) δ 4.76 (1H, s), 3.68 (3H, s), 3.45~3.30 (2H, m), 2.55~2.48 (2H, m), 2.40~2.32 (1H, m), 2.00~1.95 (1H, m), 1.90~1.80 (1H, m), 1.43 (9H, s)

Mass (EI) 300 (M$^+$+1)

(4) Synthesis of 4-aminomethyl-5,5,5-trifluoro-pentanoic acid methyl ester hydrochloric acid salt 335 mg (1.42 mmol) of the title compound was obtained in a yield of 85% in the same manner as in PREPARATION 1-(4), except that 500 mg (1.67 mmol) of 4-(t-butoxycarbonylamino-methyl)-5,5,5-trifluoro-pentanoic acid methylester obtained in the above step (3) was used.

NMR: $^1$H-NMR (CDCl$_3$) δ 8.48 (2H, s), 3.69 (3H, s), 3.50~3.40 (1H, m), 3.30~3.15 (1H, m), 2.99~2.89 (1H, m), 2.65~2.52 (2H, m), 2.11~1.91 (2H, m)

Mass (EI) 236 (M$^+$+1)

PREPARATION 10

Synthesis of (2-amino-1-methyl-ethoxy)-acetic acid ethyl ester hydrochloric acid salt

(1) Synthesis of (2-t-butoxycarbonylamino-1-methyl-ethoxy)-acetic acid ethyl ester 500 mg (2.85 mmol) of (2-hydroxy-propyl)-carbamic acid t-butyl ester was dissolved in 10 mL of dichloroethane, then 0.44 mL (4.24 mmol) of ethyl diazoacetate was added thereto. 38 mg (0.085 mmol) of rhodium acetate was added to the reaction and then heated to 80° C. for 2 hours. The solvent was distilled off under reduced pressure, and the residue was purified by column chromatography to give 381 mg (1.45 mmol) of the title compound in a yield of 50%.

NMR: $^1$H-NMR (CDCl$_3$) δ 5.39 (1H, s), 4.23 (2H, q, J=8 Hz), 4.09 (1H, d, J=16 Hz), 4.00 (1H, d, J=16 Hz), 3.60~3.35 (1H, m), 3.35~3.15 (1H, m), 3.10~3.04 (1H, m), 1.46 (9H, s), 1.31 (3H, t, J=4 Hz), 1.16 (3H, d, J=4 Hz)

Mass (EI) 262 (M$^+$+1)

(2) Synthesis of (2-amino-1-methyl-ethoxy)-acetic acid ethyl ester hydrochloric acid salt 130 mg (0.65 mmol) of the title compound was obtained in a yield of 44% in the same manner as in PREPARATION 1-(4), except that 381 mg (1.45 mmol) of 2-t-butoxycarbonylamino-1-methyl-ethoxy)-acetic acid ethyl ester obtained in the above step (the above step (1) was used.

NMR: $^1$H-NMR (CDCl$_3$) δ 8.47(2H, s), 4.23 (2H, q, J=8 Hz), 4.22~3.99 (2H, m), 3.80~3.70 (1H, m), 3.25~3.20 (1H, m), 3.10~2.98 (1H, m), 1.29 (3H, t, J=7.5 Hz), 1.20 (3H, d, J=5 Hz)

Mass (EI) 200 (M$^+$+1)

PREPARATION 11

Synthesis of 5-amino-3-trifluoromethyl-pentanoic acid ethyl ester hydrochloric acid salt

(1) Synthesis of 2-oxo-4-trifluoromethyl-piperidin-1-carboxylic acid t-butyl ester 2.82 g (3.2 mmol) of sodium methaperiodate (NaIO$_4$) was dissolved in 20 mL of water, followed by addition of 117 mg (0.88 mmol) of ruthenium oxide (RuO$_2$). To The reaction, was added a solution in which 660 mg (2.6 mmol) of 4-trifluoromethyl-piperidin-1-carboxylic acid t-butyl ester dissolved in 35 mL of ethyl acetate, followed by stirring for 2 hours and 20 minutes. The reaction solution was diluted with excess ethylacetate and washed once with water and aqueous NaCl, respectively, and then dried over anhydrous magnesium sulfate and filtered off. The filtrated solution was distilled off under reduced pressure, then the residue was purified by column chromatography (2:1 hexane:ethyl acetate) to give 0.63 g of the title compound in a yield of 90%.

$^1$H NMR (CDCl$_3$) δ 3.86 (1H, dd, J=13.5, 5.5 Hz), 3.62 (1H, m), 2.6-2.8 (2H, m), 2.56 (1H, dd, J=17, 10 Hz), 2.1-2.2 (1H, m), 1.8-1.9 (1H, m), 1.53 (9H, s)

Mass (m/e) 290 (M+Na)

(2) Synthesis of 5-t-butoxycarbonylamino-3-trifluoromethyl-pentanoic acid ethyl ester 630 mg (2.36 mmol) of 2-oxo-4-trifluoromethyl-piperidin-1-carboxylic acid t-butyl ester obtained in the above step (1) was dissolved in methanol, then 255 mg (4.5 mmol) of sodium ethoxide was added thereto, followed by stirring for 15 minutes. After concentration, the reaction was diluted with excess ethyl acetate, and the reaction solution was washed once with aqueous 1 N aqueous hydrochloric acid and aqueous NaCl, respectively, and dried over anhydrous magnesium sulfate and filtered off. The filtrated solution was distilled off under reduced pressure, then the residue was purified by column chromatography (5:1 hexane:ethyl acetate) to give 0.48 g of the title compound in a yield of 65%.

$^1$H NMR (CDCl$_3$) δ 4.76 (1H, br s), 4.17 (2H, q, J=7.0 Hz), 3.1-3.3 (2H, m), 2.7-2.8 (1H, m), 2.62 (1H, dd, J=16, 5 Hz), 2.4 (1H, dd, J=16, 8 Hz), 1.9 (1H, m), 1.6 (1H, m), 1.43 (9H, s), 1.26 (3H, t, J=7.0 Hz)

Mass (m/e) 336 (M+Na)

(3) Synthesis of 5-amino-3-trifluoromethyl-pentanoic acid ethyl ester hydrochloric acid salt 477 mg (1.5 mmol) of 5-t-butoxycarbonylamino-3-trifluoromethyl-pentanoic acid ethyl ester obtained in the above step (2) was reacted with ethyl acetate/hydrochloric acid, followed by stirring for 35 minutes. Then, the reaction solution was concentrated and solidified with diethylether to give 0.220 g of the title compound in a yield of 68%.

$^1$H NMR (CDCl$_3$) δ 4.16 (2H, q, J=7.0 Hz), 3.04 (2H, t, J=8.0 Hz), 2.9 (1H, m), 2.70 (1H, dd, J=16, 5 Hz), 2.55 (1H, dd, J=17, 8 Hz), 2.0-2.1 (1H, m), 1.8-1.9 (1H, m), 1.26 (3H, t, J=7.0 Hz)

Mass (m/e) 214 (M+1)

PREPARATION 12

Synthesis of 5-amino-4,4-difluoro-pentanoic acid methyl ester hydrochloric acid salt

(1) Synthesis of 3,3-difluoro-piperidin-1-carboxylic acid t-butyl ester 400 mg (2.0 mmol) of 3-oxo-piperidin-1-carboxylic acid t-butyl ester was dissolved in dichloromethane and cooled to −78° C., and then 0.53 mL of diethyllaminosulfur trifluoride (DAST, 4.0 mmol) was dropwise added thereto, followed by stirring for 19 hours. Thereafter, the temperature was raised to room temperature and about 0.3 mL water was added to the reaction solution. After concentration, the residue was purified by column chromatography (10:1 hexane:ethyl acetate) to give 0.29 g of the title compound in a yield of 64%.

$^1$H NMR (CDCl$_3$) δ 3.61 (2H, t, J=11 Hz), 3.4 (2H, m), 1.9-2.0 (2H, m), 1.7-1.8 (2H, m), 1.45 (9H, s)

Mass (m/e) 244 (M+Na)

(2) Synthesis of 5,5-difluoro-2-oxo-piperidin-1-carboxylic acid t-butyl ester 0.53 g (2.5 mmol) of sodium methaperiodate (NaIO$_4$) was dissolved in 4 mL of water, and then 22 mg (0.17 mmol) of ruthenium oxide (RuO$_2$) was added thereto. The resulting solution was dissolved in 7 mL of ethyl acetate. To this solution, 110 mg (0.5 mmol) of 3,3-difluoro-piperidin-1-carboxylic acid t-butyl ester obtained in the above step (1) was added, followed by stirring at room temperature for 21 hours. After stirring, the reaction solution was diluted by excess ethylacetate, and washed once with water and aqueous NaCl, respectively, and dried over anhydrous magnesium sulfate and filtered off. The filtrated solution was distilled off under reduced pressure, then the residue was purified by column chromatography (2:1 hexane:ethyl acetate) to give 91 mg of the title compound in a yield of 78%

$^1$H NMR (CDCl$_3$) δ 3.97 (2H, t, J=13 Hz), 2.66 (2H, t, J=7.0 Hz), 2.3-2.4 (2H, m), 1.53 (9H, s)

Mass (m/e) 258 (M+Na)

(3) Synthesis of 5-t-butoxycarbonylamino-4,4-difluoro-pentanoic acid methyl ester 91 mg (0.39 mmol) of 5,5-difluoro-2-oxo-piperidin-1-carboxylic acid t-butyl ester obtained in the above step (2) was dissolved in methanol, then 42 mg (0.78 mmol) of sodium methoxide was added thereto, followed by stirring for 20 minutes. After concentration, the reaction was diluted with excess ethyl acetate, and washed once with aqueous 1 N aqueous hydrochloric acid and aqueous NaCl, respectively, then dried over anhydrous magnesium sulfate and filtered off. The filtrated solution was distilled off under reduced pressure, then the residue was purified by column chromatography (2:1 hexane:ethyl acetate) to give 73 mg of the title compound in a yield of 71%

$^1$H NMR (CDCl$_3$) δ 4.83 (1H, br s), 3.69 (3H, s), 3.4-3.6 (2H, m), 2.55 (2H, t, J=8 Hz), 2.1-2.3 (2H, m), 1.44 (9H, s)

Mass (m/e) 290 (M+Na)

(4) Synthesis of 5-amino-4,4-difluoro-pentanoic acid methyl ester hydrochloric acid salt 73 mg (0.27 mmol) of 5-t-butoxycarbonylamino-4,4-difluoro-pentanoic acid methyl ester obtained in the above step (3) was reacted with ethyl acetate/hydrochloric acid, followed by stirring for 25 minutes. Thereafter, the reaction solution was concentrated and solidated with diethylether to give 40 mg of the title compound in a yield of 88%.

$^1$H NMR (CD$_3$OD) δ 3.68 (3H, s), 3.48 (2H, t, J=15 Hz), 2.59 (2H, t, J=7.5 Hz), 2.3-2.4 (2H, m)

Mass (m/e) 168 (M+1)

PREPARATION 13

Synthesis of 3S-t-butoxycarbonylamino-4-hydroxy-butyric acid benzyl ester 2S-t-butoxycarbonylamino-succinic acid 4-benzyl ester 6.46 g (20 mmol) of was dissolved in tetrahydrofuran and then cooled to 0 C. To the resulting solution, was dropwise added in sequence 1.9 mL (20 mmol) of ethyl chloroformate and 2.79 mL of triethylamine. After 30 minutes, 1.5 g (40 mmol) of sodium borohydride was added thereto, and the reaction solution was slowly poured into methanol, followed by stirring for 1 hour. Thereafter, the reaction solution was diluted with excess ethyl acetate, and washed once with aqueous 1 N aqueous HCl and aqueous NaCl, respectively, then dried over anhydrous magnesium sulfate and filtered off. The filtrated solution was distilled off under reduced pressure, then the residue was purified by column chromatography (4:1 hexane:ethyl acetate) to give 4.44 g of the title compound in a yield of 72%

$^1$H NMR (CDCl$_3$) δ 7.3-7.4 (5H, m), 5.21 (1H, d, J=8 Hz), 5.12 (2H, s), 4.0 (1H, m), 3.69 (2H, d, J=5 Hz), 2.67 (2H, d, J=5.5 Hz), 1.42 (9H, s)

Mass (m/e) 310 (M+1)

PREPARATION 14

Synthesis of 3S-t-butoxycarbonylamino-4-oxo-butyric acid benzyl ester 0.31 g (1.0 mmol) of 3S-t-butoxycarbonylamino-4-hydroxy-butyric acid benzyl ester was dissolved in dichloromethane obtained in PREPARATION 13, and then 6 mL of Dess-Martin (~0.3 M) was added thereto, followed by stirring for 4 hours. After concentration, the residue was purified by column chromatography (2:1 hexane:ethyl acetate) to give 0.23 g of the title compound in a yield of 75%

$^1$H NMR (CDCl$_3$) δ 9.64 (1H, s), 7.3-7.4 (5H, m), 5.6 (1H, d, J=7.5 Hz), 5.12 (2H, s), 4.35 (1H, m), 3.05 (1H, dd, J=15.0, 5.0 Hz), 2.88 (1H, dd, J=15.0, 5.0 Hz), 1.44 (9H, s)

Mass (m/e) 308 (M+1)

PREPARATION 15

Synthesis of 3S-t-butoxycarbonylamino-4-(2-hydroxy-ethylamino)-butyric acid benzyl ester 0.68 g (2.2 mmol) of 3S-t-butoxycarbonylamino-4-oxo-butyric acid benzyl ester obtained in PREPARATION 14 was dissolved in dichloroethane and then cooled to 0° C., then 2-aminoethanol (130 l, 2.2 mmol) of was added thereto, followed by stirring for about 30 minutes. Thereafter, sodium triacetoxyborohydride 1.4 g (6.6 mmol) of was added thereto, followed by stirring for about 1⅙ hours. The resulting solution was diluted with dichloromethane, and washed with aqueous saturated sodium bicarbonate, then dried over anhydrous magnesium sulfate and filtered off. The filtrated solution was distilled off under reduced pressure, then the residue was purified by column chromatography (1:1 hexane:ethyl acetate→10:1 CH$_2$Cl$_2$:MeOH) to give 0.14 g of the title compound in a yield of 18%

$^1$H NMR (CDCl$_3$) δ 7.3-7.4 (5H, m), 5.8-6.1 (1H, m), 5.12 (2H, s), 4.15-4.35 (1H, m), 3.7-3.8 (2H, m), 2.9-3.15 (4H, m), 2.6-2.8 (2H, m), 1.42 (9H, s)

Mass (m/e) 353 (M+1)

PREPARATION 16

Synthesis of 3S-t-butoxycarbonylamino-4-(2-oxo-oxazolidin-3-yl)-butyric acid benzyl ester 140 mg (0.4 mmol) of 3S-t-butoxycarbonylamino-4-(2-hydroxy-ethylamino)-butyric acid benzyl ester obtained in PREPARATION 15 was dissolved in dichloromethane and then cooled to 0° C., then 280 l (1.6 mmol) of N,N-diisopropylethylamine and 49 mg (0.4 mmol) of dimethylaminopyridine were added thereto, followed by addition of 0.4 g (0.6 mmol) of phosgene (20% toluene) followed by stirring for 2 hours and 40 minutes. Thereafter, the resulting solution was diluted with dichloromethane, and washed with aqueous NaCl, then dried over anhydrous magnesium sulfate and filtered off. The filtrated solution was distilled off under reduced pressure, then the residue was purified by column chromatography (1:1 hexane:ethyl acetate) to give 30 mg of the title compound in a yield of 20%

$^1$H NMR (CDCl$_3$) δ 7.3-7.4 (5H, m), 5.12 (2H, s), 5.1 (1H, m), 4.3 (2H, m), 4.2 (1H, m), 3.76 (1H, m), 3.5 (2H, m), 3.22 (1H, m), 2.63 (1H, dd, J=16, 5.5 Hz), 2.58 (1H, dd, J=16, 6.5 Hz), 1.41 (9H, s)

Mass (m/e) 379 (M+1)

PREPARATION 17

Synthesis of [3-oxo-1-(2-oxo-oxazolidin-3-ylmethyl)-3-(3-trifluoromethyl-5,6-dihydro-8H-[1,2,4]triazolo[4,3-a]pyrazin-7-yl)-propyl]-1S-carbamic acid t-butyl ester 30 mg (0.079 mmol) of 3S-t-butoxycarbonylamino-4-(2-oxo-oxazolidin-3-yl)-butyric acid benzyl ester obtained in PREPARATION 16 was dissolved in methanol, then 3 mg of palladium/carcol (Pd/C) was added thereto, followed by stirring under hydrogen atmosphere for 3 hours, 40 minutes. After completion of a reaction, the reaction solution was filtered by Cellite, and then washed with methanol, concentrated. To this reaction, 15 mg (0.079 mmol) of 3-trifluoromethyl-5,6-dihydro-8H-[1,2,4]triazolo[4,3-a]pyrazine was added immediately, then was dissolved in dichloromethane. The reaction was cooled to 0° C., then 13 mg (0.095 mmol) of HOBT was added, then stirred for 10 minutes, 23 mg (0.12 mmol) of EDC was added to thereto. After removal of an icebath, the reaction solution was stirred for about 17 hours, then the concentrated residue was purified by prep-TLC (10:1 CH$_2$Cl$_2$:MeOH) to give 21 mg of the title compound in a total yield of 57%.

$^1$H NMR (CDCl$_3$) δ 5.6-5.8 (1H, m), 4.9-5.1 (2H, m), 4.0-4.4 (6H, m), 3.6-3.8 (2H, m), 3.3-3.5 (2H, m), 2.6-2.9 (2H, m), 1.39 (9H, s)

Mass (m/e) 463 (M+1)

EXAMPLE 1

Synthesis of 3-[2S-amino-4-oxo-4-(3-trifluoromethyl-5,6-dihydro-8H-[1,2,4]triazolo[4,3-a]pyrazin-7-yl)-butyl]-oxazolidin-2-one

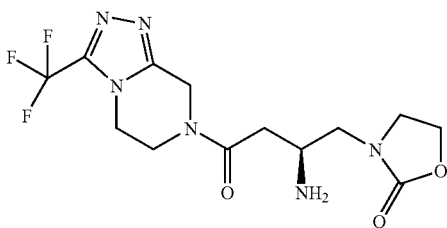

21 mg (0.045 mmol) of [3-oxo-1-(2-oxo-oxazolidin-3-yl-methyl)-3-(3-trifluoromethyl-5,6-dihydro-8H-[1,2,4]triazolo[4,3-a]pyrazin-7-yl)-propyl]-1S-carbamic acid t-butyl ester obtained in PREPARATION 17 was dissolved in ethyl acetate/hydrochloric acid, followed by stirring for about 17 hours, and then the solution was concentrated to give white solid. Thereafter, the solid was washed with diethylether and dried over to give 15 mg of the title compound in a yield of 91%

$^1$H NMR (CD$_3$OD) δ 5.06 (2H, s), 4.4 (3H, m), 4.26 (1H, m), 4.05-4.15 (2H, m), 3.9 (1H, m), 3.5-3.8 (4H, m), 3.0-3.1 (1H, m), 2.85-2.95 (1H, m),

Mass (m/e) 363 (M+1)

PREPARATION 18

Synthesis of 3S-t-butoxycarbonylamino-4-(2-hydroxy-propylamino)-butyric acid benzyl ester 0.68 g (2.2 mmol) of 3S-t-butoxycarbonylamino-4-oxo-butyric acid benzyl ester obtained in PREPARATION 14 was dissolved in dichloroethane, and then cooled to 0° C., then 2-aminoethanol (170 l, 2.2 mmol) of was added thereto, followed by stirring 30 minutes. Thereafter, 1.4 g (6.6 mmol) of sodium triacetoxyborohydride was added to the solution, followed by stirring about 1 hour, 10 minutes. Thereafter, to the solution was diluted with dichloromethane, then washed with a saturated aqueous sodium bicarbonate, and dried over anhydrous magnesium sulfate and filtered off. The filtrated solution was distilled off under reduced pressure, then the residue was purified by column chromatography (1:1 hexane: ethyl acetate→10:1 CH$_2$Cl$_2$:MeOH) to give 0.36 g of the title compound in a yield of 45%

$^1$H NMR (CDCl$_3$) δ 7.3-7.4 (5H, m), 5.8-6.0 (1H, m), 5.10 (2H, m), 3.9-4.0 (1H, m), 2.5-3.1 (6H, m), 1.40 (9H, s), 1.15 (3H, d, J=7 Hz)

Mass (m/e) 367 (M+1)

PREPARATION 19

Synthesis of 3S-t-butoxycarbonylamino-4-(5-methyl-2-oxo-oxazolidin-3-yl)-butyric acid benzyl ester 360 mg (0.98 mmol) of 3S-t-butoxycarbonylamino-4-(2-hydroxy-propylamino)-butyric acid benzyl ester obtained in PREPARATION 18 was dissolved in dichloromethane, and then cooled to 0° C., then 120 mg (0.98 mmol) of N,N-diisopropylethylamine and 680 1 (3.92 mmol) of dimethylaminopyridine were added thereto, followed by addition of 1.0 g (1.5 mmol) of phosgene (20% toluene) and then stirring for 2 hours and 40 minutes. The reaction solution was diluted with dichloromethane, and washed with aqueous NaCl, then dried over anhydrous magnesium sulfate and filtered off. The filtrated solution was distilled off under reduced pressure, then the residue was purified by column chromatography (1:1 hexane:ethyl acetate) to give 120 mg of the title compound in a yield of 31%

$^1$H NMR (CDCl$_3$) δ 7.3-7.4 (5H, m), 5.10 (2H, s), 5.10 (1H, m), 4.55-4.65 (1H, m), 4.1-4.2 (1H, m), 3.0-3.8 (3H, m), 2.5-2.8 (2H, m), 1.41 (12H, m)

Mass (m/e) 393 (M+1)

PREPARATION 20

Synthesis of [1-(5-methyl-2-oxo-oxazolidin-3-ylmethyl)-3-oxo-3-(3-trifluoromethyl-5,6-dihydro-8H-[1,2,4]triazolo[4,3-a]pyrazin-7-yl)-propyl]-1S-carbamic acid t-butyl ester 3S-t-butoxycarbonylamino-4-(5-methyl-2-oxo-oxazolidin-3-yl)-butyric acid benzyl ester 120 mg (0.31 mmol) of obtained in PREPARATION 19 was dissolved in methanol, then 12 mg of palladium/carcol (Pd/C) was added thereto, followed by stirring under hydrogen atmosphere for 3 hours, 40 minutes. After completion of a reaction, the reaction solution was filtered by Cellite, then washed with methanol, followed by concentration. 9 mg (0.31 mmol) of amine was added immediately thereto, then the resulting solution was dissolved in dichloromethane. The reaction was cooled to 0° C., then 50 mg (0.37 mmol) of HOBT was added there. After stirring for 10 minutes, 88 mg (0.47 mmol) of EDC was added to thereto. After removal of an icebath, the reaction solution was stirred for about 17 hours, then the concentrated residue was purified by prep-TLC (10:1 CH$_2$Cl$_2$:MeOH) to give 88 mg of the title compound in a total yield of 60%.

$^1$H NMR (CDCl$_3$) δ 5.6-5.9 (1H, m), 4.9-5.1 (2H, m), 4.6-4.8 (1H, m), 3.9-4.3 (5H, m), 3.6-3.8 (1H, m), 3.1-3.5 (3H, m), 2.5-2.9 (2H, m), 1.40 (12H, m)

Mass (m/e) 477 (M+1)

EXAMPLE 2

Synthesis of 3-[2S-amino-4-oxo-4-(3-trifluoromethyl-5,6-dihydro-8H-[1,2,4]triazolo[4,3-a]pyrazin-7-yl)-butyl]-5-methyl-oxazolidin-2-one

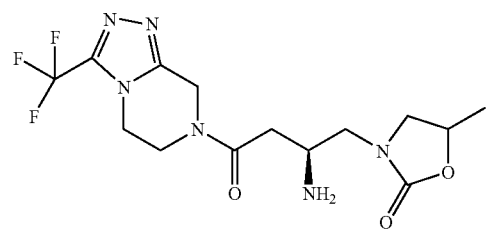

88 mg (0.045 mmol) of [1-(5-methyl-2-oxo-oxazolidin-3-ylmethyl)-3-oxo-3-(3-trifluoromethyl-5,6-dihydro-8H-[1,2,4]triazolo[4,3-a]pyrazin-7-yl)-propyl]-1S-carbamic acid t-butyl ester obtained in PREPARATION 20 was dissolved in ethyl acetate/hydrochloric acid. After stirring for about 30 minutes, the reaction solution was concentrated to give white solid. Thereafter, the solid was washed with diethylether and dried over to give 42 mg of the title compound in a yield of 60%.

$^1$H NMR (CD$_3$OD) δ 5.1-5.2 (2H, m), 4.7-4.8 (1H, m), 4.45 (1H, m), 4.3 (1H, m), 4.0-4.2 (3H, m), 3.8-3.9 (2H, m), 3.4-3.7 (2H, m), 2.9-3.1 (2H, m), 1.41 (3H, m)

Mass (m/e) 377 (M+1)

PREPARATION 21

Synthesis of 3S-t-butoxycarbonylamino-4-(t-butyl-dimethyl-silanyloxy)-butyric acid benzyl ester 4.0 g (12.9 mmol) of 3S-t-butoxycarbonylamino-4-hydroxy-butanoic acid benzyl ester obtained in PREPARATION 13 was dissolved in dimethylformamide, then 2.34 g (15.5 mmol) of imidazole and 2.34 g (32.3 mmol) of t-butyldimethylsilylchloride were added thereto, followed by stirring for about 2 hours. Thereafter, the solution was diluted with excess ethylacetate and washed once with water and aqueous NaCl, respectively, then dried over anhydrous magnesium sulfate and filtered off. The filtrated solution was distilled off under reduced pressure, then the residue was purified by column chromatography (5:1 hexane:ethyl acetate) to give 4.0 g of the title compound in a yield of 73%.

$^1$H NMR (CDCl$_3$) δ 7.3-7.4 (5H, m), 5.21 (1H, d, J=8 Hz), 5.08 (1H, m), 4.0-4.1 (1H, m), 3.6-3.7 (2H, m), 2.6-2.7 (2H, m), 1.42 (9H, s), 0.86 (9H, s), 0.01 (6H, s)

Mass (m/e) 424 (M+1)

PREPARATION 22

Synthesis of [1-(t-butyl-dimethyl-silanloxymethyl)-3-oxo-3-(3-trifluoromethyl-5,6-dihydro-8H-[1,2,4]triazolo[4,3-a]pyrazin-7-yl)-propyl]-1S-carbamic acid t-butyl ester (1) Synthesis of 3S-t-butoxycarbonylamino-4-(t-butyl-dimethyl-silanyloxy)-butanoic acid 1.0 g (2.36 mmol) of 3S-t-butoxycarbonylamino-4-(t-butyl-dimethyl-silanyloxy)-butyric acid benzyl ester obtained in PREPARATION 21 was dissolved in methanol, then 120 mg of palladium/carcol (Pd/C) was added thereto, followed by stirring under hydrogen atmosphere for 3 hours and 25 minutes. After completion of a reaction, the reaction solution was filtered by Cellite and washed with methanol, then concentrated.

$^1$H NMR (CDCl$_3$) δ 5.10 (1H, m), 4.02 (1H, m), 3.6-3.7 (2H, m), 2.61 (2H, m), 1.43 (9H, s), 0.88 (9H, s), 0.04 (6H, s)

Mass (m/e) 356 (M+Na)

(2) Synthesis of [1-(t-butyl-dimethyl-silanyloxymethyl)-3-oxo-3-(3-trifluoromethyl-5,6-dihydro-8H-[1,2,4]triazolo[4,3-a]pyrazin-7-yl)-propyl]-1S-carbamic acid t-butyl ester 333 mg (1 mmol) of 3S-t-butoxycarbonylamino-4-(t-butyl-dimethyl-silanyloxy)-butanoic acid which was obtained from step (1) was added 192 mg (1 mmol) of 3-trifluoromethyl-5,6-dihydro-8H-[1,2,4]triazolo[4,3-a]pyrazine, and the resulting mixture was dissolved in dichloromethane. The reaction solution was cooled to 0° C., and 162 mg (1.2 mmol) of HOBT was added, followed by stirring for 10 minutes and then addition of 288 mg (1.5 mmol) of EDC. After removal of an icebath, the reaction solution was stirred for about 13 hours, and then the residue, which was obtained by concentration was purified by column chromatography (1:1 hexane:ethyl acetate) to give 0.27 g of the title compound in yield of 53%.

$^1$H NMR (CDCl$_3$) δ 5.1-5.3 (1H, m), 4.9-5.1 (2H, m), 3.9-4.3 (4H, m), 3.7-3.8 (2H, m), 2.6-2.9 (2H, m), 1.40 (9H, s), 0.87 (9H, s), 0.03 (6H, s)

Mass (m/e) 508 (M+1)

PREPARATION 23

Synthesis of [1-formyl-3-oxo-3-(3-trifluoromethyl-5,6-dihydro-8H-[1,2,4]triazolo[4,3-a]pyrazin-7-yl)-propyl]-1S-carbamic acid t-butyl ester (1) Synthesis of [1-hydroxymethyl-3-oxo-3-(3-trifluoromethyl-5,6-dihydro-8H-[1,2,4]triazolo[4,3-a]pyrazin-7-yl)-propyl]-1S-carbamic acid t-butyl ester 2.3 g (4.53 mmol) of [1-(t-butyl-dimethyl-silanyloxymethyl)-3-oxo-3-(3-trifluoromethyl-5,6-dihydro-8H-[1,2,4]triazolo[4,3-a]pyrazin-7-yl)-propyl]-1S-carbamic acid t-butyl ester obtained in PREPARATION 22 was dissolved in tetrahydrofuran, then 9 mL of tetrabutylammonium fluoride (1 M in THF) was dropwise added thereto, followed by stirring for about 12 minutes. After the solution was diluted with excess ethylacetate, the diluted solution was washed once with water and aqueous NaCl, respectively and dried over anhydrous magnesium sulfate and filtered off. The filtrated solution was distilled off under reduced pressure, then the residue was purified by column chromatography (15:1 CH$_2$Cl$_2$:MeOH) to give 1.78 g of [1-hydroxymethyl-3-oxo-3-(3-trifluoromethyl-5,6-dihydro-8H-[1,2,4]triazolo[4,3-a]pyrazin-7-yl)-propyl]-1S-carbamic acid t-butyl ester in a yield of 99%.

$^1$H NMR (CDCl$_3$) δ 5.3-5.5 (1H, m), 5.0-5.2 (2H, m), 3.9-4.3 (4H, m), 3.6-3.8 (2H, m), 2.7-3.0 (2H, m), 1.41 (9H, s)

Mass (m/e) 394 (M+1)

(2) Synthesis of [1-formyl-3-oxo-3-(3-trifluoromethyl-5,6-dihydro-8H-[1,2,4]triazolo[4,3-a]pyrazin-7-yl)-propyl]-1S-carbamic acid t-butyl ester 500 mg (1.27 mmol) of [1-hydroxymethyl-3-oxo-3-(3-trifluoromethyl-5,6-dihydro-8H-[1,2,4]triazolo[4,3-a]pyrazin-7-yl)-propyl]-1S-carbamic acid t-butyl ester which was obtained from step (1) was dissolved in dichloromethane, and then 10 mL of Dess-Martin (~0.3 M) was added thereto, followed by stirring for 2 hours and 40 minutes. After concentration, the residue was purified by column chromatography (1:2 hexane:ethyl acetate) to give 0.33 g of the title compound in a yield of 66%

$^1$H NMR (CDCl$_3$) δ 9.67 (1H, s), 5.7-5.9 (1H, m), 4.9-5.1 (2H, m), 3.9-4.5 (5H, m), 3.1-3.2 (1H, m), 2.9-3.0 (1H, m), 1.42 (9H, s)

Mass (m/e) 392 (M+1)

PREPARATION 24

Synthesis of [3-oxo-1-(2-oxo-piperidin-1-ylmethyl)-3-(3-trifluoromethyl-5,6-dihydro-8H-[1,2,4]triazolo[4,3-a]pyrazin-7-yl)-propyl]-1S-carbamic acid t-butyl ester 77 mg (0.2 mmol) of [1-formyl-3-oxo-3-(3-trifluoromethyl-5,6-dihydro-8H-[1,2,4]triazolo[4,3-a]pyrazin-7-yl)-propyl]-1S-carbamic acid t-butyl ester was added 33 mg (0.2 mmol) of 5-amino-pentanoic acid methyl ester hydrochloric acid salt was dissolved in dichloroethane, followed by stirring for 30 minutes. 83 mg (0.4 mmol) of sodium triacetoxyborohydride was added to the solution, followed by stirring for about 1 hour and 40 minutes. The resulting solution was heated to 80° C. about 7 hours and concentrated, then the residue was purified by prep-TLC (10:1 $CH_2Cl_2$:MeOH) to give about 20 g of the title compound in a total yield of 21%

$^1$H NMR ($CD_3OD$) δ 6.5 (1H, m), 4.9-5.1 (2H, m), 4.0-4.4 (5H, m), 3.35-3.5 (3H, m), 2.6-2.8 (2H, m), 2.28 (2H, t, J=6.0 Hz), 1.7-1.8 (4H, m), 1.36 (9H, s)

Mass (m/e) 475 (M+1)

EXAMPLE 3

Synthesis of 1-[2S-amino-4-oxo-4-(3-trifluoromethyl-5,6-dihydro-8H-[1,2,4]triazolo[4,3-a]pyrazin-7-yl)-butyl]-piperidin-2-one

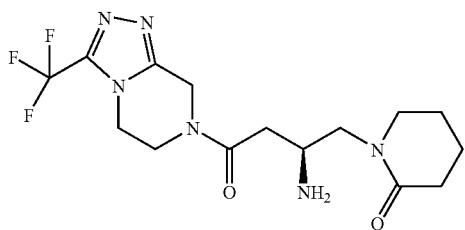

88 mg (0.045 mmol) of [3-oxo-1-(2-oxo-piperidin-1-ylmethyl)-3-(3-trifluoromethyl-5,6-dihydro-8H-[1,2,4]triazolo[4,3-a]pyrazin-7-yl)-propyl]-1S-carbamic acid t-butyl ester obtained in PREPARATION 24 was dissolved in ethyl acetate/hydrochloric acid, followed by stirring for about 30 minutes and then concentration. The residue was purified by prep-TLC (10:1 $CH_2Cl_2$:MeOH) to give about 10.4 mg of the title compound in a yield of 66%.

$^1$H NMR ($CD_3OD$) δ 4.9-5.1 (2H, m), 4.6 (1H, br), 4.0-4.4 (4H, m), 3.8-3.9 (2H, m), 3.35-3.5 (2H, m), 2.8-3.0 (2H, m), 2.0-2.4 (2H, m), 1.8-1.9 (4H, m),

Mass (m/e) 375 (M+1)

PREPARATION 25

Synthesis of [1-(4-methyl-2-oxo-pyrrolidin-1-ylmethyl)-3-oxo-3-(3-trifluoromethyl-5,6-dihydro-8H-[1,2,4]triazolo[4,3-a]pyrazin-7-yl)-propyl]-1S-carbamic acid t-butyl ester 50 mg (0.13 mmol) of [1-formyl-3-oxo-3-(3-trifluoromethyl-5,6-dihydro-8H-[1,2,4]triazolo[4,3-a]pyrazin-7-yl)-propyl]-1S-carbamic acid t-butyl ester obtained in PREPARATION 23 and 21 mg (0.13 mmol) of 4-amino-3-methyl-butyric acid methyl ester hydrochloric acid salt (product of PREPARATION 2) mmol were reacted in the same manner as in PREPARATION 24, to give 18 mg of the title compound in a yield of 30%.

$^1$H NMR ($CDCl_3$) δ 5.7-6.0 (1H, m), 4.8-5.1 (2H, m), 3.9-4.4 (5H, m), 3.3-3.7 (3H, m), 3.0-3.1 (1H, m), 2.3-2.9 (4H, m), 1.9-2.0 (1H, m), 1.40 (9H, s), 1.09 (3H, d, J=5 Hz)

Mass (m/e) 475 (M+1)

EXAMPLE 4

Synthesis of 1-[2S-amino-4-oxo-4-(3-trifluoromethyl-5,6-dihydro-8H-[1,2,4]triazolo[4,3-a]pyrazin-7-yl)-butyl]-4-methyl-pyrrolidin-2-one

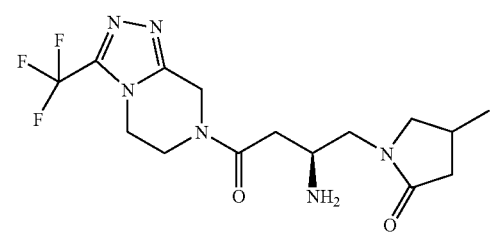

18 mg of [1-(4-methyl-2-oxo-pyrrolidin-1-ylmethyl)-3-oxo-3-(3-trifluoromethyl-5,6-dihydro-8H-[1,2,4]triazolo[4,3-a]pyrazin-7-yl)-propyl]-1S-carbamic acid t-butyl ester obtained in PREPARATION 25 was reacted with ethyl acetate/hydrochloric acid in the same manner as in EXAMPLE 3 to give 5.8 mg of the title compound in a yield of 37%.

$^1$H NMR ($CD_3OD$) δ 4.9-5.1 (2H, m), 4.0-4.3 (4H, m), 3.3-3.7 (4H, m), 3.0-3.1 (1H, m), 2.4-2.8 (4H, m), 1.9-2.0 (1H, m), 1.1 (3H, m),

Mass (m/e) 375 (M+1)

PREPARATION 26

Synthesis of [1-(3-fluoro-2-oxo-pyrrolidin-1-ylmethyl)-3-oxo-3-(3-trifluoromethyl-5,6-dihydro-8H-[1,2,4]triazolo[4,3-a]pyrazin-7-yl)-propyl]-1S-carbamic acid t-butyl ester

[1-formyl-3-oxo-3-(3-trifluoromethyl-5,6-dihydro-8H-[1,2,4]triazolo[4,3-a]pyrazin-7-yl)-propyl]-1S-carbamic acid t-butyl ester 39 mg (0.1 mmol) of obtained in PREPARATION 23 and 17 mg (0.1 mmol) of 4-amino-2-fluoro-butryic acid methyl ester hydrochloric acid salt (product of PREPARATION 3) and 42 mg (0.2 mmol) of sodium triacetoxyborohydride were reacted in the same manner as in EXAMPLE 3 to give 5.8 mg of the title compound in a yield of 37%.

$^1$H NMR ($CDCl_3$) δ 5.7-5.9 (1H, m), 4.9-5.1 (3H, m), 3.8-4.3 (5H, m), 3.3-3.7 (4H, m), 2.4-2.8 (3H, m), 2.1-2.2 (1H, m), 1.40 (9H, s),

Mass (m/e) 479 (M+1)

EXAMPLE 5

Synthesis of 1-[2S-amino-4-oxo-4-(3-trifluoromethyl-5,6-dihydro-8H-[1,2,4]triazolo[4,3-a]pyrazin-7-yl)-butyl]-3-fluoro-pyrrolidin-2-one

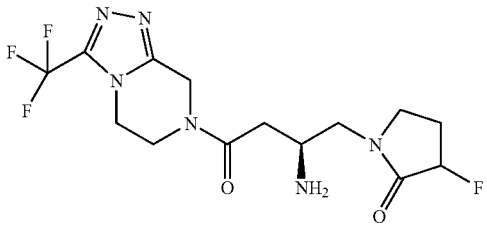

15 mg of [1-(3-fluoro-2-oxo-pyrrolidin-1-ylmethyl)-3-oxo-3-(3-trifluoromethyl-5,6-dihydro-8H-[1,2,4]triazolo[4,3-a]pyrazin-7-yl)-propyl]-1S-carbamic acid t-butyl ester obtained in PREPARATION 26 and ethyl acetate/hydrochloric acid were reacted in the same manner as in EXAMPLE 3 to give 5.9 mg of amine in a yield of 45%.

$^1$H NMR (CD$_3$OD) δ 5.0-5.3 (3H, m), 4.2-4.4 (2H, m), 4.0-4.2 (2H, m), 3.4-3.7 (5H, m), 2.5-2.8 (3H, m), 2.1-2.3 (1H, m)

Mass (m/e) 379 (M+1)

EXAMPLE 6

Synthesis of 1-[2S-amino-4-oxo-4-(3-trifluoromethyl-5,6-dihydro-8H-[1,2,4]triazolo[4,3-a]pyrazin-7-yl)-butyl]-pyrrolidin-2-one

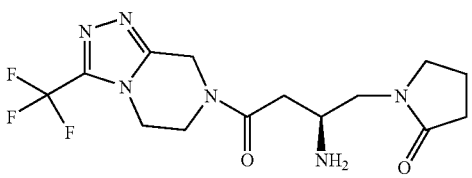

77 mg (0.2 mmol) of [1-formyl-3-oxo-3-(3-trifluoromethyl-5,6-dihydro-8H-[1,2,4]triazolo[4,3-a]pyrazin-7-yl)-propyl]-1S-carbamic acid t-butyl ester obtained in PREPARATION 23 was added to (23 mg 0.2 mmol of 4-aminobutyric acid methylester, then the resulting mixture was dissolved in dichloroethane, followed by stirring for 30 minutes. Thereafter, 84 mg (0.4 mmol) of sodium triacetoxyborohydride was added thereto, followed by stirring for about 2 hours. After concentration, the residue was reacted with ethyl acetate/hydrochloric acid in the same manner as in EXAMPLE 3 to give 15 mg of the title compound in a yield of 21%.

$^1$H NMR (CD$_3$OD) δ 5.00-4.95 (2H, m), 4.31-4.22 (2H, m), 4.10-4.01 (2H, m), 3.74 (1H, brs), 3.53-3.41 (3H, m), 2.89-2.72 (2H, m), 2.37-2.34 (2H, m), 2.08-2.05 (2H, m), 1.27 (2H, brs).

Mass (m/e) 361 (M+1)

PREPARATION 27

Synthesis of [1-(3-fluoro-2-oxo-piperidin-1-ylmethyl)-3-oxo-3-(3-trifluoromethyl-5,6-dihydro-8H-[1,2,4]triazolo[4,3-a]pyrazin-7-yl)-propyl]-1S-carbamic acid t-butyl ester 90 mg (0.1 mmol) of [1-formyl-3-oxo-3-(3-trifluoromethyl-5,6-dihydro-8H-[1,2,4]triazolo[4,3-a]pyrazin-7-yl)-propyl]-1S-carbamic acid t-butyl ester obtained in PREPARATION 23 and 43 mg (0.1 mmol) of 5-amino-2-fluoropentanoic acid methyl ester hydrochloric acid salt (product of PREPARATION 4) and 98 mg (0.2 mmol) of sodium triacetoxyborohydride were reacted in the same manner as in PREPARATION 24 to give 24 mg of the title compound in a yield of 21%.

$^1$H NMR (CDCl$_3$) δ 5.8-6.1 (1H, m), 4.6-5.2 (3H, m), 3.8-4.4 (5H, m), 3.2-3.6 (4H, m), 2.6-3.0 (2H, m), 1.7-2.1 (4H, m), 1.40 (9H, s),

Mass (m/e) 493 (M+1)

EXAMPLE 7

Synthesis of 1-[2S-amino-4-oxo-4-(3-trifluoromethyl-5,6-dihydro-8H-[1,2,4]triazolo[4,3-a]pyrazin-7-yl)-butyl]-3-fluoro-piperidin-2-one

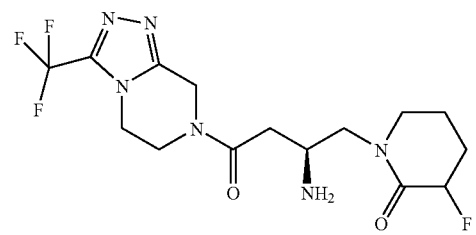

24 mg of [1-(3-fluoro-2-oxo-piperidin-1-ylmethyl)-3-oxo-3-(3-trifluoromethyl-5,6-dihydro-8H-[1,2,4]triazolo[4,3-a]pyrazin-7-yl)-propyl]-1S-carbamic acid t-butyl ester obtained in PREPARATION 27 and were reacted in the same manner as in EXAMPLE 3 to give 6 mg of the title compound in a yield of 31%.

$^1$H NMR (CD$_3$OD) δ 4.9-5.1 (2H, m), 4.7-4.9 (1H, m), 4.2-4.4 (2H, m), 4.0-4.2 (2H, m), 3.7-3.8 (1H, m), 3.3-3.6 (4H, m), 2.7-3.0 (2H, m), 1.8-2.2 (4H, m)

Mass (m/e) 393 (M+1)

PREPARATION 28

Synthesis of [1-(3-methyl-2-oxo-pyrrolidin-1-ylmethyl)-3-oxo-3-(3-trifluoromethyl-5,6-dihydro-8H-[1,2,4]triazolo[4,3-a]pyrazin-7-yl)-propyl]-1S-carbamic acid t-butyl ester 75 mg (0.1 mmol) of [1-formyl-3-oxo-3-(3-trifluoromethyl-5,6-dihydro-8H-[1,2,4]triazolo[4,3-a]pyrazin-7-yl)-propyl]-1S-carbamic acid t-butyl ester obtained in PREPARATION 25 and 32 mg (0.1 mmol) of 4-amino-2-methyl-butanoic acid methyl ester hydrochloric acid salt (product of PREPARATION 5) and 81 mg (0.2 mmol) of sodium triacetoxyborohydride were reacted in the same manner as in PREPARATION 24 to give 20 mg of the title compound in a yield of 22%.

¹H NMR (CDCl₃) δ 5.8-6.0 (1H, m), 4.8-5.1 (2H, m), 3.8-4.3 (5H, m), 3.3-3.5 (4H, m), 2.5-2.9 (2H, m), 2.1-2.4 (2H, m), 1.5-1.6 (1H, m), 1.40 (9H, s), 1.09-1.1 (3H, m)

Mass (m/e) 475 (M+1)

EXAMPLE 8

Synthesis of 1-[2S-amino-4-oxo-4-(3-trifluoromethyl-5,6-dihydro-8H-[1,2,4]triazolo[4,3-a]pyrazin-7-yl)-butyl]-3-methyl-pyrrolidin-2-one

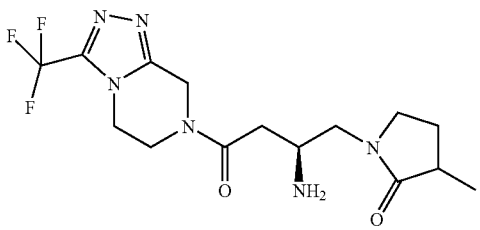

20 mg of [1-(3-methyl-2-oxo-pyrrolidin-1-ylmethyl)-3-oxo-3-(3-trifluoromethyl-5,6-dihydro-8H-[1,2,4]triazolo[4,3-a]pyrazin-7-yl)-propyl]-1S-carbamic acid t-butyl ester obtained in PREPARATION 28 and ethyl acetate/hydrochloric acid were reacted in the same manner as in EXAMPLE 3 to give 4.5 mg of the title compound in a yield of 29%.

¹H NMR (CD₃OD) δ 4.9-5.1 (2H, m), 4.2-4.4 (2H, m), 4.0-4.2 (2H, m), 3.6-3.7 (1H, m), 3.4-3.5 (4H, m), 2.6-2.9 (2H, m), 2.2-2.5 (2H, m), 1.6-1.7 (1H, m), 1.3 (1H, m), 1.1-1.2 (3H, m)

Mass (m/e) 375 (M+1)

PREPARATION 29

Synthesis of [1-(4-methyl-2-oxo-2,5-dihydro-pyrrol-1-ylmethyl)-3-oxo-3-(3-trifluoromethyl-5,6-dihydro-8H-[1,2,4]triazolo[4,3-a]pyrazin-7-yl)-propyl]-1S-carbamic acid t-butyl ester 85 mg (0.22 mmol) of [1-formyl-3-oxo-3-(3-trifluoromethyl-5,6-dihydro-8H-[1,2,4]triazolo[4,3-a]pyrazin-7-yl)-propyl]-1S-carbamic acid t-butyl ester obtained in PREPARATION 23 and 36 mg (0.22 mmol) of 4-amino-3-methyl-2-butenoic acid methyl ester hydrochloric acid salt (product of PREPARATION 6) and 92 mg (0.44 mmol) of sodium triacetoxyborohydride were reacted in the same manner as in PREPARATION 24 to give 34 mg of the title compound in a yield of 33%.

¹H NMR (CDCl₃) δ 5.9-6.2 (1H, m), 5.72 (1H, m), 4.9-5.1 (2H, m), 3.9-4.4 (7H, m), 3.6-3.7 (1H, m), 3.4-3.5 (1H, m), 2.7-2.9 (1H, m), 2.5-2.6 (1H, m), 2.04 (3H, s), 1.38 (9H, m)

Mass (m/e) 473 (M+1)

EXAMPLE 9

Synthesis of 1-[2S-amino-4-oxo-4-(3-trifluoromethyl-5,6-dihydro-8H-[1,2,4]triazolo[4,3-a]pyrazin-7-yl)-butyl]-4-methyl-1,5-dihydro-pyrrol-2-one

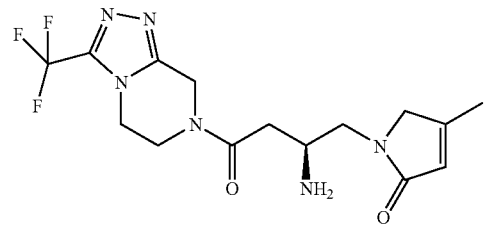

34 mg of [1-(4-methyl-2-oxo-2,5-dihydro-pyrrol-1-ylmethyl)-3-oxo-3-(3-trifluoromethyl-5,6-dihydro-8H-[1,2,4]triazolo[4,3-a]pyrazin-7-yl)-propyl]-1S-carbamic acid t-butyl ester obtained in PREPARATION 29 and ethyl acetate/hydrochloric acid were reacted in the same manner as in EXAMPLE 3 to give 25 mg of the title compound in a yield of 93%.

¹H NMR (CD₃OD) δ 5.81 (1H, m), 5.0 (2H, m), 4.2-4.4 (2H, m), 4.0-4.1 (4H, m), 3.8-3.9 (1H, m), 3.65-3.75 (2H, m), 2.9-3.0 (1H, m), 2.75-2.85 (1H, m), 2.10 (3H, s)

Mass (m/e) 373 (M+1)

PREPARATION 30

Synthesis of [1-(4-methyl-2-oxo-piperidin-1-ylmethyl)-3-oxo-3-(3-trifluoromethyl-5,6-dihydro-8H-[1,2,4]triazolo[4,3-a]pyrazin-7-yl)-propyl]-1S-carbamic acid t-butyl ester 85 mg (0.22 mmol) of [1-formyl-3-oxo-3-(3-trifluoromethyl-5,6-dihydro-8H-[1,2,4]triazolo[4,3-a]pyrazin-7-yl)-propyl]-1S-carbamic acid t-butyl ester obtained in PREPARATION 25 and 39 mg (0.22 mmol) of 5-amino-3-methyl-pentanoic acid methyl ester hydrochloric acid salt (product of PREPARATION 8) and 92 mg (0.44 mmol) of sodium triacetoxyborohydride were reacted in the same manner as in PREPARATION 24 to give 46 mg of the title compound in a yield of 43%.

¹H NMR (CDCl₃) δ 5.9-6.0 (1H, m), 4.8-5.1 (2H, m), 3.9-4.3 (6H, m), 3.5-3.6 (1H, m), 3.3-3.5 (3H, m), 2.7-2.9 (1H, m), 2.3-2.6 (2H, m), 1.8-1.9 (2H, m), 1.4-1.5 (1H, m), 1.39 (9H, s), 0.95 (3H, m)

Mass (m/e) 489 (M+1)

EXAMPLE 10

Synthesis of 1-[2S-amino-4-oxo-4-(3-trifluoromethyl-5,6-dihydro-8H-[1,2,4]triazolo[4,3-a]pyrazin-7-yl)-butyl]-4-methyl-piperidin-2-one

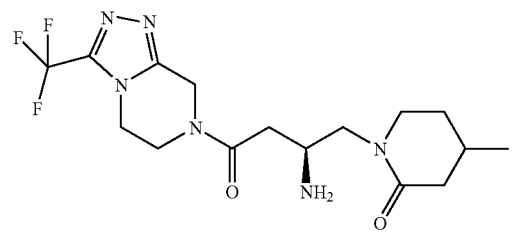

46 mg of [1-(4-methyl-2-oxo-piperidin-1-ylmethyl)-3-oxo-3-(3-trifluoromethyl-5,6-dihydro-8H-[1,2,4]triazolo[4,3-a]pyrazin-7-yl)-propyl]-1S-carbamic acid t-butyl ester obtained in PREPARATION 30 and ethyl acetate/hydrochloric acid were reacted in the same manner as in EXAMPLE 3 to give 29 mg of the title compound in a yield of 79%.

$^1$H NMR (CD$_3$OD) δ 4.9-5.1 (2H, m), 4.2-4.4 (2H, m), 4.0-4.2 (2H, m), 3.8-3.9 (2H, m), 3.3-3.8 (3H, m), 2.8-3.0 (2H, m), 2.4 (1H, m), 1.8-2.0 (3H, m), 1.5-1.6 (1H, m), 1.0 (3H, m)

Mass (m/e) 389 (M+1)

PREPARATION 31

Synthesis of [1-(5,5-difluoro-2-oxo-piperidin-1-ylmethyl)-3-oxo-3-(3-trifluoromethyl-5,6-dihydro-8H-[1,2,4]triazolo[4,3-a]pyrazin-7-yl)-propyl]-1S-carbamic acid t-butyl ester 85 mg (0.22 mmol) of [1-formyl-3-oxo-3-(3-trifluoromethyl-5,6-dihydro-8H-[1,2,4]triazolo[4,3-a]pyrazin-7-yl)-propyl]-1S-carbamic acid t-butyl ester obtained in PREPARATION 23 and 44 mg (0.22 mmol) of 5-amino-4,4-difluoro-pentanoic acid methyl ester hydrochloric acid salt (product of PREPARATION 12) and 92 mg (0.44 mmol) of sodium triacetoxyborohydride were reacted in the same manner as in PREPARATION 24 to give 25 mg of the title compound in a yield of 23%.

$^1$H NMR (CDCl$_3$) 5.8-5.9 (1H, m), 4.8-5.1 (2H, m), 4.1-4.3 (4H, m), 3.9-4.0 (1H, m), 3.6-3.8 (3H, m), 3.3-3.5 (1H, m), 2.7-2.9 (1H, m), 2.5-2.6 (2H, m), 2.4 (1H, t, J=7.0 Hz), 2.2-2.3 (2H, m), 1.40 (9H, s)

Mass (m/e) 511 (M+1)

EXAMPLE 11

Synthesis of 1-[2S-amino-4-oxo-4-(3-trifluoromethyl-5,6-dihydro-8H-[1,2,4]triazolo[4,3-a]pyrazin-7-yl)-butyl]-5,5-difluoro-piperidin-2-one

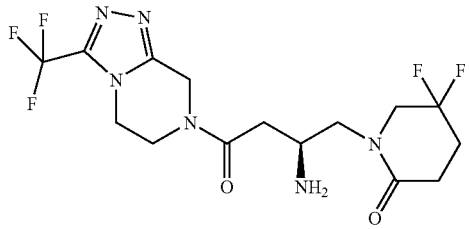

25 mg of [1-(5,5-difluoro-2-oxo-piperidin-1-ylmethyl)-3-oxo-3-(3-trifluoromethyl-5,6-dihydro-8H-[1,2,4]triazolo[4,3-a]pyrazin-7-yl)-propyl]-1S-carbamic acid t-butyl ester obtained in PREPARATION 31 and ethyl acetate/hydrochloric acid were reacted in the same manner as in EXAMPLE 3 to give 7.9 mg of the title compound in a yield of 39%.

$^1$H NMR (CD$_3$OD) δ 4.9-5.1 (2H, m), 4.2-4.4 (2H, m), 4.0-4.2 (2H, m), 3.7-3.9 (2H, m), 3.6-3.7 (2H, m), 3.4-3.5 (1H, m), 2.8 (1H, td, J=16, 5 Hz), 2.6-2.7 (1H, m), 2.5-2.6 (2H, m), 2.3-2.4 (2H, m)

Mass (m/e) 411 (M+1)

PREPARATION 32

Synthesis of [1-(5R-methyl-2-oxo-piperidin-1-ylmethyl)-3-oxo-3-(3-trifluoromethyl-5,6-dihydro-8H-[1,2,4]triazolo[4,3-a]pyrazin-7-yl)-propyl]-1S-carbamic acid t-butyl ester 80 mg (0.20 mmol) of [1-formyl-3-oxo-3-(3-trifluoromethyl-5,6-dihydro-8H-[1,2,4]triazolo[4,3-a]pyrazin-7-yl)-propyl]-1S-carbamic acid t-butyl ester obtained in PREPARATION 23 and 37 mg (0.20 mmol) of (R)-5-amino-4-methyl-pentanoic acid methyl ester hydrochloric acid salt (product of PREPARATION 7) and 87 mg (0.40 mmol) of sodium triacetoxyborohydride were reacted in the same manner as in PREPARATION 24 to give 33 mg of the title compound in a yield of 33%.

$^1$H NMR (CDCl$_3$) δ 5.9-6.0 (1H, m), 4.8-5.1 (2H, m), 3.8-4.3 (5H, m), 3.2-3.7 (3H, m), 2.9-3.1 (1H, m), 2.1-2.9 (4H, m), 1.7-2.0 (2H, m), 1.3-1.5 (1H, m), 1.40 (9H, s), 0.98 (3H, m)

Mass (m/e) 489 (M+1)

EXAMPLE 12

Synthesis of 1-[2S-amino-4-oxo-4-(3-trifluoromethyl-5,6-dihydro-8H-[1,2,4]triazolo[4,3-a]pyrazin-7-yl)-butyl]-5R-methyl-piperidin-2-one

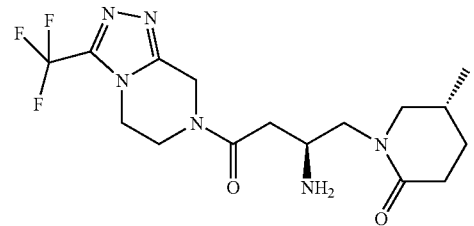

33 mg of [1-(5R-methyl-2-oxo-piperidin-1-ylmethyl)-3-oxo-3-(3-trifluoromethyl-5,6-dihydro-8H-[1,2,4]triazolo[4,3-a]pyrazin-7-yl)-propyl]-1S-carbamic acid t-butyl ester obtained in PREPARATION 32 and ethyl acetate/hydrochloric acid were reacted in the same manner as in EXAMPLE 3 to give 15.3 mg of the title compound in a yield of 58%.

$^1$H NMR (CD$_3$OD) δ 4.9-5.1 (2H, m), 4.2-4.4 (2H, m), 4.0-4.2 (2H, m), 3.8-3.9 (1H, m), 3.7-3.8 (1H, m), 3.55-3.65 (1H, m), 3.3-3.4 (1H, m), 2.8-3.1 (3H, m), 2.3-2.4 (2H, m), 2.0-2.1 (1H, m), 1.8-1.9 (1H, m), 1.5-1.6 (1H, m), 1.03 (3H, d, J=6 Hz)

Mass (m/e) 389 (M+1)

PREPARATION 33

Synthesis of [3-oxo-1-(2-oxo-4-trifluoromethyl-pyrrolidin-1-ylmethyl)-3-(3-trifluoromethyl-5,6-dihydro-8H-[1,2,4]triazolo[4,3-a]pyrazin-7-yl)-propyl]-1S-carbamic acid t-butyl ester 80 mg (0.20 mmol) of [1-formyl-3-oxo-3-(3-trifluoromethyl-5,6-dihydro-8H-[1,2,4]triazolo[4,3-a]pyrazin-7-yl)-propyl]-1S-carbamic acid t-butyl ester obtained in PREPARATION 23 and 48 mg (0.20 mmol) of 3-aminomethyl-4,4,4-trifluoro-butanoic acid ethyl ester hydrochloric acid salt (product of PREPARATION 1) and 87 mg (0.40 mmol) of sodium triacetoxyborohydride were reacted in the same manner as in PREPARATION 24 to give 4.6 mg of the title compound in a yield of 40%.

$^1$H NMR (CDCl$_3$) δ 5.6-5.7 (1H, m), 4.8-5.1 (2H, m), 3.9-4.3 (5H, m), 3.3-3.8 (4H, m), 3.0-3.1 (1H, m), 2.4-2.9 (4H, m), 1.4 (9H, s)

Mass (m/e) 529 (M+1)

EXAMPLE 13

Synthesis of 1-[2S-amino-4-oxo-4-(3-trifluoromethyl-5,6-dihydro-8H-[1,2,4]triazolo[4,3-a]pyrazin-7-yl)-butyl]-4-trifluoromethyl-pyrrolidin-2-one

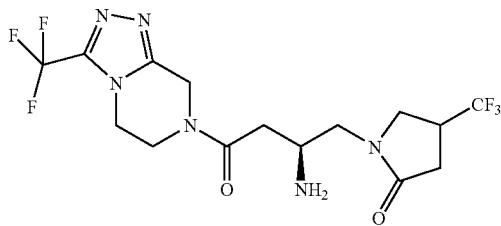

18 mg of [3-oxo-1-(2-oxo-4-trifluoromethyl-pyrrolidin-1-ylmethyl)-3-(3-trifluoromethyl-5,6-dihydro-8H-[1,2,4]triazolo[4,3-a]pyrazin-7-yl)-propyl]-1S-carbamic acid t-butyl ester obtained in PREPARATION 33 and ethyl acetate/hydrochloric acid were reacted in the same manner as in EXAMPLE 3 to give 7 mg of the title compound in a yield of 48%.

$^1$H NMR (CD$_3$OD) δ 4.9-5.1 (2H, m), 4.2-4.4 (2H, m), 4.0-4.2 (2H, m), 3.7-3.9 (2H, m), 3.5-3.7 (3H, m), 3.3-3.4 (1H, m), 2.8-3.0 (2H, m), 2.5-2.7 (2H, m)

Mass (m/e) 429 (M+1)

PREPARATION 34

Synthesis of [3-oxo-1-(2-oxo-4-trifluoromethyl-piperidin-1-ylmethyl)-3-(3-trifluoromethyl-5,6-dihydro-8H-[1,2,4]triazolo[4,3-a]pyrazin-7-yl)-propyl]-1S-carbamic acid t-butyl ester 80 mg (0.20 mmol) of [1-formyl-3-oxo-3-(3-trifluoromethyl-5,6-dihydro-8H-[1,2,4]triazolo[4,3-a]pyrazin-7-yl)-propyl]-1S-carbamic acid t-butyl ester obtained in PREPARATION 23 and 51 mg (0.20 mmol) of 5-amino-3-trifluoromethyl-pentanoic acid ethyl ester hydrochloric acid salt (product of PREPARATION 11) and 87 mg (0.40 mmol) of sodium triacetoxyborohydride were reacted in the same manner as in PREPARATION 24 to give 41 mg of the title compound in a yield of 37%.

$^1$H NMR (CDCl$_3$) δ 5.7-6.0 (1H, m), 4.8-5.1 (2H, m), 3.8-4.3 (5H, m), 3.3-3.7 (4H, m), 2.7-2.9 (1H, m), 2.4-2.6 (3H, m), 2.3-2.4 (1H, m), 2.1 (1H, m), 1.8 (1H, m), 1.4 (9H, s)

Mass (m/e) 543 (M+1)

EXAMPLE 14

Synthesis of 1-[2S-amino-4-oxo-4-(3-trifluoromethyl-5,6-dihydro-8H-[1,2,4]triazolo[4,3-a]pyrazin-7-yl)-butyl]-4-trifluoromethyl-piperidin-2-one

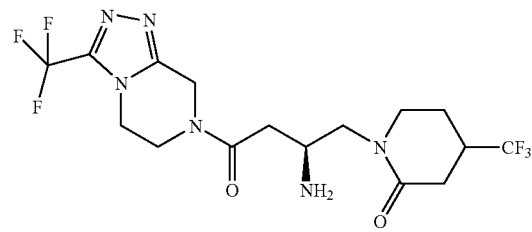

41 mg of [3-oxo-1-(2-oxo-4-trifluoromethyl-piperidin-1-ylmethyl)-3-(3-trifluoromethyl-5,6-dihydro-8H-[1,2,4]triazolo[4,3-a]pyrazin-7-yl)-propyl]-1S-carbamic acid t-butyl ester obtained in PREPARATION 34 and ethyl acetate/hydrochloric acid were reacted in the same manner as in EXAMPLE 3 to give 28.3 mg of the title compound in a yield of 85%.

$^1$H NMR (CD$_3$OD) δ 4.9-5.1 (2H, m), 4.2-4.4 (2H, m), 4.0-4.2 (2H, m), 3.7-3.9 (2H, m), 3.4-3.7 (3H, m), 2.8-3.1 (3H, m), 2.5-2.7 (1H, m), 2.3-2.5 (1H, m), 2.1-2.2 (1H, m), 1.8-2.0 (1H, m), 1.3 (1H, m)

Mass (m/e) 443 (M+1)

PREPARATION 35

[3-oxo-1-(2-oxo-5-trifluoromethyl-piperidin-1-ylmethyl)-3-(3-trifluoromethyl-5,6-dihydro-8H-[1,2,4]triazolo[4,3-a]pyrazin-7-yl)-propyl]-1S-carbamic acid t-butyl ester 286 mg (0.73 mmol) of [1-formyl-3-oxo-3-(3-trifluoromethyl-5,6-dihydro-8H-[1,2,4]triazolo[4,3-a]pyrazin-7-yl)-propyl]-1S-carbamic acid t-butyl ester obtained in PREPARATION 23 and 172 mg (0.73 mmol) of 4-aminomethyl-5,5,5-trifluoro-pentanoic acid methyl ester hydrochloric acid salt (product of PREPARATION 9) and 310 mg (1.46 mmol) of sodium triacetoxyborohydride were reacted in the same manner as in PREPARATION 24 to give 260 mg of the title compound in a yield of 37%.

$^1$H NMR (CDCl$_3$) δ 5.7-6.0 (1H, m), 4.8-5.1 (2H, m), 4.1-4.3 (4H, m), 3.7-4.0 (2H, m), 3.3-3.7 (3H, m), 2.2-2.9 (5H, m), 2.0-2.1 (1H, m), 1.8-1.9 (1H, m), 1.39 (9H, s)

Mass (m/e) 543 (M+1)

EXAMPLE 15

Synthesis of 1-[2S-amino-4-oxo-4-(3-trifluoromethyl-5,6-dihydro-8H-[1,2,4]triazolo[4,3-a]pyrazin-7-yl)-butyl]-5-trifluoromethyl-piperidin-2-one

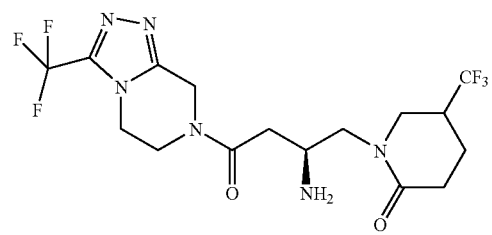

260 mg of [3-oxo-1-(2-oxo-5-trifluoromethyl-piperidin-1-ylmethyl)-3-(3-trifluoromethyl-5,6-dihydro-8H-[1,2,4]triazolo[4,3-a]pyrazin-7-yl)-propyl]-1S-carbamic acid t-butyl ester obtained in PREPARATION 35 and ethyl acetate/hydrochloric acid were reacted in the same manner as in EXAMPLE 3 to give 15 mg of the title compound in a yield of 7%.

$^1$H NMR (CD$_3$OD) δ 4.9-5.1 (2H, m), 4.2-4.4 (2H, m), 4.0-4.2 (2H, m), 3.8-3.9 (2H, m), 3.4-3.8 (3H, m), 2.8-3.0 (3H, m), 2.4-2.5 (2H, m), 2.0-2.1 (1H, m), 1.8-2.0 (1H, m)

Mass (m/e) 443 (M+1)

PREPARATION 36

Synthesis of [1-(2-methyl-5-oxo-morpholin-4-ylmethyl)-3-oxo-3-(3-trifluoromethyl-5,6-dihydro-8H-[1,2,4]triazolo[4,3-a]pyrazin-7-yl)-propyl]-1S-carbamic acid t-butyl ester 140 mg (0.36 mmol) of [1-formyl-3-oxo-3-(3-trifluoromethyl-5,6-dihydro-8H-[1,2,4]triazolo[4,3-a]pyrazin-7-yl)-propyl]-1S-carbamic acid t-butyl ester obtained in PREPARATION 23 and 71 mg (0.36 mmol) of (2-amino-1-methyl-ethoxy)-acetic acid ethyl ester hydrochloric acid salt (product of PREPARATION 10) and 151 mg (0.72 mmol) of sodium triacetoxyborohydride were reacted in the same manner as in PREPARATION 24 to give 78 mg of the title compound in a yield of 44%.

$^1$H NMR (CDCl$_3$) δ 5.8-6.0 (1H, m), 4.8-5.1 (2H, m), 3.9-4.3 (7H, m), 3.7-3.9 (1H, m), 3.5-3.7 (1H, m), 3.1-3.5 (3H, m), 2.5-2.9 (2H, m), 1.33 (9H, s), 1.19 (3H, br s)

Mass (m/e) 491 (M+1)

EXAMPLE 16

Synthesis of 4-[2S-amino-4-oxo-4-(3-trifluoromethyl-5,6-dihydro-8H-[1,2,4]triazolo[4,3-a]pyrazin-7-yl)-butyl]-6-methyl-morpholin-3-one

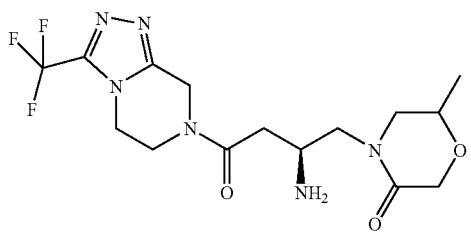

78 mg of [1-(2-methyl-5-oxo-morpholin-4-ylmethyl)-3-oxo-3-(3-trifluoromethyl-5,6-dihydro-8H-[1,2,4]triazolo[4,3-a]pyrazin-7-yl)-propyl]-1S-carbamic acid t-butyl ester obtained in PREPARATION 36 and ethyl acetate/hydrochloric acid were reacted in the same manner as in EXAMPLE 3 to give 25.7 mg of the title compound in a yield of 451%.

$^1$H NMR (CD$_3$OD) δ 4.9-5.1 (2H, m), 4.2-4.4 (2H, m), 4.1-4.2 (2H, m), 3.8-4.1 (4H, m), 3.68 (1H, m), 3.2-3.5 (3H, m), 2.8-3.1 (2H, m), 1.24 (3H, d, J=6.5 Hz)

Mass (m/e) 391 (M+1)

PREPARATION 37

Synthesis of [1-(t-butyl-dimethyl-silanyloxymethyl)-3-(3,4-dihydro-1H-isoquinolin-2-yl)-3-oxo-propyl]-1S-carbamic acid t-butyl ester 100 mg of 3S-t-butoxycarbonylamino-4-(t-butyl-dimethyl-silanyloxy)-butyric acid obtained in PREPARATION 22(1) and 110 l of 3,4-dihydro-1H-isoquinoline were reacted in the same manner as in PREPARATION 22-(2) to give 34 mg of the title compound in a yield of 87%.

$^1$H NMR (CDCl$_3$) δ 7.1-7.3 (4H, m), 5.5-5.6 (1H, m), 4.7-4.8 (2H, m), 4.0-4.1 (1H, m), 3.6-3.9 (4H, m), 2.8-3.0 (3H, m), 2.6-2.7 (1H, m), 1.47 (9H, s), 0.92 (9H, s), 0.19 (3H, s), 0.14 (3H, s)

Mass (m/e) 449 (M+1)

PREPARATION 38

Synthesis of [3-(3,4-dihydro-1H-isoquinolin-2-yl)-1-formyl-3-oxo-propyl]-1S-carbamic acid t-butyl ester (1) Synthesis of [3-(3,4-dihydro-1H-isoquinolin-2-yl)-1-hydroxymethyl-3-oxo-propyl]-1S-carbamic acid t-butyl ester 250 mg of [3-(3,4-dihydro-1H-isoquinolin-2-yl)-1-hydroxymethyl-3-oxo-propyl]-1S-carbamic acid t-butyl ester was obtained in a yield of 96% in the same manner as in PREPARATION 23-(1), using 349 mg of [1-(t-butyl-dimethyl-silanyloxymethyl)-3-(3,4-dihydro-1H-isoquinolin-2-yl)-3-oxo-propyl]-1S-carbamic acid t-butyl ester obtained in PREPARATION 37

$^1$H NMR (CDCl$_3$) δ 7.1-7.2 (4H, m), 5.5-5.6 (1H, m), 4.6-4.8 (2H, m), 3.7-4.0 (5H, m), 3.3-3.4 (2H, m), 2.7-3.0 (2H, m), 1.41 (9H, s), 0.90 (9H, s), 0.10 (6H, s)

Mass (m/e) 357 (M+Na)

(2) Synthesis of [3-(3,4-dihydro-1H-isoquinolin-2-yl)-1-formyl-3-oxo-propyl]-1S-carbamic acid t-butyl ester 250 mg of [3-(3,4-dihydro-1H-isoquinolin-2-yl)-1-hydroxymethyl-3-oxo-propyl]-1S-carbamic acid t-butyl ester (product of step 1) obtained in the same manner as in PREPARATION 23-(2) and 10 mL of Dess-Martin (~0.3 M) were reacted in the same manner as in EXAMPLE 3 to give 180 mg of the title compound in a yield of 72%

$^1$H NMR (CDCl$_3$) δ 9.72 (1H, s), 7.1-7.2 (4H, m), 5.97 (1H, m), 4.3-4.8 (4H, m), 3.6-3.8 (2H, m), 2.8-3.0 (2H, m), 1.45 (9H, s)

Mass (m/e) 333 (M+1)

PREPARATION 39

Synthesis of [3-(3,4-dihydro-1H-isoquinolin-2-yl)-3-oxo-1-(2-oxo-piperidin-1-ylmethyl)-propyl]-1S-carbamic acid t-butyl ester 60 mg (0.18 mmol) of [3-(3,4-dihydro-1H-isoquinolin-2-yl)-1-formyl-3-oxo-propyl]-1S-carbamic acid t-butyl ester obtained in PREPARATION 30 and 5-amino-pentanoic acid methyl ester hydrochloric acid salt mmol of and 77 mg (0.36 mmol) of sodium triacetoxyborohydride was reacted in the same manner as in PREPARATION 24 to give 9 mg of the title compound in a yield of 12%

Mass (m/e) 416 (M+1)

EXAMPLE 17

Synthesis of Synthesis of 1-[2S-amino-4-(3,4-dihydro-1H-isoquinolin-2-yl)-4-oxo-butyl]-piperidin-2-one

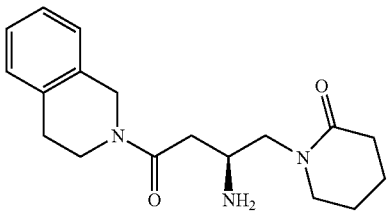

9 mg of [3-(3,4-dihydro-1H-isoquinolin-2-yl)-3-oxo-1-(2-oxo-piperidin-1-ylmethyl)-propyl]-1S-carbamic acid t-butyl ester obtained in PREPARATION 39 and ethyl acetate/hydrochloric acid were reacted in the same manner as in EXAMPLE 3 to give 4.4 mg of the title compound in a yield of 64%.

$^1$H NMR (CD$_3$OD) δ 7.1-7.2 (4H, m), 4.67 (2H, d, J=13 Hz), 3.6-3.8 (4H, m), 3.3-3.5 (3H, m), 2.8-3.0 (3H, m), 2.6-2.7 (1H, m), 2.3-2.4 (2H, m), 1.7-1.9 (4H, m)

Mass (m/e) 316 (M+1)

PREPARATION 40

Synthesis of [3-(3,4-dihydro-1H-isoquinolin-2-yl)-1-(4-methyl-2-oxo-pyrrolidin-1-ylmethyl)-3-oxo-propyl]-1S-carbamic acid t-butyl ester 59 mg (0.18 mmol) of [3-(3,4-dihydro-1H-isoquinolin-2-yl)-1-formyl-3-oxo-propyl]-1S-carbamic acid t-butyl ester obtained in PREPARATION 38 and 30 mg (0.18 mmol) of 4-amino-3-methyl-butanoic acid methyl ester and 77 mg (0.36 mmol) of sodium triacetoxyborohydride were reacted in the same manner as in PREPARATION 24 to give 20 mg of the title compound in a yield of 27%

Mass (m/e) 416 (M+1)

EXAMPLE 18

Synthesis of 1-[2S-amino-4-(3,4-dihydro-1H-isoquinolin-2-yl)-4-oxo-butyl]-4-methyl-pyrrolidin-2-one

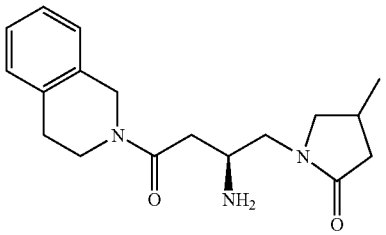

20 mg of [3-(3,4-dihydro-1H-isoquinolin-2-yl)-1-(4-methyl-2-oxo-pyrrolidin-1-ylmethyl)-3-oxo-propyl]-1S-carbamic acid t-butyl ester obtained in PREPARATION 40 and ethyl acetate/hydrochloric acid were reacted in the same manner as in EXAMPLE 3 to give 11 mg of the title compound in a yield of 72%.

$^1$H NMR (CD$_3$OD) δ 7.1-7.2 (4H, m), 4.67 (2H, d, J=13 Hz), 3.6-3.8 (4H, m), 3.5 (1H, d, J=6 Hz), 3.3-3.4 (1H, m), 3.0-3.2 (1H, m), 2.8-3.0 (3H, m), 2.6-2.8 (1H, m), 2.4-2.6 (2H, m), 2.0-2.1 (1H, m), 1.1 (3H, m)

Mass (m/e) 316 (M+1)

PREPARATION 41

Synthesis of 3S-t-butoxycarbonylamino-4-oxo-butryic acid t-butyl ester 0.69 mL (9.72 mmol) of dimethylsulfoxide was dissolved in 20 mL of methylene chloride, and cooled to −78° C. by dryice/acetone, then 0.42 mL (4.81 mmol) of oxalylchloride was added slowly thereto. After 20 minute, to the resulting solution, was slowly added at same temperature for 5 minutes a solution in which 666 mg (2.42 mmol) of 3S-t-butoxycarbonylamino-4-hydroxy-butyric acid t-butylester synthesized from Boc-L-Asp(O-tBu)-OH with reference to J. Med. Chem. 1999, 42, 3557-3571 was dissolved in 9 mL of dichloromethane. After stirring at same temperature for 20 minute, a solution in which 2.0 mL of triethylamine (11.7 mmol) was dissolved in 5 mL of dichloromethane was dropwise added to the reaction solution over 5 minutes. Thereafter, the temperature was gradually raised to −70° C., and the reaction solution was diluted with diethylether and then washed once with aqueous 0.5 N KHSO$_4$ and water and aqueous NaCl, respectively. An organic layer was dried over anhydrous magnesium sulfate, and filtered off, then concentrated to give the title compound. The compound was used at the next reaction without any further purification.

$^1$H NMR (CDCl$_3$) δ 9.65 (1H, s), 5.65 (1H, brs), 4.54 (1H, brs), 2.92-2.72 (2H, m), 1.52-1.44 (18H, m)

Mass (m/e) 274 (M+1)

PREPARATION 42

Synthesis of 3S-t-butoxycarbonylamino-4-(2-oxo-piperidin-1-yl)-butyric acid t-butylester A solution in which 576 mg (3.44 mg) of 5-amino-pentanoic acid methylester hydrochloric acid salt was dissolved in 1,2-dichloroethane 5 mL was added at room temperature to a solution in which 1.80 g of 3S-t-butoxycarbonylamino-4-oxo-butyric acid t-butylester (product of PREPARATION 41) was dissolved in 50 mL of 1,2-dichloroethane. After stirring at room temperature for 15 minutes, 1.46 g (6.88 mmol) of sodium triacetoxyborohydride was added thereto. After stirring at room temperature for 5 hours, the resulting solution was diluted with methyl chloridem and then washed with 1N aqueous hydrochloric acid and saline, sequently. An organic layer thus obtained was dried over anhydrous magnesium sulfate, and the solvent was distilled off under reduced pressure, then the residue, which was obtained by concentration under reduced pressure, was purified by column chromatography to give 568 mg of the title compound in a total yield of 46%.

¹H NMR (CDCl₃) δ 5.34-5.29 (1H, m), 4.17 (1H, brs), 3.92-3.84 (1H, m), 3.51-3.46 (1H, m), 3.27-3.23 (1H, m), 3.10-3.05 (1H, m), 2.56-2.51 (1H, m), 2.41-2.31 (3H, m), 1.82-1.75 (4H, m), 1.45 (9H, s)

Mass (m/e) 357 (M+1)

PREPARATION 43

Synthesis of 3S-t-butoxycarbonylamino-4-(2-oxo-piperidin-1-yl)-butanoic acid (1) Synthesis of 3S-amino-4-(2-oxo-piperidin-1-yl)-butanoic acid 214 mg (0.60 mmol) of t-butoxycarbonylamino-4-(2-oxo-piperidin-1-yl)-butyric acid t-butylester obtained in PREPARATION 42 was dissolved in 2 mL of chloromethane/trifluoroacetic acid (1/1) solution, followed by stirring at room temperature for 18 hours. Excess trifluoroacetic acid and dichloromethane was removed under reduced pressure to obtain 280 mg of the title compound. The compound was used at the next reaction without any further purification.

¹H NMR (CD₃OD) δ 4.00-3.77 (2H, m), 3.48-3.38 (3H, m), 2.80-2.70 (2H, s), 2.43-2.40 (2H, m), 1.89-1.82 (4H, m)

Mass (m/e) 200 (M+1)

(2) Synthesis of 3S-t-butoxycarbonylamino-4-(2-oxo-piperidin-1-yl)-butanoic acid 280 mg of 3S-amino-4-(2-oxo-piperidin-1-yl)-butanoic acid obtained in the above step (1) was dissolved in 10 mL of water/1,4-dioxane (1/1) solvent, followed by addition of 144 mg (0.66 mmol) of di-butyldicarbonate. 2.3 mL of aqueous 1N sodium hydroxide solution was added thereto and then stirred for at room temperature 18 hours. The reaction solution was diluted with dichloromethane, and an organic layer was washed once with aqueous 1N aqueous hydrochloric acid and aqueous NaCl, respectively, then dried over anhydrous magnesium sulfate, followed by filtering and concentration under reduced pressure. The resulting compound was isolated and then the residue was purified by column chromatography to give 110 mg of the title compound in a yield of 61%.

¹H NMR (CD₃OD) δ 4.28-4.25 (1H, m), 3.67-3.58 (1H, m), 3.54-3.49 (1H, m), 3.40-3.32 (3H, m), 2.59-2.47 (2H, m), 2.37-2.30 (2H, m), 1.83-1.81 (4H, m), 1.44 (9H, s).

Mass (m/e) 301 (M+1)

PREPARATION 44

Synthesis of 3-trifluoromethyl-4,5,6,7-tetrahydro-isooxazol[3,4-c]pyridine 365 mg (1.24 mmol) of tert-butyl 3-oxo-4-(trifluoro-acetyl)-piperidine-1-carboxylate, which was obtained with reference to WO 04/064778, was diluted with 7 mL of acetic acid, then 107 mg (1.53 mmol) of hydroxylamine was added thereto, followed by refluxing. After refluxing for 6 hours, the reaction solution was cooled to room temperature, and acetic acid was removed under reduced pressure. The resulting compound was isolated and then the residue was purified by prep-TLC to give 45 mg of the title compound in a yield of 19%.

¹H NMR (CDCl₃) δ 4.05 (1H, s), 3.04-3.02 (2H, m), 2.70-2.69 (2H, m)

Mass (m/e) 193 (M+1)

PREPARATION 45

Synthesis of [3-oxo-1-(2-oxo-piperidin-1-ylmethyl)-3-(3-trifluoromethyl-4,5-dihydro-7H-isooxazolo[3,4-c]pyridin-6-yl)-propyl]-1S-carbamic acid t-butylester 11.8 mg (0.087 mmol) of 1-hydroxybenzotriazole and 166 mg (0.087 mmol) of EDC were dropwise added in sequence at room temperature to a solution in which 20 mg (0.067 mmol) of 3S-t-butoxycarbonylamino-4-(2-oxo-piperidin-1-yl)-butyric acid obtained in PREPARATION 42 was dissolved in 10 mL of dimethylformamide. After stirring for 10 minutes, to the reaction solution, was dropwise added a solution in which 14 mg (0.073 mmol) of 3-trifluoromethyl-4,5,6,7-tetrahydro-isooxazol[3,4-c]pyridine obtained in PREPARATION 44 was dissolved in 3 mL of dimethyl-formamide. After stirring at room temperature for 10 minutes, 0.035 mL (0.20 mmol) of diisopropylethylamine was added to the solution. After stirring at room temperature for 12 hours, the reaction solution was diluted with ethylacetate, and washed in sequence with aqueous 1N hydrochloric acid and aqueous NaCl, then an organic layer was dried over anhydrous magnesium sulfate and filtered off. The filtrated solution was distilled off under reduced pressure, then the residue was isolated and purified by prep-TLC to give 23 mg of the title compound in a yield of 73%.

¹H NMR (CDCl₃) δ 5.87-5.86 (1H, m), 4.86 (1H, brs), 4.76-4.70 (1H, m), 4.14 (1H, brs), 3.81 (1H, brs), 3.70-3.64 (2H, m), 3.44-3.30 (3H, m), 2.85-2.77 (2H, m), 2.50-2.45 (1H, m), 2.33-2.32 (2H, m), 1.83 (1H, brs), 1.77-1.75 (4H, m), 1.39 (9H, s).

Mass (m/e) 475 (M+1)

PREPARATION 46

Synthesis of [3-oxo-1-(2-oxo-piperidin-1-ylmethyl)-3-(3-trifluoromethyl-1,4,5,7-tetrahydro-pyrazolo[3,4-c]pyridin-6-yl)-propyl]-1S-carbamic acid t-butylester 25 mg of the title compound was obtained in a yield of 93% in the same manner as in PREPARATION 45, except that 14 mg (0.062 mmol) of 3-(trifluoromethyl)-4,5,6,7-tetrahydro-1H-pyrazolo[3,4-c]pyridine hydrochloric acid salt obtained with reference to WO 04/064778 and 17 mg (0.057 mmol) of 3S-t-butoxycarbonylamino-4-(2-oxo-piperidin-1-yl)-butanoic acid obtained in PREPARATION 43 were used.

¹H NMR (CDCl₃) δ 5.99-5.90 (1H, m), 4.82-4.64 (2H, m), 4.30-20 (1H, m), 3.90-3.84 (1H, m), 3.68-3.66 (1H, m), 3.64-3.31 (5H, m), 2.96-2.71 (3H, m), 2.66-2.56 (1H, m), 2.41-2.37 (2H, m), 1.93 (1H, brs), 1.79 (2H, brs), 1.39 (9H, m)

Mass (m/e) 474 (M+1)

EXAMPLE 19

Synthesis of 1-[2S-amino-4-oxo-4-(3-trifluoromethyl-4,5-dihydro-7H-isooxazolo[3,4-c]pyridin-6-yl)butyl]-piperidin-2-one

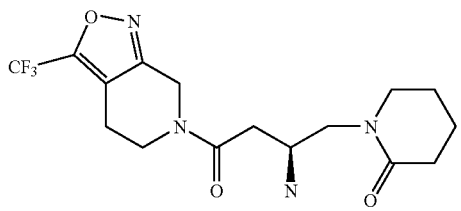

9.9 mg of the title compound in was obtained in a yield of 50% in the same manner as in EXAMPLE 3, except that 23 mg (0.048 mmol) of [3-oxo-1-(2-oxo-piperidin-1-ylmethyl)-3-(3-trifluoromethyl-4,5-dihydro-7H-isooxazolo[3,4-c]pyridin-6-yl)-propyl]-1S-carbamic acid t-butylester obtained in PREPARATION 45 was used.

$^1$H NMR (CD$_3$OD) δ 5.45-5.47 (1H, m), 3.86-3.68 (3H, m), 3.45-3.28 (4H, m), 2.90-2.68 (4H, m), 2.37-2.34 (2H, m), 1.89-1.78 (5H, m).

Mass (m/e) 375 (M+1)

EXAMPLE 20

Synthesis of 1-[2S-amino-4-oxo-4-(3-trifluoromethyl-1,4,5,7-tetrahydro-pyrazolo[3,4-c]pyridin-6-yl)-butyl]-piperidin-2-one

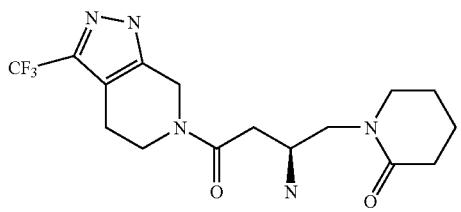

8.9 mg of the title compound was obtained in a yield of 41% in the same manner as in EXAMPLE 3, except that 25 mg (0.053 mmol) of [3-oxo-1-(2-oxo-piperidin-1-ylmethyl)-3-(3-trifluoromethyl-1,4,5,7-tetrahydro-pyrazol o[3,4-c]pyridin-6-yl)-propyl]-1S-carbamic acid t-butylester obtained in PREPARATION 46 was used.

$^1$H NMR (CD$_3$OD) δ 4.84-4.73 (1H, m), 4.12-3.73 (3H, m), 3.54-3.37 (4H, m), 2.30-2.70 (4H, m), 2.46-2.34 (2H, m), 1.94-1.80 (5H, m)

Mass (m/e) 374 (M+1)

PREPARATION 47

Synthesis of t-butyl 3-oxo-4-(trifluoroacetyl)piperidin-1-carboxylate 5.0 g (25 mmol) of t-butyl 3-oxopiperidin-1-carboxylate was dissolved in dimethoxyethane, and the resulting solution was cooled to −78° C., then 30 mL (30 mmol) of lithium hexamethyldisilazane (LHMDS, 1M in THF) was dropwise added and stirred for about 1 hour, followed by dropwise addition of 3.9 mL (33 mmol) of ethyltrifluoroacetate. After stirring for 1 hour, a dryice/acetone bath was removed and then further stirred for about 2 hours and 30 minutes with the reaction solution being heated to room temperature. After the reaction solution was washed with a saturated aqueous ammonium chloride, extraction was conduced three times with ethyl acetate. An organic layer was dried over anhydrous magnesium sulfate, and the solvent was distilled off under reduced pressure, then the residue was purified by column chromatography (20:1 dichloromethane:methanol) to give 6.0 g of the title compound in a yield of 81%.

$^1$H NMR (CDCl$_3$) δ 4.22 (2H, br s), 3.56 (2H, m), 2.57 (2H, br s), 1.49 (9H, s)

Mass (m/e) 296 (M+1)

PREPARATION 48

Synthesis of 4-trifluoromethyl-5,8-dihydro-6H-pyrido[3,4-d]pyrimidin-7-carboxylic acid t-butylester 0.52 mL of sodium ethoxide (21% wt. ethanol solution) was added at room temperature to a solution in which 95 mg (1.18 mmol) of formamidine hydrochloric acid salt was dissolved in 2 mL of anhydrous ethanol at room temperature. After stirring at room temperature for 10 minutes, to the resulting solution, was added a solution in which 232 mg (0.786 mmol) of tert-butyl-3-oxo-4-(trifluoroacetyl)-piperidine-1-carboxylate (product of PREPARATION 47) was diluted with 2 mL of anhydrous ethanol. Thereafter, the temperature of the solution was raised to 80° C., followed by stirring for about 18 hours. After cooling to room temperature, ethanol was removed under reduced pressure, and the reaction solution was diluted with ethylacetate, then washed in sequence aqueous NaCl. An organic layer was dried over anhydrous magnesium sulfate and filtered off. The filtrated solution was distilled off under reduced pressure and then, the residue was isolated and purified by prep-TLC (ethylacetate 20% normal hexane in solvent) to give 30 mg of the title compound in a yield of 13%

$^1$H NMR (CDCl$_3$) δ 9.11 (1H, s), 4.73 (2H, s), 3.72 (2H, t, J=5.5 Hz), 3.02 (2H, br s), 1.48 (9H, s)

Mass (m/e) 248 (M+1-t-butyl)

PREPARATION 49

Synthesis of Synthesis of 4-trifluoromethyl-5,6,7,8-tetrahydropyrido[3,4-d]pyrimidine hydrochloric acid salt 30 mg (0.099 mmol) of 4-trifluoromethyl-5,8-dihydro-6H-pyrido[3,4-d]pyrimidin-7-carboxylic acid t-butylester obtained in PREPARATION 48 was added to 1.8 mL of 3N HCl-ethylacetate solution under room temperature. After stirring at room temperature 10 minutes, excess HCl-ethylacetate solution was removed and concentrated to give the title compound. The compound was used at the next reaction without any further purification.

$^1$H NMR (CD$_3$OD) δ 4.44 (2H, s), 3.55-3.52 (2H, m), 3.23-3.20 (2H, m)

Mass (m/e) 204 (M+1)

PREPARATION 50

Synthesis of Synthesis of (3S)-t-butoxycarbony-lamino-4-[(5R)-methyl-2-oxo-piperidin-1-yl]-butanoic acid t-butyl ester 359 mg of the title compound was obtained in a yield of 73% in the same manner as in PREPARATION 42, except that 363 mg (1.33 mmol) of 3S-t-butoxycarbonylamino-4-oxo-butyric acid t-butyl ester (product of PREPARATION 41) and 220 mg (1.21 mmol) of (R)-5-amino-4-methyl-pentanoic acid methyl ester hydrochloric acid salt obtained in PREPARATION 7 were used.

$^1$H NMR (CDCl$_3$) δ 5.40-5.31 (1H, m), 4.17 (1H, br s), 3.89-3.80 (1H, m), 3.25-3.03 (3H, m), 2.58-2.29 (2H, m), 1.98-1.88 (1H, m), 1.84-1.80 (1H, m), 1.46 (9H, s), 1.42 (9H, s), 1.01 (3H, d, J=6.4 Hz)

Mass (m/e) 371 (M+1)

PREPARATION 51

Synthesis of (3S)-3-[(t-butoxycarbonyl)amino]-4-(5R-methyl-2-oxo-piperidin-1-yl)-butanoic acid 116 mg of the title compound was obtained in a yield of 38% in the same manner as in PREPARATION 43, except that (3S)-t-butoxycarbonylamino-4-[(5R)-methyl-2-oxo-piperidin-1-yl]-butanoic acid t-butyl ester 359 mg (0.97 mmol) of obtained in PREPARATION 50 were used.

$^1$H NMR (CDCl$_3$) δ 8.50 (1H, br s), 5.75-5.73 (1H, m), 4.16 (1H, br s), 3.76-3.54 (2H, m), 3.44-3.34 (1H, m), 3.16-2.97 (1H, m), 2.59-2.38 (4H, m), 1.98 (1H, br s), 1.86-1.84 (1H, m), 1.45 (9H, s), 1.04 (3H, d, J=6.8 Hz)

Mass (m/e) 315 (M+1)

PREPARATION 52

Synthesis of [1-(5R-methyl-2-oxo-piperidin-1-ylmethyl)-3-oxo-3-(4-trifluoromethyl-5,8-dihydro-6H-pyrido[3,4-d]pyrimidin-7-yl)-propyl]-1S-carbamic acid t-butylester 35 mg of the title compound was obtained in a yield of 65% in the same manner as in PREPARATION 45, except that 34.1 mg (0.108 mmol) of (3S)-3-[(t-butoxycarbonyl)amino]-4-[(5R)-methyl-2-oxo-piperidin-1-yl]-butanoic acid obtained in PREPARATION 51 and 26 mg (0.109 mmol) of 4-trifluoromethyl-5,6,7,8-tetrahydropyrido[3,4-d]pyrimidine hydrochloric acid salt obtained in PREPARATION 49 were used.

$^1$H NMR (CDCl$_3$) δ 9.15 (1H, s), 5.95-5.88 (1H, m), 4.95-4.70 (2H, m), 4.15 (1H, br s), 3.92-3.89 (1H, m), 3.86-3.80 (1H, m), 3.57-3.55 (1H, m), 3.36 (1H, br s), 3.09-3.00 (3H, m), 2.89-2.81 (1H, m), 2.54-2.30 (3H, m), 1.94 (1H, br s), 1.81 (1H, br s), 1.64 (2H, br s), 1.42-1.40 (9H, m), 1.02-1.00 (3H, m)

Mass (m/e) 500 (M+1)

EXAMPLE 21

Synthesis of 1-[2S-amino-4-oxo-4-(4-trifluoromethyl-5,8-dihydro-6H-pyrido[3,4-d]pyrimidin-7-yl-butyl]-5R-methyl-1-piperidin-2-one

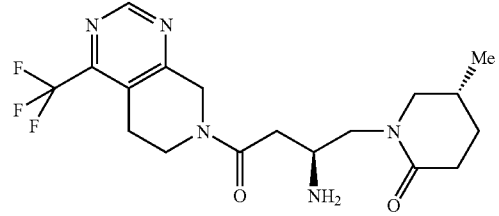

14.5 mg of the title compound was obtained in a yield of 51% in the same manner as in EXAMPLE 3, except that 35 mg (0.053 mmol) of 1-(5R-methyl-2-oxo-piperidin-1-ylmethyl)-3-oxo-3-(4-trifluoromethyl-5,8-dihydro-6H-pyrido[3,4-d]pyrimidin-7-yl)-propyl]-1S-carbamic acid t-butylester obtained in PREPARATION 52 was used.

$^1$H NMR (CD$_3$OD) δ 9.15-9.14 (1H, m), 9.95 (1H, t, J=6.0 Hz), 3.90-3.86 (1H, m), 3.80-3.77 (1H, m), 3.71-3.65 (1H, m), 3.58-3.53 (1H, m), 3.48-3.37 (3H, m), 3.18-3.07 (3H, m), 2.94-2.87 (1H, m), 2.80-2.75 (1H, m), 2.58-2.34 (2H, m), 2.05-2.03 (1H, m), 1.89-1.85 (1H, m), 1.60-1.47 (1H, m), 1.06 (3H, d, J=2.8 Hz)

Mass (m/e) 374 (M+1)

PREPARATION 53

Synthesis of (S)-(2-amino-1-methyl-ethoxy)-acetic acid ethyl ester hydrochloric acid salt (1) Synthesis of (S)-(2-hydroxy-propyl)-carbamic acid t-butyl ester 500 mg (6.65 mmol) of (S)-1-amino-propane-2-ol was dissolved in 20 mL of methanol and 5 mL of water, then 1.85 g (8.45 mmol) of di-t-butyl dicarbonate was added thereto, followed by stirring for 3 hours. 200 mL of ethyl acetate was added thereto, and the reaction solution was washed with water. An organic layer was dried over anhydrous magnesium sulfate, and the solvent was distilled off under reduced pressure, then the residue was purified by column chromatography to give 802 g (4.57 mmol) of the title compound in a yield of 68%.

NMR: $^1$H-NMR (CDCl$_3$) δ 4.91 (1H, brs), 3.95~3.85 (1H, m), 3.30~3.22 (1H, m), 3.04~2.97 (1H, m), 2.31 (1H, brs), 1.45 (9H, s), 1.18 (3H, d, J=8 Hz)

Mass (EI) 176 (M$^+$+1)

(2) Synthesis of (S)-(2-t-butoxycarbonylamino-1-methyl-ethoxy)-acetic acid ethyl ester 1.16 g (6.61 mmol) of (S)-(2-hydroxy-propyl)-carbamic acid t-butyl ester was dissolved in 20 mL of dichloroethane, then 0.66 mL (9.84 mmol) of ethyl diazoacetate was added thereto. 57 mg (0.12 mmol) of rhodium acetate was dropwise added thereto, and then heated to at 80° C. for 2 hour. The solvent was distilled off under reduced pressure, and the residue was purified by column chromatography to give 1.2 g (4.59 mmol) of the title compound in a yield of 69%.

NMR: $^1$H-NMR (CDCl$_3$) δ 5.39 (1H, s), 4.23 (2H, q, J=8 Hz), 4.09 (1H, d, J=16 Hz), 4.00 (1H, d, J=16 Hz), 3.60~3.35 (1H, m), 3.35~3.15 (1H, m), 3.10~3.04 (1H, m), 1.46 (9H, s), 1.31 (3H, t, J=4 Hz), 1.16 (3H, d, J=4 Hz)

Mass (EI) 262 (M$^+$+1)

(3) Synthesis of (S)-(2-amino-1-methyl-ethoxy)-acetic acid ethyl ester hydrochloric acid salt 1.2 g (4.59 mmol) of (S)-(2-t-butoxycarbonylamino-1-methyl-ethoxy)-acetic acid ethyl ester was dissolved in 20 mL of ethyl acetate saturated with hydrochloric acid gas, followed by stirring at room temperature for 3 hours. The solvent was distilled off under reduced pressure, then the residue was purified by column chromatography to give 699 mg (3.49 mmol) of the title compound in a yield of 76%.

NMR: $^1$H-NMR (CD$_3$OD) δ 5.05 (2H, s), 4.32~4.19 (4H, m), 3.88~3.83 (1H, m), 3.16~3.12 (1H, m), 2.96~2.90 (1H, m), 1.32 (3H, t, J=7.2 Hz), 1.25 (3H, d, J=6 Hz)

Mass (EI) 200 (M$^+$+1)

PREPARATION 54

Synthesis of t-butyl (3S)-3-[(t-butoxycarbonyl)amino]-4-[(2S)-2-methyl-5-oxomorpholin-4-yl]-butanoate 3S-t-butoxycarbonylamino-4-oxo-butyric acid t-butyl ester obtained in the same manner as in PREPARATION 41 and 457 mg (2.31 mmol) of (S)-(2-amino-1-methyl-ethoxy)-acetic acid ethyl ester hydrochloric acid salt obtained in PREPARATION 53 were reacted at the manner as in PREPARATION 50 to give 767 mg of the title compound in a total yield of 81%.

$^1$H NMR (CDCl$_3$) δ 5.22 (1H, d, J=8.5 Hz), 4.17 (2H, Abq, J=18 Hz), 3.87 (1H, m), 3.66 (1H, dd, J=13.5, 8.5 Hz), 3.41 (1H, t, J=11.0 Hz), 3.31 (1H, dd, J=13.5 5.0 Hz), 2.90 (1H, dd, J=12.0, 2.5 Hz), 2.52 (1H, dd, J=16.0, 5.0 Hz), 2.41 (1H, dd, J=16.0, 6.5 Hz), 1.44 (9H, s), 1.41 (9H, s), 1.25 (3H, d, J=6.0 Hz)

Mass (m/e) 395 (M+Na)

PREPARATION 55

Synthesis of (3S)-3-[(t-butoxycarbonyl)amino]-4-[(2S)-2-methyl-5-oxomorpholin-4-yl]-butanoic acid 580 mg of the title compound was obtained in a total yield of 89% at the same manner as in PREPARATION 43, except that 767 mg (2.06 mmol) of t-butyl (3S)-3-[(t-butoxycarbonyl)amino]-4-[(2S)-2-methyl-5-oxomorpholin-4-yl]-butanoate obtained in PREPARATION 54

$^1$H NMR (CD$_3$OD) δ 4.23 (1H, m), 4.11 (2H, s), 3.88 (1H, m), 3.50 (1H, dd, J=13.5 8.5 Hz), 3.39 (2H, m), 2.50 (1H, dd, J=16, 6 Hz), 2.44 (1H, dd, J=16, 7 Hz), 1.41 (9H, s), 1.22 (3H, d, J=7 Hz)

Mass (m/e) 317 (M+1)

PREPARATION 56

Synthesis of t-butyl (3S)-3-[(t-butoxycarbonyl)amino]-4-(5,5-difluoro-2-oxopiperidin-1-yl)-butanoate 900 mg of the title compound was obtained in a yield of 90% in the same manner as in PREPARATION 42, except that 3S-t-butoxycarbonylamino-4-oxo-butyric acid t-butyl ester (product of PREPARATION 41) and 471 mg (2.31 mmol) of 5-amino-4,4-difluoropentanoic acid methyl ester hydrochloric acid salt obtained in PREPARATION 12 were used.

$^1$H NMR (CDCl$_3$) δ 5.19 (1H, d, J=8.0 Hz), 3.5-4.0 (4H, m), 3.20 (1H, dd, J=14, 4 Hz), 2.6 (2H, m), 2.5 (1H, dd, J=16, 4 Hz), 2.4 (1H, dd, J=16, 8 Hz), 2.2-2.3 (2H, m), 1.46 (9H, s), 1.42 (9H, s)

Mass (m/e) 393 (M+1)

PREPARATION 57

Synthesis of (3S)-3-[(t-butoxycarbonyl)amino]-4-(5,5-difluoro-2-oxopiperidin-1-yl)-butanoic acid 298 mg of the title compound was obtained in a yield of 39% in the same manner as in PREPARATION 43, except that 900 mg (2.29 mmol) of t-butyl (3S)-3-[(t-butoxycarbonyl)amino]-4-(5,5-difluoro-2-oxopiperidin-1-yl)-butanoate obtained in PREPARATION 56 was used.

$^1$H NMR (CD$_3$OD) δ 4.19 (1H, m), 3.87 (1H, br q, J=13 Hz), 3.7 (1H, br q, J=13 Hz), 3.52 (1H, dd, J=14, 9 Hz), 3.37 (1H, m), 2.4-2.6 (4H, m), 2.2-2.3 (2H, m), 1.40 (9H, s)

Mass (m/e) 337 (M+1)

PREPARATION 58

Synthesis of 2-(4-fluorophenyl)-4-(trifluoromethyl)-5,6,7,8-tetrahydropyrido[3,4-d]pyrimidine hydrochloric acid salt

(1) Synthesis of 4-fluorobenzenecarboximidamide 4.12 mL (8.24 mmol) of trimethyl aluminum (2.0 M toluene solution) was dropwise added to a 10 mL of toluene containing 441 mg (8.24 mmol) of ammonium chloride at room temperature. After stirring for 1.5 hours, 1 g (8.25 mmol) of 4-fluorobenzonitrile was added thereto and the resulting mixture was heated to 85° C. for 9 hours. After completion of a reaction, the reaction solution was cooled, then poured into 100 mL of chloroform containing 500 g of silica gel and filtered off. The residue was washed with 100 mL of methanol and distillation was conducted to give 821 mg (5.9 mmol) of the title compound in a yield of 71%.

NMR: $^1$H-NMR (DMSO d6) δ 9.44 (1H, brs), 9.25 (1H, brs), 7.96~7.92 (2H, m), 7.52~7.31 (2H, m)

Mass (EI) 139 (M$^+$+1)

(2) Synthesis of t-butyl 2-(4-fluorophenyl)-4-(trifluoromethyl)-5,8-dihydropyrido[3,4-d]pyrimidin-7(6H)-carboxylate 500 mg (1.69 mmol) of t-butyl 3-oxo-4-(trifluoroacetyl) of piperidin-1-carboxylate obtained in PREPARATION 47 and 351 m (2.54 mmol) of 4-fluorobenzenecarboximidamide obtained in the above step (1) were reacted in the same manner as in PREPARATION 48 to give 108 mg of the title compound in a yield of 16%.

$^1$H NMR (CDCl$_3$) δ 8.47 (2H, m), 7.16 (2H, t, J=8.5 Hz), 4.76 (2H, s), 3.74 (2H, t, J=6.0 Hz), 3.02 (2H, br s), 1.51 (9H, s)

Mass (m/e) 398 (M+1)

(3) Synthesis of 2-(4-fluorophenyl)-4-(trifluoromethyl)-5,6,7,8-tetrahydropyrido[3,4-d]pyrimidine hydrochloric acid salt 108 mg (0.306 mmol) of t-butyl 2-(4-fluorophenyl)-4-(trifluoromethyl)-5,8-dihydropyrido[3,4-d]pyrimidin-7(6H)-carboxylate obtained in the above step (2) was added to 7.5 mL of 4 N HCl/1,4-dioxane solution at room temperature. After stirring at room temperature for 25 minutes, excess HCl/1,4-dioxane solution was removed, and the resulting solution was concentrated to give 69 mg of the title compound. The compound was used at the next reaction without any further purification.

$^1$H NMR (CD$_3$OD) δ 8.54 (2H, m), 7.29 (2H, t, J=10.0 Hz), 4.60 (2H, s), 3.67 (2H, t, J=6.0 Hz), the remaining two protons are anticipated to be buried in CD$_3$OD of 3.3 ppm.

Mass (m/e) 298 (M+1)

PREPARATION 59

Synthesis of 2-(3,4-difluorophenyl)-4-(trifluoromethyl)-5,6,7,8-tetradropyrido[3,4-d]pyrimidine hydrochloric acid salt (1) Synthesis of 3,4-difluorobenzenecarboximidamide 3.6 mL (7.2 mmol) of trimethyl aluminum (2.0 M toluene solution) was dropwise added to a 10 mL of toluene containing 384 mg (7.17 mmol) of ammonium chloride at room temperature. After stirring for 1.5 hours, 1 g (7.1 mmol) of 3,4-difluorobenzonitrile was added thereto and the resulting mixture was heated to 85° C. for 9 hours. After completion of a reaction, the reaction solution was poured into 100 mL of chloroform containing 200 g of silicagel and filtered off. The residue was washed with 200 mL of methanol and distillation was conducted to give 370 mg (2.36 mmol) of the title compound in a yield of 33%.

NMR: $^1$H-NMR (CD$_3$OD) δ 7.87~7.82 (1H, m), 7.72~7.70 (1H, m), 7.63~7.55 (1H, m)

Mass (EI) 157 (M$^+$+1)

(2) Synthesis of t-butyl 2-(3,4-difluorophenyl)-4-(trifluoromethyl)-5,8-dihydropyrido[3,4-d]pyrimidin-7(6H)-carboxylate 25 mg of the title compound was obtained in a yield of 4.7% in the same manner as in PREPARATION 58-(2), except that 380 mg (1.28 mmol) of t-butyl 3-oxo-4-(trifluoroacetyl)piperidin-1-carboxylate obtained in PREPARATION 47 and 300 mg (1.92 mmol) of 3,4-difluorobenzenecarboximidamide obtained in the above (1) were used.

$^1$H NMR (CDCl$_3$) δ 8.3 (2H, m), 7.25 (1H, m), 4.76 (2H, s), 3.75 (2H, t, J=6.0 Hz), 3.03 (2H, br s), 1.51 (9H, s)

Mass (m/e) 416 (M+1)

(3) Synthesis of 2-(3,4-difluorophenyl)-4-(trifluoromethyl)-5,6,7,8-tetradropyrido[3,4-d]pyrimidine hydrochloric acid salt 14 mg of the title compound was obtained in a yield of 74% in the same manner as in PREPARATION 59(3), except that 25 mg (0.62 mmol) of t-butyl 2-(3,4-difluorophenyl)-4-(trifluoromethyl)-5,8-dihydropyrido[3,4-d]pyrimidin-7(6H)-carboxylate obtained in the above step (2) was used.

$^1$H NMR (CD$_3$OD) δ 8.36 (2H, m), 7.48 (1H, m), 4.60 (2H, s), 3.66 (2H, t, J=7.5 Hz), 3.12 (2H, m)

Mass (m/e) 316 (M+1)

PREPARATION 60

Synthesis of 2-(3-fluorophenyl)-4-(trifluoromethyl)-5,6,7,8-tetrahydropyrido[3,4-d]pyrimidine hydrochloric acid salt (1) Synthesis of 3-fluorobenzenecarboximidamide 4.12 mL (8.24 mmol) of trimethyl aluminum (2.0 M toluene solution) was added to a 10 mL of toluene containing 441 mg (8.24 mmol) of ammonium chloride at room temperature. After stirring for 1.5 hours, 2 g (28.9 mmol) of isobutyronitrile was added thereto and the resulting mixture was heated to 85° C. for 9 hours. After completion of a reaction, the reaction solution was poured into 200 mL of chloroform containing 200 g of silicagel and filtered off. The residue was washed with 100 mL of methanol and distillation was conducted to give 731 mg (5.29 mmol) of the title compound in a yield of 64%.

NMR: $^1$H-NMR (CD$_3$OD) δ 7.71~7.44 (4H, m)

Mass (EI) 139 (M$^+$+1)

(2) Synthesis of t-butyl 2-(3-fluorophenyl)-4-(trifluoromethyl)-5,8-dihydropyrido[3,4-d]pyrimidin-7(6H)-carboxylate 159 mg of the title compound was obtained in a yield of 20% in the same manner as in PREPARATION 61-58(2), except that 600 mg (2.03 mmol) of t-butyl 3-oxo-4-(trifluoroacetyl)piperidin-1-carboxylate obtained in PREPARATION 47 and 421 mg (3.05 mmol) of 3-fluorobenzenecarboximidamide obtained in the above step (1) were used.

$^1$H NMR (CDCl$_3$) δ 8.25 (1H, d, J=8.0 Hz), 8.15 (1H, m), 7.45 (1H, m), 7.18 (1H, m), 4.78 (2H, s), 3.75 (2H, t, J=6.0 Hz), 3.13 (2H, br s), 1.52 (9H, s)

Mass (m/e) 398 (M+1)

(3) Synthesis of 2-(3-fluorophenyl)-4-(trifluoromethyl)-5,6,7,8-tetradropyrido[3,4-d]pyrimidine hydrochloric acid salt 88 mg of the title compound was obtained in a yield of 67% in the same manner as in PREPARATION 58(3), except that 159 mg (0.62 mmol) of t-butyl 2-(3-fluorophenyl)-4-(trifluoromethyl)-5,8-dihydropyrido[3,4-d]pyrimidin-7(6H)-carboxylate obtained in above step (2) was used.

$^1$H NMR (CD$_3$OD) δ 8.33 (1H, m), 8.17 (1H, m), 7.58 (1H, m), 7.34 (1H, m), 4.62 (2H, s), 3.67 (2H, t, J=6.5 Hz), 3.35 (2H, m)

Mass (m/e) 298 (M+1)

PREPARATION 61

Synthesis of 2-cyclopropyl-4-(trifluoromethyl)-5,6,7,8-tetrahydropyrido[3,4-d]pyrimidine hydrochloric acid salt (1) Synthesis of t-butyl 2-cyclopropyl-4-(trifluoromethyl)-5,8-dihydropyrido[3,4-d]pyrimidin-7(6H)-carboxylate 1.27 g of sodiumethoxide (21% wt. Ethanol solution) was added at room temperature to a solution in which 500 mg (4.13 mmol) of cyclopropanecarboximidamide hydrochloric acid salt was dissolved in 50 mL of isopropanol. After stirring for 30 minutes, concentration and filtration was conducted, and 940 mg (3.17 mmol) of t-butyl 3-oxo-4-(trifluoroacetyl) piperidin-1-carboxylate obtained in PREPARATION 47 was added thereto, followed by addition of $BF_2OEt_2$ 12 1 (3% catalyst amount). The resulting solution was heated to 80° C., followed by stirring for 19 hours. After cooling to room temperature, isopropaneol was removed under reduced pressure. The residue was purified by column chromatography (10:1 hexane:ethyl acetate) to give 400 mg of the title compound in a yield of 37%.

$^1$H NMR ($CDCl_3$) δ 4.62 (2H, s), 3.68 (2H, t, J=5.5 Hz), 2.93 (2H, br s), 2.25 (1H, m), 1.49 (9H, s), 1.1-1.2 (4H, m)

Mass (m/e) 344 (M+1)

(2) Synthesis of 2-cyclopropyl-4-(trifluoromethyl)-5,6,7,8-tetrahydropyrido[3,4-d]pyrimidine hydrochloric acid salt 264 mg of the title compound was obtained in a yield of 81% in the same manner as in PREPARATION 58-(3), except that 400 mg (1.16 mmol) of t-butyl 2-cyclopropyl-4-(trifluoromethyl)-5,8-dihydropyrido[3,4-d]pyrimidin-7(6H)-carboxylate obtained in the above step (1) was used.

$^1$H NMR ($CD_3OD$) δ 4.40 (2H, s), 3.56 (2H, t, J=6.5 Hz), 3.20 (2H, t, J=6.5 Hz), 2.29 (1H, m), 1.20 (4H, m)

Mass (m/e) 244 (M+1)

PREPARATION 62

2-cyclopentyl-4-(trifluoromethyl)-5,6,7,8-tetradropyrido[3,4-d]pyrimidine hydrochloric acid salt (1) Synthesis of t-butyl 2-cyclopentyl-4-(trifluoromethyl)-5,8-dihydropyrido[3,4-d]pyrimidin-7(6H)-carboxylate 1.0 g (3.39 mmol) of t-butyl 3-oxo-4-(trifluoroacetyl)piperidin-1-carboxylate obtained in PREPARATION 47 was dissolved in 10 mL of pyridine, and then 380 mg (3.39 mmol) of cyclopentane carboximidamide hydrochloric acid salt was added thereto, and the reaction solution was heated to 120° C. and stirred for 1 hour, 20 minutes. After cooling to room temperature, pyridine was removed under reduced pressure. The residue was purified by column chromatography (10:1 hexane:ethyl acetate) to give 688 mg of the title compound in a yield of 55%.

$^1$H NMR ($CDCl_3$) δ 4.67 (2H, s), 3.70 (2H, t, J=5.5 Hz), 3.34 (1H, m), 2.96 (2H, br s), 2.07 (2H, m), 1.8-2.0 (4H, m), 1.70 (2H, m), 1.49 (9H, s)

Mass (m/e) 372 (M+1)

(2) Synthesis of 2-cyclopentyl-4-(trifluoromethyl)-5,6,7,8-tetrahydropyrido[3,4-d]pyrimidine hydrochloric acid salt 480 mg of the title compound was obtained in a yield of 84% in the same manner as in PREPARATION 58(3), except that 688 mg (1.85 mmol) of t-butyl 2-cyclopentyl-4-(trifluoromethyl)-5,8-dihydropyrido[3,4-d]pyrimidin-7(6H)-carboxylate obtained in above step (1) was used.

$^1$H NMR ($CD_3OD$) δ 4.44 (2H, s), 3.58 (2H, t, J=6.5 Hz), 3.4 (1H, m), 3.20 (2H, t, J=6.5 Hz), 2.07 (2H, m), 1.8-2.0 (4H, m), 1.70 (2H, m)

Mass (m/e) 272 (M+1)

PREPARATION 63

Synthesis of 2-phenyl-4-(trifluoromethyl)-5,6,7,8-tetradropyrido[3,4-d]pyrimidine hydrochloric acid salt (1) Synthesis of t-butyl 2-phenyl-4-(trifluoromethyl)-5,8-dihydropyrido[3,4-d]pyrimidin-7(6H)-carboxylate 900 mg of the title compound was obtained in a yield of 70% in the same manner as in PREPARATION 61-(1), except that 1.0 g (3.39 mmol) of t-butyl 3-oxo-4-(trifluoroacetyl) piperidin-1-carboxylate obtained in PREPARATION 47 and 530 mg (3.39 mmol) of benzenecarboximidamide hydrochloric acid salt were used.

$^1$H NMR ($CDCl_3$) δ 8.46 (2H, m), 7.49 (3H, m), 4.78 (2H, s), 3.75 (2H, t, J=5.5 Hz), 3.03 (2H, br s), 1.51 (9H, s)

Mass (m/e) 380 (M+1)

(2) Synthesis of 2-phenyl-4-(trifluoromethyl)-5,6,7,8-tetrahydropyrido[3,4-d]pyrimidine hydrochloric acid salt 730 mg of the title compound was obtained in a yield of 97% in the same manner as in PREPARATION 58(3), except that 900 mg (2.37 mmol) of t-butyl 2-phenyl-4-(trifluoromethyl)-5,8-dihydropyrido[3,4-d]pyrimidin-7(6H)-carboxylate obtained in above step (1) was used.

$^1$H NMR ($CD_3OD$) δ 8.50 (2H, m), 7.57 (3H, m), 4.61 (2H, s), 3.67 (2H, t, J=7.5 Hz), 3.30 (2H, m)

Mass (m/e) 280 (M+1)

PREPARATION 64

Synthesis of t-butyl {(1S)-1-{[(5R)-5-methyl-2-oxopiperidin-1-yl]methyl}-3-oxo-3-[2-phenyl-4-(trifluoromethyl)-5,8-dihydropyrido[3,4-d]pyrimidin-7(6H)-yl]propyl}carbamate 77 mg (0.24 mmol) of (3S)-3-[(t-butoxycarbonyl)amino]-4-(5R-methyl-2-oxopiperidin-1-yl)-butanoic acid obtained in PREPARATION 51 and 70 mg (0.22 mmol) of 2-phenyl-4-(trifluoromethyl)-5,6,7,8-tetrahydropyrido[3,4-d]pyrimidine hydrochloric acid salt obtained in PREPARATION 63 were reacted in the same manner as in PREPARATION 45 to give 120 mg of the title compound in a yield of 94%.

$^1$H NMR ($CDCl_3$) δ 8.46 (2H, m), 7.50 (3H, m), 5.86 (1H, m), 4.93 (1H, s), 4.8 (1H, ABq, J=16 Hz), 4.2 (1H, m), 3.92 (1H, m), 3.8 (1H, m), 3.63 (1H, m), 3.36 (1H, m), 3.0-3.2 (3H, m), 2.88 (1H, m), 2.3-2.6 (3H, m), 1.8-2.0 (2H, m), 1.40 (9H, m), 1.00 (3H, d, J=6.5 Hz)

Mass (m/e) 576 (M+1)

EXAMPLE 22

Synthesis of (5R)-1-{(2S)-2-amino-4-oxo-4-[2-phenyl-4-(trifluoromethyl)-5,8-dihydropyrido[3,4-d]pyrimidin-7(6H)-yl]butyl}-5-methylpiperidin-2-one

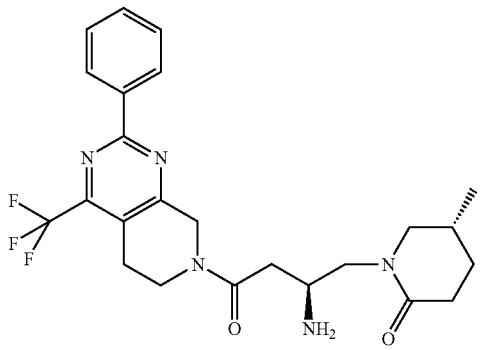

120 mg (0.21 mmol) of t-butyl {(1S)-1-{[(5R)-5-methyl-2-oxopiperidin-1-yl]methyl}-3-oxo-3-[2-phenyl-4-(trifluoromethyl)-5,8-dihydropyrido[3,4-d]pyrimidin-7(6H)-yl]propyl}carbamate obtained in PREPARATION 64 was dissolved in 1,4-dioxane/hydrochloric acid. After stirring for 30 minutes and then concentration under reduced pressure, the residue was purified by prep-TLC (10:1 $CH_2Cl_2$:MeOH) to give 83 mg of the title compound in a yield of 84%.

$^1$H NMR ($CD_3OD$) δ 8.46 (2H, m), 7.50 (3H, m), 5.0-4.8 (2H, m), 3.94 (1H, t, J=6.5 Hz), 3.86 (1H, m), 3.75 (1H, m), 3.64 (1H, m), 3.53 (1H, m), 3.3-3.4 (1H, m), 3.0-3.2 (3H, m), 2.86 (1H, m), 2.70 (1H, m), 2.3-2.5 (2H, m), 2.0 (1H, m), 1.84 (1H, m), 1.52 (1H, m), 1.02 (3H, m)

Mass (m/e) 476 (M+1)

PREPARATION 65

Synthesis of t-butyl [(1S)-1-{[(2S)-2-methyl-5-oxomorpholin-4-yl]methyl}3-oxo-3-[2-phenyl-4-(trifluoromethyl)-5,8-dihydropyrido[3,4-d]pyrimidin-7(6H)-yl]propyl]carbamate 182 mg of the title compound was obtained in a yield of 99% in the same manner as in PREPARATION 45, except that 77 mg (0.24 mmol) of (3S)-3-[(t-butoxycarbonyl)amino]-4-[(2S)-2-methyl-5-oxomorpholin-4-yl]-butanoic acid obtained in PREPARATION 55 and 70 mg (0.22 mmol) of 2-phenyl-4-(trifluoromethyl)-5,6,7,8-tetrahydropyrido[3,4-d]pyrimidine hydrochloric acid salt obtained in PREPARATION 63 were used.

$^1$H NMR ($CDCl_3$) δ 8.46 (2H, m), 7.51 (3H, m), 5.80 (1H, m), 4.93 (1H, s), 4.8 (1H, ABq, J=16 Hz), 4.2-4.3 (2H, m), 3.8-4.0 (3H, m), 3.6-3.7 (1H, m), 3.5-3.6 (1H, m), 3.3-3.4 (2H, m), 3.0-3.2 (2H, m), 2.8-2.9 (1H, m), 2.5-2.6 (1H, m), 1.41 (9H, m), 1.26 (3H, d, J=6.5 Hz)

Mass (m/e) 578 (M+1)

EXAMPLE 23

Synthesis of (6S)-4-{(2S-2-amino-4-oxo-4-[2-phenyl-4-(trifluoromethyl)-5,8-dihydropyrido[3,4-d]pyrimidin-7(6H)-yl]butyl}-6-methylmorpholine-3-one

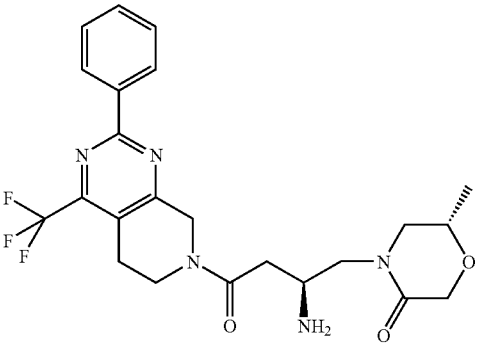

91 mg of the title compound was obtained in a yield of 87% in the same manner as in EXAMPLE 23, except that 127 mg (0.22 mmol) of t-butyl [(1S)-1-{[(2S)-2-methyl-5-oxomorpholin-4-yl]methyl}3-oxo-3-[2-phenyl-4-(trifluoromethyl)-5,8-dihydropyrido[3,4-d]pyrimidin-7(6H)-yl]propyl]carbamate obtained in PREPARATION 65 was used.

$^1$H NMR ($CD_3OD$) δ 8.46 (2H, m), 7.50 (3H, m), 5.0-4.8 (2H, m), 4.0-4.2 (2H, m), 3.8-4.0 (3H, m), 3.7-3.8 (1H, m), 3.5-3.6 (2H, m), 3.53 (1H, m), 3.3-3.4 (2H, m), 3.0-3.2 (2H, m), 2.8-2.9 (1H, m), 2.6-2.7 (1H, m), 1.23 (3H, m)

Mass (m/e) 478 (M+1)

PREPARATION 66

Synthesis of t-butyl {(1S)-1-[(5,5-difluoro-2-oxopiperidin-1-yl)methyl]3-oxo-3-[2-phenyl-4-(trifluoromethyl)-5,8-dihydropyrido[3,4-d]pyrimidin-7(6H)-yl]propyl}carbamate 108 mg of the title compound was obtained in a yield of 82% in the same manner as in PREPARATION 45, except that 82 mg (0.24 mmol) of (3S)-3-[(t-butoxycarbonyl)amino]-4-(5,5-difluoro-2-oxopiperidin-1-yl)-butanoic acid obtained in PREPARATION 57 and 70 mg (0.22 mmol) of 2-phenyl-4-(trifluoromethyl)-5,6,7,8-tetrahydropyrido[3,4-d]pyrimidine hydrochloric acid salt obtained in PREPARATION 63 were used.

$^1$H NMR ($CDCl_3$) δ 8.46 (2H, m), 7.50 (3H, m), 5.78 (1H, m), 4.93 (1H, s), 4.78 (1H, ABq, J=16 Hz), 4.22 (1H, m), 3.92 (1H, m), 3.7-3.8 (3H, m), 3.5-3.7 (2H, m), 3.0-3.2 (2H, m), 2.84 (1H, m), 2.56 (3H, m), 2.27 (2H, m), 1.41 (9H, m)

Mass (m/e) 598 (M+1)

EXAMPLE 24

Synthesis of 1-{(2S)-2-amino-4-oxo-4-[2-phenyl-4-(trifluoromethyl)-5,8-dihydropyrido[3,4-d]pyrimidin-7(6H)-yl]butyl}-5,5-difluoropiperidin-2-one

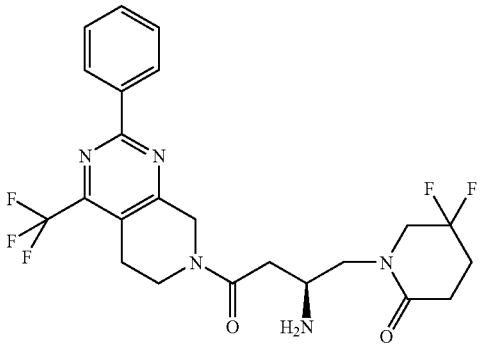

78 mg of the title compound was obtained in a yield of 87% in the same manner as in EXAMPLE 23, except that 108 mg (0.18 mmol) of t-butyl {(1S)-1-[(5,5-difluoro-2-oxopiperidin-1-yl)methyl]3-oxo-3-[2-phenyl-4-(trifluoromethyl)-5,8-dihydropyrido[3,4-d]pyrimidin-7(6H)-yl]propyl}carbamate obtained in PREPARATION 65 was used.

$^1$H NMR (CD$_3$OD) δ 8.46 (2H, m), 7.50 (3H, m), 5.0-4.8 (2H, m), 3.6-4.0 (6H, m), 3.48 (1H, m), 3.0-3.2 (2H, m), 2.83 (1H, m), 2.71 (1H, m), 2.57 (2H, m), 2.34 (2H, m)

Mass (m/e) 498 (M+1)

PREPARATION 67 t-butyl {(1S)-1-[(5,5-difluoro-2-oxopiperidin-1-yl)methyl]-3-[2-cyclopropyl-4-(trifluoromethyl)-5,8-dihydropyrido[3,4-d]pyrimidin-7(6H)-yl]-3-oxpropyl}carbamate 12 mg (0.021 mmol) of the title compound was obtained in a yield of 87% in the same manner as in PREPARATION 45, except that 8.4 mg (0.024 mmol) of (3S)-3-[(t-butoxycarbonyl)amino]-4-(5,5-difluoro-2-oxopiperidin-1-yl)butanoic acid obtained in PREPARATION 57 and 7 mg (0.025 mmol) of 2-cyclopropyl-4-(trifluoromethyl)-5,6,7,8-tetrahydropyrido[3,4-d]pyrimidine hydrochloric acid salt obtained in PREPARATION 61 were used.

Mass (EI) 562 (M$^+$+1)

EXAMPLE 25

Synthesis of 1-{(2S)-2-amino-4-[2-cyclopropyl-4-(trifluoromethyl)-5,8-dihydropyrido[3,4-d]pyrimidin-7(6H)-yl]-4-oxobutyl}-5,5-difluoropiperidin-2-one

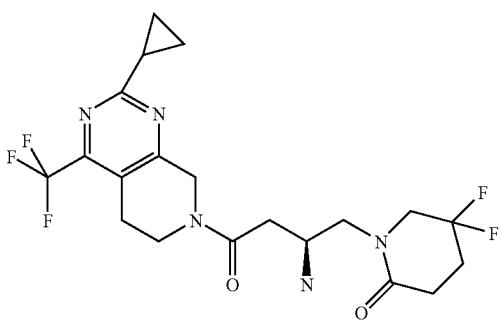

6 mg (0.012 mmol) of the title compound was obtained in a yield of 57% in the same manner as in EXAMPLE 23, except that 12 mg (0.021 mmol) of t-butyl {(1S)-1-[(5,5-difluoro-2-oxopiperidin-1-yl)methyl]-3-[2-cyclopropyl-4-(trifluoromethyl)-5,8-dihydropyrido[3,4-d]pyrimidin-7(6H)-yl]-3-oxpropyl}carbamate obtained in PREPARATION 67 was used.

NMR: $^1$H-NMR (CD$_3$OD) δ 4.84~4.73 (2H, m), 3.89~3.76 (4H, m), 3.55~3.47 (3H, m), 3.10~2.96 (2H, m), 2.69~2.55 (4H, m), 2.39~2.17 (3H, m), 1.17~1.12 (4H, m)

Mass (EI) 462 (M$^+$+1)

PREPARATION 68

Synthesis of t-butyl (1S)-{[(5R)-5-methyl-2-oxopiperidin-1-yl]methyl]-3-[2-cyclopropyl-4-(trifluoromethyl)-5,8-dihydropyrido[3,4-d]pyrimidin-7(6H)-yl]-3-oxpropyl}carbamate 11 mg (0.020 mmol) of the title compound was obtained in a yield of 80% in the same manner as in PREPARATION 45, except that 8.0 mg (0.025 mmol) of (3S)-3-[(t-butoxycarbonyl)amino]-4-[(5R)-5-methyl-2-oxopiperidin-1-yl]butanoic acid obtained in PREPARATION 51 and 7 mg (0.025 mmol) of 2-cyclopropyl-4-(trifluoromethyl)-5,6,7,8-tetrahydropyrido[3,4-d]pyrimidine hydrochloric acid salt obtained in PREPARATION 61 were used.

Mass (EI) 540 (M$^+$+1)

EXAMPLE 26

Synthesis of 1-{(2S)-2-amino-4-[2-cyclopropyl-4-(trifluoromethyl)-5,8-dihydropyrido[3,4-d]pyrimidin-7(6H)-yl]-4-oxobutyl}-5-methylpiperidin-2-one

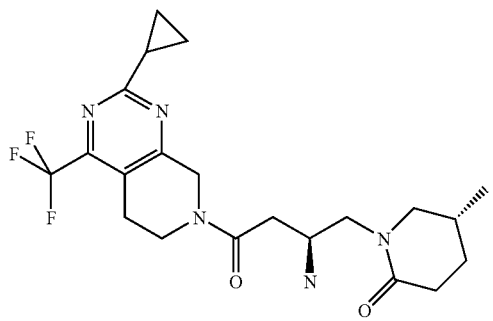

7 mg (0.014 mmol) of the title compound was obtained in a yield of 70% in the same manner as in EXAMPLE 23, except that 11 mg (0.020 mmol) of t-butyl (1S)-1-{[(5R)-5-methyl-2-oxopiperidin-1-yl]methyl}-3-[2-cyclopropyl-4-(trifluoromethyl)-5,8-dihydropyrido[3,4-d]pyrimidin-7(6H)-yl]-3-oxpropyl}carbamate obtained in PREPARATION 68 was used.

NMR: $^1$H-NMR (CD$_3$OD) δ 4.80~4.73 (2H, m), 3.89~3.81 (2H, m), 3.70~3.60 (1H, m), 3.52~3.50 (2H, m), 3.40~3.37 (1H, m), 3.10~2.90 (3H, m), 2.77~2.72 (1H, m), 2.65~2.59 (1H, m), 2.42~2.17 (3H, m), 2.10~1.95 (1H, m), 1.90~1.80 (1H, m), 1.58~1.49 (1H, m), 1.13 (3H, d, J=6.4 Hz), 1.04 (4H, d, J=6.4 Hz)

Mass (EI) 440 (M$^+$+1)

PREPARATION 69

Synthesis of t-butyl (1S)-1-{[(2R)-2-methyl-5-oxo-morpholin-4-yl]methyl]-3-[2-cyclopropyl-4-(trifluoromethyl)-5,8-dihydropyrido[3,4-d]pyrimidin-7(6H)-yl]-3-oxpropyl}carbamate 12 mg (0.022 mmol) of the title compound was obtained in a yield of 88% in the same manner as in PREPARATION 45, except that 8.0 mg (0.025 mmol) of (3S)-3-[(t-butoxycarbonyl)amino]-4-[(2S)-2-methyl-5-oxopiperidin-morpholin-4-yl]butanoic acid obtained in PREPARATION 55 and 7 mg (0.025 mmol) of 2-cyclopropyl-4-(trifluoromethyl)-5,6,7,8-tetrahydropyrido[3,4-d]pyrimidine hydrochloric acid salt obtained in PREPARATION 61 was used.

Mass (EI) 528 (M$^+$+1)

EXAMPLE 27

Synthesis of (6S)-4-{(2S)-2-amino-4-[2-cyclopropyl-4-(trifluoromethyl)-5,8-dihydropyrido[3,4-d]pyrimidin-7(6H)-yl]-4-oxobutyl}-6-methylmorpholine-3-one

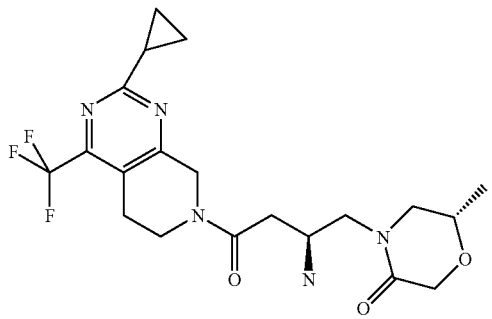

7 mg (0.014 mmol) of the title compound was obtained in a yield of 63% in the same manner as in EXAMPLE 23, except that 12 mg (0.022 mmol) of t-butyl (1S)-1-{[(2R)-2-methyl-5-oxomorpholin-4-yl]methyl}-3-[2-cyclopropyl-4-(trifluoromethyl)-5,8-dihydropyrido[3,4-d]pyrimidin-7(6H)-yl]-3-oxpropyl}carbamate obtained in PREPARATION 69 was used.

NMR: $^1$H-NMR (CD$_3$OD) δ 4.80~4.73 (2H, m), 4.20~4.13 (2H, m), 3.97~3.82 (3H, m), 3.60~3.52 (2H, m), 3.46~3.32 (3H, m), 3.10~3.05 (1H, m), 3.00~2.94 (1H, m), 2.73~2.68 (1H, m), 2.62~2.56 (1H, m), 2.30~2.17 (1H, m), 1.25 (3H, d, J=6.0 Hz), 1.15 (4H, d, J=9.2 Hz)

Mass (EI) 442 (M$^+$+1)

PREPARATION 70

Synthesis of t-butyl {(1S)-1-[(5,5-difluoro-2-oxopiperidin-1-yl)methyl]-3-oxo-3-[5-(trifluoromethyl)-3,4-dihydroisoquinolin-2(1H)-yl]propyl}carbamate 12 mg (0.023 mmol) of the title compound was obtained in a yield of 25% in the same manner as in PREPARATION 45, except that 31 mg (0.092 mmol) of (3S)-3-[(t-butoxycarbonyl)amino]-4-(5,5-difluoro-2-oxopiperidin-1-yl)butanoic acid obtained in PREPARATION 57 and 20 mg (0.099 mmol) of 5-(trifluoromethyl)-1,2,3,4-tetrahydroisoquinoline obtained with reference to WO 03/093231 were used.

Mass (EI) 520 (M$^+$+1)

EXAMPLE 28

Synthesis of 1-{(2S)-2-amino-4-oxo-4-[5-(trifluoromethyl)-3,4-dihydroisoquinolin-2(1H)-yl]butyl}5,5-difluoropiperidin-2-one

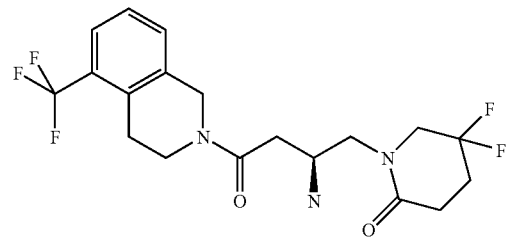

6 mg (0.012 mmol) of the title compound was obtained in a yield of 57% in the same manner as in EXAMPLE 23, except that 12 mg (0.023 mmol) of t-butyl {(1S)-1-[(5,5-difluoro-2-oxopiperidin-1-yl)methyl]-3-oxo-3-[5-(trifluoromethyl)-3,4-dihydroisoquinolin-2(1H)-yl]propyl}carbamate obtained in PREPARATION 70 was used.

NMR: $^1$H-NMR (CD$_3$OD) δ 7.61~7.38 (3H, m), 4.79~4.78 (2H, m), 3.84~3.75 (4H, m), 3.67~3.62 (2H, m), 3.48~3.46 (1H, m), 3.15~3.12 (1H, m), 3.04~3.02 (1H, m), 2.81~2.70 (1H, m), 2.66~2.56 (3H, m), 2.41~2.32 (2H, m)

Mass (EI) 420 (M$^+$+1)

PREPARATION 71

Synthesis of t-butyl {(1S)-1-{[(2S)-2-methyl-5-oxomorpholin-4-yl]methyl}-3-oxo-3-[5-(trifluoromethyl)-3,4-dihydroisoquinolin-2(1H)-yl]propyl}carbamate 10 mg (0.020 mmol) of the title compound was obtained in a yield of 20% in the same manner as in PREPARATION 45, except that 31 mg (0.097 mmol) of (3S)-3-[(t-butoxycarbonyl)amino]-4-[(2S)-2-methyl-5-oxopiperidin-morpholin-4-yl]butanoic acid obtained in PREPARATION 55 and 5-(trifluoromethyl)-1,2,3,4-tetrahydroisoquinoline 20 mg (0.099 mmol) of obtained with reference to WO 03/093231 was used.

Mass (EI) 500 (M$^+$+1)

EXAMPLE 29

Synthesis of (6S)-4-{(2S)-2-amino-4-oxo-4-[5-(trifluoromethyl)-3,4-dihydroisoquinolin-2(1H)-yl]butyl}-6-methylmorpholine-3-one

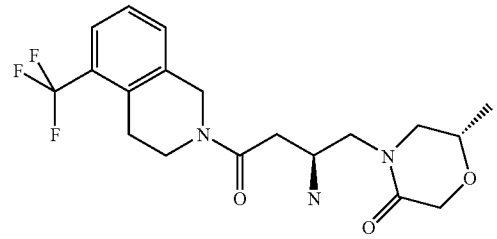

6 mg (0.013 mmol) of the title compound was obtained in a yield of 65% in the same manner as in EXAMPLE 23, except that 10 mg (0.020 mmol) of t-butyl {(1S)-1-{[(2S)-2-methyl-5-oxomorpholin-4-yl]methyl}-3-oxo-3-[5-(trifluoromethyl)-3,4-dihydroisoquinolin-2(1H)-yl]propyl}carbamate obtained in PREPARATION 76 was used.

NMR: $^1$H-NMR (CD$_3$OD) δ 7.61~7.40 (3H, m), 4.87~4.79 (2H, m), 4.20~4.07 (2H, m), 3.94~3.90 (1H, m), 3.82~3.76 (2H, m), 3.66~3.49 (3H, m), 3.40~3.35 (2H, m), 3.14~3.00 (2H, m), 2.73~2.60 (2H, m), 1.24 (3H, d, J=6 Hz)

Mass (EI) 400 (M$^+$+1)

PREPARATION 72

Synthesis of t-butyl {(1S)-1-[(5,5-difluoro-2-oxopiperidin-1-yl)methyl]-3-[2-(4-fluorophenyl)-4-(trifluoromethyl)-5,8-dihydropyrido[3,4-d]pyrimidin-7(6H)-yl]-3-oxpropyyl}carbamate 22 mg of the title compound was obtained in a yield of 53% in the same manner as in PREPARATION 45, except that 16 mg (0.067 mmol) of (3S)-3-[(t-butoxycarbonyl)amino]-4-(5,5-difluoro-2-oxopiperidin-1-yl) butanoic acid obtained in PREPARATION 57 and 20 mg (0.067 mmol) of 2-(4-fluorophenyl)-4-(trifluoromethyl)-5,6,7,8-tetrahydropyrido[3,4-d]pyrimidine hydrochloric acid salt obtained in PREPARATION 58 were used.

$^1$H NMR (CDCl$_3$) δ 8.48-8.46 (2H, m), 7.18-7.16 (2H, m), 5.79-5.77 (1H, m), 4.94-4.88 (1H, m), 4.82-4.72 (1H, m), 4.21 (1H, brs), 3.94-3.88 (1H, m), 3.80-3.70 (3H, m), 3.62-3.58 (1H, m), 3.12-3.03 (2H, m), 2.87-2.82 (1H, m), 2.60-2.52 (4H, m), 2.28-2.23 (2H, m), 1.41-1.40 (9H, m)

Mass (m/e) 516 (M+1-BOC)

EXAMPLE 30

Synthesis of 1-{(2S)-2-amino-4-[2-(4-fluorophenyl)-4-(trifluoromethyl)-5,8-dihydropyrido[3,4-d]pyrimidin-7(6H)-yl]-4-oxobutyl}-5,5-difluoropiperidin-2-one

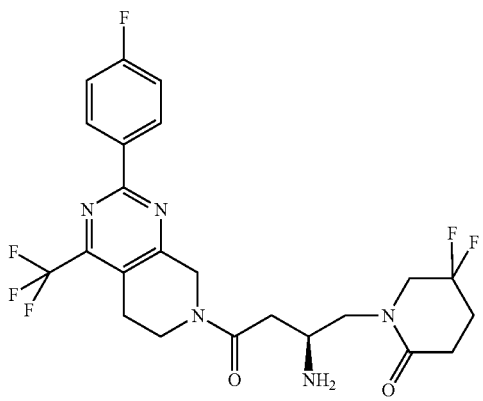

15.3 mg of the title compound was obtained in a yield of 78% in the same manner as in EXAMPLE 22, except that 22 mg (0.036 mmol) of t-butyl {(1S)-1-[(5,5-difluoro-2-oxopiperidin-1-yl)methyl]-3-[2-(4-fluorophenyl)-4-(trifluoromethyl)-5,8-dihydropyrido[3,4-d]pyrimidin-7(6H)-yl]-3-oxpropyl}carbamate obtained in PREPARATION 72 was used.

$^1$H NMR (CD$_3$OD) δ 8.49-8.48 (2H, m), 7.23-7.20 (2H, m), 4.90-4.85 (2H, m), 3.95-3.70 (5H, m), 3.50-3.46 (1H, m), 3.30-3.28 (1H, m), 3.13 (1H, brs), 3.03 (1H, brs), 2.90-2.86 (1H, m), 2.76-2.72 (1H, m), 2.58-2.54 (2H, m), 2.37-2.32 (2H, m)

Mass (m/e) 516 (M+1)

PREPARATION 73

Synthesis of t-butyl [(1S)-3-[2-(4-fluoro phenyl)-4-(trifluoromethyl)-5,8-dihydropyrido[3,4-d]pyrimidin-7(6H)-yl]-1-{[(2S)-2-methyl-5-oxomorpholin-4-yl]methyl}3-oxpropyl]carbamate 26 mg of the title compound was obtained in a yield of 40% in the same manner as in PREPARATION 45, except that 21.2 mg (0.067 mmol) of (3S)-3-[(t-butoxycarbonyl)amino]-4-[2(S)-2-methyl-5-oxomorpholin-4-yl]butanoic acid obtained in PREPARATION 55 and 20 mg (0.067 mmol) of 2-(4-fluorophenyl)-4-(trifluoromethyl)-5,6,7,8-tetrahydropyrido[3,4-d]pyrimidine hydrochloric acid salt obtained in PREPARATION 58 were used.

$^1$H NMR (CDCl$_3$) δ 8.49-8.46 (2H, m), 7.17-7.15 (2H, m), 5.81-5.76 (1H, m), 4.96-4.88 (1H, m), 4.83-4.72 (1H, m), 4.23-4.09 (3H, m), 3.93-3.85 (2H, m), 3.79 (1H, brs), 3.68-3.61 (1H, m), 3.54-3.48 (1H, m), 3.39-3.30 (2H, m), 3.10-3.03 (3H, m), 2.60-2.53 (1H, m), 1.42-1.41 (9H, m), 1.25 (3H, d, J=6.1 Hz), Mass (m/e) 496 (M+1-BOC)

EXAMPLE 31

Synthesis of (6S)-4-{(2S-2-amino-4-[2-(4-fluorophenyl)-4-(trifluoromethyl)-5,8-dihydropyrido[3,4-d]pyrimidin-7(6H)-yl]-4-oxobutyl}-6-methylmorpholine-2-one

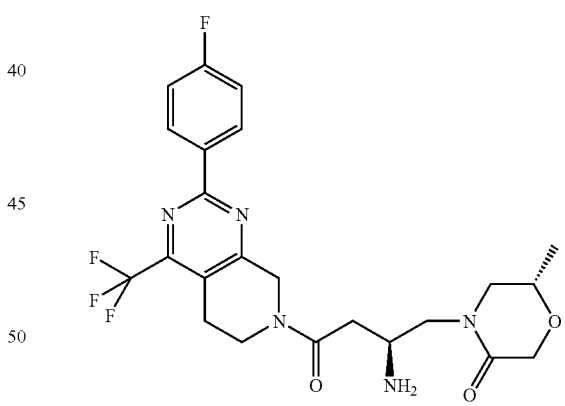

17.8 mg of the title compound was obtained in a yield of 77% in the same manner as in EXAMPLE 22, except that 26 mg (0.044 mmol) of t-butyl [(1S)-3-[2-(4-fluorophenyl)-4-(trifluoromethyl)-5,8-dihydropyrido[3,4-d]pyrimidin-7(6H)-yl]-1-{[(2S)-2-methyl-5-oxomorpholin-4-yl]methyl}3-oxpropyl]carbamate of obtained in PREPARATION 73 was used.

$^1$H NMR (CD$_3$OD) δ 8.49-8.48 (2H, m), 7.24-7.21 (2H, m), 4.97-4.85 (2H, m), 4.20-4.10 (2H, m), 3.96-3.93 (2H, m), 3.87-3.84 (1H, m), 3.79 (1H, brs), 3.67-3.55 (2H, m), 3.33-3.30 (2H, m), 2.13 (1H, brs), 3.03 (1H, brs), 2.91-2.87 (1H, m), 2.76-2.71 (1H, m), 1.24-1.22 (3H, m)

Mass (m/e) 496 (M+1)

PREPARATION 74

Synthesis of t-butyl {(1S)-1-[(5,5-difluoro-2-oxopiperidin-1-yl)methyl]-3-{2-(3-fluorophenyl)-4-(trifluoromethyl)-5,8-dihydropyrido[3,4-d]pyrimidin-7(6H)-yl}-3-oxpropyl}carbamate 27 mg of the title compound was obtained in a yield of 72% in the same manner as in PREPARATION 45, except that 22.6 mg (0.067 mmol) of (3S)-3-[(t-butoxycarbonyl)amino]-4-(5,5-difluoro-2-oxopiperidin-1-yl)butanoic acid obtained in PREPARATION 57 and 20 mg (0.067 mmol) of 2-(3-fluorophenyl)-4-(trifluoromethyl)-5,6,7,8-tetrahydropyrido[3,4-d]pyrimidine hydrochloric acid salt obtained in PREPARATION 60 were used.

$^1$H NMR (CDCl$_3$) δ 8.29-8.25 (1H, m), 8.18-8.15 (1H, m), 7.53-7.44 (1H, m), 7.24-7.19 (1H, m) 5.81-5.79 (1H, m), 4.99-4.88 (1H, m), 4.85-4.75 (1H, m), 4.23 (1H, brs), 3.94-3.91 (1H, m), 3.81-3.67 (4H, m), 3.64-3.58 (2H, m), 3.12-3.06 (2H, m), 2.88-2.84 (1H, m), 2.63-2.54 (3H, m), 2.27-2.24 (1H, m), 1.43-1.41 (9H, m)

Mass (m/e) 516 (M+1-BOC)

EXAMPLE 32

Synthesis of 1-{(2S)-2-amino-4-[2-(3-fluorophenyl)-4-(trifluoromethyl)-5,8-dihydropyrido[3,4-d]pyrimidin-7(6H)-yl]-4-oxobutyl}-5,5-difluoropiperidin-2-one

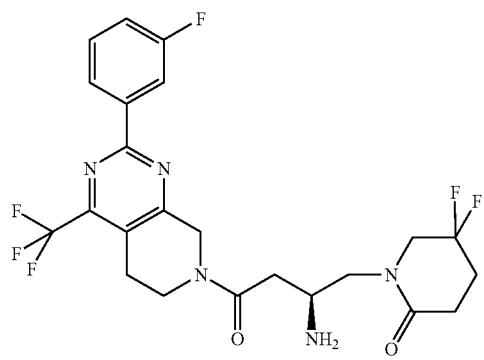

18.5 mg of the title compound was obtained in a yield of 76% in the same manner as in EXAMPLE 22, except that 27 mg (0.044 mmol) of t-butyl {(1S)-1-[(5,5-difluoro-2-oxopiperidin-1-yl)methyl]-3-{2-(3-fluorophenyl)-4-(trifluoromethyl)-5,8-dihydropyrido[3,4-d]pyrimidin-7(6H)-yl}-3-oxpropyl}carbamate obtained in PREPARATION 74 was used.

$^1$H NMR (CD$_3$OD) δ 8.31-8.28 (1H, m), 8.16-8.12 (1H, m), 7.57-7.51 (1H, m), 7.31-7.26 (1H, m) 5.00-4.88 (2H, m), 3.99-3.88 (2H, m), 3.85-3.77 (2H, m), 3.58-3.53 (1H, m), 3.51-3.46 (2H, m), 3.16 (1H, brs), 3.06 (1H, brs), 2.75-2.70 (1H, m), 2.63-2.52 (3H, m), 2.40-2.32 (2H, m)

Mass (m/e) 516 (M+1)

PREPARATION 75

Synthesis of t-butyl [(1S)-3-[2-(3-fluorophenyl)-4-(trifluoro)-5,8-dihydropyrido[3,4-d]pyrimidin-7(6)-yl]-1-{[(2S)-2-methyl-5-oxomorpholin-4-yl]methyl}-3-oxpropyl]carbamate 27 mg of the title compound was obtained in a yield of 68% in the same manner as in PREPARATION 45, except that 21.2 mg (0.067 mmol) of (3S)-3-[(t-butoxycarbonyl)amino]-4-[2(S)-2-methyl-5-oxomorpholin-4-yl]butanoic acid obtained in PREPARATION 55 and 20 mg (0.067 mmol) of 2-(3-fluorophenyl)-4-(trifluoromethyl)-5,6,7,8-tetrahydropyrido[3,4-d]pyrimidine hydrochloric acid salt obtained in PREPARATION 60 were used.

$^1$H NMR (CDCl$_3$) δ 8.33-8.29 (1H, m), 8.22-8.19 (1H, m), 7.54-7.48 (1H, m), 7.28-7.23 (1H, m) 5.86-5.81 (1H, m), 5.03-4.92 (1H, m), 4.90-4.79 (1H, m), 4.29-4.23 (2H, m), 4.19-4.15 (1H, m), 4.00-3.90 (2H, m), 3.85 (1H, brs), 3.75-3.68 (1H, m), 3.59-3.52 (1H, m), 3.45-3.35 (2H, m), 3.15-3.10 (2H, m), 2.96-2.90 (1H, m), 2.64-2.60 (1H, m), 1.47-1.46 (9H, m), 1.32-1.28 (3H, m)

Mass (m/e) 496 (M+1-BOC)

EXAMPLE 33

Synthesis of (6S)-4-{(2S)-amino-4-[2-(3-fluorophenyl)-4-trifluoromethyl)-5,8-dihydropyrido[3,4-d]pyrimidin-7(6H)-yl]-4-oxobutyl}-6-methylmorpholine-3-one

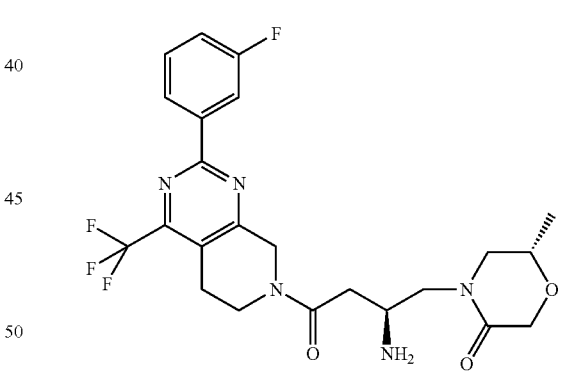

16.5 mg of the title compound was obtained in a yield of 68% in the same manner as in EXAMPLE 22, except that 27 mg (0.045 mmol) of t-butyl [(1S)-3-[2-(3-fluorophenyl)-4-(trifluoro)-5,8-dihydropyrido[3,4-d]pyrimidin-7(6H)-yl]-1-{[(2S)-2-methyl-5-oxomorpholin-4-yl]methyl}-3-oxpropyl]carbamate obtained in PREPARATION 75 was used.

$^1$H NMR (CD$_3$OD) δ 8.30-8.28 (1H, m), 8.16-8.12 (1H, m), 7.57-7.51 (1H, m), 7.31-7.26 (1H, m) 5.01-4.88 (2H, m), 4.21-4.09 (2H, m), 4.00-3.84 (3H, m), 3.64-3.54 (2H, m), 3.46-3.35 (3H, m), 3.16 (1H, brs), 3.06 (1H, brs), 2.78-2.72 (1H, m), 2.64-2.57 (1H, m), 1.27-1.24 (3H, m)

Mass (m/e) 496 (M+1)

PREPARATION 76

Synthesis of t-butyl [(1S)-3-[2-(4-fluorophenyl)-4-(trifluoromethyl)-5,8-dihydropyrido[3,4-d]pyrimidin-7(6H)-yl]-1-{[(5R)-5-methyl-2-oxopiperidin-1-yl]methyl}-3-oxpropyl]carbamate 29 mg of the title compound was obtained in a yield of 52% in the same manner as in PREPARATION 45, except that 28 mg (0.094 mmol) of (3S)-3-[(t-butoxycarbonyl)amino]-4-[(5R)-5-methyl-2-oxopiperidin-1-yl]butanoic acid obtained in PREPARATION 51 and 30 mg (0.094 mmol) of 2-(4-fluorophenyl)-4-(trifluoromethyl)-5,6,7,8-tetrahydropyrido[3,4-d]pyrimidine hydrochloric acid salt obtained in PREPARATION 58 were used.

$^1$H NMR (CDCl$_3$) δ 8.50-8.46 (2H, m), 7.26-7.00 (2H, m) 5.88-5.87 (1H, m), 4.92 (1H, s), 4.86-4.74 (1H, m), 4.21 (1H, brs), 3.92 (1H, brs), 3.82-3.79 (1H, m), 3.64-3.52 (2H, m), 3.38-3.35 (1H, m), 3.10-3.04 (3H, m), 2.87-2.85 (1H, m), 2.55-2.45 (1H, m), 2.41-2.21 (2H, m), 1.95-1.88 (1H, m), 1.82-1.80 (1H, m), 1.43-1.41 (10H, m), 1.01-0.99 (3H, m)

Mass (m/e) 494 (M+1-BOC)

EXAMPLE 34

Synthesis of (5R)-1-{(2S)-2-amino-4-[2-(4-fluorophenyl)-4-(trifluoromethyl)-5,8-dihydropyrido[3,4-d]pyrimidin-7(6H)-yl]-4-oxobutyl}-5-methylpiperidin-2-one

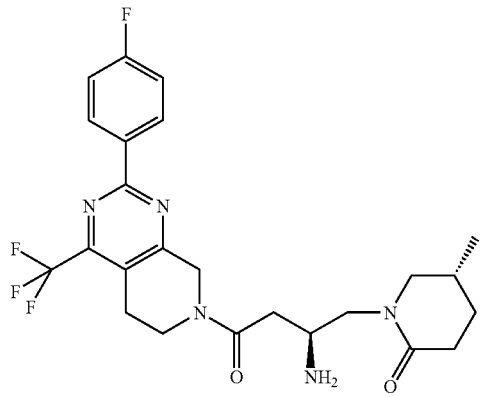

20 mg of the title compound was obtained in a yield of 77% in the same manner as in EXAMPLE 22, except that 29 mg (0.049 mmol) of t-butyl [(1S)-3-[2-(4-fluorophenyl)-4-(trifluoromethyl)-5,8-dihydropyrido[3,4-d]pyrimidin-7(6H)-yl]-1-{[(5R)-5-methyl-2-oxopiperidin-1-yl]methyl}-3-oxpropyl]carbamate obtained in PREPARATION 76 was used.

$^1$H NMR (CD$_3$OD) δ 8.51-8.48 (2H, m), 7.25-7.20 (2H, m) 4.93-4.86 (2H, m), 3.95-3.92 (1H, m), 3.87-3.84 (1H, m), 3.77-3.76 (1H, m), 3.68-3.61 (1H, m), 3.54-3.50 (1H, m), 3.35-3.32 (1H, m), 3.30-3.29 (1H, m), 3.13-3.02 (2H, m), 2.90-2.83 (1H, m), 2.75-2.70 (1H, m), 2.44-2.32 (2H, m), 1.99 (1H, brs), 1.82 (1H, brs), 1.52-1.46 (1H, m), 1.03-1.01 (3H, m)

Mass (m/e) 494 (M+1)

PREPARATION 77

Synthesis of t-butyl {(1S)-1-[(5,5-difluoro-2-oxopiperidin-1-yl)methyl]-3-[2-(3,4-difluorophenyl)-4-(trifluoromethyl)-5,8-dihydropyrido[3,4-d]pyrimidin-7(6H)-yl]-3-oxpropyl}carbamate 6.0 mg of the title compound was obtained in a yield of 47% in the same manner as in PREPARATION 45, except that 7.0 mg (0.020 mmol) of (3S)-3-[(t-butoxycarbonyl)amino]-4-(5,5-difluoro-2-oxopiperidin-1-yl)butanoic acid obtained in PREPARATION 57 and 7.0 mg (0.020 mmol) of 2-(3,4-difluorophenyl)-4-(trifluoromethyl)-5,6,7,8-tetrahydropyrido[3,4-d]pyrimidine hydrochloric acid salt obtained in PREPARATION 59 were used.

$^1$H NMR (CDCl$_3$) δ 8.33-8.28 (2H, m), 7.31-7.25 (1H, m) 5.79-5.78 (1H, m), 4.98-4.87 (1H, m), 4.84-4.73 (1H, m), 4.22-4.21 (1H, m), 3.93-3.91 (1H, m), 3.79-3.64 (3H, m), 3.62-3.56 (2H, m), 3.12-3.05 (2H, m), 2.88-2.84 (1H, m), 2.62-2.54 (3H, m), 2.27-2.24 (2H, m), 1.43-1.41 (9H, m)

Mass (m/e) 534 (M+1-BOC)

EXAMPLE 35

Synthesis of 1-{(2S)-2-amino-4-[2-(3,4-difluorophenyl)-4-(trifluoromethyl)-5,8-dihydropyrido[3,4-d]pyrimidin-7(6H)-yl]-4-oxobutyl}-5,5-difluoropiperidin-2-one

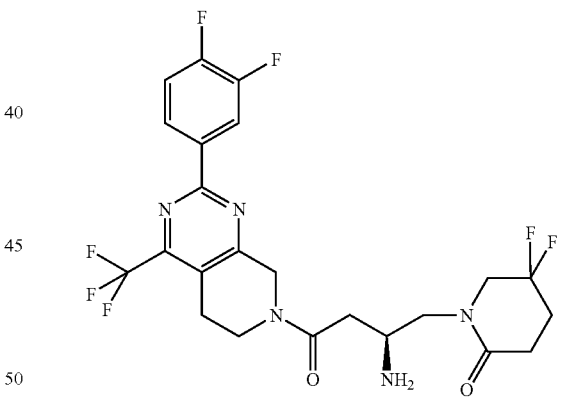

4.0 mg of the title compound was obtained in a yield of 74% in the same manner as in EXAMPLE 22, except that 6.0 mg (0.009 mmol) of t-butyl {(1S)-1-[(5,5-difluoro-2-oxopiperidin-1-yl)methyl]-3-[2-(3,4-difluorophenyl)-4-(trifluoromethyl)-5,8-dihydropyrido[3,4-d]pyrimidin-7(6H)-yl]-3-oxpropyl}carbamate obtained in PREPARATION 77 was used.

$^1$H NMR (CD$_3$OD) δ 8.31-8.28 (2H, m), 7.41-7.39 (1H, m), 4.96-4.85 (2H, m), 3.93-3.84 (2H, m), 3.80-3.74 (2H, m), 3.53-3.49 (1H, m), 3.47-3.44 (2H, m), 3.12 (1H, brs), 3.03 (1H, brs), 2.70-2.66 (1H, m), 2.58-2.52 (3H, m), 2.34-2.32 (2H, m)

Mass (m/e) 534 (M+1)

PREPARATION 77

Synthesis of t-butyl [(1S)-3-[2-(3,4-difluorophenyl)-4-(trifluoromethyl)-5,8-dihydropyrido[3,4-d]pyrimidin-7(6H)-yl]-1-{[(2S)-2-methyl-5-oxomorpholin-4-yl]methyl}-3-oxpropyl]carbamate 6.0 m of the title compound was obtained in a yield of 49% in the same manner as in PREPARATION 45, except that 6.3 mg (0.020 mmol) of (3S)-3-[(t-butoxycarbonyl)amino]-4-[2(S)-2-methyl-5-oxomorpholin-4-yl]butanoic acid obtained in PREPARATION 55 and 7.0 mg (0.020 mmol) of 2-(3,4-difluorophenyl)-4-(trifluoromethyl)-5,6,7,8-tetrahydropyrido[3,4-d]pyrimidine hydrochloric acid salt obtained in PREPARATION 59 were used.

$^1$H NMR (CDCl$_3$) δ 8.32-8.24 (2H, m), 7.30-7.23 (1H, m), 5.84-5.79 (1H, m), 4.98-4.74 (2H, m), 4.24-4.19 (2H, m), 4.15-4.09 (1H, m), 3.94-3.84 (2H, m), 3.81 (1H, brs), 3.74-3.67 (1H, m), 3.66-3.46 (1H, m), 3.40-3.31 (2H, m), 3.12-3.00 (2H, m), 2.91-2.86 (1H, m), 2.63-2.57 (1H, m), 1.43-1.42 (9H, m), 1.28-1.24 (3H, m)

Mass (m/e) 514 (M+1-BOC)

PREPARATION 79

Synthesis of Synthesis of t-butyl [(1S)-3-[2-(3,4-difluorophenyl)-4-(trifluoromethyl)-5,8-dihydropyrido[3,4-d]pyrimidin-7(6H)-yl]-1-{[(5R)-5-methyl-2-oxopiperidin-1-yl]methyl}-3-oxpropyl]carbamate 82 mg of the title compound was obtained in a yield of 96% in the same manner as in PREPARATION 45, except that 44 mg (0.139 mmol) of (3S)-3-[(t-butoxycarbonyl)amino]-4-[(5R)-5-methyl-2-oxopiperidin-1-yl]butanoic acid obtained in PREPARATION 51 and 49 mg (0.139 mmol) of 2-(3,4-difluorophenyl)-4-(trifluoromethyl)-5,6,7,8-tetrahydropyrido[3,4-d]pyrimidine hydrochloric acid salt obtained in PREPARATION 59 were used.

$^1$H NMR (CDCl$_3$) δ 8.33-8.26 (2H, m), 7.32-7.25 (1H, m), 5.93-5.92 (1H, m), 5.00-4.90 (1H, m), 4.89-4.77 (1H, m), 4.22 (1H, brs), 3.96-3.93 (1H, m), 3.85-3.82 (1H, m), 3.76-3.55 (2H, m), 3.52-3.48 (2H, m), 3.42-3.38 (1H, m), 3.19-3.07 (4H, m), 2.92-2.87 (1H, m), 2.60-2.54 (1H, m), 2.47-2.29 (2H, m), 1.99-1.96 (1H, m), 1.90-1.83 (1H, m), 1.45-1.43 (9H, m), 1.02 (3H, d, J=6.8 Hz)

Mass (m/e) 512 (M+1-BOC)

EXAMPLE 36

Synthesis of (6S)-4-{(2S-2-amino-4-[2-(3,4-difluorophenyl)-4-(trifluoromethyl)-5,8-dihydropyrido[3,4-d]pyrimidin-7(6H)-yl]-4-oxobutyl}-6-methylmorpholine-3-one

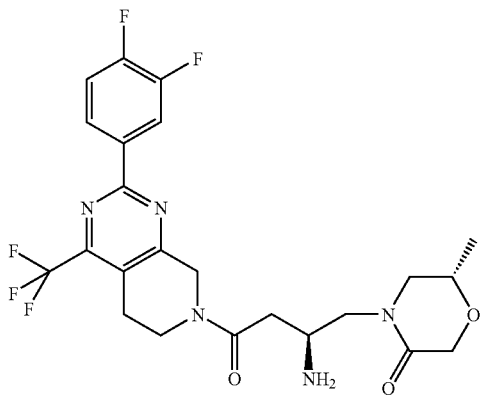

3.6 mg of the title compound was obtained in a yield of 56% in the same manner as in EXAMPLE 22, except that 6.0 mg (0.012 mmol) of t-butyl [(1S)-3-[2-(3,4-difluorophenyl)-4-(trifluoro)-5,8-dihydropyrido[3,4-d]pyrimidin-7(6H)-yl]-1-{[(2S)-2-methyl-5-oxomorpholin-4-yl]methyl}-3-oxpropyl]carbamate obtained in PREPARATION 78 was used.

$^1$H NMR (CD$_3$OD) δ 8.33-8.26 (2H, m), 7.45-7.38 (1H, m), 5.00-4.87 (2H, m), 4.18-4.11 (2H, m), 3.99-3.89 (3H, m), 3.66-3.55 (2H, m), 3.51-3.48 (1H, m), 3.38-3.29 (2H, m), 3.16 (1H, brs), 3.06 (1H, brs), 2.81-2.76 (1H, m), 2.69-2.61 (1H, m), 1.27-1.23 (3H, m)

Mass (m/e) 514 (M+1)

EXAMPLE 37

Synthesis of (5R)-1-{(2S)-2-amino-4-[2-(3,4-difluorophenyl)-4-(trifluoromethyl)-5,8-dihydropyrido[3,4-d]pyrimidin-7(6H)-yl]-4-oxobutyl}-5-methylpiperidin-2-one

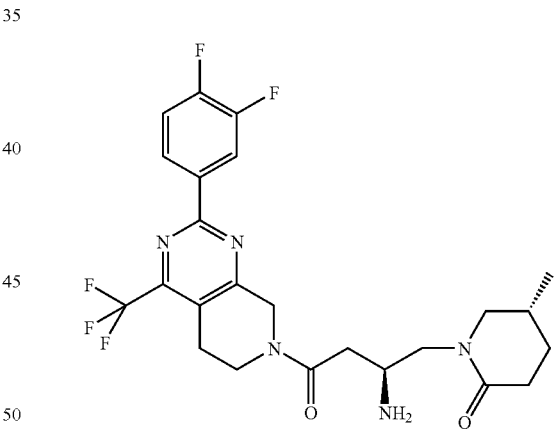

58.3 mg of the title compound was obtained in a yield of 79% in the same manner as in EXAMPLE 22, except that 82 mg (0.134 mmol) of t-butyl [(1S)-3-[2-(3,4-difluorophenyl)-4-(trifluoromethyl)-5,8-dihydropyrido[3,4-d]pyrimidin-7(6H)-yl]-1-{[(5R)-5-methyl-2-oxopiperidin-1-yl]methyl}-3-oxpropyl]carbamate obtained in PREPARATION 79 was used.

$^1$H NMR (CD$_3$OD) δ 8.32-8.24 (2H, m), 7.45-7.37 (1H, m), 5.00-4.88 (2H, m), 3.98-3.95 (1H, m), 3.92-3.89 (1H, m), 3.79-3.76 (1H, m), 3.65-3.56 (2H, m), 3.42-3.37 (1H, m), 3.17-3.07 (3H, m), 2.93-2.87 (1H, m), 2.80-2.76 (1H, m), 2.44-2.36 (2H, m), 2.05-2.02 (1H, m), 1.88-1.85 (1H, m), 1.60-1.49 (1H, m), 1.06-1.04 (3H, m)

Mass (m/e) 512 (M+1)

PREPARATION 80

Synthesis of t-butyl {(1S)-3-[2-cyclopentyl-4-(trifluoromethyl)-5,8-dihydropyrido[3,4-d]pyrimidin-7(6H)-yl]-1-{[(5R)-5-methyl-2-oxopiperidin-1-yl]methyl}-3-oxpropyl}carbamate 65 mg of the title compound was obtained in a yield of 84% in the same manner as in PREPARATION 45, except that 112 mg (0.357 mmol) of (3S)-3-[(t-butoxycarbonyl)amino]-4-[(5R)-5-methyl-2-oxopiperidin-1-yl]butanoic acid obtained in PREPARATION 51 and 100 mg (0.325 mmol) of 2-cyclopentyl-4-(trifluoromethyl)-5,6,7,8-tetrahydropyrido[3,4-d]pyrimidine hydrochloric acid salt obtained in PREPARATION 62 were used.

$^1$H NMR (CDCl$_3$) δ 5.88 (1H, brs), 4.88 (1H, s), 4.76-4.64 (1H, m), 4.18 (1H, brs), 3.88 (1H, brs), 3.77 (1H, brs), 3.63-3.47 (2H, m), 3.39-3.35 (2H, m), 3.01-2.97 (3H, m), 2.88-2.81 (1H, m), 2.55-2.30 (3H, m), 2.17-2.04 (3H, m), 1.93-1.85 (6H, m), 1.70 (2H, brs), 1.42-1.40 (9H, m), 1.00 (3H, d, J=5.6 Hz)

Mass (m/e) 468 (M+1-BOC)

EXAMPLE 38

Synthesis of (5R)-1-{(2S)-2-amino-4-[2-cyclopentyl-4-(trifluoromethyl)-5,8-dihydropyrido[3,4-d]pyrimidin-7(6H)-yl]-4-oxobutyl}-5-methylpiperidin-2-one

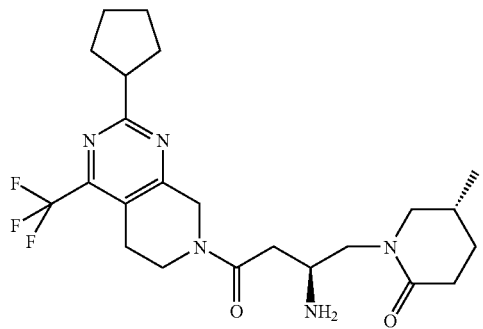

120 mg of the title compound was obtained in a yield of 83% in the same manner as in EXAMPLE 22, except that 176 mg (0.310 mmol) of t-butyl {(1S)-1-[2-cyclopentyl-4-(trifluoromethyl)-5,8-dihydropyrido[3,4-d]pyrimidin-7(6H)-yl]-1-{[(5R)-5-methyl-2-oxopiperidin-1-yl]methyl}-3-oxpropyl}carbamate obtained in PREPARATION 80 was used.

$^1$H NMR (CD$_3$OD) δ 4.91-4.80 (2H, m), 4.15-4.11 (1H, m), 3.94-3.80 (2H, m), 3.75-3.67 (1H, m), 3.58-3.53 (1H, m), 3.44-3.37 (2H, m), 3.15-3.10 (2H, m), 3.01 (1H, s), 2.96-2.89 (1H, m), 2.81-2.72 (1H, m), 2.46-2.34 (2H, m), 2.12-2.03 (3H, m), 1.98-1.82 (5H, m), 1.79-1.73 (2H, m), 1.59-1.49 (1H, m), 1.05 (3H, d, J=6.4 Hz)

Mass (m/e) 468 (M+1)

PREPARATION 81

Synthesis of t-butyl [(1S)-3-[2-cyclopentyl-4-(trifluoromethyl)-5,8-dihydropyrido[3,4-d]pyrimidin-7(6H)-yl]-1-{[(2S)-2-methyl-5-oxomorpholin-4-yl]methyl}-3-oxpropyl]carbamate 180 mg of the title compound was obtained in a yield of 97% in the same manner as in PREPARATION 45, except that 113 mg (0.357 mmol) of (3S)-3-[(t-butoxycarbonyl)amino]-4-[2(S)-2-methyl-5-oxomorpholin-4-yl]butanoic acid obtained in PREPARATION 55 and 100 mg (0.325 mmol) of 2-cyclopentyl-4-(trifluoromethyl)-5,6,7,8-tetrahydropyrido[3,4-d]pyrimidine hydrochloric acid salt obtained in PREPARATION 62 were used.

$^1$H NMR (CDCl$_3$) δ 5.82-5.77 (1H, m), 4.89-4.78 (1H, m), 4.75-4.63 (1H, m), 4.31-4.19 (2H, m), 4.15-4.09 (1H, m), 3.94-3.84 (2H, m), 3.69 (1H, brs), 3.68-3.62 (1H, m), 3.54-3.45 (1H, m), 3.41-3.30 (2H, m), 3.09-2.98 (2H, m), 2.87-2.82 (1H, m), 2.60-2.51 (1H, m), 2.10-2.07 (2H, m), 1.97-1.85 (5H, m), 1.72-1.68 (2H, brs), 1.43-1.42 (9H, m), 1.28-1.24 (3H, m)

Mass (m/e) 470 (M+1)

EXAMPLE 39

Synthesis of (6S)-4-{(2S-2-amino-4-[2-cyclopentyl-4-(trifluoromethyl)-5,8-dihydropyrido[3,4-d]pyrimidin-7(6H)-yl]-4-oxobutyl}-6-methylmorpholine-3-one

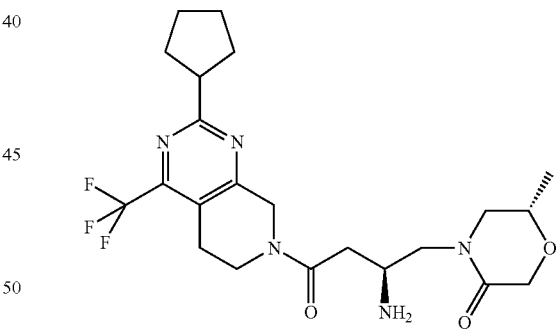

117 mg of the title compound was obtained in a yield of 79% in the same manner as in EXAMPLE 22, except that 180 mg (0.316 mmol) of t-butyl [(1S)-3-[2-cyclopentyl-4-(trifluoromethyl)-5,8-dihydropyrido[3,4-d]pyrimidin-7(6H)-yl]-1]-{[(2S)-2-methyl-5-oxomorpholin-4-yl]methyl}-3-oxpropylicarbamate obtained in PREPARATION 81 was used.

$^1$H NMR (CD$_3$OD) δ 4.83-4.78 (2H, m), 4.22-4.10 (2H, m), 4.00-3.81 (3H, m), 3.69-3.66 (1H, m), 3.59-3.47 (2H, m), 3.45-3.36 (4H, m), 3.10 (1H, brs), 3.00 (1H, brs), 2.82-2.76 (1H, m), 2.68-2.59 (1H, m), 2.12-2.10 (2H, m), 1.97-1.82 (4H, m), 1.79-1.73 (1H, m), 1.26 (3H, d, J=6.0 Hz)

Mass (m/e) 470 (M+1)

PREPARATION 82

Synthesis of t-butyl {(1S)-3-[2-cyclopentyl-4-(trifluoromethyl)-5,8-dihydropyrido[3,4-d]pyrimidin-7(6H)-yl]-1-[(5,5-difluoro-2-oxopiperidin-1-yl)methyl]-3-oxpropyl}carbamate 182 mg of the title compound was obtained in a yield of 95% in the same manner as in PREPARATION 45, except that 120 mg (0.357 mmol) of (3S)-3-[(t-butoxycarbonyl)amino]-4-(5,5-difluoro-2-oxopiperidin-1-yl)butanoic acid obtained in PREPARATION 57 and 100 mg (0.325 mmol) of 2-cyclopentyl-4-(trifluoromethyl)-5,6,7,8-tetrahydropyrido[3,4-d]pyrimidine hydrochloric acid salt obtained in PREPARATION 62 were used.

$^1$H NMR (CDCl$_3$) δ 4.78 (1H, brs), 4.87 (1H, s), 4.77-4.63 (1H, m), 4.20 (1H, brs), 3.89-3.86 (1H, m), 3.75-3.63 (3H, m), 3.60-3.53 (2H, m), 3.41-3.33 (1H, m), 3.05-2.98 (2H, m), 2.82-2.80 (1H, m), 2.60-2.51 (3H, m), 2.31-2.21 (2H, m), 2.10-2.07 (2H, m), 1.95-1.85 (4H, m), 1.75-1.70 (2H, m), 1.42-1.41 (9H, m)

Mass (m/e) 490 (M+1-BOC)

EXAMPLE 40

Synthesis of 1-{(2S)-2-amino-4-[2-cyclopentyl-4-(trifluoromethyl)-5,8-dihydropyrido[3,4-d]pyrimidin-7(6H)-yl]-4-oxobutyl}-5,5-difluoropiperidin-2-one

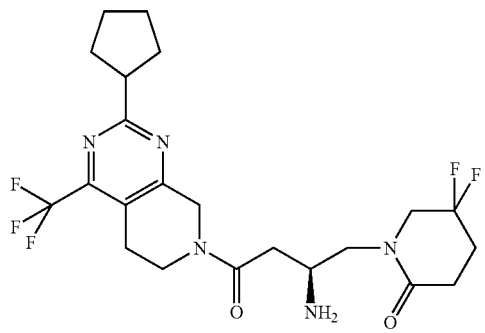

105 mg of the title compound was obtained in a yield of 70% in the same manner as in, except that 182 mg (0.309 mmol) of t-butyl {(1S)-3-[2-cyclopentyl-4-(trifluoromethyl)-5,8-dihydropyrido[3,4-d]pyrimidin-7(6H)-yl]-1-[(5,5-difluoro-2-oxopiperidin-1-yl)methyl]-3-oxpropyl}carbamate obtained in PREPARATION 82 was used.

$^1$H NMR (CD$_3$OD) δ 4.90-4.79 (2H, m), 3.93-3.77 (4H, m), 3.64-3.56 (2H, m), 3.49-3.37 (2H, m), 3.15 (1H, brs), 3.00 (1H, brs), 2.79-2.73 (1H, m), 2.66-2.52 (3H, m), 2.42-2.31 (2H, m), 2.12-2.08 (2H, m), 1.97-1.83 (4H, m), 1.79-1.73 (2H, m), Mass (m/e) 490 (M+1)

PREPARATION 83

Synthesis of t-butyl-3-amino-4-hydroxypiperidin-1-carboxylate (1) Synthesis of t-butyl 3,6-dihydroxypyridine-1(2H)-carboxylate 1 g (12 mmol) of 1,2,3,6-tetrahydroxypyridine and 2.76 g (12.6 mmol) of t-butyl dicarbonate was dissolved in 40 mL of tetrahydrofurane/water (1:1), and after stirring for 5 hour, 100 mL of ethylacetate was added thereto. After washing with water, an organic layer was dried over anhydrous magnesium sulfate. The solvent was distilled off under reduced pressure, and the residue was purified by column chromatography to give 2.1 g (11.5 mmol) of the title compound in a yield of 91%.

NMR: $^1$H-NMR (CDCl$_3$) δ 5.81 (1H, m), 5.66 (1H, m), 3.88 (2H, s), 3.49 (2H, t, J=6 Hz), 2.13 (2h, brs), 1.47 (9H, s)

(2) Synthesis of t-butyl 7-oxa-3-azabicyclo[4.1.0]heptane-3-carboxylate 2.1 g (11.5 mmol) of t-butyl 3,6-dihydroxypyridin-1(2H)-carboxylate (product of step 1) and 3.1 g (12.6 mmol) of m-chloro benzoic acid was dissolved in 30 mL of methylene chloride, and after stirring for 5 hour, 100 mL of ethylacetate was added thereto. After washing with water, an organic layer was dried over anhydrous magnesium sulfate. The solvent was distilled off under reduced pressure and the residue was purified by column chromatography to give 2.1 g (10.5 mmol) of the title compound in a yield of 87%.

Mass (m/e) 200 (M+1)

(3) Synthesis of t-butyl-3-amino-4-hydroxypiperidin-1-carboxylate 2.9 g (10.0 mmol) of t-butyl 7-oxa-3-azabicyclo[4.1.0]heptane-3-carboxylate (product of step 2) and 1.2 g (10.0 mmol) of (S)-1-phenylethylamine was dissolved in 30 mL of water, and stirred under reflux for 12 hours, then 100 mL of ethylacetoacetate was added thereto. The reaction mixture was washed with water, then an organic layer was dried over anhydrous magnesium sulfate. The solvent was distilled off under reduced pressure and the resulting solution was dissolved in methanol. A reaction was conducted with 120 mg of 20% palladium/carbon under hydrogen atmosphere for 9 hours, and the solvent was filtered off by Cellite. The filtrated solution was distilled off under reduced pressure, then the residue was purified by column chromatography to give 0.50 g (2.3 mmol) of the title compound in a yield of 23%.

Mass (m/e) 217 (M+1)

PREPARATION 84

Synthesis of 2-[4-(trifluoromethyl)phenyl]-4,5,6,7-tetrahydro[1,3]thiazolo[4,5-c]pyridine hydrochloride (1) Synthesis of t-butyl 4-hydroxy-3-{[4-(trifluoromethyl)benzoyl]amino}piperidin-1-carboxylate 0.50 g (2.3 mmol) of t-butyl 3-amino-4-hydroxypiperidin-1-carboxylate (product of PREPARATION 83) and 0.32 mL, (2.3 mmol) of triethylamine was dissolved in 30 mL of methylene chloride, and 0.34 mL, (2.3 mmol) of 4-trifluoromethyl benzylchloride was dropwise added thereto while stirring at 0° C. for 1 hour, followed by addition of 100 mL of ethylacetoacetate and then washing with water. An organic layer dried over anhydrous magnesium sulfate. The reaction solution was filtered off and distilled off under reduced pressure, then the residue was purified by column chromatography to give 0.48 g (1.2 mmol) of the title compound in a total yield of 54%.

Mass (m/e) 335 (M+1)

(2) Synthesis of t-butyl 4-oxo-3-{[4-(trifluoromethyl)benzoyl]amino}piperidin-1-carboxylate 0.48 g (1.2 mmol) of t-butyl 4-hydroxy-3-{[4-(trifluoromethyl)benzoyl]amino}piperidin-1-carboxylate (product of step 1) was dissolved in 10 mL of methylene chloride, and 5.24 g (1.9 mmol) of Dess-Martin periodinane was dropwise added thereto. After stirring for 5 hours, 50 mL of ethylacetoacetate was dropwise added thereto, and the resulting solution was washed with water. An organic layer dried over anhydrous magnesium sulfate. The reaction solution was filtered off and distilled off under reduced pressure, then the residue was purified by column chromatography to give 0.30 g (0.78 mmol) of the title compound in a total yield of 65%.

NMR: $^1$H-NMR (CDCl$_3$) δ 7.94 (2H, d, J=8 Hz), 7.73 (2H, d, J=8 Hz), 7.16 (1H, brs), 5.05~5.00 (1H, m), 4.70~4.60 (1H, m), 4.55~4.45 (1H, m), 3.12~3.00 (1H, m), 2.77~2.66 (2H, m), 2.61~2.57 (2H, m), 1.55 (9H, s)

Mass (m/e) 387 (M+1)

(3) Synthesis of t-butyl 2-[4-(trifluoromethyl)phenyl]-6,7-dihydro[1,3]thiazolo[4,5-c]pyridin-5(4H)-carboxylate 0.40 g (1.0 mmol) of t-butyl 4-oxo-3-{[4-(trifluoromethyl) benzoyl]amino}piperidin-1-carboxylate (product of step 2) was dissolved in 0.47 g (1.2 mmol) of Lawesson's reagent, and the resulting solution was stirred under refluxing of 30 mL of toluene for 4 hours and distilled off under reduced pressure. The residue was purified by column chromatography to give 0.30 g (0.91 mmol) of the title compound in a total yield of 91%.

NMR: $^1$H-NMR (CDCl$_3$) δ 8.00 (2H, d, J=8 Hz), 7.68 (2H, d, J=8 Hz), 4.70 (2H, s), 3.79 (2H, s), 2.93 (2H, m), 1.50 (9H, s)

Mass (m/e) 331 (M+1)

(4) Synthesis of 2-[4-(trifluoromethyl)phenyl]-4,5,6,7-tetrahydro[1,3]thiazolo[4,5-c]pyridine hydrochloride 0.30 g (0.91 mmol) of t-butyl 2-[4-(trifluoromethyl)phenyl]-6,7-dihydro[1,3]thiazol o[4,5-c]pyridin-5(4H)-carboxylate (product of step 3) was dissolved in 15 mL of 4.0 M HCl/Dioxan solution, followed by stirring for 2 hours. The solvent was distilled off under reduced pressure, and the residue was purified by column chromatography to give 0.15 g (0.53 mmol) of the title compound in a yield of 58%.

NMR: $^1$H-NMR (CD$_3$OD) δ 8.08 (2H, d, J=8 Hz), 7.77 (2H, d, J=8 Hz), 4.03 (2H, s), 3.16 (2H, t, J=6 Hz), 2.96 (2H, m)

Mass (m/e) 285 (M+1)

PREPARATION 88

Synthesis of t-butyl [(1S)-{[(5R)-5-methyl-2-oxopiperidin-1-yl]methyl}-3-oxo-3-{2-[4-(trifluoromethyl) phenyl]-6,7-dihydro[1,3]thiazolo[4,5-c]pyridin-5 (4H)-yl}propyl]carbamate 30.0 mg (0.095 mmol) of (3S)-3-[(t-butoxycarbonyl) amino]-4-[(5R)-methyl-2-oxopiperidin-1-yl]-butanoic acid obtained in PREPARATION 51 and 30.0 mg (0.095 mmol) of 2-[4-(trifluoromethyl)phenyl]-4,5,6,7-tetrahydro[1,3]thiazolo[4,5-c]pyridine obtained in PREPARATION 68 were reacted in the same manner as in PREPARATION 45 to give 30 mg of the title compound in a yield of 13%.

NMR: $^1$H-NMR (CDCl$_3$) δ 8.00 (2H, m), 7.69 (2H, m), 5.84 (1H, m), 4.84 (1H, s), 4.70 (1H, m), 4.22 (1H, m), 4.03~3.89 (1H, m), 3.81 (1H, t, J=6 Hz), 3.65 (1H, m), 3.52 (2H, m), 3.36 (1H, m), 3.10~2.80 (4H, m), 2.55~2.35 (3H, m), 1.95 (1H, m), 1.80 (1H, m), 1.42 (9H, s), 1.00 (3H, m)

Mass (m/e) 581 (M+1)

EXAMPLE 41

Synthesis of (5R)-1-[(2S)-2-amino-4-oxo-4-{2-[4-(trifluoromethyl)phenyl]-6,7-dihydro[1,3]thiazolo[4,5,c]pyridin-5(4H)-yl}butyl]-5-methylpiperidin-2-one

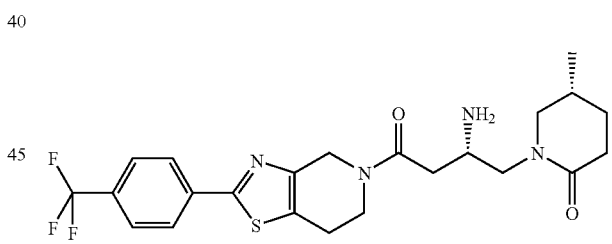

1.2 mg of the title compound was obtained in a total yield of 29% in the same manner as in EXAMPLE 3, using 5 mg (0.0086 mmol) of t-butyl [(1S)-1-{[(5R)-5-methyl-2-oxopiperidin-1-yl]methyl}-3-oxo-3-{2-[4-(trifluoromethyl)phenyl]-6,7-dihydro[1,3]thiazolo[4,5,c]pyridin-5(4H)-yl}propyl]carbamate obtained in

PREPARATION 85

NMR: $^1$H-NMR (CD$_3$OD) δ 8.12 (2H, d, J=8 Hz), 7.80 (2H, d, J=8 Hz), 4.85 (1H, s), 4.79 (1H, s), 4.03 (1H, t, J=6 Hz), 3.89 (2H, m), 3.79 (1H, m), 3.55 (1H, m), 3.36 (1H, m), 3.13 (2H, m), 2.98 (2H, m), 2.81 (1H, m), 2.42 (2H, m), 2.03 (1H, m), 1.86 (1H, m), 1.53 (9H, s), 1.05 (3H, d, J=7 Hz)

Mass (m/e) 481 (M+1)

EXAMPLE 42

Synthesis of (6S)-4-[(2S)-2-amino-4-oxo-4-{2-[4-(trifluoromethyl)phenyl]-6,7-dihydro[1,3]thiazolo[4,5,c]pyridin-5(4H)-yl}butyl]-6-methylmorpholine-3-one

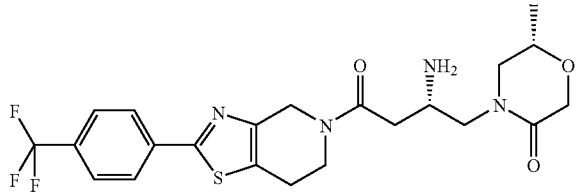

29 mg of the title compound was obtained in a yield of 43% in the same manner as in PREPARATION 45 and EXAMPLE 3 in sequence, except that 45 mg (0.14 mmol) of 2-[4-(trifluoromethyl)phenyl]-4,5,6,7-tetrahydro[1,3]thiazolo[4,5-c]pyridine obtained in PREPARATION 84 and 45 mg (0.14 mmol) of (3S)-3-[(t-butoxycarbonyl)amino]-4-[2(S)-2-methyl-5-oxomorpholin-4-yl]butanoic acid obtained in PREPARATION 55 were used.

NMR: $^1$H-NMR (CD$_3$OD) δ 8.12 (2H, d, J=8 Hz), 7.79 (2H, d, J=8 Hz), 4.85 (1H, s), 4.79 (1H, s), 4.20 (2H, m), 4.02 (1H, t, J=6 Hz), 3.98 (1H, m), 3.90 (1H, M), 3.88 (1H, m), 3.72 (1H, m), 3.60 (1H, m), 3.38 (2H, m), 3.09 (1H, m), 2.99 (1H, m), 2.96 (1H, m), 2.77 (1H, m), 1.26 (3H, d, J=6 Hz)

Mass (m/e) 483 (M+1)

EXAMPLE 43

Synthesis of 1-[(2S)-2-amino-4-oxo-4-{2-[4-(trifluoromethyl)phenyl]-6,7-dihydro[1,3]thiazolo[4,5,c]pyridin-5(4H)-yl}butyl]-5,5-difluoropiperidin-2-one

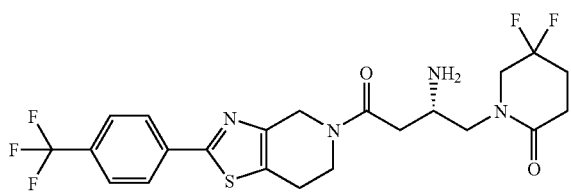

45 mg of the title compound was obtained in a yield of 64% in the same manner as in PREPARATION 45 and EXAMPLE 3 in sequence, except that 45 mg (0.14 mmol) of 2-[4-(trifluoromethyl)phenyl]-4,5,6,7-tetrahydro[1,3]thiazolo[4,5-c]pyridine obtained in PREPARATION 84 and 47 mg (0.14 mmol) of (3S)-3-[(t-butoxycarbonyl)amino]-4-(5,5-difluoro-2-oxopiperidin-1-yl)butanoic acid obtained in PREPARATION 57 were used.

NMR: $^1$H-NMR (CD$_3$OD) δ 8.12 (2H, d, J=8 Hz), 7.79 (2H, d, J=8 Hz), 4.85 (1H, s), 4.79 (1H, s), 4.02 (1H, t, J=6 Hz), 3.90 (2H, m), 3.81 (3H, m), 3.50 (1H, m), 3.09 (1H, m), 3.00 (1H, m), 2.91 (1H, m), 2.62 (2H, m), 2.37 (2H, m)

Mass (m/e) 503 (M+1)

PREPARATION 89

Synthesis of 2-(4-fluorophenyl)-4,5,6,7-tetrahydro[1,3]thiazolo[4,5,c]pyridine hydrochloride 70 mg of the title compound was obtained in a yield of 32% in the same manner as in PREPARATION 84, except that 0.20 g (0.92 mmol) of t-butyl-3-amino-4-hydroxypiperidin-1-carboxylate obtained in PREPARATION 83 and 0.11 mL (0.92 mmol) of 4-fluorobenzoylchloride were used.

NMR: $^1$H-NMR (CD$_3$OD) δ 7.90 (2H, m), 7.20 (2H, m), 4.98 (2H, s), 3.13 (2H, t, J=6 Hz), 2.89 (2H, m)

Mass (m/e) 235 (M+1)

EXAMPLE 44

Synthesis of (5R)-1-{(2S)-2-amino-4-[2-(4-fluorophenyl)-6,7-dihydro[1,3]thiazolo[4,5,c]pyridin-5(4H)-yl]-4-oxobutyl}-5-methylpiperidin-2-one

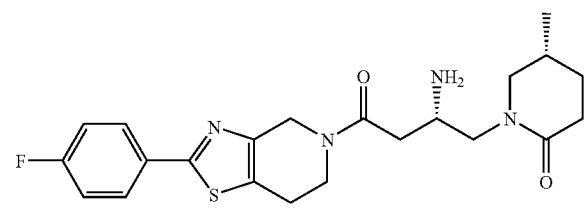

5.8 mg of the title compound was obtained in a yield of 36% in the same manner as in PREPARATION 45 and EXAMPLE 3 in sequence, except that 10 mg (0.037 mmol) of 2-(4-fluorophenyl)-4,5,6,7-tetrahydro[1,3]thiazolo[4,5,c]pyridine obtained in PREPARATION 86 and 12.0 mg (0.037 mmol) of (3S)-3-[(t-butoxycarbonyl)amino]-4-[(5R)-methyl-2-oxopiperidin-1-yl]-butanoic acid obtained in PREPARATION 51 were used.

NMR: $^1$H-NMR (CD$_3$OD) δ 7.92 (2H, m), 7.20 (2H, m), 4.78 (1H, s), 4.71 (1H, s), 3.98 (1H, m), 3.89 (2H, m), 3.71 (1H, m), 3.51 (1H, m), 3.36 (1H, m), 3.13 (2H, m), 2.98 (2H, m), 2.80 (1H, m), 2.38 (2H, m), 1.98 (1H, m), 1.82 (1H, m), 1.50 (9H, s), 1.00 (3H, m)

Mass (m/e) 431 (M+1)

EXAMPLE 45

Synthesis of (6S)-4-{(2S)-2-amino-4-oxo-4-[2-(4-fluorophenyl)6,7-dihydro[1,3]thiazolo[4,5,c]pyridin-5(4H)-yl]butyl}-6-methylmorpholine-3-one

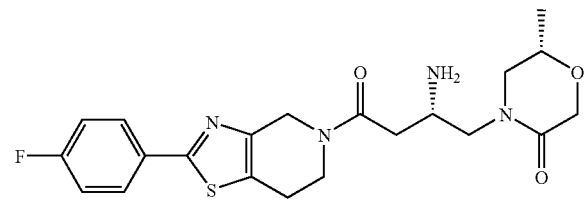

5.0 mg of the title compound was obtained in a yield of 31% in the same manner as in PREPARATION 45 and EXAMPLE 3 in sequence, except that 10 mg (0.037 mmol) of 2-(4-fluorophenyl)-4,5,6,7-tetrahydro[1,3]thiazolo[4,5,c]pyridine obtained in PREPARATION 86 and 12.0 mg (0.037 mmol) of (3S)-3-[(t-butoxycarbonyl)amino]-4-[2(S)-2-methyl-5-oxomorpholin-4-yl]butanoic acid obtained in PREPARATION 55 were used.

NMR: $^1$H-NMR (CD$_3$OD) δ 7.91 (2H, m), 7.18 (2H, m), 4.78 (1H, s), 4.71 (1H, s), 4.15 (2H, m), 4.02 (1H, t, J=6 Hz), 3.91 (2H, m), 3.81 (2H, M), 3.70 (1H, m), 3.65 (2H, m), 3.55 (1H, m), 3.00 (2H, m), 2.93 (1H, m), 2.80 (1H, m), 1.22 (3H, m)

Mass (m/e) 433 (M+1)

EXAMPLE 46

Synthesis of 1-{(2S)-2-amino-4-[2-(4-fluorophenyl)-6,7-dihydro[1,3]thiazolo[4,5,c]pyridin-5(4H)-yl]-4-oxobutyl}-5,5-difluoropiperidin-2-one

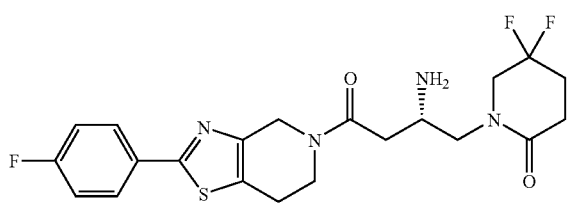

8.0 mg of the title compound was obtained in a yield of 48% in the same manner as in PREPARATION 45 and EXAMPLE 3 in sequence, except that 10 mg (0.037 mmol) of 2-(4-fluorophenyl)-4,5,6,7-tetrahydro[1,3]thiazolo[4,5,c]pyridine obtained in PREPARATION 86 and 14.0 mg (0.037 mmol) of (3S)-3-[(t-butoxycarbonyl)amino]-4-(5,5-difluoro-2-oxopiperidin-1-yl)butanoic acid obtained in PREPARATION 57 were used.

NMR: $^1$H-NMR (CD$_3$OD) δ 7.91 (2H, dm), 7.20 (2H, m), 4.79 (1H, s), 4.71 (1H, s), 3.95 (1H, m), 3.90 (3H, m), 3.82 (2H, m), 3.45 (1H, m), 3.00 (2H, m), 2.92 (1H, m), 2.80 (1H, m), 2.59 (2H, m), 2.34 (2H, m)

Mass (m/e) 453 (M+1)

PREPARATION 87

Synthesis of 2-(tetrahydro-2H-pyran-4-yl)-4,5,6,7-tetrahydro[1,3]thiazolo[4,5,c]pyridine 45 mg of the title compound was obtained in a yield of 17% in the same manner as in PREPARATION 45, except that 0.22 g (11.0 mmol) of t-butyl-3-amino-4-hydroxypiperidin-1-carboxylate obtained in PREPARATION 83 and (1.0 mmol) of tetrahydro-2H-pyran-4-carbonylchloride 0.15 mg was used.

Mass (m/e) 225 (M+1)

EXAMPLE 47

Synthesis of (5R)-1-{(2S)-2-amino-4-oxo-4-[2-(tetrahydro-2H-pyran-4-yl)-6,7-dihydro[1,3]thiazolo[4,5,c]pyridin-5(4H)-yl]butyl}-5-methylpiperidin-2-one

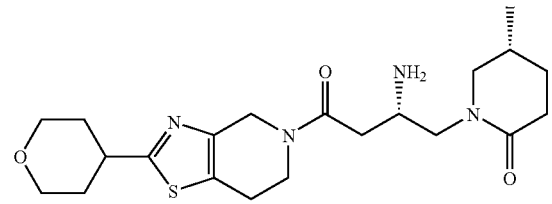

3.2 mg of the title compound was obtained in a yield of 25% in the same manner as in PREPARATION 45 and EXAMPLE 42 in sequence, except that 8.0 mg (0.031 mmol) of 2-(tetrahydro-2H-pyran-4-yl)-4,5,6,7-tetrahydro[1,3]thiazolo[4,5,c]pyridine obtained in PREPARATION 87 and 9.6 mg (0.031 mmol) of (3S)-3-[(t-butoxycarbonyl)amino]-4-[(5R)-methyl-2-oxopiperidin-1-yl]-butanoic acid obtained in PREPARATION 51 were used.

NMR: $^1$H-NMR (CD$_3$OD) δ 4.73 (1H, s), 4.65 (1H, s), 4.03 (2H, m), 3.96 (1H, t, J=6 Hz), 3.83 (2H, m), 3.76 (1H, m), 3.69 (1H, m), 3.60 (3H, m), 3.52 (1H, m), 3.35 (1H, m), 3.25 (1H, m), 3.11 (1H, m), 2.97 (1H, m), 2.88 (2H, m), 2.75 (1H, m), 2.43 (2H, m), 1.99 (2H, m), 1.85 (2H, m), 1.55 (1H, m), 1.05 (3H, d, J=7 Hz)

Mass (m/e) 421 (M+1)

EXAMPLE 48

Synthesis of (6S)-4-{(2R)-2-amino-4-oxo-4-[2-(tetrahydro-2H-pyran-4-yl)-6,7-dihydro[1,3]thiazolo[4,5,c]pyridin-5(4H)-yl]butyl}-6-methylmorpholine-3-one

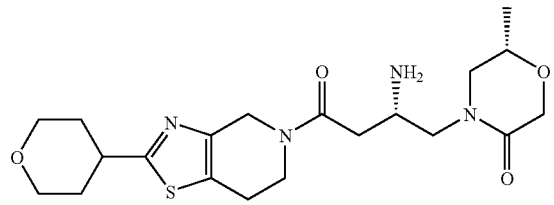

2.5 mg of the title compound was obtained in a yield of 19% in the same manner as in PREPARATION 45 and EXAMPLE 42 in sequence, except that 8.0 mg (0.031 mmol) of 2-(tetrahydro-2H-pyran-4-yl)-4,5,6,7-tetrahydro[1,3]thiazolo[4,5,c]pyridine obtained in PREPARATION 87 and 10 mg (0.031 mmol) of the (3S)-3-[(t-butoxycarbonyl)amino]-4-[2(S)-2-methyl-5-oxomorpholin-4-yl]butanoic acid obtained in PREPARATION 55 were used.

NMR: $^1$H-NMR (CD$_3$OD) δ 4.88 (1H, s), 4.66 (1H, s), 4.21 (2H, m), 4.05 (2H, m), 3.95 (2H, m), 3.83 (1H, m), 3.75 (1H, m), 3.58 (4H, m), 3.36 (2H, m), 3.25 (1H, m), 2.97 (1H, m), 2.86 (2H, m), 2.68 (1H, m), 2.00 (2H, m), 1.85 (2H, m), 1.26 (3H, d, J=7 Hz)

Mass (m/e) 423 (M+1)

EXAMPLE 49

Synthesis of 1-{(2S)-2-amino-4-oxo-4-[2-(tetrahydro-2H-pyran-4-yl)-6,7-dihydro[1,3]thiazolo[4,5,c]pyridin-5(4H)-yl]butyl}-5,5-difluoropiperidin-2-one

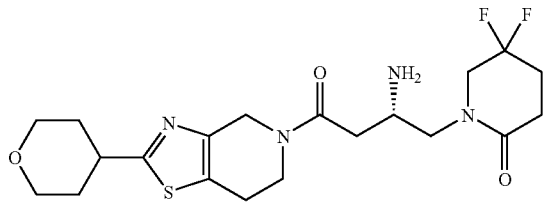

3.6 mg of the title compound was obtained in a yield of 26% in the same manner as in PREPARATION 45 and EXAMPLE 3 in sequence, except that 8.0 mg (0.031 mmol) of 2-(tetrahydro-2H-pyran-4-yl)-4,5,6,7-tetrahydro[1,3]thiazolo[4,5,c]pyridine obtained in PREPARATION 87 and 10 mg (0.031 mmol) of (3S)-3-[(t-butoxycarbonyl)amino]-4-(5,5-difluoro-2-oxopiperidin-1-yl)butanoic acid obtained in PREPARATION 57 were used.

NMR: $^1$H-NMR (CD$_3$OD) δ 4.88 (1H, s), 4.73 (1H, s), 4.03 (2H, m), 3.95 (1H, t, J=6 Hz), 3.83 (2H, m), 3.77 (3H, m), 3.58 (2H, m), 3.48 (1H, m), 3.25 (1H, m), 2.97 (1H, m), 2.88 (2H, m), 2.70 (1H, m), 2.61 (2H, m), 2.37 (2H, m), 2.01 (2H, m), 1.85 (2H, m)

Mass (m/e) 443 (M+1)

PREPARATION 88

Synthesis of 2-(trifluoromethyl-4,5,6,7-tetrahydro[1,3]thiazolo[4,5,c]pyridine 20 mg of the title compound was obtained in a yield of 9.3% in the same manner as in PREPARATION 84, except that 0.30 g (1.4 mmol) of t-butyl-3-amino-4-hydroxypiperidin-1-carboxylate obtained in PREPARATION 83 and 0.19 mL (1.4 mmol) of trifluoroacetic anhydride were used.

NMR: $^1$H-NMR (CDCl$_3$) δ 4.52 (2H, brs), 3.64 (2H, brs), 3.41 (2H, brs)

Mass (m/e) 209 (M+1)

EXAMPLE 50

Synthesis of (6S)-4-{(2S)-2-amino-4-oxo-4-[2-(trifluoromethyl)-6,7-dihydro[1,3]thiazolo[4,5,c]pyridin-5(4H)-yl]butyl}-6-methylmorpholine-3-one

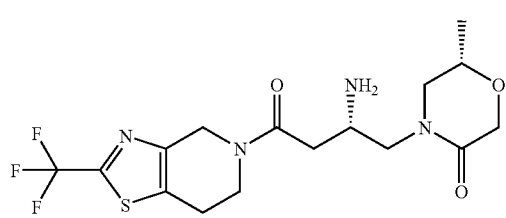

2.0 mg of the title compound was obtained in a yield of 15% in the same manner as in PREPARATION 45 and EXAMPLE 3 in sequence, except that 5.0 mg (0.032 mmol) of 2-(trifluoromethyl)-4,5,6,7-tetrahydro[1,3]thiazolo[4,5,c]pyridine obtained in PREPARATION 88 and 11 mg (0.032 mmol) of the (3S)-3-[(t-butoxycarbonyl)amino]-4-[2(S)-2-methyl-5-oxomorpholin-4-yl]butanoic acid obtained in PREPARATION 55 were used.

NMR: $^1$H-NMR (CD$_3$OD) δ 4.80 (1H, s), 4.75 (1H, s), 4.11 (3H, m), 3.95 (2H, m), 3.85 (2H, m), 3.80 (1H, m), 3.67 (1H, m), 3.56 (2H, m), 3.08 (1H, m), 2.99 (1H, m), 2.89 (1H, m), 2.72 (1H, m)

Mass (m/e) 407 (M+1)

EXAMPLE 51

Synthesis of 1-{(2S)-2-amino-4-oxo-4-[2-(trifluoromethyl)-6,7-dihydro[1,3]thiazolo[4,5,c]pyridin-5(4H)-yl]butyl}-5,5-difluoropiperidin-2-one

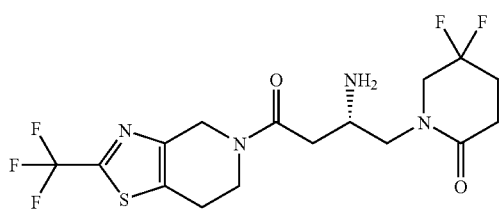

3.0 mg of the title compound was obtained in a yield of 22% in the same manner as in PREPARATION 45 and EXAMPLE 3 in sequence, except that 5.0 mg (0.032 mmol) of 2-(trifluoromethyl)-4,5,6,7-tetrahydro[1,3]thiazolo[4,5,c]pyridine obtained in PREPARATION 88 and 11 mg (0.032 mmol) of (3S)-3-[(t-butoxycarbonyl)amino]-4-(5,5-difluoro-2-oxopiperidin-1-yl)butanoic acid obtained in PREPARATION 57 were used.

NMR: $^1$H-NMR (CD$_3$OD) δ 4.82 (1H, s), 4.75 (1H, s), 3.96 (1H, t, J=6 Hz), 3.85 (2H, m), 3.80 (1H, m), 3.72 (2H, m), 3.45 (1H, m), 3.08 (1H, m), 2.99 (1H, m), 2.85 (1H, m), 2.72 (1H, m), 2.57 (2H, m), 2.33 (2H, m)

Mass (m/e) 427 (M+1)

PREPARATION 89

Synthesis of 2-(2-methoxymethyl)-4-(trifluoromethyl)-5,6,7,8-tetrahydropyrido[3,4-d]pyrimidine hydrochloric acid salt (1) Synthesis of 3-methoxypropaneimidamide 11.7 mL of trimethyl aluminum (23.4 mmol, 2.0M in toluene) was dropwise added at room temperature to 20 mL (23.4 mmol) of toluene containing 1.26 g of ammonium chloride. After stirring for 1.5 hours, 2 g (23.4 mmol) of 3-methoxypropanenitrile was added thereto, followed by heating at 85° C. for 9 hours. After a reaction, the solution was cooled, then 100 mL of chloroform containing 200 g of silica gel was added thereto, followed by filtering. After washing with 100 mL of methanol and then distillation, 2.35 g (23 mmol) of the title compound was obtained in a yield of 98%.

NMR: $^1$H-NMR (CD$_3$OD) δ 3.70 (2H, t, J=7.0 Hz), 3.39 (3H, s), 2.73 (2H, t, J=7.0 Hz)

(2) Synthesis of t-butyl 2-(2-methoxyethyl)-4-(trifluoromethyl)-5,8-dihydropyrido[3,4-d]pyrimidin-7(6H)-carboxylate 500 mg (1.69 mmol) of t-butyl 3-oxo-4-(trifluoroacetyl)piperidin-1-carboxylate obtained in PREPARATION 47 and 173 mg (1.69 mmol) of 3-methoxypropaneimidamide obtained in the above step (1) were added to 20 mL of pyridine and then heated to 90° C., followed by stirring for about 1.5 hours. After cooling to room temperature, pyridine was distilled off under reduced pressure, the residue was purified by column chromatography (10:1 hexane:ethyl acetate) to give 220 mg of the title compound in a total yield of 36%.

$^1$H NMR (CDCl$_3$) δ 4.69 (2H, s), 3.90 (2H, t, J=7.0 Hz), 3.70 (2H, t, J=5.5 Hz), 3.35 (3H, s), 3.23 (2H, t, J=7.0 Hz), 2.97 (2H, br s), 1.47 (9H, s)

Mass (m/e) 362 (M+1)

(3) Synthesis of 2-(2-methoxyethyl)-4-(trifluoromethyl)-5,6,7,8-tetradropyrido[3,4-d]pyrimidine hydrochloric acid salt 120 mg of the title compound was obtained in a yield of 75% in the same manner of PREPARATION 58 (3), using 220 mg (0.609 mmol) of t-butyl 2-(2-methoxyethyl)-4-(trifluoromethyl)-5,8-dihydropyrido[3,4-d]pyrimidin-7(6H)-carboxylate obtained in the above step (2)

$^1$H NMR (CD$_3$OD) δ 4.51 (2H, s), 3.93 (2H, t, J=6.0 Hz), 3.63 (2H, t, J=6.0 Hz), 3.2-3.4 (7H, m)

Mass (m/e) 262 (M+1)

PREPARATION 90

Synthesis of 2-(cyclopropylmethyl)-4-(trifluoromethyl)-5,6,7,8-tetradropyrido[3,4-d]pyrimidine hydrochloric acid salt (1) Synthesis of cyclopropylethaneimidamide 1.61 g of the title compound was obtained in a yield of 66% at the same manner as in PREPARATION 89(1) using 2.0 g (25 mmol) of cyclopropylacetonitrile.

NMR: $^1$H-NMR (CD$_3$OD) δ 2.39 (2H, d, J=7.2 Hz), 1.09 (1H, m), 0.66 (2H, m), 0.35 (2H, m)

(2) Synthesis of t-butyl 2-(cyclopropylmethyl)-4-(trifluoromethyl)-5,8-dihydropyrido[3,4-d]pyrimidin-7(6H-carboxylate 155 mg of the title compound was obtained in a yield of 26% at the same manner as in PREPARATION 89(2) using 500 mg (1.69 mmol) of t-butyl 3-oxo-4-(trifluoroacetyl)piperidin-1-carboxylate (product of PREPARATION 47) and 166 mg (1.69 mmol) of cyclopropylethaneimidamide obtained in the above step (1).

$^1$H NMR (CDCl$_3$) δ 4.70 (2H, s), 3.71 (2H, t, J=6.0 Hz), 2.98 (2H, br s), 2.84 (2H, d, J=7.5 Hz), 1.49 (9H, s), 1.25 (1H, m), 0.51 (2H, m), 0.29 (2H, m)

Mass (m/e) 358 (M+1)

(3) Synthesis of 2-(cyclopropylmethyl)-4-(trifluoromethyl)-5,6,7,8-tetradropyrido[3,4-d]pyrimidine hydrochloric acid salt 85 mg of the title compound was obtained in a yield of 76% at the same manner as in PREPARATION 58 (3) using 155 mg (0.43 mmol) of t-butyl 2-(cyclopropylmethyl)-4-(trifluoromethyl)-5,8-dihydropyrido[3,4-d]pyrimidin-7(6H)-carboxylate obtained in the above step (2).

$^1$H NMR (CD$_3$OD) δ 4.33 (2H, s), 3.37 (2H, t, J=6.5 Hz), 2.63 (2H, d, J=6.0 Hz), 1.0 (1H, m), 0.30 (2H, m), 0.1 (2H, m)

Mass (m/e) 258 (M+1)

PREPARATION 91

Synthesis of 2-pyridin-4-yl-4-(trifluoromethyl)-5,6,7,8-tetradropyrido[3,4-d]pyrimidine hydrochloric acid salt (1) Synthesis of pyridin-4-carboximidamide 1.06 g of the title compound was obtained in a yield of 45% at the same manner as in PREPARATION 89(1) using 2.0 g (19.2 mmol) of isonicotinonitrile.

NMR: $^1$H-NMR (CD$_3$OD) δ 8.86 (2H, m), 7.79 (2H, m)

(2) Synthesis of t-butyl 2-pyridin-4-yl-4-(trifluoromethyl)-5,8-dihydropyrido[3,4-d]pyrimidin-7(6H)-carboxylate 240 mg of the title compound was obtained in a yield of 37% at the same manner as in PREPARATION 89(2) using 500 mg (1.69 mmol) of t-butyl 3-oxo-4-(trifluoroacetyl)piperidin-1-carboxylate (product of PREPARATION 47) and 210 mg (1.69 mmol) of pyridin-4-carboximidamide obtained in the above step (1).

$^1$H NMR (CDCl$_3$) δ 8.78 (2H, d, J=5.5 Hz), 8.30 (2H, d, J=5.5 Hz), 4.81 (2H, s), 3.76 (2H, t, J=6.0 Hz), 3.07 (2H, br s), 1.51 (9H, s)

Mass (m/e) 381 (M+1)

(3) Synthesis of 2-pyridin-4-yl-4-(trifluoromethyl)-5,6,7,8-tetrahydropyrido[3,4-d]pyrimidine hydrochloric acid salt 160 mg of the title compound was obtained in a yield of 90% at the same manner as in PREPARATION 58 (3) using 240 mg (0.63 mmol) of t-butyl-2-pyridin-4-yl-4-(trifluoromethyl)-5,8-dihydropyrido[3,4-d]pyrimidin-7(6H)-carboxylate obtained in the above step (2).

$^1$H NMR (CD$_3$OD) δ 9.07 (2H, d, J=6.0 Hz), 9.02 (2H, d, J=6.0 Hz), 4.71 (2H, s), 3.70 (2H, br t, J=6.0 Hz), 3.43 (2H, br s)

Mass (m/e) 281(M+1)

PREPARATION 92

Synthesis of 2-(4-fluorobenzyl)-4-(trifluoromethyl)-5,6,7,8-tetrahydro pyrido[3,4-d]pyrimidine hydrochloric acid salt (1) Synthesis of 2-(4-fluorophenyl)ethaneimidamide 2.0 g of the title compound was obtained in a yield of 89% at the same manner as in PREPARATION 89(1) using 2.0 g (14.8 mmol) of (4-fluorophenyl)acetonitrile.

NMR: $^1$H-NMR (CD$_3$OD) δ 7.50 (2H, m), 7.15 (2H, m), 3.90 (2H, s)

(2) Synthesis of t-butyl 2-(4-fluorobenzyl)-4-(trifluoromethyl)-5,8-dihydropyrido[3,4-d]pyrimidin-7(6H)-carboxylate 250 mg of the title compound was obtained in a yield of 36% at the same manner as in PREPARATION 89(2) using 500 mg (1.69 mmol) of t-butyl 3-oxo-4-(trifluoroacetyl)piperidin-1-carboxylate (product of PREPARATION 47) and 258 mg (1.69 mmol) of 2-(4-fluorophenyl)ethaneimidamide obtained in the above step (1).

$^1$H NMR (CDCl$_3$) δ 7.37 (2H, m), 6.95 (2H, t, J=8.0 Hz), 4.67 (2H, s), 4.24 (2H, s), 3.69 (2H, t, J=6.0 Hz), 2.96 (2H, br s), 1.49 (9H, s)

Mass (m/e) 412 (M+1)

(3) Synthesis of 2-(4-fluorobenzyl)-4-(trifluoromethyl)-5,6,7,8-tetradropyrido[3,4-d]pyrimidine hydrochloric acid salt 77 mg of the title compound was obtained in a yield of 41% at the same manner as in PREPARATION 58 (3) using 250 mg (0.61 mmol) of t-butyl 2-(4-fluorobenzyl)-4-(trifluoromethyl)-5,8-dihydropyrido[3,4-d]pyrimidin-7(6H)-carboxylate obtained in the above step (2).

$^1$H NMR (CD$_3$OD) δ 7.35 (2H, m), 6.99 (2H, t, J=9.0 Hz), 4.45 (2H, s), 4.27 (2H, s), 3.57 (2H, t, J=6.5 Hz), 3.23 (2H, t, J=6.5 Hz)

Mass (m/e) 312 (M+1)

PREPARATION 93

Synthesis of 2-(3-thienyl)-4-(trifluoromethyl)-5,6,7,8-tetradropyrido[3,4-d]pyrimidine hydrochloric acid salt

(1) Synthesis of thiophen-3-carboximidamide 1.81 g of the title compound was obtained in a yield of 95% at the same manner as in PREPARATION 89(1) using 1.64 g (15 mmol) of thiophen-3-carbonitrile.

NMR: $^1$H-NMR (CD$_3$OD) δ 8.41 (1H, m), 7.69 (1H, m), 7.59 (1H, m)

(2) Synthesis of t-butyl 2-(3-thienyl)-4-(trifluoromethyl)-5,8-dihydropyrido[3,4-d]pyrimidin-7(6H)-carboxylate 228 mg of the title compound was obtained in a yield of 35% at the same manner as in PREPARATION 89(2) using 500 mg (1.69 mmol) of t-butyl 3-oxo-4-(trifluoroacetyl)piperidin-1-carboxylate (product of PREPARATION 47) and 214 mg (1.69 mmol) of thiophen-3-carboximidamide obtained in the above step (1).

$^1$H NMR (CDCl$_3$) δ 8.34 (1H, m), 7.90 (1H, m), 7.38 (1H, m), 4.74 (2H, s), 3.74 (2H, t, J=6.0 Hz), 3.00 (2H, br s), 1.51 (9H, s)

Mass (m/e) 386 (M+1)

(3) Synthesis of 2-(3-thienyl)-4-(trifluoromethyl)-5,6,7,8-tetrahydropyrido[3,4-d]pyrimidine hydrochloric acid salt 168 mg of the title compound was obtained in a yield of 61% at the same manner as in PREPARATION 58 (3) using 228 mg (0.59 mmol) of t-butyl 2-(3-thienyl)-4-(trifluoromethyl)-5,8-dihydropyrido[3,4-d]pyrimidin-7(6H)-carboxylate obtained in the above step (2).

$^1$H NMR (CD$_3$OD) δ 8.42 (1H, m), 7.86 (1H, m), 7.53 (1H, m), 4.53 (2H, s), 3.62 (2H, t, J=6.5 Hz), 3.30 (2H, m)

Mass (m/e) 286 (M+1)

PREPARATION 94

Synthesis of 2-(2-triethyl)-4-(trifluoromethyl)-5,6,7,8-tetradropyrido[3,4-d]pyrimidine hydrochloric acid salt

(1) Synthesis of thiophen-2-carboximidamide 1.8 g of the title compound was obtained in a yield of 95% at the same manner as in PREPARATION 89(1) using 1.64 g (15 mmol) of thiophen-2-carbonitrile.

NMR: $^1$H-NMR (CD$_3$OD) δ 7.94 (1H, m), 7.89 (1H, m), 7.24 (1H, m)

(2) Synthesis of t-butyl 2-(2-thienyl)-4-(trifluoromethyl)-5,8-dihydropyrido[3,4-d]pyrimidin-7(6H)-carboxylate 144 mg of the title compound was obtained in a yield of 25% at the same manner as in PREPARATION 89(2) using 500 mg (1.69 mmol) of t-butyl 3-oxo-4-(trifluoroacetyl)piperidin-1-carboxylate (product of PREPARATION 47) and 146 mg (1.69 mmol) of thiophen-2-carboximidamide obtained in the above step (1).

$^1$H NMR (CDCl$_3$) δ 8.04 (1H, d, J=4.0 Hz), 7.50 (1H, d, J=5.0 Hz), 7.14 (1H, m), 4.72 (2H, s), 3.72 (2H, t, J=5.5 Hz), 2.99 (2H, br s), 1.54 (9H, s)

Mass (m/e) 386 (M+1)

(3) Synthesis of 2-(2-thienyl)-4-(trifluoromethyl)-5,6,7,8-tetrahydropyrido[3,4-d]pyrimidine hydrochloric acid salt 72 mg of the title compound was obtained in a yield of 61% at the same manner as in PREPARATION 58 (3) using 144 mg (0.42 mmol) of t-butyl 2-(2-thienyl)-4-(trifluoromethyl)-5,8-dihydropyrido[3,4-d]pyrimidin-7(6H)-carboxylate obtained in the above step (2).

$^1$H NMR (CD$_3$OD) δ 8.09 (1H, m), 7.72 (1H, m), 7.23 (1H, m), 4.55 (2H, s), 3.64 (2H, t, J=6.5 Hz), 3.30 (2H, m)

Mass (m/e) 286 (M+1)

PREPARATION 95

Synthesis of 2-(2-furyl)-4-(trifluoromethyl)-5,6,7,8-tetradropyrido[3,4-d]pyrimidine hydrochloric acid salt

(1) Synthesis of furan-2-carboximidamide 2.1 g of the title compound was obtained in a yield of 64% at the same manner as in PREPARATION 89(1) using 2.77 g (30 mmol) of 2-furonitrile.

NMR: $^1$H-NMR (CD$_3$OD) δ 7.94 (1H, s), 7.58 (1H, d, J=3.6 Hz), 6.78 (1H, m)

(2) Synthesis of t-butyl-2-(2-furyl)-4-(trifluoromethyl)-5,8-dihydropyrido[3,4-d]pyrimidin-7(6H)-carboxylate 2.55 g of the title compound was obtained in a yield of 68% at the same manner as in PREPARATION 89(2) using 3 g (10.2 mmol) of t-butyl 3-oxo-4-(trifluoroacetyl)piperidin-1- carboxylate (product of PREPARATION 47) and 1.12 g (10.2 mmol) of furan-2-carboximidamide obtained in the above step (1).

$^1$H NMR (CDCl$_3$) δ 7.65 (1H, s), 7.39 (1H, d, J=3.0 Hz), 6.58 (1H, m), 4.78 (2H, s), 3.73 (2H, t, J=5.5 Hz), 3.0 (2H, br s), 1.49 (9H, s)

Mass (m/e) 370 (M+1)

(3) Synthesis of 2-(2-furyl)-4-(trifluoromethyl)-5,6,7,8-tetrahydropyrido[3,4-d]pyrimidine hydrochloric acid salt 1.42 g of the title compound was obtained in a yield of 67% at the same manner as in PREPARATION 58 (3) using 2.55 g (6.9 mmol) of t-butyl 2-(2-furyl)-4-(trifluoromethyl)-5,8-dihydropyrido[3,4-d]pyrimidin-7(6H)-carboxylate obtained in the above step (2).

$^1$H NMR (CD$_3$OD) δ 7.58 (1H, s), 7.43 (1H, d, J=3.7 Hz), 6.67 (1H, m), 4.51 (2H, s), 3.61 (2H, t, J=6.5 Hz), 3.26 (2H, t, J=6.5 Hz)

Mass (m/e) 270 (M+1)

PREPARATION 96

Synthesis of 2-(3-furyl)-4-(trifluoromethyl)-5,6,7,8-tetrahydropyrido[3,4-d]pyrimidine hydrochloric acid salt (1) Synthesis of furan-3-carboximidamide 1.56 g of the title compound was obtained in a yield of 94% at the same manner as in PREPARATION 89(1) using 1.4 g (15 mmol) of 3-furonitrile.

NMR: $^1$H-NMR (CD$_3$OD) δ 8.4 (1H, s), 7.76 (1H, m), 6.96 (1H, m)

(2) Synthesis of t-butyl 2-(3-furyl)-4-(trifluoromethyl)-5,8-dihydropyrido[3,4-d]pyrimidin-7(6H)-carboxylate 170 mg of the title compound was obtained in a yield of 27% at the same manner as in PREPARATION 89(2) using 500 mg (1.69 mmol) of t-butyl 3-oxo-4-(trifluoroacetyl)piperidin-1-carboxylate (product of PREPARATION 47) and 186 mg (1.69 mmol) of furan-3-carboximidamide obtained in the above step (1).

$^1$H NMR (CDCl$_3$) δ 8.26 (1H, s), 7.49 (1H, s), 7.06 (1H, s), 4.70 (2H, s), 3.72 (2H, t, J=5.5 Hz), 3.0 (2H, br s), 1.54 (9H, s)

Mass (m/e) 370 (M+1)

(3) Synthesis of 2-(3-furyl)-4-(trifluoromethyl)-5,6,7,8-tetrahydropyrido[3,4-d]pyrimidine hydrochloric acid salt 86 mg of the title compound was obtained in a yield of 69% at the same manner as in PREPARATION 58 (3) using 170 mg (0.46 mmol) of t-butyl 2-(3-furyl)-4-(trifluoromethyl)-5,8-dihydropyrido[3,4-d]pyrimidin-7(6H)-carboxylate obtained in the above step (2).

$^1$H NMR (CD$_3$OD) δ 8.39 (1H, s), 7.67 (1H, m), 7.09 (1H, m), 4.54 (2H, s), 3.65 (2H, t, J=6.0 Hz), 3.29 (2H, t, J=6.0 Hz)

Mass (m/e) 270 (M+1)

PREPARATION 97

Synthesis of 2-pyridin-3-yl-4-(trifluoromethyl)-5,6,7,8-tetradropyrido[3,4-d]pyrimidine hydrochloric acid salt (1) Synthesis of t-butyl 2-pyridin-3-yl-4-(trifluoromethyl)-5,8-dihydropyrido[3,4-d]pyrimidin-7(6H)-carboxylate 640 mg of the title compound was obtained in a yield of 71% at the same manner as in PREPARATION 89(2) using 700 mg (2.37 mmol) of t-butyl 3-oxo-4-(trifluoroacetyl)piperidin-1-carboxylate (product of PREPARATION 47) and 370 mg (2.37 mmol) of pyridin-3-carboximidamide obtained in the above step (1).

$^1$H NMR (CDCl$_3$) δ 9.65 (1H, s), 8.73 (2H, m), 7.43 (1H, m), 4.80 (2H, s), 3.76 (2H, t, J=5.5 Hz), 3.05 (2H, br s), 1.51 (9H, s)

Mass (m/e) 381 (M+1)

(2) Synthesis of 2-pyridin-3-yl-4-(trifluoromethyl)-5,6,7,8-tetrahydropyrido[3,4-d]pyrimidine hydrochloric acid salt 500 mg of the title compound was obtained in a yield of 94% at the same manner as in PREPARATION 58(3) using 640 mg (1.68 mmol) of t-butyl 2-pyridin-3-yl-4-(trifluoromethyl)-5,8-dihydropyrido[3,4-d]pyrimidin-7(6H)-carboxylate obtained in the above step (2).

$^1$H NMR (CD$_3$OD) δ 9.72 (1H, s), 9.49 (1H, m), 9.00 (1H, br s), 8.23 (1H, m), 4.67 (2H, s), 3.66 (2H, t, J=5.5 Hz), 3.39 (2H, br s)

Mass (m/e) 281 (M+1)

PREPARATION 98

Synthesis of 2-(1H-pyrrol-2-yl)-4-(trifluoromethyl)-5,6,7,8-tetradropyrido[3,4-d]pyrimidine hydrochloric acid salt (1) Synthesis of 1H-pyrrol-2-carboximidamide 1.09 g of the title compound was obtained in a yield of 67% at the same manner as in PREPARATION 89-(1) using 1.38 g (15 mmol) of 1H-pyrrol-2-carbonitrile.

NMR: $^1$H-NMR (CD$_3$OD) δ 7.12 (2H, m), 6.31 (1H, t, J=3.3 Hz)

(2) Synthesis of t-butyl 2-(1H-pyrrol-2-yl)-4-(trifluoromethyl)-5,8-dihydropyrido[3,4-d]pyrimidin-7(6H)-carboxylate 185 mg of the title compound was obtained in a yield of 19% at the same manner as in PREPARATION 89(2) using 800 mg (2.7 mmol) of t-butyl 3-oxo-4-(trifluoroacetyl)piperidin-1-carboxylate (product of PREPARATION 47) and 300 mg (2.7 mmol) of 1H-pyrrol-2-carboximidamide obtained in the above step (1).

$^1$H NMR (CDCl$_3$) δ 7.14 (1H, m), 6.98 (1H, m), 6.34 (1H, m), 7.18 (1H, m), 4.67 (2H, s), 3.71 (2H, t, J=5.5 Hz), 2.95 (2H, br s), 1.49 (9H, s)

Mass (m/e) 369 (M+1)

(3) Synthesis of 2-(1H-pyrrol-2-yl)-4-(trifluoromethyl)-5,6,7,8-tetrahydropyrido[3,4-d]pyrimidine hydrochloric acid salt 48 mg of the title compound was obtained in a yield of 36% at the same manner as in PREPARATION 58-(3) using 185 mg (0.50 mmol) of t-butyl 2-(1H-pyrrol-2-yl)-4-(trifluoromethyl)-5,8-dihydropyrido[3,4-d]pyrimidin-7(6H)-carboxylate obtained in the above (2).

$^1$H NMR (CD$_3$OD) δ 11.25 (1H, m), 7.08 (1H, m), 7.00 (1H, m), 6.26 (1H, m), 4.45 (2H, s), 3.59 (2H, t, J=5.5 Hz), 3.20 (2H, t, J=5.5 Hz)

Mass (m/e) 269 (M+1)

PREPARATION 99

Synthesis of t-butyl [(1S)-3-[2-(2-methoxyethyl)-4-trifluoromethyl-5,8-dihydropyrido[3,4-d]pyrimidin-7(6H)-yl]-1-{[(5R)-5-methyl-2-oxopiperidin-1-yl]methyl}-3-oxpropyl]carbamate 61 mg of the title compound was obtained in a yield of 79% at the same manner as in PREPARATION 45, except that 44.0 mg (0.139 mmole) of (3S)-3-t-butoxycarbonylamino-4-[(5R)-5-methyl-2-oxopiperidin-1-yl]butanoic acid obtained in PREPARATION 51 and 37.5 mg (0.126 mmole) of 2-(2-methoxyethyl)-4-(trifluoromethyl)-5,6,7,8-tetrahydropyrido[3,4-d]pyrimidine hydrochloric acid salt obtained in PREPARATION 89 were used.

$^1$H NMR (CDCl$_3$) δ 5.89-5.87 (1H, m), 4.90-4.79 (1H, m), 4.78-4.67 (1H, m), 4.20-4.15 (1H, m), 3.92-3.82 (2H, m), 3.78-3.75 (1H, m), 3.64-3.47 (4H, m), 3.39-3.36 (4H, m), 3.26-3.23 (2H, m), 3.11-2.99 (3H, m), 2.87-2.80 (1H, m), 2.55-2.27 (3H, m), 1.97-1.93 (1H, m), 1.84-1.81 (1H, m), 1.42-1.41 (9H, m), 1.00 (3H, d, J=5.6 Hz)

Mass (m/e) 558 (M+1)

EXAMPLE 52

Synthesis of (5R)-1-{(2S)-2-amino-4-[2-(2-methoxyethyl)-4-(trifluoromethyl)-5,8-dihydropyrido[3,4-d]pyrimidin-7(6H)-yl]-4-oxobutyl}-5-methylpiperidin-2-one

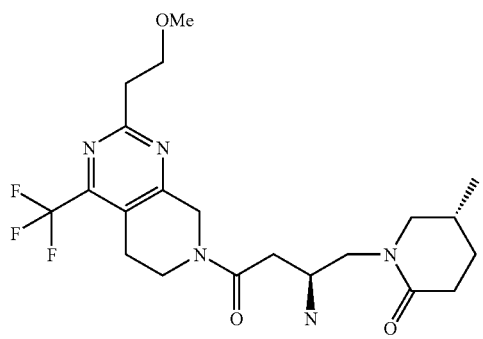

51.9 mg of the title compound was obtained in a yield of 96% at the same manner as in EXAMPLE 22, using 61 mg (0.109 mmole) of t-butyl [(1S)-3-[2-(2-methoxyethyl)-4-trifluoromethyl-5,8-dihydropyrido[3,4-d]pyrimidin-7(6H)-yl]-1-{[(5R)-5-methyl-2-oxopiperidin-1-yl]methyl}-3-oxpropyl]carbamate obtained in PREPARATION 99

$^1$H NMR (CD$_3$OD) δ 4.92-4.80 (2H, m), 3.94-3.83 (4H, m), 3.67 (1H, brs), 3.54-3.53 (2H, m), 3.42-3.34 (4H, m), 3.24-3.21 (2H, m), 3.12-3.01 (3H, m), 2.82-2.77 (1H, m), 2.70-2.60 (1H, m), 2.47-2.32 (2H, m), 2.05-2.00 (1H, m), 1.88-1.85 (1H, m), 1.59-1.48 (1H, m), 1.04 (3H, d, J=6.4 Hz)

Mass (m/e) 458 (M+1)

PREPARATION 100

Synthesis of t-butyl {(1S)-1-[(5,5-difluoro-2-oxopiperidin-1-yl)methyl]-3-[2-(2-methoxyethyl)-4-(trifluoromethyl)-5,8-dihydropyrido[3,4-d]pyrimidin-7(6H)-yl]-3-oxpropyl}carbamate 47 mg of the title compound was obtained in a yield of 58% at the same manner as in PREPARATION 45, using 47.0 mg (0.139 mmole) of (3S)-3-[(t-butoxycarbonyl)amino]-4-(5,5-difluoro-2-oxopiperidin-1-yl)butanoic acid obtained PREPARATION 57 and 37.5 mg (0.126 mmole) of 2-(2-methoxyethyl)-4-(trifluoromethyl)-5,6,7,8-tetrahydropyrido[3,4-d]pyrimidine hydrochloric acid salt obtained in PREPARATION 89.

$^1$H NMR (CDCl$_3$) δ 5.79-5.78 (1H, m), 4.90-4.79 (1H, m), 4.76-4.65 (1H, m), 4.25-4.20 (1H, m), 3.92-3.86 (3H, m), 3.80-3.68 (3H, m), 3.63-3.53 (2H, m), 3.36 (3H, s), 3.26-3.23 (2H, m), 3.01-2.99 (2H, m), 2.85-2.78 (1H, m), 2.61-2.50 (3H, m), 2.32-2.20 (2H, m), 1.42-1.41 (9H, m)

Mass (m/e) 580 (M+1)

EXAMPLE 53

Synthesis of 1-{(2S)-2-amino-4-[2-(2-methoxyethyl)-4-(trifluoromethyl)-5,8-dihydropyrido[3,4-d]pyrimidin-7(6H)-yl]-4-oxobutyl}-5,5-difluoropiperidin-2-one

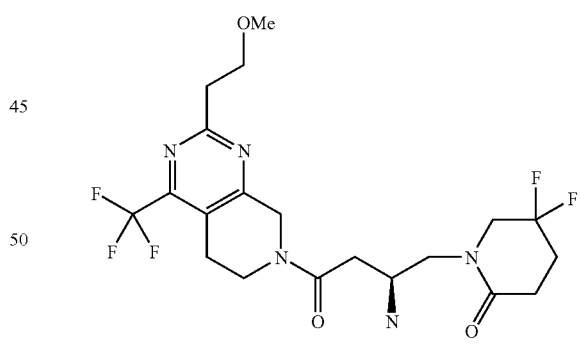

25.4 mg of the title compound was obtained in a yield of 61% at the same manner as in EXAMPLE 22, using 47 mg (0.081 mmole) of t-butyl {(1S)-1-[(5,5-difluoro-2-oxopiperidin-1-yl)methyl]-3-[2-(2-methoxyethyl)-4-(trifluoromethyl)-5,8-dihydropyrido[3,4-d]pyrimidin-7(6H)-yl]-3-oxpropyl}carbamate obtained in PREPARATION 100.

$^1$H NMR (CD$_3$OD) δ 4.86-4.80 (2H, m), 3.94-3.90 (3H, m), 3.89-3.75 (3H, m), 3.57-3.45 (3H, m), 3.34-3.32 (3H, m), 3.24-3.21 (2H, m), 3.11-3.01 (2H, m), 2.73-2.51 (4H, m), 2.41-2.30 (2H, m)

Mass (m/e) 480 (M+1)

PREPARATION 101

Synthesis of t-butyl {(1S)-3-[2-(cyclopropylmethyl)-4-(trifluoromethyl)-5,8-dihydropyrido[3,4-d]pyrimidin-7(6H)-yl]-1-{[(5R)-5-methyl-2-oxopiperidin-1-yl]methyl}-3-oxpropyl}carbamate 66 mg of the title compound was obtained in a yield of 75% at the same manner as in PREPARATION 45, using 50.0 mg (0.159 mmole) of (3S)-3-[(t-butoxycarbonyl)amino]-4-[(5R)-5-methyl-2-oxopiperidin-1-yl]butanoic acid obtained in PREPARATION 51 and 43.0 mg (0.145 mmole) of 2-(cyclopropylmethyl)-4-(trifluoromethyl)-5,6,7,8-tetrahydropyrido[3,4-d]pyrimidine hydrochloric acid salt obtained in PREPARATION 90.

$^1$H NMR (CDCl$_3$) δ 5.88 (1H, brs), 4.90-4.80 (1H, m), 4.78-4.66 (1H, m), 4.20-4.18 (1H, m), 3.93-3.85 (1H, m), 3.79-3.76 (1H, m), 3.65-3.47 (2H, m), 3.43-3.33 (1H, m), 3.11-2.99 (3H, m), 2.86-2.81 (3H, m), 2.56-2.27 (3H, m), 2.02-1.93 (1H, m), 1.84-1.81 (1H, m), 1.42-1.41 (9H, m), 1.30-1.17 (2H, m), 1.00 (3H, d, J=6.4 Hz), 0.55-0.49 (2H, m), 0.34-0.28 (2H, m)

Mass 554 (m/e) (M+1)

EXAMPLE 54

Synthesis of (5R)-1-{(2S)-2-amino-4-[2-(cyclopropylmethyl)-4-(trifluoromethyl)-5,8-dihydropyrido[3,4-d]pyrimidin-7(6H)-yl]-4-oxobutyl}-5-methylpiperidin-2-one

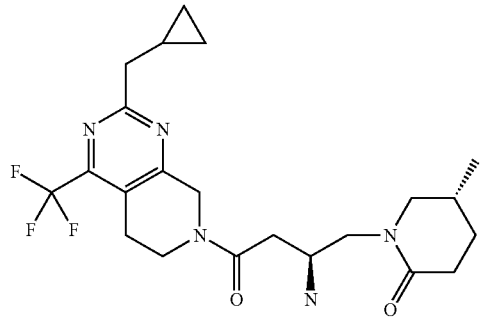

47.9 mg of the title compound was obtained in a yield of 82% at the same manner as in EXAMPLE 22, using 66 mg (0.119 mmole) of t-butyl {(1S)-3-[2-(cyclopropylmethyl)-4-(trifluoromethyl)-5,8-dihydropyrido[3,4-d]pyrimidin-7(6H)-yl]-1-{[(5R)-5-methyl-2-oxopiperidin-1-yl]methyl}-3-oxpropyl}carbamate obtained in PREPARATION 101.

$^1$H NMR (CD$_3$OD) δ 4.68-4.56 (2H, m), 3.70-3.58 (2H, m), 3.40-3.37 (1H, m), 3.31-3.21 (2H, m), 3.17-3.12 (1H, m), 2.87-2.77 (3H, m), 2.62-2.60 (2H, m), 2.53-2.48 (1H, m), 2.41-2.35 (1H, m), 2.20-2.11 (2H, m), 1.79-1.76 (1H, m), 1.63-1.59 (1H, m), 1.34-1.23 (1H, m), 1.06-0.97 (1H, m), 0.80 (3H, d, J=6.4 Hz), 0.31-0.23 (2H, m), 0.11-0.04 (2H, m),

Mass (m/e) 454 (M+1)

PREPARATION 102

Synthesis of t-butyl {(1S)-3-[2-(cyclopropylmethyl)-4-(trifluoromethyl)-5,8-dihydropyrido[3,4-d]pyrimidin-7(6H)-yl]-1-[(5,5-difluoro-2-oxopiperidin-1-yl)methyl]-3-oxpropyl}carbamate 66 mg of the title compound was obtained in a yield of 75% at the same manner as in PREPARATION 45, using 53.5 mg (0.159 mmole) of (3S)-3-[(t-butoxycarbonyl)amino]-4-(5,5-difluoro-2-oxopiperidin-1-yl)butanoic acid obtained in PREPARATION 57 and 43.0 mg (0.145 mmole) of 2-(cyclopropylmethyl)-4-(trifluoromethyl)-5,6,7,8-tetrahydropyrido[3,4-d]pyrimidine hydrochloric acid salt obtained in PREPARATION 90.

$^1$H NMR (CDCl$_3$) δ 5.77 (1H, brs), 4.87-4.80 (1H, m), 4.73-4.62 (1H, m), 4.19 (1H, brs), 3.89-3.86 (1H, m), 3.78-3.68 (3H, m), 3.61-3.55 (2H, m), 3.05-2.92 (2H, m), 2.84-2.79 (3H, m), 2.59-2.47 (3H, m), 2.29-2.15 (2H, m), 1.40-1.39 (9H, m), 1.24-1.23 (1H, m), 0.53-0.49 (2H, m), 0.28-0.27 (2H, m)

Mass (m/e) 576 (M+1)

EXAMPLE 55

Synthesis of 1-{(2S)-2-amino-4-[2-(cyclopropylmethyl)-4-(trifluoromethyl)-5,8-dihydropyrido[3,4-d]pyrimidin-7(6H)-yl]-4-oxobutyl}-5,5-difluoropiperidin-2-one

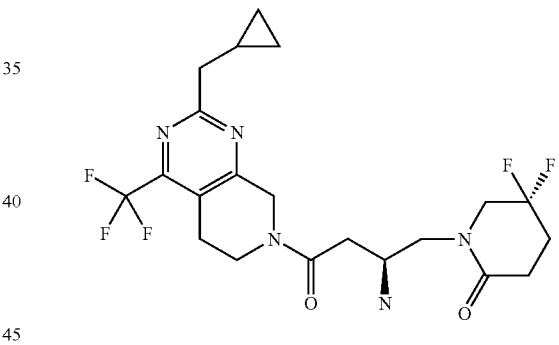

35.9 mg of the title compound was obtained in a yield of 66% at the same manner as in EXAMPLE 22, using 61 mg (0.106 mmole) of t-butyl {(1S)-3-[2-(cyclopropylmethyl)-4-(trifluoromethyl)-5,8-dihydropyrido[3,4-d]pyrimidin-7(6H)-yl]-1-[(5,5-difluoro-2-oxopiperidin-1-yl)methyl]-3-oxpropyl}carbamate obtained in PREPARATION 102.

$^1$H NMR (CD$_3$OD) δ 4.67-4.55 (2H, m), 3.62-3.54 (4H, m), 3.30-3.23 (3H, m), 2.87-2.77 (2H, m), 2.62-2.60 (2H, m), 2.48-2.27 (4H, m), 2.17-2.06 (2H, m), 1.03-0.98 (1H, m), 0.31-0.26 (2H, m), 0.07-0.04 (2H, m)

Mass (m/e) 476 (M+1)

PREPARATION 103

Synthesis of t-butyl {(1S)-1-{[(5R)-5-methyl-2-oxopiperidin-1-yl]methyl}-3-oxo-3-[2-pyridin-4-yl-4-(trifluoromethyl)-5,8-dihydropyrido[3,4-d]pyrimidin-7(6H)-yl]propyl}carbamate 50 mg of the title compound was obtained in a yield of 62% at the same manner as in PREPARATION 45, using 44.0 mg (0.140 mmole) of (3S)-3-[(t-butoxycarbonyl)amino]-4-[(5R)-5-methyl-2-oxopiperidin-1-yl]butanoic acid obtained in PREPARATION 51 and 45.0 mg (0.127 mmole) of 2-pyridin-4-yl-4-(trifluoromethyl)-5,6,7,8-tetrahydropyrido[3,4-d]pyrimidine hydrochloric acid salt obtained in PREPARATION 91.

$^1$H NMR (CDCl$_3$) δ 8.80-8.79 (2H, m), 8.31 (2H, m), 5.89 (1H, brs), 5.03-4.79 (2H, m), 4.20 (1H, brs), 3.94 (1H, brs), 3.70 (1H, brs), 3.60-3.46 (2H, m), 3.39-3.36 (1H, m), 3.17-3.04 (3H, m), 2.87 (1H, brs), 2.56-2.51 (1H, m), 2.44-2.31 (2H, m), 1.96 (1H, brs), 1.82 (2H, brs), 1.43-1.41 (9H, m), 1.00 (3H, d, J=6.4 Hz)

Mass 577 (m/e) (M+1)

EXAMPLE 56

Synthesis of (5R)-1-{(2S)-2-amino-4-oxo-4-[2-pyridin-4-yl-4-(trifluoromethyl)-5,8-dihydropyrido[3,4-d]pyrimidin-7(6H)-yl]butyl}-5-methylpiperidin-2-one

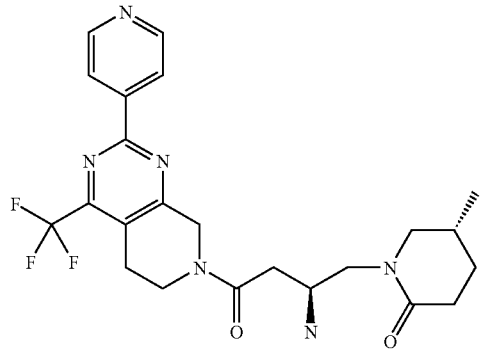

33.6 mg of the title compound was obtained in a yield of 81% at the same manner as in EXAMPLE 22, using 50 mg (0.087 mmole) of t-butyl {(1S)-1-{[(5R)-5-methyl-2-oxopiperidin-1-yl]methyl}-3-oxo-3-[2-pyridin-4-yl-4-(trifluoromethyl)-5,8-dihydropyrido[3,4-d]pyrimidin-7(6H)-yl]propyl}carbamate obtained in PREPARATION 103.

$^1$H NMR (CD$_3$OD) δ 8.77-8.75 (2H, m), 8.44-8.42 (2H, m), 5.05-4.93 (2H, m), 3.98-3.91 (2H, m), 3.57-3.39 (4H, m), 3.22-3.20 (1H, m), 3.12-3.05 (2H, m), 2.78-2.73 (1H, m), 2.66-2.58 (1H, m), 2.47-2.32 (2H, m), 2.05-2.03 (1H, m), 1.88-1.84 (1H, m), 1.60-1.48 (1H, m), 1.06-1.03 (3H, m)

Mass (m/e) 477 (M+1)

PREPARATION 104

Synthesis of t-butyl {(1S)-1-[(5,5-difluoro-2-oxopiperidin-1-yl)methyl]-3-oxo-3-[2-pyridin-4-yl-4-(trifluoromethyl)-5,8-dihydropyrido[3,4-d]pyrimidin-7(6H)-yl]propyl}carbamate 65 mg of the title compound was obtained in a yield of 78% at the same manner as in PREPARATION 45, using 47.0 mg (0.140 mmole) of (3S)-3-[(t-butoxycarbonyl)amino]-4-(5,5-difluoro-2-oxopiperidin-1-yl)butanoic acid obtained in PREPARATION 57 and 45.0 mg (0.127 mmole) of 2-pyridin-4-yl-4-(trifluoromethyl)-5,6,7,8-tetrahydropyrido[3,4-d]pyrimidine hydrochloric acid salt obtained PREPARATION 91.

$^1$H NMR (CDCl$_3$) δ 8.81 (2H, brs), 8.32-8.31 (2H, m), 5.81 (1H, brs), 4.98-4.96 (1H, m), 4.85-4.83 (1H, m), 4.23 (1H, brs), 3.95 (1H, brs), 3.81-3.73 (3H, m), 3.62-3.49 (2H, m), 3.16-3.10 (2H, m), 2.89-2.85 (1H, m), 2.62-2.55 (3H, m), 2.28 (2H, m), 1.42 (9H, s)

Mass (m/e) 599 (M+1)

EXAMPLE 57

Synthesis of 1-{(2S)-2-amino-4-oxo-4-[2-pyridin-4-yl-4-(trifluoromethyl)-5,8-dihydropyrido[3,4-d]pyrimidin-7(6H)-yl]butyl}-5,5-difluoropiperidin-2-one

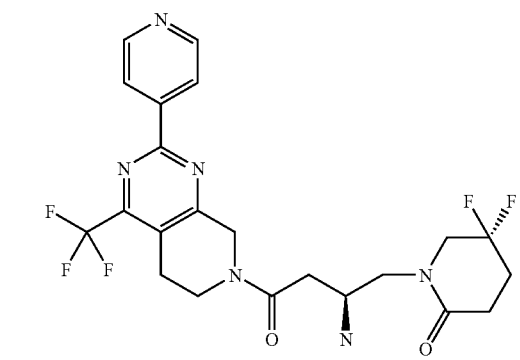

34.4 mg of the title compound was obtained in a yield of 64% at the same manner as in EXAMPLE 22, using 65 mg (0.109 mmole) of t-butyl {(1S)-1-[(5,5-difluoro-2-oxopiperidin-1-yl)methyl]-3-oxo-3-[2-pyridin-4-yl-4-(trifluoromethyl)-5,8-dihydropyrido[3,4-d]pyrimidin-7(6H)-yl]propyl}carbamate obtained in PREPARATION 104.

$^1$H NMR (CD$_3$OD) δ 8.77-8.75 (2H, m), 8.45-8.43 (2H, m), 5.06-4.86 (2H, m), 4.00-3.88 (2H, m), 3.85-3.78 (2H, m), 3.58-3.49 (3H, m), 3.21-3.11 (2H, m), 2.75-2.70 (1H, m), 2.64-2.54 (3H, m), 2.37-2.33 (2H, m)

Mass (m/e) 499 (M+1)

PREPARATION 105

Synthesis of t-butyl [(1S)-3-[2-(4-fluorobenzyl)-4-(trifluoromethyl)-5,8-dihydropyrido[3,4-d]pyrimidin-7(6H)-yl]-1-{[(5R)-5-methyl-2-oxopiperidin-1-yl]methyl}-3-oxpropyl]carbamate 70 mg of the title compound was obtained in a yield of 96% at the same manner as in PREPARATION 45, using 38.0 mg (0.120 mmole) of (3S)-3-[(t-butoxycarbonyl)amino]-4-[(5R)-5-methyl-2-oxopiperidin-1-yl]butanoic acid obtained in PREPARATION 51 and 38.0 mg (0.109 mmole) of 2-(4-fluorobenzyl)-4-(trifluoromethyl)-5,6,7,8-tetrahydropyrido[3,4-d]pyrimidine hydrochloric acid salt obtained in PREPARATION 92.

$^1$H NMR (CDCl$_3$) δ 7.34-7.32 (2H, m), 7.00-6.96 (2H, m), 5.86-5.85 (1H, m), 4.85-4.80 (1H, m), 4.73-4.61 (1H, m), 4.23-4.15 (2H, m), 3.86-3.83 (1H, m), 3.74-3.68 (2H, m), 3.56-3.47 (2H, m), 3.36-3.33 (1H, m), 3.06-2.95 (3H, m), 2.85-2.77 (1H, m), 2.50-2.83 (4H, m), 1.92 (1H, brs), 1.79 (2H, brs), 1.40-1.38 (9H, m), 0.99 (3H, d, J=6.7 Hz)

Mass (m/e) 608 (M+1)

EXAMPLE 58

Synthesis of (5R)-1-{(2S)-2-amino-4-[2-(4-fluorobenzyl)-4-(trifluoromethyl)-5,8-dihydropyrido[3,4-d]pyrimidin-7(6H)-yl]-4-oxobutyl}-5-methylpiperidin-2-one

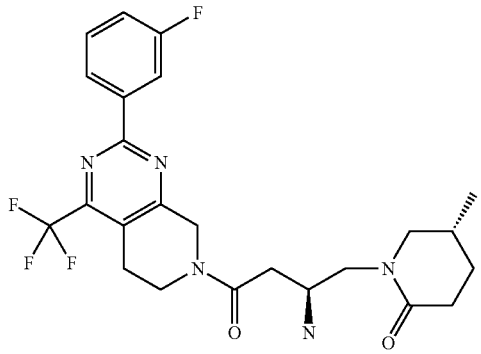

49.7 mg of the title compound was obtained in a yield of 85% at the same manner as in EXAMPLE 22, using 77 mg (0.115 mmole) of t-butyl [(1S)-3-[2-(4-fluorobenzyl)-4-(trifluoromethyl)-5,8-dihydropyrido[3,4-d]pyrimidin-7(6H)-yl]-1-{[(5R)-5-methyl-2-oxopiperidin-1-yl]methyl}-3-oxpropyl]carbamate obtained in PREPARATION 105.

$^1$H NMR (CD$_3$OD) δ 7.39-7.36 (2H, m), 7.04-7.00 (2H, m), 4.86-4.77 (2H, m), 4.28-4.27 (2H, m), 3.86-3.83 (2H, m), 3.50-3.37 (4H, m), 3.09-2.99 (3H, m), 2.73-2.66 (1H, m), 2.61-2.53 (1H, m), 2.43-2.29 (2H, m), 2.02-1.98 (1H, m), 1.85-1.82 (1H, m), 1.56-1.46 (1H, m), 1.03 (3H, d, J=6.4 Hz)

Mass (m/e) 508 (M+1)

PREPARATION 106

Synthesis of t-butyl {(1S)-1-[(5,5-difluoro-2-oxopiperidin-1-yl)methyl]-3-[2-(4-fluorobenzyl)-4-(trifluoromethyl)-5,8-dihydropyrido[3,4-d]pyrimidin-7(6H)-yl]-3-oxpropyl}carbamate 66 mg of the title compound was obtained in a yield of 87% at the same manner as in PREPARATION 45, using 40.3 mg (0.120 mmole) of (3S)-3-[(t-butoxycarbonyl)amino]-4-(5,5-difluoro-2-oxopiperidin-1-yl)butanoic acid obtained in PREPARATION 57 and 38.0 mg (0.109 mmole) of 2-(4-fluorobenzyl)-4-(trifluoromethyl)-5,6,7,8-tetrahydropyrido[3,4-d]pyrimidine hydrochloric acid salt obtained in PREPARATION 92.

$^1$H NMR (CDCl$_3$) δ 7.35-7.26 (2H, m), 7.00-6.97 (2H, m), 5.77-5.75 (1H, m), 4.85-4.80 (1H, m), 4.70-4.61 (1H, m), 4.24-4.18 (3H, m), 3.86-3.84 (1H, m), 3.76-3.67 (2H, m), 3.59-3.48 (3H, m), 3.07-2.97 (2H, m), 2.83-2.76 (1H, m), 2.57-2.49 (3H, m), 2.28-2.19 (2H, m) 1.40 (9H, s)

Mass (m/e) 630 (M+1-Boc)

EXAMPLE 59

Synthesis of 1-{(2S)-2-amino-4-[2-(4-fluorobenzyl)-4-(trifluoromethyl)-5,8-dihydropyrido[3,4-d]pyrimidin-7(6H)-yl]-4-oxobutyl}-5,5-difluoropiperidin-2-one

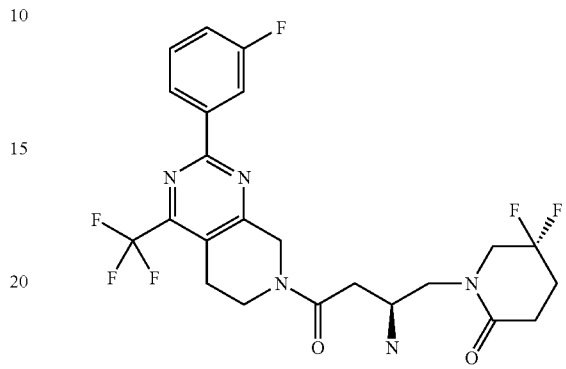

44.4 mg of the title compound was obtained in a yield of 80% at the same manner as in EXAMPLE 22, using 66.0 mg (0.105 mmole) of t-butyl {(1S)-1-[(5,5-difluoro-2-oxopiperidin-1-yl)methyl]-3-[2-(4-fluorobenzyl)-4-(trifluoromethyl)-5,8-dihydropyrido[3,4-d]pyrimidin-7(6H)-yl]-3-oxpropyl}carbamate obtained in PREPARATION 106.

$^1$H NMR (CD$_3$OD) δ 7.39-7.36 (2H, m), 7.04-7.00 (2H, m), 4.89-4.81 (2H, m), 4.28-4.27 (2H, m), 3.88-3.77 (4H, m), 3.53-3.47 (3H, m), 3.09-2.99 (2H, m), 2.66-2.61 (1H, m), 2.58-2.49 (3H, m), 2.40-2.29 (2H, m)

Mass (m/e) 530 (M+1)

PREPARATION 107

Synthesis of t-butyl {(1S)-1-{[(5R)-5-methyl-2-oxopiperidin-1-yl]methyl}-3-oxo-3-[2-(3-thienyl)-4-(trifluoromethyl)-5,8-dihydropyrido[3,4-d]pyrimidin-7(6H)-yl]propyl}carbamate 75.0 mg of the title compound was obtained in a yield of 94% at the same manner as in PREPARATION 45, using 43.0 mg (0.137 mmole) of (3S)-3-[(t-butoxycarbonyl)amino]-4-[(5R)-5-methyl-2-oxopiperidin-1-yl]butanoic acid PREPARATION 51 and 40.0 mg (0.124 mmole) of 2-(3-thienyl)-4-(trifluoromethyl)-5,6,7,8-tetrahydropyrido[3,4-d]pyrimidine hydrochloric acid salt obtained in PREPARATION 95.

$^1$H NMR (CDCl$_3$) δ 8.38-8.37 (1H, m), 7.93-7.91 (1H, m), 7.43-7.40 (1H, m), 5.90-5.88 (1H, m), 5.33 (1H, s), 4.92-4.74 (1H, m), 4.23-4.13 (1H, m), 3.98-3.92 (1H, m), 3.84-3.81 (1H, m), 3.73-3.51 (2H, m), 3.42-3.28 (1H, m), 3.13-3.04 (3H, m), 2.93-2.87 (1H, m), 2.59-2.54 (1H, m), 2.48-2.32 (2H, m), 2.00-1.84 (3H, m), 1.46-1.44 (9H, m) 1.04-1.03 (3H, m)

Mass (m/e) 582 (M+1)

EXAMPLE 60

Synthesis of (5R)-1-{(2S)-2-amino-4-oxo-4-[2-(3-thienyl)-4-(trifluoromethyl)-5,8-dihydropyrido[3,4-d]pyrimidin-7(6H)-yl]butyl}-5-methylpiperidin-2-one

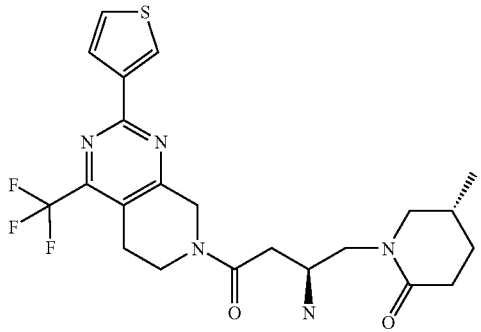

54.4 mg of the title compound was obtained in a yield of 88% at the same manner as in EXAMPLE 22, using 75.0 mg (0.129 mmole) of t-butyl {(1S)-1-{[(5R)-5-methyl-2-oxopiperidin-1-yl]methyl}-3-oxo-3-[2-(3-thienyl)-4-(trifluoromethyl)-5,8-dihydropyrido[3,4-d]pyrimidin-7(6H)-yl]propyl}carbamate obtained in PREPARATION 107.

$^1$H NMR (CD$_3$OD) δ 8.41-8.40 (1H, m), 7.90-7.88 (1H, m), 7.54-7.52 (1H, m), 4.97-4.86 (2H, m), 3.96-3.86 (2H, m), 3.67-3.63 (1H, m), 3.57-3.45 (2H, m), 3.42-3.37 (1H, m), 3.13-3.03 (3H, m), 2.80-2.76 (1H, m), 2.68-2.59 (1H, m), 2.46-2.32 (2H, m), 2.01 (1H, brs), 1.84-1.82 (1H, m), 1.58-1.51 (1H, m), 1.06-1.03 (3H, m)

Mass (m/e) 482 (M+1)

PREPARATION 108

Synthesis of t-butyl {(1S)-1-[(5,5-difluoro-2-oxopiperidin-1-yl)methyl]-3-oxo-3-[2-(3-thienyl)-4-(trifluoromethyl)-5,8-dihydropyrido[3,4-d]pyrimidin-7(6H)-yl]propyl}carbamate 66.0 mg of the title compound was obtained in a yield of 80% at the same manner as in PREPARATION 45, using 43 mg (0.137 mmole) of (3S)-3-[(t-butoxycarbonyl)amino]-4-(5,5-difluoro-2-oxopiperidin-1-yl) butanoic acid obtained in PREPARATION 57 and 40.0 mg (0.124 mmole) of 2-(3-thienyl)-4-(trifluoromethyl)-5,6,7,8-tetrahydropyrido[3,4-d]pyrimidine hydrochloric acid salt obtained in PREPARATION 93.

$^1$H NMR (CD$_3$OD) δ 8.35-8.34 (1H, m), 7.89-7.87 (1H, m), 7.40-7.37 (1H, m), 5.79-5.77 (1H, m), 4.88 (1H, s), 4.80-4.69 (1H, m), 4.23 (1H, brs), 3.92-3.89 (1H, m), 3.78-3.66 (3H, m), 3.60-3.55 (2H, m), 3.08-3.01 (2H, m), 2.87-2.83 (1H, m), 2.62-2.53 (3H, m), 2.35-2.23 (2H, m), 1.42-1.41 (9H, m)

Mass (m/e) 604 (M+1)

EXAMPLE 61

Synthesis of 1-{(2S)-2-amino-4-oxo-4-[2-(3-thienyl)-4-(trifluoromethyl)-5,8-dihydropyrido[3,4-d]pyrimidin-7(6H)-yl]butyl}-5,5-difluoropiperidin-2-one

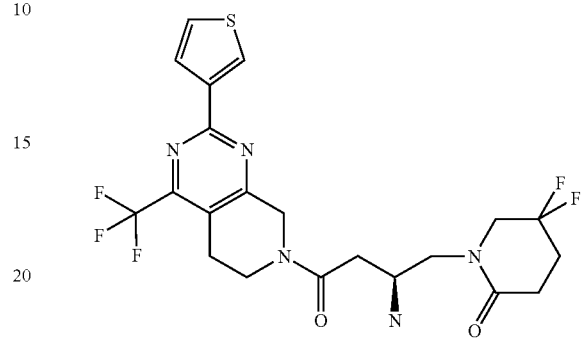

44.0 mg of the title compound was obtained in a yield of 80% at the same manner as in EXAMPLE 22, using 66 mg (0.109 mmole) of t-butyl {(1S)-1-[(5,5-difluoro-2-oxopiperidin-1-yl)methyl]-3-oxo-3-[2-(3-thienyl)-4-(trifluoromethyl)-5,8-dihydropyrido[3,4-d]pyrimidin-7(6H)-yl]propyl}carbamate obtained in PREPARATION 108.

$^1$H NMR (CD$_3$OD) δ 8.41-8.40 (1H, m), 7.90-7.88 (1H, m), 7.55-7.52 (1H, m), 4.95-4.89 (2H, m), 3.88-3.79 (4H, m), 3.58-3.53 (1H, m), 3.50-3.45 (2H, m), 3.12-3.02 (2H, m), 2.74-2.68 (1H, m), 2.62-2.51 (3H, m), 2.40-2.33 (2H, m)

Mass (m/e) 504 (M+1)

PREPARATION 109

Synthesis of t-butyl {(1S)-1-{[(5R)-5-methyl-2-oxopiperidin-1-yl]methyl}-3-oxo-3-[2-(2-thienyl)-4-(trifluoromethyl)-5,8-dihydropyrido[3,4-d]pyrimidin-7(6H)-yl]propyl}carbamate 80.0 mg of the title compound was obtained in a yield of 100% at the same manner as in PREPARATION 45, using 43.0 mg (0.137 mmole) of (3S)-3-[(t-butoxycarbonyl)amino]-4-[(5R)-5-methyl-2-oxopiperidin-1-yl]butanoic acid obtained in PREPARATION 51 and 40.0 mg (0.124 mmole) of 2-(2-thienyl)-4-(trifluoromethyl)-5,6,7,8-tetrahydropyrido[3,4-d]pyrimidine hydrochloric acid salt obtained in PREPARATION 94.

$^1$H NMR (CDCl$_3$) δ 8.05-8.04 (1H, m), 7.52-7.51 (1H, m), 7.16-7.13 (1H, m), 5.89 (1H, brs), 4.87 (1H, s), 4.76-4.69 (1H, m), 4.25-4.18 (1H, m), 3.91-3.88 (1H, m), 3.80-3.77 (1H, m), 3.67-3.51 (3H, m), 3.38-3.27 (1H, m), 3.11-2.99 (3H, m), 2.89-2.83 (1H, m), 2.56-2.28 (3H, m), 2.01-1.91 (1H, m), 1.85-1.81 (1H, m), 1.42-1.41 (9H, m), 1.00 (3H, d, J=6.8 Hz)

Mass (m/e) 582 (M+1)

EXAMPLE 62

Synthesis of (5R)-1-{(2S)-2-amino-4-oxo-4-[2-(2-thienyl)-4-(trifluoromethyl)-5,8-dihydropyrido[3,4-d]pyrimidin-7(6H)-yl]butyl}-5-methylpiperidin-2-one

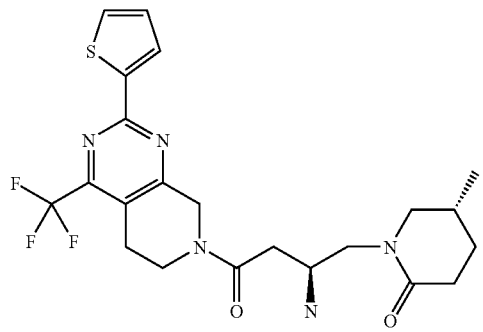

58.6 mg of the title compound was obtained in a yield of 89% at the same manner as in EXAMPLE 22, using 80.0 mg (0.138 mmole) of t-butyl {(1S)-1-{[(5R)-5-methyl-2-oxopiperidin-1-yl]methyl}-3-oxo-3-[2-(2-thienyl)-4-(trifluoromethyl)-5,8-dihydropyrido[3,4-d]pyrimidin-7(6H)-yl]propyl}carbamate obtained in PREPARATION 109.

$^1$H NMR (CD$_3$OD) δ 8.04-8.03 (1H, m), 7.68-7.66 (1H, m), 7.21-7.18 (1H, m), 4.93-4.82 (2H, m), 3.93-3.86 (2H, m), 3.70-3.63 (1H, m), 3.56-3.44 (2H, m), 3.42-3.37 (1H, m), 3.10-3.00 (3H, m), 2.79-2.74 (1H, m), 2.66-2.58 (1H, m), 2.45-2.32 (2H, m), 2.05-2.00 (1H, m), 1.85-1.81 (1H, m), 1.58-1.50 (1H, m), 1.05-1.03 (3H, m)

Mass (m/e) 482 (M+1)

PREPARATION 110

Synthesis of t-butyl {(1S)-1-[(5,5-difluoro-2-oxopiperidin-1-yl)methyl]-3-oxo-3-[2-(2-thienyl)-4-(trifluoromethyl)-5,8-dihydropyrido[3,4-d]pyrimidin-7(6H)-yl]propyl}carbamate 29.0 mg of the title compound was obtained in a yield of 35% at the same manner as in PREPARATION 45, using 43.0 mg (0.137 mmole)
(3S)-3-[(t-butoxycarbonyl)amino]-4-(5,5-difluoro-2-oxopiperidin-1-yl) butanoic acid obtained in PREPARATION 57 and 40.0 mg (0.124 mmole) of 2-(2-thienyl)-4-(trifluoromethyl)-5,6,7,8-tetrahydropyrido[3,4-d]pyrimidine hydrochloric acid salt obtained in PREPARATION 94.

$^1$H NMR (CDCl$_3$) δ 8.10-8.09 (1H, m), 7.57-7.55 (1H, m), 7.21-7.18 (1H, m), 5.83-5.81 (1H, m), 4.95-4.82 (1H, m), 4.81-4.72 (1H, m), 4.30-4.20 (1H, m), 3.95-3.93 (1H, m), 3.82-3.73 (3H, m), 3.63-3.62 (2H, m), 3.11-3.04 (2H, m), 2.90-2.86 (1H, m), 2.66-2.57 (3H, m), 2.36-2.27 (2H, m), 1.46-1.45 (9H, m)

Mass (m/e) 604 (M+1)

EXAMPLE 63

Synthesis of 1-{(2S)-2-amino-4-oxo-4-[2-(2-thienyl)-4-(trifluoromethyl)-5,8-dihydropyrido[3,4-d]pyrimidin-7(6H)-yl]butyl}-5,5-difluoropiperidin-2-one

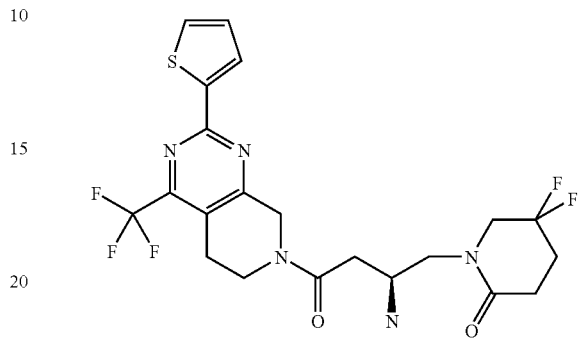

20.3 mg of the title compound was obtained in a yield of 84% at the same manner as in EXAMPLE 22, using 29 mg (0.048 mmole) of t-butyl {(1S)-1-[(5,5-difluoro-2-oxopiperidin-1-yl)methyl]-3-oxo-3-[2-(2-thienyl)-4-(trifluoromethyl)-5,8-dihydropyrido[3,4-d]pyrimidin-7(6H)-yl]propyl}carbamate obtained in PREPARATION 110.

$^1$H NMR (CD$_3$OD) δ 8.06-8.05 (1H, m), 7.67-7.66 (1H, m), 7.21-7.19 (1H, m), 4.94-4.82 (2H, m), 3.94-3.78 (4H, m), 3.54-3.48 (3H, m), 3.11-3.02 (2H, m), 2.74-2.69 (1H, m), 2.62-2.56 (3H, m), 2.40-2.35 (2H, m)

Mass (m/e) 504 (M+1)

PREPARATION 111

Synthesis of t-butyl {(1S)-3-[2-(2-furyl-4-(trifluoromethyl)-5,8-dihydropyrido[3,4-d]pyrimidin-7(6H)-yl]-1-{[(5R)-5-methyl-2-oxopiperidin-1-yl]methyl}3-oxpropyl}carbamate 70.0 mg of the title compound was obtained in a yield of 86% at the same manner as in PREPARATION 45, using 45.3 mg (0.144 mmole) of (3S)-3-[(t-butoxycarbonyl)amino]-4-[(5R)-5-methyl-2-oxopiperidin-1-yl]butanoic acid obtained in PREPARATION 51 and 40.0 mg (0.131 mmole) of 2-(2-furyl)-4-(trifluoromethyl)-5,6,7,8-tetrahydropyrido[3,4-d]pyrimidine hydrochloric acid salt obtained in PREPARATION 95.

$^1$H NMR (CDCl$_3$) δ 7.68-7.65 (1H, m), 7.43-7.38 (1H, m), 6.61-6.59 (1H, m), 5.91-5.89 (1H, m), 4.98-4.87 (1H, m), 4.85-4.74 (1H, m), 4.20 (1H, brs), 3.94-3.89 (1H, m), 3.82-3.78 (1H, m), 3.62-3.48 (3H, m), 3.44-3.36 (1H, m), 3.08-3.01 (3H, m), 2.88-2.81 (1H, m), 2.58-2.28 (3H, m), 2.04 (1H, brs), 1.84-1.82 (1H, m), 1.42-1.40 (9H, m), 1.00 (3H, d, J=6.4 Hz)

Mass (m/e) 566 (M+1-Boc)

EXAMPLE 64

Synthesis of (5R)-1-{(2S)-2-amino-4-[2-(2-furyl)-4-(trifluoromethyl)-5,8-dihydropyrido[3,4-d]pyrimidin-7(6H)-yl]-4-oxobutyl}-5-methylpiperidin-2-one

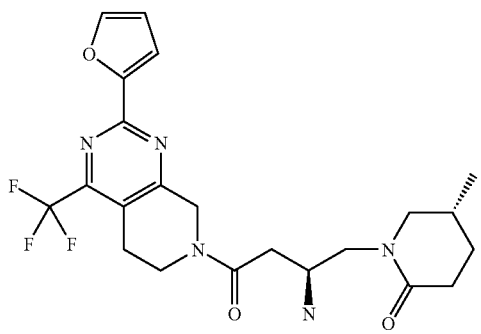

57.7 mg of the title compound was obtained in a yield of 93% at the same manner as in EXAMPLE 22, using 70.0 mg (0.124 mmole) of t-butyl {(1S)-3-[2-(2-furyl)-4-(trifluoromethyl)-5,8-dihydropyrido[3,4-d]pyrimidin-7(6H)-yl]-1-{[(5R)-5-methyl-2-oxopiperidin-1-yl]methyl}3-oxpropyl}carbamate obtained in PREPARATION 111.

$^1$H NMR (CD$_3$OD) δ 7.81 (1H, m), 7.43-7.42 (1H, m), 6.70-6.68 (1H, m), 4.99-4.87 (2H, m), 3.98-3.83 (5H, m), 3.59-3.55 (1H, m), 3.17-3.11 (2H, m), 3.04-2.98 (2H, m), 2.88-2.79 (1H, m), 2.48-2.41 (2H, m), 2.10-2.06 (1H, m), 1.90-1.85 (1H, m), 1.60-1.53 (1H, m), 1.06 (3H, d, J=6.8 Hz)

Mass (m/e) 466 (M+1)

PREPARATION 112

Synthesis of t-butyl {(1S)-1-[(5,5-difluoro-2-oxopiperidin-1-yl)methyl]-3-[2-(2-furyl)-4-(trifluoromethyl)-5,8-dihydropyrido[3,4-d]pyrimidin-7(6H)-yl]-3-oxpropyl}carbamate 75.0 mg of the title compound was obtained in a yield of 89% at the same manner as in PREPARATION 45, using 48 mg (0.144 mmole) of (3S)-3-[(t-butoxycarbonyl)amino]-4-(5,5-difluoro-2-oxopiperidin-1-yl) butanoic acid PREPARATION 57 and 40.0 mg (0.131 mmole) of 2-(2-furyl)-4-(trifluoromethyl)-5,6,7,8-tetrahydropyrido[3,4-d]pyrimidine hydrochloric acid salt obtained in PREPARATION 95.

$^1$H NMR (CDCl$_3$) δ 7.64 (1H, m), 7.40-7.38 (1H, m), 6.60-6.56 (1H, m), 5.82-5.79 (1H, m), 4.95-4.88 (1H, m), 4.80-4.71 (1H, m), 4.20 (1H, brs), 3.92-3.85 (1H, m), 3.78-3.68 (3H, m), 3.60-3.50 (1H, m), 3.10-3.00 (2H, m), 2.85-2.78 (1H, m), 2.60-2.50 (3H, m), 2.30-2.20 (2H, m), 1.40 (9H, s)

Mass (m/e) 588 (M+1)

EXAMPLE 65

Synthesis of 1-{(2S)-2-amino-4-[2-(2-furyl)-4-(trifluoromethyl)-5,8-dihydropyrido[3,4-d]pyrimidin-7(6H)-yl]-4-oxobutyl}-5,5-difluoropiperidin-2-one

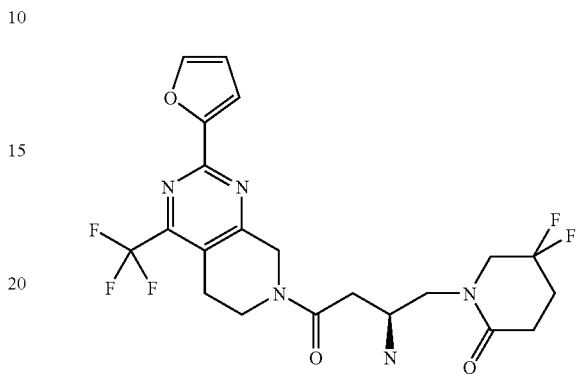

48.9 mg of the title compound was obtained in a yield of 73% at the same manner as in EXAMPLE 22, using 75 mg (0.128 mmole) of t-butyl {(1S)-1-[(5,5-difluoro-2-oxopiperidin-1-yl)methyl]-3-[2-(2-furyl)-4-(trifluoromethyl)-5,8-dihydropyrido[3,4-d]pyrimidin-7(6H)-yl]-3-oxpropyl}carbamate obtained in PREPARATION 112.

$^1$H NMR (CD$_3$OD) δ 7.81-7.80 (1H, m), 7.43-7.42 (1H, m), 6.70-6.68 (1H, m), 4.98-4.88 (2H, m), 3.98-3.75 (6H, m), 3.61-3.50 (1H, m), 3.20-3.10 (1H, m) 3.07-2.99 (2H, m), 2.91-2.83 (1H, m), 2.69-2.62 (2H, m), 2.44-2.34 (2H, m)

Mass (m/e) 488 (M+1)

PREPARATION 113

Synthesis of t-butyl [(1S)-3-[2-(3-furyl)-4-(trifluoromethyl)-5,8-dihydropyrido[3,4-d]pyrimidin-7(6H)-yl]-1-{[(5R)-5-methyl-2-oxopiperidin-1-yl]methyl}3-oxpropyl]carbamate 80.0 mg of the title compound was obtained in a yield of 91% at the same manner as in PREPARATION 45, using 49.0 mg (0.155 mmole) of (3S)-3-[(t-butoxycarbonyl)amino]-4-[(5R)-5-methyl-2-oxopiperidin-1-yl]butanoic acid obtained in PREPARATION 51 and 43.0 mg (0.141 mmole) of 2-(3-furyl)-4-(trifluoromethyl)-5,6,7,8-tetrahydropyrido[3,4-d]pyrimidine hydrochloric acid salt obtained in PREPARATION 96.

$^1$H NMR (CDCl$_3$) δ 8.25 (1H, s), 7.49-7.48 (1H, m), 7.04-7.03 (1H, m), 5.87-5.83 (1H, m), 4.85 (1H, s), 4.74-4.67 (1H, m), 4.18-4.13 (1H, m), 3.89-3.87 (1H, m), 3.80-3.75 (1H, m), 3.62-3.47 (3H, m), 3.40-3.30 (1H, m), 3.07-2.95 (3H, m), 2.87-2.82 (1H, m), 2.52-2.31 (3H, m), 1.93 (1H, brs), 1.80 (1H, brs), 1.41-1.39 (9H, m), 0.99 (3H, d, J=6.9 Hz)

Mass (m/e) 566 (M+1)

EXAMPLE 66

Synthesis of (5R)-1-{(2S)-2-amino-4-[2-(3-furyl)-4-(trifluoromethyl)-5,8-dihydropyrido[3,4-d]pyrimidin-7(6H)-yl]-4-oxobutyl}-5-methylpiperidin-2-one

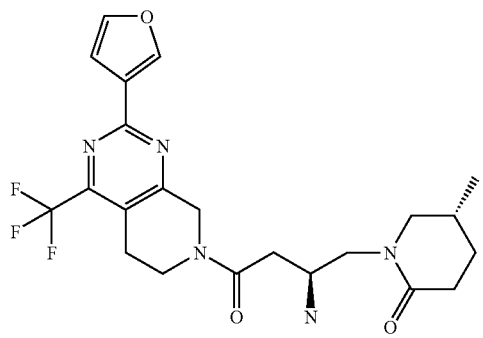

68.1 mg of the title compound was obtained in a yield of 95% at the same manner as in EXAMPLE 22, using 80.0 mg (0.076 mmole) of t-butyl [(1S)-3-[2-(3-furyl)-4-(trifluoromethyl)-5,8-dihydropyrido[3,4-d]pyrimidin-7(6H)-yl]-1-{[(5R)-5-methyl-2-oxopiperidin-1-yl]methyl}3-oxpropyl] carbamate obtained in PREPARATION 113.

$^1$H NMR (CD$_3$OD) δ 8.53 (1H, s), 7.65-7.64 (1H, m), 7.08 (1H, s), 4.97-4.86 (2H, m), 3.96-3.83 (4H, m), 3.69-3.59 (1H, m), 3.43-3.37 (1H, m) 3.20-3.15 (4H, m), 2.88-2.75 (1H, m), 2.50-2.40 (2H, m), 2.06 (1H, brs), 1.88-1.84 (1H, m), 1.60-1.51 (1H, m), 1.07 (3H, d, J=6.4 Hz)

Mass (m/e) 466 (M+1)

PREPARATION 114

Synthesis of t-butyl {(1S)-1-[(5,5-difluoro-2-oxopiperidin-1-yl)methyl]-3-[2-(3-furyl)-4-(trifluoromethyl)-5,8-dihydropyrido[3,4-d]pyrimidin-7(6H)-yl]-3-oxpropyl}carbamate 85.0 mg of the title compound was obtained in a yield of 93% at the same manner as in PREPARATION 45, using 52 mg (0.155 mmole) of (3S)-3-[(t-butoxycarbonyl)amino]-4-(5,5-difluoro-2-oxopiperidin-1-yl) butanoic acid PREPARATION 57 and 43.0 mg (0.141 mmole) of 2-(3-furyl)-4-(trifluoromethyl)-5,6,7,8-tetrahydropyrido[3,4-d]pyrimidine hydrochloric acid salt obtained in PREPARATION 96.

$^1$H NMR (CDCl$_3$) δ 8.26 (1H, s), 7.49 (1H, s), 7.04-7.03 (1H, m), 5.77 (1H, brs), 4.84 (1H, s), 4.75-4.70 (1H, m), 4.20 (1H, brs), 3.88 (1H, brs), 3.75-3.68 (3H, m), 3.59-3.55 (2H, m), 3.06-2.99 (2H, m), 2.83-2.80 (1H, m), 2.58-2.53 (3H, m), 2.25 (2H, m), 1.41-1.40 (9H, m)

Mass (m/e) 588 (M+1)

EXAMPLE 67

Synthesis of 1-{(2S)-2-amino-4-[2-(3-furyl)-4-(trifluoromethyl)-5,8-dihydropyrido[3,4-d]pyrimidin-7(6H)-yl]-4-oxobutyl}-5,5-difluoropiperidin-2-one

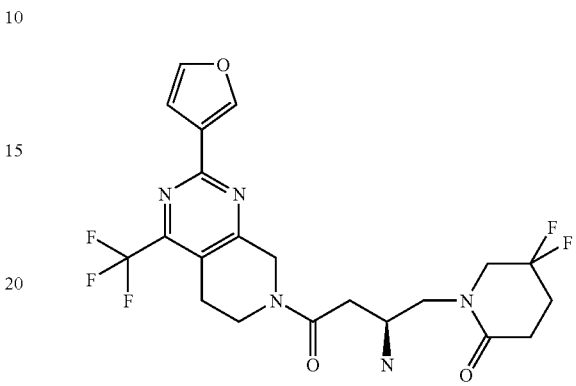

68.8 mg of the title compound was obtained in a yield of 91% at the same manner as in EXAMPLE 22, using 85 mg (0.145 mmole) of t-butyl {(1S)-1-[(5,5-difluoro-2-oxopiperidin-1-yl)methyl]-3-[2-(3-furyl)-4-(trifluoromethyl)-5,8-dihydropyrido[3,4-d]pyrimidin-7(6H)-yl]-3-oxpropyl}carbamate obtained in PREPARATION 114.

$^1$H NMR (CD$_3$OD) δ 8.36 (1H, s), 7.65-7.64 (1H, m), 7.09 (1H, s), 4.97-4.80 (2H, m), 3.98-3.79 (6H, m), 3.54-3.51 (1H, m), 3.15-3.01 (3H, m), 2.89-2.83 (1H, m), 2.65-2.61 (2H, m), 2.42-2.36 (2H, m)

Mass (m/e) 488 (M+1)

PREPARATION 115

Synthesis of t-butyl {(1S)-1-{[(5R)-5-methyl-2-oxopiperidin-1-yl]methyl}-3-oxo-3-[2-(1H-pyrrol-2-yl)-4-(trifluoromethyl)-5,8-dihydropyrido[3,4-d]pyrimidin-7(6H)-yl]propyl}carbamate 43.0 mg of the title compound was obtained in a yield of 88% at the same manner as in PREPARATION 45, using 27.3 mg (0.087 mmole) of (3S)-3-[(t-butoxycarbonyl)amino]-4-[(5R)-5-methyl-2-oxopiperidin-1-yl]butanoic acid obtained in PREPARATION 51 and 24.0 mg (0.079 mmole) of 2-(1H-pyrrol-2-yl)-4-(trifluoromethyl)-5,6,7,8-tetrahydropyrido[3,4-d]pyrimidine hydrochloric acid salt obtained in PREPARATION 98.

$^1$H NMR (CDCl$_3$) δ 9.55 (1H, brs), 7.20-7.18 (1H, m), 7.04 (1H, s), 6.39 (1H, s), 5.91-5.88 (1H, m), 4.86 (1H, s), 4.80-4.69 (1H, m), 4.23-4.17 (1H, m), 3.92-3.90 (1H, m), 3.81-3.79 (1H, m), 3.66-3.54 (1H, m), 3.66-3.54 (2H, m), 3.41-3.38 (1H, m), 3.14-2.87 (4H, m), 2.57-2.37 (3H, m), 1.98 (1H, m), 1.85 (1H, m), 1.45-1.44 (9H, m), 1.06-1.03 (3H, m)

Mass (m/e) 565 (M+1)

EXAMPLE 68

Synthesis of (5R)-1-{(2S)-2-amino-4-oxo-4-[2-(1H-pyrrol-2-yl)-4-(trifluoromethyl)-5,8-dihydropyrido[3,4-d]pyrimidin-7(6H)-yl]butyl}-5-methylpiperidin-2-one

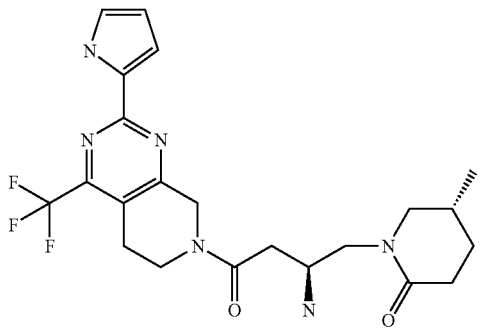

35.2 mg of the title compound was obtained in a yield of 86% at the same manner as in EXAMPLE 22, using 43.0 mg (0.076 mmole) of t-butyl {(1S)-1-{[(5R)-5-methyl-2-oxopiperidin-1-yl]methyl}-3-oxo-3-[2-(1H-pyrrol-2-yl)-4-(trifluoromethyl)-5,8-dihydropyrido[3,4-d]pyrimidin-7(6H)-yl]propyl}carbamate obtained in PREPARATION 115.

$^1$H NMR (CD$_3$OD) δ 7.10-7.09 (1H, m), 7.03-7.00 (1H, m), 6.28-6.26 (1H, m), 4.92-4.83 (2H, m), 3.96-3.93 (2H, m), 3.86-3.83 (2H, m), 3.77-3.66 (1H, m), 3.41-3.36 (1H, m), 3.23-2.83 (5H, m), 2.45-2.41 (2H, m), 2.06 (1H, brs), 1.86 (1H, m), 1.57-1.30 (1H, m), 1.05 (3H, d, J=6.8 Hz)

Mass (m/e) 465 (M+1)

PREPARATION 116

Synthesis of t-butyl {(1S)-1-[(5,5-difluoro-2-oxopiperidin-1-yl)methyl]-3-oxo-3-[2-(1H-pyrrol-2-yl)-4-(trifluoromethyl)-5,8-dihydropyrido[3,4-d]pyrimidin-7(6H)-yl]propyl}carbamate 37.0 mg of the title compound was obtained in a yield of 73% at the same manner as in PREPARATION 45, using 20.0 mg (0.087 mmole) of (3S)-3-[(t-butoxycarbonyl)amino]-4-(5,5-difluoro-2-oxopiperidin-1-yl) butanoic acid obtained in PREPARATION 57 and 24.0 mg (0.079 mmole) of 2-(1H-pyrrol-2-yl)-4-(trifluoromethyl)-5,6,7,8-tetrahydropyrido[3,4-d]pyrimidine hydrochloric acid salt obtained in PREPARATION 98.

$^1$H NMR (CDCl$_3$) δ 9.55 (1H, brs), 7.20-7.18 (1H, m), 7.04 (1H, s), 6.40-6.38 (1H, m), 5.83-5.81 (1H, m), 4.86 (1H, s), 4.77-4.67 (1H, m), 4.27 (1H, brs), 3.94-3.90 (1H, m), 3.83-3.73 (3H, m), 3.64-3.62 (2H, m), 3.07-3.00 (2H, m), 2.90-2.80 (1H, m), 2.65-2.58 (3H, m), 2.36-2.27 (2H, m), 1.46-1.45 (9H, s), Mass (m/e) 587 (M+1)

EXAMPLE 69

Synthesis of 1-{(2S)-2-amino-4-oxo-4-[2-(1H-pyrrol-2-yl)-4-(trifluoromethyl)-5,8-dihydropyrido[3,4-d]pyrimidin-7(6H)-yl]butyl}-5,5-difluoropiperidin-2-one

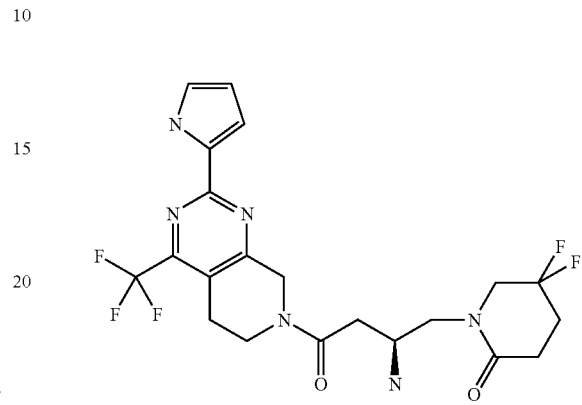

34.9 mg of the title compound was obtained in a yield of 99% at the same manner as in EXAMPLE 22, using 37 mg (0.063 mmole) of t-butyl {(1S)-1-[(5,5-difluoro-2-oxopiperidin-1-yl)methyl]-3-oxo-3-[2-(1H-pyrrol-2-yl)-4-(trifluoromethyl)-5,8-dihydropyrido[3,4-d]pyrimidin-7(6H)-yl]propyl}carbamate obtained in PREPARATION 116.

$^1$H NMR (CD$_3$OD) δ 7.10-7.08 (1H, m), 7.03-7.02 (1H, m), 6.28-6.26 (1H, m), 4.93-4.82 (2H, m), 3.97-3.74 (6H, m), 3.70-3.54 (1H, m), 3.09-2.87 (4H, m), 2.68-2.58 (2H, m), 2.43-2.35 (2H, m)

Mass (m/e) 488 (M+1)

PREPARATION 117

Synthesis of t-butyl {(1S)-1-{[(5R)-5-methyl-2-oxopiperidin-1-yl]methyl}-3-oxo-3-[2-pyridin-3-yl-4-(trifluoromethyl)-5,8-dihydropyrido[3,4-d]pyrimidin-7(6H)-yl]propyl}carbamate 65.6 mg of the title compound was obtained in a yield of 90% at the same manner as in PREPARATION 45, using 40.0 mg (0.127 mmole) of (3S)-3-[(t-butoxycarbonyl)amino]-4-[(5R)-5-methyl-2-oxopiperidin-1-yl]butanoic acid PREPARATION 51 and 40.0 mg (0.126 mmole) of 2-pyridin-3-yl-4-(trifluoromethyl)-5,6,7,8-tetrahydropyrido[3,4-d] pyrimidine hydrochloric acid salt PREPARATION 97.

$^1$H NMR (CDCl$_3$) δ 9.68 (1H, s), 8.78-8.76 (2H, m), 7.50-7.44 (1H, m), 5.94-5.92 (1H, m), 5.04-4.81 (2H, m), 4.24 (1H, brs), 3.98-3.95 (1H, m), 3.87-3.84 (1H, m), 3.62-3.52 (2H, m), 3.44-3.39 (1H, m), 3.18-3.11 (3H, m), 2.89 (1H, m), 2.61-2.57 (1H, m), 2.45-2.35 (3H, m), 1.98 (1H, brs), 1.84 (1H, brs), 1.46-1.44 (9H, m), 1.04 (3H, d, J=8.0 Hz)

Mass (m/e) 577 (M+1)

EXAMPLE 70

Synthesis of (5R)-1-{(2S)-2-amino-4-oxo-4-[2-pyridin-3-yl-4-(trifluoromethyl)-5,8-dihydropyrido[3,4-d]pyrimidin-7(6H)-yl]butyl}-5-methylpiperidin-2-one

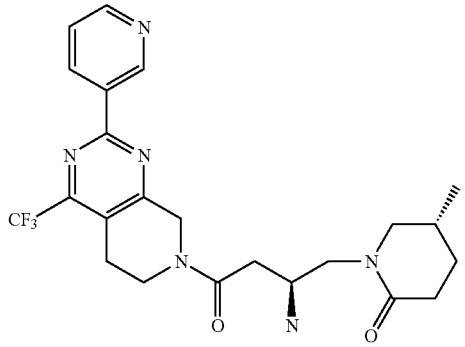

59.7 mg of the title compound was obtained in a yield of 95% at the same manner as in EXAMPLE 22, using 65.6 mg (0.114 mmole) of t-butyl {(1S)-1-{[(5R)-5-methyl-2-oxopiperidin-1-yl]methyl}-3-oxo-3-[2-pyridin-3-yl-4-(trifluoromethyl)-5,8-dihydropyrido[3,4-d]pyrimidin-7(6H)-yl]propyl}carbamate obtained in PREPARATION 117.

$^1$H NMR (CD$_3$OD) δ 9.78 (1H, s), 9.62 (1H, d, 8.4 Hz), 9.07 (1H, d, 5.2 Hz), 8.35-8.32 (1H, m), 5.12-5.01 (2H, m), 4.03-3.95 (3H, m), 3.86-3.75 (1H, m), 3.70-3.59 (1H, m), 3.44-3.37 (1H, m), 3.28 (1H, brs), 3.19-2.96 (2H, m), 2.95-2.90 (2H, m), 2.45-2.42 (2H, m), 2.17 (1H, brs), 1.89-1.84 (1H, m), 1.59-1.54 (1H, m), 1.07 (3H, d, J=6.4 Hz)

Mass (m/e) 477 (M+1)

PREPARATION 118

Synthesis of t-butyl {(1S)-1-[(5,5-difluoro-2-oxopiperidin-1-yl)methyl]-3-oxo-3-[2-pyridin-3-yl-4-(trifluoromethyl)-5,8-dihydropyrido[3,4-d]pyrimidin-7(6H)-yl]propyl}carbamate 71.0 mg of the title compound was obtained in a yield of 93% at the same manner as in PREPARATION 45, using 42.4 mg (0.127 mmole) of (3S)-3-[(t-butoxycarbonyl)amino]-4-(5,5-difluoro-2-oxopiperidin-1-yl) butanoic acid obtained in PREPARATION 57 and 40.0 mg (0.126 mmole) of 2-pyridin-3-yl-4-(trifluoromethyl)-5,6,7,8-tetrahydropyrido[3,4-d]pyrimidine hydrochloric acid salt obtained in PREPARATION 97.

$^1$H NMR (CDCl$_3$) δ 9.67 (1H, s), 8.78-8.74 (2H, m), 7.50-7.41 (1H, m), 5.85-5.84 (1H, m), 5.03-4.92 (1H, m), 4.91-4.78 (1H, m), 4.27-4.22 (1H, m), 3.98-3.95 (1H, m), 3.90-3.73 (3H, m), 3.67-3.57 (2H, m), 3.21-3.09 (2H, m), 2.91-2.87 (1H, m), 2.67-2.56 (3H, m), 2.35-2.30 (2H, m), 1.45 (9H, s)

Mass (m/e) 599 (M+1)

EXAMPLE 71

Synthesis of 1-{(2S)-2-amino-4-oxo-4-[2-pyridin-3-yl-4-(trifluoromethyl)-5,8-dihydropyrido[3,4-d]pyrimidin-7(6H)-yl]butyl}-5,5-difluoropiperidin-2-one

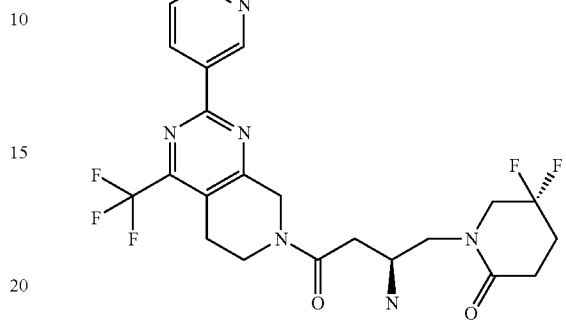

34.4 mg of the title compound was obtained in a yield of 64% at the same manner as in EXAMPLE 22, using 65 mg (0.109 mmole) of t-butyl {(1S)-1-[(5,5-difluoro-2-oxopiperidin-1-yl)methyl]-3-oxo-3-[2-pyridin-3-yl-4-(trifluoromethyl)-5,8-dihydropyrido[3,4-d]pyrimidin-7(6H)-yl]propyl}carbamate obtained in PREPARATION 118.

$^1$H NMR (CD$_3$OD) δ 9.78 (1H, s), 9.62 (1H, d, 8.0 Hz), 9.08 (1H, d, 4.0 Hz), 8.36-8.33 (1H, m), 5.12-5.01 (2H, m), 4.02-3.67 (6H, m), 3.62-3.51 (1H, m), 3.29 (1H, brs), 3.20-3.09 (2H, m), 3.03-2.95 (1H, m), 2.71-2.57 (2H, m), 2.43-2.37 (2H, m)

Mass (m/e) 499 (M+1)

PREPARATION 119

Synthesis of (R)-(2-amino-1-methyl-ethoxy)-acetic acid ethyl ester hydrochloric acid salt (1) Synthesis of (R)-(2-hydroxy-propyl)-carbamic acid t-butyl ester 723 mg (4.1 mmol) of the title compound was obtained in a yield of 61% at the same manner as in PREPARATION 6-(1), except that 500 mg of (R)-1-amino-propane-2-ol (6.65 mmol) was used.

NMR: $^1$H-NMR (CDCl$_3$) δ 4.91 (1H, brs), 3.95~3.85 (1H, m), 3.30-3.22 (1H, m), 3.05~2.95 (1H, m), 1.43 (9H, s), 1.16 (3H, d, J=4 Hz)

Mass (EI) 176 (M$^+$+1)

(2) Synthesis of (R)-(2-t-butoxycarbonylamino-1-methyl-ethoxy)-acetic acid ethyl ester 4.5 g (17.1 mmol) of the title compound was obtained in a yield of 60% at the same manner as in PREPARATION 10-(1), except that 4.93 g (28.1 mmol) of (R)-(2-hydroxy-propyl)-carbamic acid t-butyl ester (product of step 1) was used.

NMR: $^1$H-NMR (CDCl$_3$) δ 5.39 (1H, s), 4.23 (2H, q, J=8 Hz), 4.09 (1H, d, J=16 Hz), 4.00 (1H, d, J=16 Hz), 3.60~3.35 (1H, m), 3.35~3.15 (1H, m), 3.10~3.04 (1H, m), 1.46 (9H, s), 1.31 (3H, t, J=4 Hz), 1.16 (3H, d, J=4 Hz)

Mass (EI) 262 (M$^+$+1)

(3) Synthesis of (R)-(2-amino-1-methyl-ethoxy)-acetic acid ethyl ester hydrochloric acid salt 2.8 g (14 mmol) of the title compound was obtained in a yield of 81% at the same manner as in PREPARATION 10-(2), except that 4.5 g (17.1 mmol) of (R)-(2-t-butoxycarbonylamino-1-methyl-ethoxy)-acetic acid ethyl ester (product of step 1) was used.

NMR: $^1$H-NMR (CDCl$_3$) δ 8.55 (2H, s), 4.25 (2H, q, J=8 Hz), 4.22 (1H, d, J=20 Hz), 4.03 (1H, d, J=20 Hz), 3.80~3.70 (1H, m), 3.27~3.23 (1H, m), 3.03~2.97 (1H, m), 1.29 (3H, t, J=4 Hz), 1.23 (3H, d, J=4 Hz)

Mass (EI) 200 (M$^+$+1)

PREPARATION 120

Synthesis of (S)-5-amino-4-methyl-pentanoic acid methyl ester hydrochloric acid salt

(1) Synthesis of (R)-3-azido-2-methyl-propionic acid methyl ester (R)-3-methanesulfonyloxy-2-methyl-propionic acid methyl ester was obtained at the same manner as in PREPARATION 1-(4) using 5 g of (R)-3-hydroxy-2-methyl-propionic acid methyl ester (42.3 mmol), which was used at the next reaction without any further purification.

(R)-3-methanesulfonyloxy-2-methyl-propionic acid methyl ester was dissolved in 100 mL of dimethylformamide, and then 8.2 g (126 mmol) of sodium azide was added thereto at 60° C., followed by stirring for 24 hours. After addition of 400 mL of ethylacetoacetate and washing with water, an organic layer was dried over anhydrous magnesium sulfate. The solvent was distilled off under reduced pressure, and then the residue was purified by column chromatography to give 2 g (13.9 mmol) of the title compound in a yield of 32%.

2 g (13.9 mmol) of the title compound was obtained in a yield of 32% at the same manner as in PREPARATION 7-(1), PREPARATION 7-(2) in sequence, except that (R)-3-methanesulfonyloxy-2-methyl-propionic acid methyl ester and 5 g (42.3 mmol) of (R)-3-hydroxy-2-methyl-propionic acid methyl ester were used.

NMR: $^1$H-NMR (CDCl$_3$) δ 3.71 (3H, s), 3.54~3.52 (1H, m), 3.40~3.30 (1H, m), 2.80~2.65 (1H, m), 1.20 (3H, d, J=7.2 Hz)

Mass (EI) 144 (M$^+$+1)

(2) Synthesis of (R)-3-t-butoxycarbonylamino-2-methyl-propionic acid methyl ester 1.9 g (8.7 mmol) of the title compound was obtained in a yield of 63% at the same manner in PREPARATION 7-(3), using 2 g (13.7 mmol) of (R)-3-azido-2-methyl-propionic acid methyl ester obtained in the above step (1).

NMR: $^1$H-NMR (CDCl$_3$) δ 4.92 (1H, brs), 3.70 (3H, s), 3.31~3.20 (2H, m), 2.70~2.55 (1H, m), 1.43 (9H, s), 1.15 (3H, d, J=12 Hz)

Mass (EI) 218 (M$^+$+1)

(3) Synthesis of (R)-(3-hydroxy-2-methyl-propyl)-carbamic acid t-butylester 900 mg (4.7 mmol) of the title compound was obtained in a yield of 54% at the same manner in PREPARATION 7-(4), using 1.9 g (8.7 mmol) of (R)-3-t-butoxycarbonylamino-2-methyl-propionic acid methyl ester obtained in the above step (2).

NMR: $^1$H-NMR (CDCl$_3$) δ 4.78 (1H, brs), 3.55~3.50 (1H, m), 3.33~3.20 (2H, m), 3.05~2.98 (1H, m), 1.75~1.65 (1H, m), 1.46 (9H, s), 0.87 (3H, d, J=12 Hz)

Mass (EI) 190 (M$^+$+1)

(4) Synthesis of (R)-(2-methyl-3-oxo-propyl)-carbamic acid t-butylester 850 mg (4.5 mmol) of the title compound was obtained in a yield of 95% at the same manner as in PREPARATION 6-(2), except that 900 mg (4.7 mmol) of (R)-(3-hydroxy-2-methyl-propyl)-carbamic acid t-butylester obtained in the above step (3) was used.

Mass (EI) 188 (M++1)

(5) Synthesis of (S)-5-t-butoxycarbonylamino-4-methyl-2-pentenoic acid methylester 1.19 g (4.4 mmol) of the title compound was obtained in a yield of 97% at the same manner as in PREPARATION 6-(3), except that 850 mg (4.5 mmol) of (R)-(2-methyl-3-oxo-propyl)-carbamic acid t-butylester obtained in the above step (4) was used.

NMR: 1H-NMR (CDCl$_3$) δ 6.84 (1H, dd, J=15 Hz, 10 Hz), 5.84 (1H, d, J=15 Hz), 4.55 (1H, brs), 3.72 (3H, s), 3.25~3.15 (1H, m), 3.06~3.00 (1H, m), 2.54~2.47 (1H, m), 1.42 (9H, s), 1.03 (3H, d, J=15 Hz)

Mass (EI) 244 (M$^+$+1)

(6) Synthesis of (S)-5-t-butoxycarbonylamino-4-methyl-pentanoic acid methylester 790 mg (3.2 mmol) was obtained in a yield of 72% at the same manner as in PREPARATION 7-(7), except that 1.09 g (4.4 mmol) of (S)-5-t-butoxycarbonylamino-4-methyl-2-pentenoic acid methylester obtained in the above step (5) was used NMR: $^1$H-NMR (CDCl$_3$) δ 4.90 (1H, brs), 3.67 (3H, s), 3.06~2.84 (2H, m), 2.43~2.27 (2H, m), 1.75~1.58 (2H, m), 1.48~1.44 (1H, m), 1.44 (9H, s), 0.88 (3H, d, J=6.8 Hz)

Mass (EI) 246 (M$^+$+1)

(7) Synthesis of (S)-5-amino-4-methyl-pentanoic acid methyl ester hydrochloric acid salt 570 mg (3.1 mmol) of the title compound was obtained in a yield of 96% at the same manner as in PREPARATION 1-(4), except that 790 mg (3.2 mmol) of (S)-5-t-butoxycarbonylamino-4-methyl-pentanoic acid methylester obtained in the above step (6) was used.

NMR: $^1$H-NMR (CD$_3$OD) δ 3.69 (3H, s), 2.94~2.89 (1H, m), 2.79~2.74 (1H, m), 2.52~2.36 (2H, m), 1.86~1.74 (2H, m), 1.54~1.47 (1H, m), 1.04 (3H, d, J=7.2 Hz)

Mass (EI) 182 (M$^+$+1)

PREPARATION 121

Synthesis of t-butyl (3S)-3-[(t-butoxycarbonyl)amino]-4-[(5S)-5-methyl-2-oxopiperidin-1-yl]-butanoate 770 mg of the title compound was obtained in a yield of 54% at the same manner as in PREPARATION 42, except that 3S-t-butoxycarbonylamino-4-oxo-butryic acid t-butyl ester (product of PREPARATION 41) and 700 mg (3.85 mmol) of (S)-5-amino-4-methyl-pentanoic acid methyl ester hydrochloric acid salt (product of PREPARATION 120) were used.

$^1$H NMR (CDCl$_3$) δ 5.37 (1H, d, J=7.0 Hz), 4.1-4.2 (1H, m), 3.8-3.9 (1H, m), 3.4-3.5 (1H, m), 3.0-3.1 (1H, m), 2.9 (1H, m), 2.3-2.6 (4H, m), 1.8-2.0 (2H, m), 1.45 (9H, s), 1.41 (9H, s), 1.0 (3H, d, J=7.0 Hz)

Mass (m/e) 371 (M+1)

PREPARATION 122

Synthesis of (3S)-3-[(t-butoxycarbonyl)amino]-4-[(5S)-5-methyl-2-oxopiperidin-1-yl]-butanoic acid 528 mg of the title compound was obtained in a total yield of 81% at the same manner as in PREPARATION 43, except that 770 mg (0.97 mmol) of t-butyl (3S)-3-[(t-butoxycarbonyl)amino]-4-[(5S)-5-methyl-2-oxopiperidin-1-yl]-butanoate (product of PREPARATION 121) was used.

$^1$H NMR (CDCl$_3$) δ 5.6 (1H, m), 3.4-3.7 (3H, m), 3.0-3.1 (2H, m), 2.3-2.6 (4H, m), 1.8-2.0 (2H, m), 1.41 (9H, s), 1.01 (3H, d, J=6.5 Hz)

Mass (m/e) 315 (M+1)

PREPARATION 123

Synthesis of methyl [(2-amino-1-methylethyl)thio]actate (1) Synthesis of t-butyl 3-[(2-methoxy-2-oxoethyl)thio]butanoate A mixture of methyl thioglycolate (0.8 mL, 8.9 mmol), piperidine (0.12 mL, 1.2 mmol) and 2 g (14 mmol) of t-butyl crotonate was stirred at room temperature for 12 hours, followed by distillation under reduced pressure. The reaction solution was purified by column chromatography to give 2.05 g (8.2 mmol) of the title compound in a yield of 92%.

NMR: $^1$H-NMR (CDCl$_3$) δ 3.74 (3H, s), 3.34~3.25 (2H, m), 2.57 (1H, dd, J=6.0 Hz, 15.2 Hz), 2.37 (1H, dd, J=8.4 Hz, 15.6 Hz), 1.84 (1H, dd, J=2 Hz, 7.2 Hz), 1.45 (9H, s), 1.34 (3H, d, J=6.8 Hz)

Mass (EI) 249 (M$^+$+1)

(2) Synthesis of 3-[(2-methoxy-2-oxoethyl)thio]butanoic acid 1.5 g (6.0 mmol) of t-butyl 3-[(2-methoxy-2-oxoethyl)thio]butanoate (product of step 1) was stirred at room temperature with 10 mL of dichloromethane and 5 mL of trifluoroacetic acid for 6 hours, followed by distillation under reduced pressure. After addition of 40 mL of ethylacetoacetate 40 mL and washing with water, an organic layer was dried over anhydrous magnesium sulfate. The solvent was distilled off under reduced pressure and then the residue was purified by column chromatography to give 1 g (5.1 mmol) of the title compound in a yield of 85%.

NMR: $^1$H-NMR (CDCl$_3$) δ 3.75 (3H, s), 3.39~3.27 (3H, m), 2.73 (1H, dd, J=6.4 Hz, 16 Hz), 2.55 (1H, dd, J=7.6 Hz, 16 Hz), 1.39 (3H, d, J=6.8 Hz)

Mass (EI) 193 (M$^+$+1)

(3) Synthesis of methyl [(2-amino-1-methylethyl)thio]acetate 300 mg (1.56 mmol) of 3-[(2-methoxy-2-oxoethyl)thio] butanoic acid (product of step 2) was dissolved in 12 mL of tetrahydrofurane, and then 0.55 mL (3.93 mmol) of triethylamine was dropwise added thereto. 0.4 mL (3.08 mmol) of isobutyl chloroformate was dropwise added at 0° C. After stirring for 1 hour, a solution in which 1.8 g (27.6 mmol) of sodium azide was dissolved in 6 mL of water was poured into the resulting mixture, and then a reaction was conducted for 30 minutes. After addition of 50 mL of ethylacetoacetate and washing with water, an organic layer was dried over anhydrous magnesium sulfate. After the solved was distilled off under reduced pressure, the resulting solution was used without any further purification.

The solution was dissolved in 5 mL of benzene 5 mL, and then triethylamine (0.45 mL, 3.2 mmol) and 4-methoxy benzyl alcohol (0.39 mL, 3.12 mmol) were added thereto, followed by stirring at 80° C. for 1 hour. The solvent was distilled off under reduced pressure, and then the residue was purified by column chromatography to obtain methyl [(2-(4-methoxybenzylamino)-1-methylethyl)thio]acetate.

The above compound was stirred with 4 mL of dichloromethane and 2 mL of trifluoroacetic acid at room temperature for 3 hours. The solvent was distilled off under reduced pressure and then the residue was purified by column chromatography to give 250 mg (1.4 mmol) of the title compound in a yield of 89%.

NMR: $^1$H-NMR (CDCl$_3$) δ 8.05 (2H, s), 3.76 (3H, s), 3.45~3.30 (2H, m), 3.27~3.20 (1H, m), 3.15~3.05 (1H, m), 2.90~2.78 (1H, m), 1.40 (3H, d, J=6.4 Hz)

Mass (EI) 164 (M$^+$+1)

PREPARATION 124

Synthesis of t-butyl (3S)-3-[(t-butoxycarbonyl)amino]-4-(2-methyl-5-oxothiomorpholin-4-yl)-butanoate 210 mg of the title compound was obtained in a yield of 75% at the same manner as in PREPARATION 42, except that 3S-t-butoxycarbonylamino-4-oxo-butryic acid t-butyl ester (product of PREPARATION 41) and 200 mg (0.72 mmol) of methyl [(2-amino-1-methylethyl)thio]acetate obtained in PREPARATION 123 were used.

$^1$H NMR (CDCl$_3$) δ 5.21 (1H, m), 3.9-4.0 (1H, m), 3.7-3.8 (3H, m), 3.2-3.3 (3H, m), 2.5-2.6 (2H, m), 2.3-2.4 (1H, m), 1.44 (9H, s), 1.43 (9H, s), 1.2-1.3 (3H, m)

Mass (m/e) 389 (M+1)

PREPARATION 125

Synthesis of (3S)-3-[(t-butoxycarbonyl)amino]-4-(2-methyl-5-oxothiomorpholin-4-yl)-butanoic acid 50 mg of the title compound was obtained in a total yield of 28% at the same manner as in PREPARATION 43, except that 210 mg (0.54 mmol) of t-butyl (3S)-3-[(t-butoxycarbonyl)amino]-4-(2-methyl-5-oxothiomorpholin-4-yl)-butanoate obtained in PREPARATION 124 was used.

$^1$H NMR (CDCl$_3$) δ 5.61 (1H, br s), 3.5-3.8 (4H, m), 3.2-3.4 (3H, m), 2.5-2.7 (3H, m), 1.41 (9H, s), 1.29 (3H, d, J=7.0 Hz)

Mass (m/e) 233 (M-tBoc)

PREPARATION 126

Synthesis of 2-methyl-4-(trifluoromethyl)-5,6,7,8-tetrahydropyrido[3,4-d]pyrimidine hydrochloric acid salt

(1) Synthesis of t-butyl 2-methyl-4-(trifluoromethyl)-5,8-dihydropyrido[3,4-d]pyrimidin-7(6H)-carboxylate 1.3 mL of sodiumethoxide (21% wt. ethanol solution) was added at room temperature to a solution in which 283 mg (3.0 mmol) of acetamidine hydrochloric acid salt was dissolved in 5 mL of absolute ethanol. After stirring of 15 minutes, to the resulting solution, was added a solution in which 590 mg (2.0 mmol) of t-butyl 3-oxo-4-(trifluoroacetyl)-piperidin-1-carboxylate obtained in PREPARATION 47 was diluted with 5 mL of absolute ethanol. The resulting mixture was heated to 80° C. and stirred for 18 hours. After cooling to room temperature, ethanol was distilled off under reduced pressure, followed by washing with saline which was diluted with ethylacetate. An organic layer was dried over anhydrous magnesium sulfate, the solvent was distilled off under reduced pressure and then the residue was purified by column chromatography (10:1 hexane:ethyl acetate) to give 98 mg of the title compound in a yield of 16%.

$^1$H NMR (CDCl$_3$) δ 4.70 (2H, s), 3.72 (2H, t, J=8.0 Hz), 3.00 (2H, br s), 1.50 (9H, s)

Mass (m/e) 318 (M+1)

(2) Synthesis of 2-methyl-4-(trifluoromethyl)-5,6,7,8-tetrahydropyrido[3,4-d]pyrimidine hydrochloric acid salt 70 mg of the title compound was obtained in a yield of 90% at the same manner in PREPARATION 49, using 98 mg (0.306 mmol) of t-butyl 2-methyl-4-(trifluoromethyl)-5,8-dihydropyrido[3,4-d]pyrimidin-7(6H)-carboxylate obtained in the above step (1).

$^1$H NMR (CD$_3$OD) δ 4.45 (2H, s), 3.59 (2H, t, J=7.0 Hz), 3.29 (2H, m), 2.72 (3H, s)

Mass (m/e) 218 (M+1)

PREPARATION 127

Synthesis of 2,4-bis(trifluoromethyl)-5,6,7,8-tetrahydropyrido[3,4-d]pyrimidine hydrochloric acid salt

(1) Synthesis of t-butyl 2,4-bis(trifluoromethyl)-5,8-dihydropyrido[3,4-d]pyrimidin-7(6H)-carboxylate 800 mg (2.71 mmol) of t-butyl 3-oxo-4-(trifluoroacetyl)piperidin-1-carboxylate obtained in PREPARATION 47 and 455 mg (4.06 mmol) of trifluoroacetamidine were stirred in 25 mL of ethanol for 15 hours, with heating to 90° C. After cooling to room temperature, ethanol was removed, then the resulting solution was diluted with ethylacetate, followed by washing with saline. An organic layer was dried over anhydrous magnesium sulfate, the solvent was distilled off under reduced pressure and then the residue was purified by column chromatography (10:1 hexane:ethyl acetate) to give 230 mg of the title compound in a yield of 23%.

$^1$H NMR (CDCl$_3$) δ 4.67 (2H, s), 3.72 (2H, t, J=8.0 Hz), 3.12 (2H, br s), 1.52 (9H, s)

Mass (m/e) 372 (M+1)

(2) Synthesis of 2,4-bis(trifluoromethyl)-5,6,7,8-tetrahydropyrido[3,4-d]pyrimidine hydrochloric acid salt 184 mg of the title compound was obtained in a yield of 96% at the same manner as in PREPARATION 49, except that 230 mg (0.62 mmol) of t-butyl 2,4-bis(trifluoromethyl)-5,8-dihydropyrido[3,4-d]pyrimidin-7(6H)-carboxylate obtained in the above step (1) was used.

$^1$H NMR (CD$_3$OD) δ 4.66 (2H, s), 3.69 (2H, t, J=7.5 Hz), 3.42 (2H, t, J=7.5 Hz)

Mass (m/e) 272 (M+1)

PREPARATION 128

Synthesis of 2-ethyl-4-(trifluoromethyl)-5,6,7,8-tetrahydropyrido[3,4-d]pyrimidine hydrochloric acid salt

(1) Synthesis of propaneimidamide 9.07 mL (18.14 mmol) of trimethyl aluminum (in 2.0 M toluene) was dropwise added to 40 mL of toluene containing 971 mg (18.1 mmol) of ammonium chloride at room temperature. After stirring for 1.5 hours, 1 g (18.1 mmol) of propionitrile was added thereto, followed by heating to 85° C. for 9 hours. After completion of a reaction, the resulting solution was cooled and then poured in 100 mL of chloroform containing 200 g of silica gel, followed by filtering. The residue was washed with 100 mL of methanol 100 mL and then distillation was conducted to give 1.01 g (14 mmol) of the title compound in a yield of 77%.

NMR: $^1$H-NMR (CD$_3$OD) δ 2.46-2.44 (2H, m), 1.28~1.24 (3H, m)

Mass (EI) 73 (M$^+$+1)

(2) Synthesis of t-butyl 2-ethyl-4-(trifluoromethyl)-5,8-dihydropyrido[3,4-d]pyrimidin-7(6H)-carboxylate 160 mg of the title compound was obtained in a yield of 9% at the same manner as in PREPARATION 48, except that 1.6 g (1.69 mmol) of t-butyl 3-oxo-4-(trifluoroacetyl)piperidin-1-carboxylate obtained in PREPARATION 47 and 508 mg (7.04 mmol) of propaneimidamide obtained in the above step (1) were used.

$^1$H NMR (CDCl$_3$) δ 4.70 (2H, s), 3.72 (2H, t, J=7.0 Hz), 3.0 (2H, m), 3.0 (2H, q, J=7.5 Hz), 1.50 (9H, s), 1.37 (3H, t, J=7.5 Hz)

Mass (m/e) 332 (M+1)

(3) Synthesis of 2-ethyl-4-(trifluoromethyl)-5,6,7,8-tetrahydropyrido[3,4-d]pyrimidine hydrochloric acid salt 60 mg of the title compound was obtained in a yield of 54% at the same manner as in PREPARATION 49, except that 160 mg (0.62 mmol) of t-butyl 2-ethyl-4-(trifluoromethyl)-5,8-dihydropyrido[3,4-d]pyrimidin-7(6H)-carboxylate obtained in the above step (2) was used.

$^1$H NMR (CD$_3$OD) δ 4.29 (2H, s), 3.42 (2H, t, J=7.0 Hz), 3.12 (2H, br s), 2.98 (2H, q, J=7.5 Hz), 1.32 (3H, t, J=7.5 Hz)

Mass (m/e) 232 (M+1)

PREPARATION 129

Synthesis of 2-(pentafluoroethyl)-4-(trifluoromethyl)-5,6,7,8-tetradropyrido[3,4-d]pyrimidine hydrochloric acid salt (1) Synthesis of t-butyl 2-(pentafluoroethyl)-4-(trifluoromethyl)-5,8-dihydropyrido[3,4-d]pyrimidin-7(6H)-carboxylate 820 mg (2.78 mmol) of t-butyl 3-oxo-4-(trifluoroacetyl)piperidin-1-carboxylate obtained in PREPARATION 47 and 585 mg (3.61 mmol) of 2,2,3,3,3-pentafluoropropaneimidadide were added to 50 mL of isopropanol, then 101 of $BF_3OEt_2$ (3%: catalyst amount) was dropwise added, and the resulting mixture was heated to 120° C. and stirred for 17 hours. 1~2 drops of a saturated sodium bicarbonate was added at room temperature, followed by cooling to room temperature. Isopropanol was distilled off under reduced pressure and then the residue was purified by column:chromatography (10:1 hexane:ethyl acetate) to give 690 mg of the title compound in a yield of 59%.

$^1$H NMR (CDCl$_3$) δ 4.84 (2H, s), 3.77 (2H, t, J=5.5 Hz), 3.11 (2H, br s), 1.50 (9H, s)

Mass (m/e) 422 (M+1)

(2) Synthesis of 2-(pentafluoroethyl)-4-(trifluoromethyl)-5,6,7,8-tetradropyrido[3,4-d]pyrimidine hydrochloric acid salt 506 mg of the title compound was obtained in a yield of 96% at the same manner as in PREPARATION 49, except that 690 mg (0.08 mmol) of t-butyl-2-(pentafluoroethyl)-4-(trifluoromethyl)-5,8-dihydropyrido[3,4-d]pyrimidin-7(6H)-carboxylate obtained in the above step (1) was used.

$^1$H NMR (CD$_3$OD) δ 4.65 (2H, s), 3.66 (2H, t, J=6.0 Hz), 3.40 (2H, m)

Mass (m/e) 322 (M+1)

PREPARATION 130

Synthesis of 2-isopropyl-4-(trifluoromethyl)-5,6,7,8-tetradropyrido[3,4-d]pyrimidine hydrochloric acid salt (1) Synthesis of 2-methylpropaneimidamide 14.5 mL (29 mmol) of trimethyl aluminum (2.0 M toluene solution) was dropwise added to a 20 mL of toluene containing 1.55 g (28.9 mmol) of ammonium chloride at room temperature. After stirring for 1.5 hours, 2 g (28.9 mmol) of isobutironitrile was added thereto and the resulting mixture was heated to 85° C. for 9 hours. After completion of a reaction, the reaction solution was poured into 200 mL of chloroform containing 500 g of silicagel and filtered. The residue was washed with 200 mL of methanol and distillation was conducted to give 2.3 g (26.7 mmol) of the title compound in a yield of 92%.

Mass (EI) 87 (M$^+$+1)

(2) Synthesis of t-butyl 2-isopropyl-4-(trifluoromethyl)-5,8-dihydropyrido[3,4-d]pyrimidin-7(6H)-carboxylate 174 mg of the title compound was obtained in a yield of 17% at the same manner as in PREPARATION 61, except that 900 mg (3.05 mmol) of t-butyl 3-oxo-4-(trifluoroacetyl)piperidin-1-carboxylate obtained in PREPARATION 47 and 394 mg (4.58 mmol) of 2-methylpropane imidamide obtained in the above step (1) were used.

$^1$H NMR (CDCl$_3$) δ 4.68 (2H, s), 3.70 (2H, t, J=5.5 Hz), 3.21 (1H, m), 2.96 (2H, m), 1.50 (9H, s), 1.33 (6H, d, J=7.0 Hz),

Mass (m/e) 346 (M+1)

(3) Synthesis of 2-isopropyl-4-(trifluoromethyl)-5,6,7,8-tetrahydropyrido[3,4-d]pyrimidine hydrochloric acid salt 80 mg of the title compound was obtained in a yield of 56% at the same manner as in PREPARATION 49, except that 174 mg (0.5 mmol) of t-butyl 2-isopropyl-4-(trifluoromethyl)-5,8-dihydropyrido[3,4-d]pyrimidin-7(6H)-carboxylate obtained in the above step (2) was used.

$^1$H NMR (CD$_3$OD) δ 4.71 (2H, s), 3.59 (2H, t, J=6.0 Hz), 3.22 (3H, m), 1.33 (6H, d, J=7.0 Hz)

Mass (m/e) 246 (M+1)

PREPARATION 131

Synthesis of 2-t-butyl-4-(trifluoromethyl)-5,6,7,8-tetrahydropyrido[3,4-d]pyrimidine hydrochloric acid salt (1) Synthesis of t-butyl 2-t-butyl-4-(trifluoromethyl)-5,8-dihydropyrido[3,4-d]pyrimidin-7(6H)-carboxylate 29 mg of the title compound was obtained in a yield of 3.4% at the same manner as in PREPARATION 48, except that 700 mg (2.37 mmol) of t-butyl 3-oxo-4-(trifluoroacetyl)piperidin-1-carboxylate obtained in PREPARATION 47 and 356 mg (3.56 mmol) of 2,2-dimethylpropaneimidamide were used.

$^1$H NMR (CDCl$_3$) δ 4.67 (2H, s), 3.71 (2H, t, J=6.0 Hz), 2.96 (2H, m), 1.51 (9H, s), 1.39 (9H, s),

Mass (m/e) 360 (M+1)

(2) Synthesis of 2-t-butyl-4-(trifluoromethyl)-5,6,7,8-tetrahydropyrido[3,4-d]pyrimidine hydrochloric acid salt 18 mg of the title compound was obtained in a yield of 90% at the same manner as in PREPARATION 49, except that 29 mg (0.08 mmol) of t-butyl obtained in the above step (1) was used.

$^1$H NMR (CD$_3$OD) δ 4.45 (2H, s), 3.56 (2H, t, J=6.0 Hz), 3.22 (2H, br t, J=6.0 Hz), 1.39 (9H, s)

Mass (m/e) 260 (M+1)

PREPARATION 132

Synthesis of t-butyl {(1S)-[(5,5-difluoro-2-oxopiperidin-1-yl)methyl]-3-[2-ethyl-4-(trifluoromethyl)-5,8-dihydropyrido[3,4-d]pyrimidin-7(6H)-yl]-3-oxpropyl}carbamate 21 mg (0.038 mmol) of the title compound was obtained in a yield of 82% at the same manner as in PREPARATION 45, except that 16 mg (0.047 mmol) of (3S)-3-[(t-butoxycarbonyl)amino]-4-(5,5-difluoro-2-oxopiperidin-1-yl)butanoic acid obtained in PREPARATION 57 and 12 mg (0.046 mmol)

of 2-ethyl-4-(trifluoromethyl)-5,6,7,8-tetrahydropyrido[3,4-d]pyrimidine hydrochloric acid salt obtained in PREPARATION 128 were used.

NMR: $^1$H-NMR (CDCl$_3$) δ 5.79~5.77 (1H, brs), 4.89~4.78 (1H, m), 4.73~4.64 (1H, m), 4.25~4.15 (1H, m), 3.90~3.80 (1H, m), 3.74~3.71 (3H, m), 3.60~3.52 (2H, m), 3.05~2.97 (4H, m), 2.85~2.79 (1H, m), 2.60~2.50 (3H, m), 2.32~2.20 (2H, m), 1.41 (9H, s), 1.38~1.34 (3H, m)

Mass (EI) 550 (M$^+$+1)

EXAMPLE 72

Synthesis of 1-{(2S)-2-amino-4-[2-ethyl-4-(trifluoromethyl)-5,8-dihydropyrido[3,4-d]pyrimidin-7(6H)-yl]-4-oxobutyl}-5,5-difluoropiperidin-2-one hydrochloric acid salt

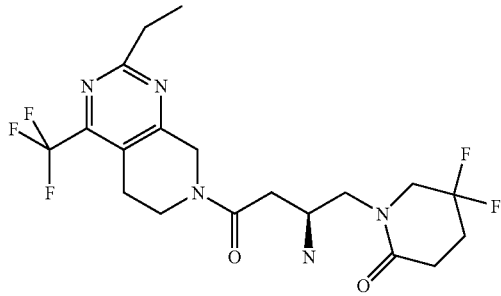

13 mg (0.026 mmol) of the title compound was obtained in a yield of 68% at the same manner as in EXAMPLE 22, except that 21 mg (0.038 mmol) of t-butyl {(1S)-1-[(5,5-difluoro-2-oxopiperidin-1-yl)methyl]-3-[2-ethyl-4-(trifluoromethyl)-5,8-dihydropyrido[3,4-d]pyrimidin-7(6H)-yl]-3-oxpropyl}carbamate obtained in PREPARATION 132 was used.

NMR: $^1$H-NMR (CD$_3$OD) δ 4.73~4.68 (2H, m), 3.80~3.67 (4H, m), 3.56~3.53 (2H, m), 3.38~3.36 (1H, m), 3.00~2.97 (1H, m), 2.91~2.85 (3H, m), 2.69~2.45 (4H, m), 2.27~2.22 (2H, m), 1.27~1.13 (3H, m)

Mass (EI) 450 (M$^+$+1)

PREPARATION 133

Synthesis of t-butyl (1S)-(3-[2-ethyl-4-(trifluoromethyl)-5,8-dihydropyrido[3,4-d]pyrimidin-7(6H)-yl]-1-{[(2S)-2-methyl-5-oxomorpholin-4-yl]methyl}-3-oxopropyl)carbamate 13 mg (0.024 mmol) of the title compound was obtained in a yield of 51% at the same manner as in PREPARATION 45, except that 15 mg (0.047 mmol) of 3S-3-[(t-butoxycarbonyl)amino]-4-[(2S)-2-methyl-5-oxomorpholin-4-yl]butanoic acid obtained in PREPARATION 55 and 12 mg (0.046 mmol) 2-ethyl-4-(trifluoromethyl)-5,6,7,8-tetrahydropyrido[3,4-d]pyrimidine hydrochloric acid salt (product of PREPARATION 128) were used.

NMR: $^1$H-NMR (CDCl$_3$) δ 5.82~5.77 (1H, brs), 4.90~4.78 (1H, m), 4.75~4.64 (1H, m), 4.24~4.09 (3H, m), 3.93~3.83 (2H, m), 3.76~3.74 (1H, m), 3.69~3.62 (1H, m), 3.53~3.47 (1H, m), 3.37~3.30 (2H, m), 3.03~2.97 (4H, m), 2.88~2.81 (1H, m), 2.59~2.49 (1H, m), 1.41 (9H, s), 1.38~1.34 (3H, m), 1.27~1.24 (3H, m)

Mass (EI) 530 (M$^+$+1)

EXAMPLE 73

Synthesis of (6S)-4-{(2S)-2-amino-4-[2-ethyl-4-(trifluoromethyl)-5,8-dihydropyrido[3,4-d]pyrimidin-7(6H)-yl]-4-oxobutyl}-6-methylmorpholine-3-one hydrochloric acid salt

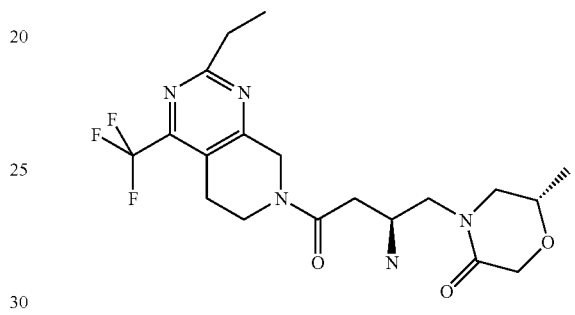

9 mg (0.019 mmol) of the title compound was obtained in a yield of 79% at the same manner as in EXAMPLE 22, except that 13 mg (0.024 mmol) of t-butyl (1S)-(3-[2-ethyl-4-(trifluoromethyl)-5,8-dihydropyrido[3,4-d]pyrimidin-7(6H)-yl]1-{[(2S)-2-methyl-5-oxomorpholin-4-yl]methyl}-3-oxpropyl)carbamate obtained in PREPARATION 133 was used.

NMR: $^1$H-NMR (CD$_3$OD) δ 4.92~4.79 (2H, m), 4.21~4.14 (2H, m), 3.97~3.92 (2H, m), 3.87~3.83 (1H, m), 3.71~3.68 (1H, m), 3.56~3.53 (2H, m), 3.37~3.33 (2H, m), 3.10~2.97 (4H, m), 2.83~2.70 (1H, m), 2.69~2.61 (1H, m), 1.39~1.35 (3H, m), 1.26 (3H, d, J=6.4 Hz)

Mass (EI) 430 (M$^+$+1)

PREPARATION 134

Synthesis of t-butyl {(1S)-1-{[(5,5-difluoro-2-oxopiperidin-1-yl]methyl}-3-[2-isopropyl-4-(trifluoromethyl)-5,8-dihydropyrido[3,4-d]pyrimidin-7(6H)-yl]-3-oxpropyyl}carbamate 26 mg (0.046 mmol) of the title compound was obtained in a yield of 50% at the same manner as in PREPARATION 45, except that 34 mg (0.10 mmol) of (3S)-3-[(t-butoxycarbonyl)amino]-4-(5,5-difluoro-2-oxopiperidin-1-yl)butanoic acid obtained in PREPARATION 57 and 26 mg (0.092 mmol) 2-isopropyl-4-(trifluoromethyl)-5,6,7,8-tetrahydropyrido[3,4-d]pyrimidine hydrochloric acid salt (product of PREPARATION 130) were used.

Mass (EI) 564 (M$^+$+1)

EXAMPLE 74

Synthesis of 1-{(2S)-2-amino-4-[2-isopropyl-4-(trifluoromethyl)-5,8-dihydropyrido[3,4-d]pyrimidin-7(6H)-yl]-4-oxobutyl}-5,5-difluoropiperidin-2-one hydrochloric acid salt

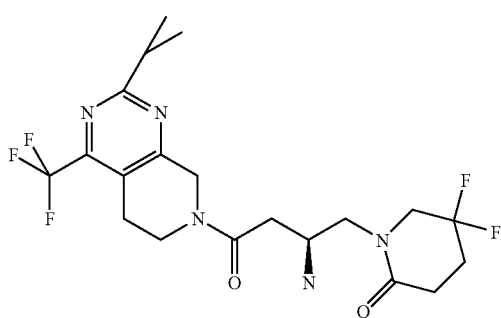

20 mg (0.040 mmol) of the title compound was obtained in a yield of 86% at the same manner as in EXAMPLE 22, except that 26 mg (0.046 mmol) of t-butyl {(1S)-1-[(5,5-difluoro-2-oxopiperidin-1-yl)methyl]-3-[2-isopropyl-4-(trifluoromethyl)-5,8-dihydropyrido[3,4-d]pyrimidin-7(6H)-yl]-3-oxpropyl}carbamate obtained in PREPARATION 134 was used.

NMR: $^1$H-NMR (CD$_3$OD) δ 4.79~4.68 (2H, m), 3.83~3.66 (4H, m), 3.55~3.48 (2H, m), 3.38~3.36 (1H, m), 3.15~3.07 (1H, m), 3.01~2.85 (2H, m), 2.69~2.64 (1H, m), 2.58~2.40 (3H, m), 2.29~2.19 (2H, m), 1.24~1.14 (6H, m)

Mass (EI) 464 (M$^+$+1)

PREPARATION 135

Synthesis of t-butyl (1S)-1-{[(5R)-5-methyl-2-oxopiperidin-1-yl]methyl}-3-[2-isopropyl-4-(trifluoromethyl)-5,8-dihydropyrido[3,4-d]pyrimidin-7(6H)-yl]-3-oxpropyl}carbamate 24 mg (0.044 mmol) of the title compound was obtained in a yield of 47% at the same manner as in PREPARATION 45, except that 32.0 mg (0.10 mmol) of (3S)-3-[(t-butoxycarbonyl)amino]-4-[(5R)-5-methyl-2-oxopiperidin-1-yl]butanoic acid obtained in PREPARATION 51 and 26 mg (0.092 mmol) 2-isopropyl-4-(trifluoromethyl)-5,6,7,8-tetrahydropyrido[3,4-d]pyrimidine hydrochloric acid salt (product of PREPARATION 130) were used.

Mass (EI) 542 (M$^+$+1)

EXAMPLE 75

Synthesis of 1-{(2S)-2-amino-4-[2-isopropyl-4-(trifluoromethyl)-5,8-dihydropyrido[3,4-d]pyrimidin-7(6H)-yl]-4-oxobutyl}-5-methylpiperidin-2-one hydrochloric acid salt

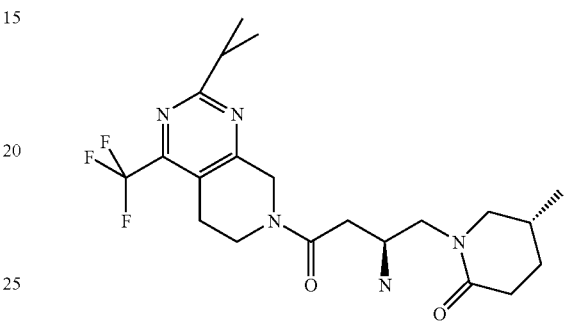

18 mg (0.037 mmol) of the title compound was obtained in a yield of 84% at the same manner as in EXAMPLE 22, except that 24 mg (0.044 mmol) of t-butyl (1S)-1-{[(5R)-5-methyl-2-oxopiperidin-1-yl]methyl}-3-[2-isopropyl-4-(trifluoromethyl)-5,8-dihydropyrido[3,4-d]pyrimidin-7(6H)-yl]-3-oxpropyl}carbamate obtained in PREPARATION 135 was used.

NMR: $^1$H-NMR (CD$_3$OD) δ 4.86~4.78 (2H, m), 3.92~3.83 (2H, m), 3.67~3.62 (1H, m), 3.52~3.48 (2H, m), 3.41~3.37 (1H, m), 3.25~3.20 (1H, m), 3.25~3.20 (2H, m), 3.10~3.00 (1H, m), 2.78~2.72 (1H, m), 2.65~2.58 (1H, m), 2.46~2.32 (2H, m), 2.05~2.00 (1H, m), 1.87~1.80 (1H, m), 1.58~1.47 (1H, m), 1.36~1.36 (6H, m), 1.04 (3H, d, J=6.8 Hz)

Mass (EI) 442 (M$^+$+1)

PREPARATION 136

Synthesis of t-butyl (1S)-1-{[(2R)-2-methyl-5-oxomorpholin-4-yl]methyl}-3-[2-isopropyl-4-(trifluoromethyl)-5,8-dihydropyrido[3,4-d]pyrimidin-7(6H)-yl]-3-oxpropyyl}carbamate 24 mg (0.044 mmol) of the title compound was obtained in a yield of 47% at the same manner as in PREPARATION 45, except that 32.0 mg (0.10 mmol) of (3S)-3-[(t-butoxycarbonyl)amino]-4-[(2S)-2-methyl-5-oxomorpholin-4-yl]butanoic acid obtained in PREPARATION 55 and 26 mg (0.092 mmol) 2-isopropyl-4-(trifluoromethyl)-5,6,7,8-tetrahydropyrido[3,4-d]pyrimidine hydrochloric acid salt (product of PREPARATION 130) were used.

Mass (EI) 544 (M$^+$+1)

EXAMPLE 76

Synthesis of (6S)-4-{(2S)-2-amino-4-[2-isopropyl-4-(trifluoromethyl)-5,8-dihydropyrido[3,4-d]pyrimidin-7(6H)-yl]-4-oxobutyl}-6-methylmorpholine-3-one hydrochloric acid salt

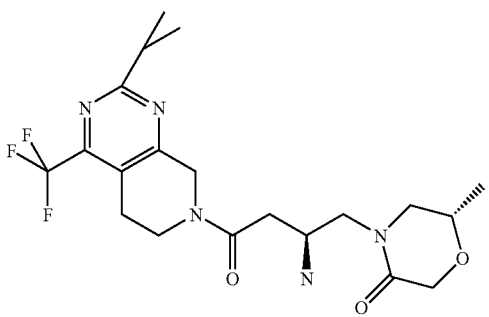

21 mg (0.043 mmol) of the title compound was obtained in a yield of 97% at the same manner as in EXAMPLE 22, except that 24 mg (0.044 mmol) of t-butyl (1S)-1-{[(2R)-2-methyl-5-oxomorpholin-4-yl]methyl}-3-[2-isopropyl-4-(trifluoromethyl)-5,8-dihydropyrido[3,4-d]pyrimidin-7(6H)-yl]-3-oxpropyl}carbamate obtained in PREPARATION 136 was used.

NMR: $^1$H-NMR (CD$_3$OD) δ 4.80~4.78 (2H, m), 4.20~4.08 (2H, m), 3.98~3.79 (3H, m), 3.59~3.52 (2H, m), 3.45~3.32 (3H, m), 3.25~3.20 (1H, m), 3.09~2.94 (2H, m), 2.74~2.69 (1H, m), 2.61~2.53 (1H, m), 1.36~1.34 (6H, m), 1.25 (3H, d, J=6.4 Hz)

Mass (EI) 444 (M$^+$+1)

PREPARATION 137

Synthesis of t-butyl {(1S)-1-{[(2R)-2-methyl-5-oxomorpholin-4-yl]methyl}-3-oxo-3-[3-(trifluoromethyl)-5,6-dihydro[1,2,4]triazolo[4,3-a]pyrazin-7(8H)-yl]propyl}carbamate 300 mg (0.77 mmol) of [1-formyl-3-oxo-3-(3-trifluoromethyl-5,6-dihydro-8H-[1,2,4]triazolo[4,3-a]pyrazin-7-yl)-propyl]-1S-carbamic acid t-butyl ester obtained in PREPARATION 24 and 152 mg (0.77 mmol) of (R)-(2-amino-1-methyl-ethoxy)-acetic acid ethyl ester hydrochloric acid salt (product of PREPARATION 119) and 325 mg (1.54 mmol) of sodium triacetoxyborohydride were reacted in the same manner as in PREPARATION 24 to give 150 mg of the title compound in a yield of 40%

$^1$H NMR (CDCl$_3$) δ 5.8-6.0 (1H, m), 4.8-5.1 (2H, m), 3.8-4.3 (9H, m), 3.6 (1H, m), 3.2-3.4 (2H, m), 2.7-2.9 (1H, m), 2.4-2.6 (1H, m), 1.40 (9H, s), 1.20 (3H, br d, J=6.0 Hz)

Mass (m/e) 491 (M+1)

EXAMPLE 77

Synthesis of (6R)-4-{(2S)-2-amino-4-oxo-4-[3-(trifluoromethyl)-5,6-dihydro[1,2,4]triazolo[4,3-a]pyrazin-7(8H)-yl]butyl}-6-methylmorpholine-3-one

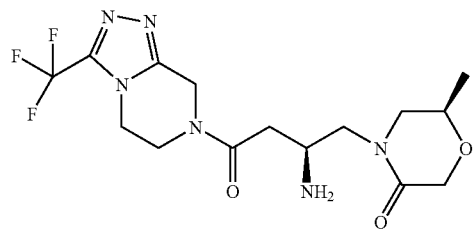

80 mg of the title compound was obtained in a yield of 67% at the same manner as in EXAMPLE 22, except that 150 mg of t-butyl {(1S)-1-{[(2R)-2-methyl-5-oxomorpholin-4-yl]methyl}-3-oxo-3-[3-(trifluoromethyl)-5,6-dihydro[1,2,4]triazolo[4,3-a]pyrazin-7(8H)-yl]propyl}carbamate ethyl acetate/hydrochloric acid obtained in PREPARATION 137 was used.

$^1$H NMR (CD$_3$OD) δ 4.9-5.1 (2H, m), 4.1-4.4 (4H, m), 3.8-4.1 (4H, m), 3.3-3.5 (2H, m), 2.7-3.0 (2H, m), 1.22 (3H, m)

Mass (m/e) 391 (M+1)

PREPARATION 138

Synthesis of t-butyl {(1S)-1-{[(2S)-2-methyl-5-oxomorpholin-4-yl]methyl}-3-oxo-3-[3-(trifluoromethyl)-5,6-dihydro[1,2,4]triazolo[4,3-a]pyrazin-7(8H)-yl]propyl}carbamate 100 mg of the title compound was obtained in a yield of 56% at the same manner as in PREPARATION 45, except that 115 mg (0.36 mmol) of (3S)-3-[(t-butoxycarbonyl)amino]-4-[(2S)-2-methyl-5-oxomorpholin-4-yl]-butanoic acid obtained in PREPARATION 55 and 70 mg (0.36 mmol) of 3-(trifluoromethyl)-5,6-dihydro-8H-[1,2,4]triazolo[4,3-a]pyrazine, which was synthesized with reference to WO 03/004498 were used.

$^1$H NMR (CDCl$_3$) δ 5.87 (1H, m), 4.8-5.1 (2H, m), 3.9-4.3 (7H, m), 3.8-3.9 (1H, m), 3.6-3.7 (1H, m), 3.2-3.4 (3H, m), 2.6-2.9 (2H, m), 1.39 (9H, s), 0.9 (3H, br d, J=7.0 Hz)

Mass (m/e) 491 (M+1)

EXAMPLE 78

Synthesis of (6S)-4-{(2S)-2-amino-4-oxo-4-[3-(trifluoromethyl)-5,6-dihydro[1,2,4]triazolo[4,3-a]pyrazin-7(8H)-yl]butyl}-6-methylmorpholine-3-one

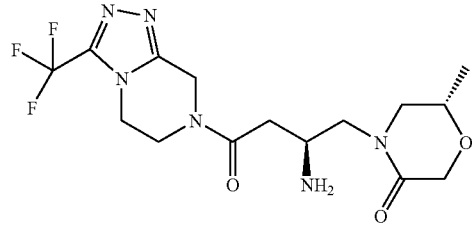

37 mg of the title compound was obtained in a yield of 47% at the same manner as in EXAMPLE 22, except that 100 mg of t-butyl {(1S)-1-{[(2S)-2-methyl-5-oxomorpholin-4-yl]methyl}-3-oxo-3-[3-(trifluoromethyl)-5,6-dihydro[1,2,4]triazolo[4,3-a]pyrazin-7(8H)-yl]propyl}carbamate obtained in PREPARATION 138 was reacted with ethyl acetate/hydrochloric acid.

$^1$H NMR (CD$_3$OD) δ 4.9-5.1 (2H, m), 4.0-4.4 (7H, m), 3.8-4.0 (2H, m), 3.6-3.7 (2H, m), 3.3-3.4 (2H, m), 2.8-3.0 (2H, m), 1.3 (3H, d, J=6.5 Hz)

Mass (m/e) 391 (M+1)

PREPARATION 139

Synthesis of t-butyl {(1S)-1-{[(5S)-5-methyl-2-oxopiperidin-1-yl]methyl}-3-oxo-3-[3-(trifluoromethyl)-5,6-dihydro[1,2,4]triazolo[4,3-a]pyrazin-7(8H)-yl]propyl}carbamate 30 mg of the title compound was obtained in a yield of 38% at the same manner as in PREPARATION 45, except that 50 mg (0.16 mmol) of (3S)-3-[(t-butoxycarbonyl)amino]-4-[(5S)-5-methyl-2-oxopiperidin-1-yl]-butanoic acid obtained in PREPARATION 122 and 31 mg (0.16 mmol) of 3-(trifluoromethyl)-5,6-dihydro-8H-[1,2,4]triazolo[4,3-a]pyrazine synthesized with reference to WO 03/004498 were used.

$^1$H NMR (CDCl$_3$) δ 5.97 (1H, m), 4.8-5.1 (2H, m), 3.9-4.3 (6H, m), 3.3-3.7 (3H, m), 2.7-3.0 (2H, m), 2.2-2.5 (3H, m), 1.7-2.0 (2H, m), 1.39 (9H, s), 0.99 (3H, br d, J=6.5 Hz)

Mass (m/e) 489 (M+1)

EXAMPLE 79

Synthesis of (5S)-1-{(2S)-2-amino-4-oxo-4-[3-(trifluoromethyl)-5,6-dihydro[1,2,4]triazolo[4,3-a]pyrazin-7(8H)-yl]butyl}-5-methylpiperidin-2-one

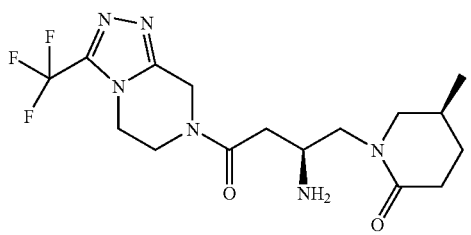

11.6 mg of the title compound was obtained in a yield of 49% at the same manner as in EXAMPLE 22, except that 30 mg of t-butyl {(1S)-1-{[(5S)-5-methyl-2-oxopiperidin-1-yl]methyl}-3-oxo-3-[3-(trifluoromethyl)-5,6-dihydro[1,2,4]triazolo[4,3-a]pyrazin-7(8H)-yl]propyl}carbamate obtained in PREPARATION 139 was used.

$^1$H NMR (CD$_3$OD) δ 4.9-5.1 (2H, m), 4.0-4.4 (4H, m), 3.7-3.9 (2H, m), 3.3-3.5 (2H, m), 2.7-3.1 (3H, m), 2.37 (2H, br), 1.9-2.1 (1H, br s), 1.8-1.9 (1H, m), 1.4-1.6 (1H, m), 1.03 (3H, m)

Mass (m/e) 389 (M+1)

PREPARATION 140

Synthesis of t-butyl [(1S)-3-[2,4-bis(trifluoromethyl)-5,8-dihydropyrido[3,4-d]pyrimidin-7(6H)-yl]-1-{[(5S)-5-methyl-2-oxopiperidin-1-yl]methyl}-3-oxpropyl]carbamate 3 mg of the title compound was obtained in a yield of 6.4% at the same manner as in PREPARATION 45, except that 26 mg (0.08 mmol) of (3S)-3-[(t-butoxycarbonyl)amino]-4-[(5S)-5-methyl-2-oxopiperidin-1-yl]-butanoic acid obtained in PREPARATION 122 and 25 mg (0.08 mmol) of 2,4-bis(trifluoromethyl)-5,6,7,8-tetrahydropyrido[3,4-d]pyrimidine hydrochloric acid salt (product of PREPARATION 127) were used.

$^1$H NMR (CDCl$_3$) δ 5.94 (1H, m), 4.8-5.1 (2H, m), 4.1-4.2 (2H, m), 3.7-3.8 (2H, m), 3.5-3.6 (1H, m), 3.3-3.5 (2H, m), 3.1-3.3 (2H, m), 2.8-3.0 (1H, m), 2.3-2.5 (3H, m), 1.8-2.0 (2H, m), 1.6-1.7 (1H, m), 1.40 (9H, s), 1.01 (3H, d, J=7 Hz)

Mass (m/e) 568 (M+1)

EXAMPLE 80

Synthesis of (5S)-1-{(2S-2-amino-4-[2,4-bis(trifluoromethyl)-5,8-dihydropyrido[3,4-d]pyrimidin-7(6H)-yl]-4-oxobutyl}-5-methylpiperidin-2-one

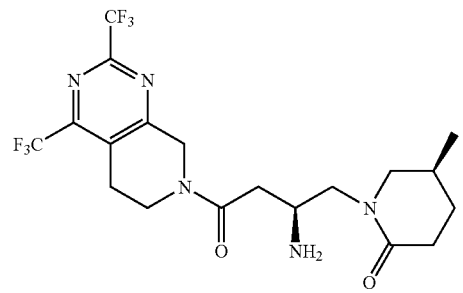

2.3 mg of the title compound was obtained in a yield of 93% at the same manner as in EXAMPLE 22, except that 3.0 mg of t-butyl [(1S)-3-[2,4-bis(trifluoromethyl)-5,8-dihydropyrido[3,4-d]pyrimidin-7(6H)-yl]-1-{[(5S)-5-methyl-2-oxopiperidin-1-yl]methyl}-3-oxpropyl]carbamate obtained in PREPARATION 140 was used.

$^1$H NMR (CD$_3$OD) δ 4.8-5.0 (2H, m), 3.8-4.0 (1H, m), 3.3-3.7 (5H, m), 3.0-3.2 (3H, m), 2.5-2.7 (2H, m), 2.3-2.4 (2H, m), 1.8-2.0 (2H, m), 1.4-1.5 (1H, m), 1.02 (3H, m)

Mass (m/e) 468 (M+1)

PREPARATION 141

Synthesis of t-butyl {(1S)-1-{[(5R)-5-methyl-2-oxopiperidin-1-yl]methyl}-3-[2-methyl-4-(trifluoromethyl-5,8-dihydropyrido[3,4-d]pyrimidin-7(6H)-yl]-3-oxpropyl}carbamate 137 mg of the title compound was obtained in a yield of 64% at the same manner as in PREPARATION 45, except that 131 mg (0.418 mmol) of (3S)-3-[(t-butoxycarbonyl)amino]-4-[(5R)-5-methyl-2-oxopiperidin-1-yl]butanoic acid obtained in PREPARATION 51 and 106 mg (0.418 mmol) of 2-methyl-4-(trifluoromethyl)-5,6,7,8-tetrahydropyrido[3,4-d]pyrimidine hydrochloric acid salt obtained in PREPARATION 126 were used.

¹H NMR (CDCl₃) δ 5.88 (1H, brs), 4.89-4.78 (1H, m), 4.76-4.64 (1H, m), 4.17-4.10 (1H, m), 3.78-3.73 (1H, m), 3.62-3.48 (2H, m), 3.39-3.33 (1H, m), 3.11-2.96 (3H, m), 2.84-2.79 (1H, m), 2.76 (3H, s), 2.60-2.20 (3H, m), 1.96-1.93 (1H, m), 1.84-1.81 (1H, m), 1.49-1.42 (1H, m), 1.40 (9H, s), 1.00 (3H, d, J=6.8 Hz)

Mass (m/e) 414 (M+1-Boc)

EXAMPLE 81

Synthesis of (5R)-1-{(2S)-2-amino-4-[2-methyl-4-(trifluoromethyl)-5,8-dihydropyrido[3,4-d]pyrimidin-7(6H)-yl]-4-oxobutyl}-5-methylpiperidin-2-one

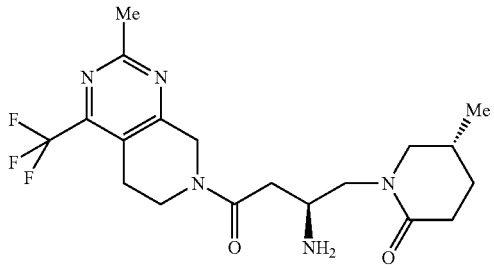

99 mg of the title compound was obtained in a yield of 83% at the same manner as in EXAMPLE 1, except that 137 mg (0.267 mmol) of t-butyl {(1S)-1-{[(5R)-5-methyl-2-oxopiperidin-1-yl]methyl}-3-[2-methyl-4-(trifluoromethyl)-5,8-dihydropyrido[3,4-d]pyrimidin-7(6H)-yl]-3-oxpropyl}carbamate obtained in PREPARATION 141 was used.

¹H NMR (CD₃OD) δ 4.89-4.79 (2H, m), 3.94-3.91 (1H, m), 3.89-3.81 (1H, m), 3.77-3.73 (1H, m), 3.67-3.61 (1H, m), 3.56-3.52 (1H, m), 3.41-3.52 (1H, m), 3.14-3.08 (2H, m), 3.02-2.98 (1H, m), 2.90-2.66 (2H, m), 2.73 (3H, s), 2.50-2.33 (2H, m), 2.05-2.00 (1H, m), 1.89-1.84 (1H, m), 1.59-1.49 (1H, m), 1.07 (3H, d, J=6.8 Hz)

Mass (m/e) 414 (M+1)

PREPARATION 142

Synthesis of t-butyl {(1S)-3-[2,4-bis(trifluoromethyl)-5,8-dihydropyrido[3,4-d]pyrimidin-7(6H)-yl]-1-{[(5R)-5-methyl-2-oxopiperidin-1-yl]methyl}-3-oxpropyl}carbamate 28 mg of the title compound was obtained in a yield of 24% at the same manner as in PREPARATION 42, except that 64 mg (0.205 mmol) of (3S)-3-[(t-butoxycarbonyl)amino]-4-[(5R)-5-methyl-2-oxopiperidin-1-yl]butanoic acid obtained in PREPARATION 51 was reacted with 63 mg (0.205 mmol) of 2,4-bis(trifluoromethyl)-5,6,7,8-tetrahydropyrido[3,4-d]pyrimidine hydrochloric acid salt (product of PREPARATION 127).

¹H NMR (CDCl₃) δ 5.96-5.91 (1H, m), 5.08-4.88 (1H, m), 4.90-4.67 (1H, m), 4.15-4.10 (1H, m), 4.03-3.80 (2H, m), 3.62-3.57 (1H, m), 3.53-3.44 (1H, m), 3.40-3.31 (1H, m), 3.27-3.01 (3H, m), 2.90-2.79 (1H, m), 2.57-2.17 (4H, m), 1.94 (1H, brs), 1.81 (1H, brs), 1.42-1.40 (9H, m), 1.01 (3H, d, J=6.4 Hz)

Mass (m/e) 468 (M+1-Boc)

EXAMPLE 82

Synthesis of (5R)-1-{(2S)-2-amino-4-[2,4-bis(trifluoromethyl)-5,8-dihydropyrido[3,4-d]pyrimidin-7(6H)-yl]-4-oxobutyl}-5-methylpiperidin-2-one

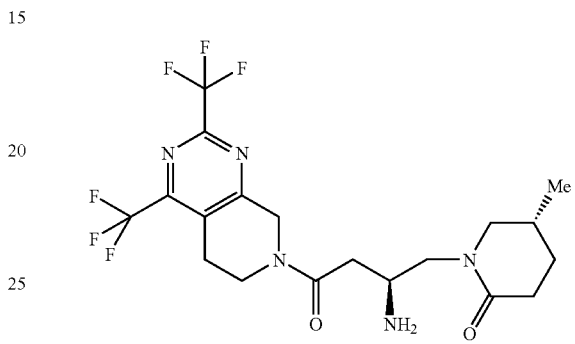

33 mg of the title compound was obtained in a yield of 80% at the same manner as in EXAMPLE 1, except that 47 mg (0.083 mmol) of t-butyl {(1S)-3-[2,4-bis(trifluoromethyl)-5,8-dihydropyrido[3,4-d]pyrimidin-7(6H)-yl]-1-{[(5R)-5-methyl-2-oxopiperidin-1-yl]methyl}-3-oxpropyl}carbamate obtained in PREPARATION 142 was used.

¹H NMR (CD₃OD) δ 5.05-4.89 (2H, m), 3.98-3.90 (2H, m), 3.73-3.70 (1H, m), 3.64-3.49 (2H, m), 3.42-3.30 (3H, m), 3.24 (1H, brs), 3.13-3.05 (2H, m), 2.88-2.81 (1H, m), 2.75-2.62 (1H, m), 2.49-2.36 (2H, m), 2.03 (1H, brs), 1.86 (1H, brs), 1.60-1.48 (1H, m), 1.06 (3H, d, J=6.4 Hz)

Mass (m/e) 468 (M+1)

PREPARATION 143

Synthesis of t-butyl {(1S)-3-[2,4-bis(trifluoromethyl)-5,8-dihydropyrido[3,4-d]pyrimidin-7(6H)-yl]-1-[(5,5-difluoro-2-oxopiperidin-1-yl)methyl]-3-oxpropyl}carbamate 42 mg of the title compound was obtained in a yield of 51% at the same manner as in PREPARATION 45, except that 46.4 mg (0.138 mmol) of (3S)-3-[(t-butoxycarbonyl)amino]-4-(5,5-difluoro-2-oxopiperidin-1-yl)-butanoic acid obtained in PREPARATION 57 and 42.5 mg (0.138 mmol) of 2,4-bis(trifluoromethyl)-5,6,7,8-tetrahydropyrido[3,4-d]pyrimidine hydrochloric acid salt (product of PREPARATION 127) were used.

¹H NMR (CDCl₃) δ 5.83-5.79 (1H, m), 5.05-4.91 (1H, m), 4.89-4.78 (1H, m), 4.17 (1H, brs), 4.00-3.58 (5H, m), 3.52-3.48 (1H, m), 3.20-3.12 (2H, m), 2.85-2.78 (1H, m), 2.59-2.48 (3H, m), 2.29-2.25 (2H, m), 1.48-1.40 (9H, m)

Mass (m/e) 490 (M+1-Boc)

EXAMPLE 83

Synthesis of 1-{(2S)-2-amino-4-[2,4-bis(trifluoromethyl)-5,8-dihydropyrido[3,4-d]pyrimidin-7(6H)-yl]-4-oxobutyl}-5,5-difluoropiperidin-2-one

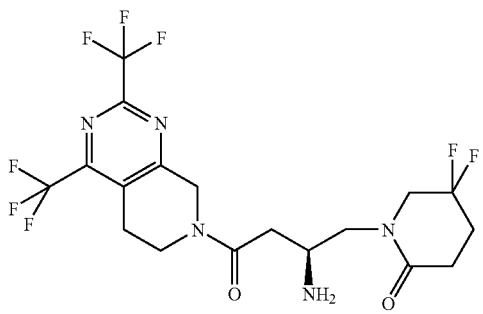

21 mg of the title compound was obtained in a yield of 56% at the same manner as in EXAMPLE 1, except that 42 mg (0.071 mmol) of t-butyl {(1S)-3-[2,4-bis(trifluoromethyl)-5,8-dihydropyrido[3,4-d]pyrimidin-7(6H)-yl]-1-[(5,5-difluoro-2-oxopiperidin-1-yl)methyl]-3-oxpropyl}carbamate obtained in PREPARATION 143 was used.

$^1$H NMR (CD$_3$OD) δ 5.05-4.92 (2H, m), 3.98-3.91 (2H, m), 3.85-3.79 (2H, m), 3.70-3.59 (2H, m), 3.54-3.48 (1H, m), 3.36-3.33 (2H, m), 3.24 (1H, brs), 3.14 (1H, brs), 2.83-2.76 (1H, m), 2.72-2.53 (3H, m), 2.43-2.34 (2H, m)

Mass (m/e) 490 (M+1)

PREPARATION 144

Synthesis of t-butyl {(1S)-3-[2,4-bis(trifluoromethyl)-5,8-dihydropyrido[3,4-d]pyrimidin-7(6H)-yl]-1-{[(2S)-2-methyl-5-oxomorpholin-4-yl]methyl}-3-oxpropyl}carbamate 14 mg of the title compound was obtained in a yield of 17% at the same manner as in PREPARATION 45, except that 43.7 mg (0.138 mmol) of (3S)-3-[(t-butoxycarbonyl)amino]-4-[2(S)-2-methyl-5-oxomorpholin-4-yl]-butanoic acid obtained in PREPARATION 55 and 42.5 mg (0.138 mmol) of 2,4-bis(trifluoromethyl)-5,6,7,8-tetrahydropyrido[3,4-d]pyrimidine hydrochloric acid salt (product of PREPARATION 127) were used.

$^1$H NMR (CDCl$_3$) δ 5.85-5.83 (1H, m), 5.09-4.92 (1H, m), 4.95-4.78 (1H, m), 4.23-4.08 (3H, m), 4.04-3.76 (3H, m), 3.73-3.66 (1H, m), 3.46-3.38 (1H, m), 3.36-3.21 (2H, m), 3.18-3.10 (2H, m), 2.96-2.81 (1H, m), 2.61-2.50 (1H, m), 1.43-1.41 (9H, m), 1.28-1.24 (3H, m)

Mass (m/e) 470 (M+1-Boc)

EXAMPLE 84

Synthesis of (6S)-4-{(2S-2-amino-4-[2,4-bis(trifluoromethyl)-5,8-dihydropyrido[3,4-d]pyrimidin-7(6H)-yl]-4-oxobutyl}-6-methylmorpholine-3-one

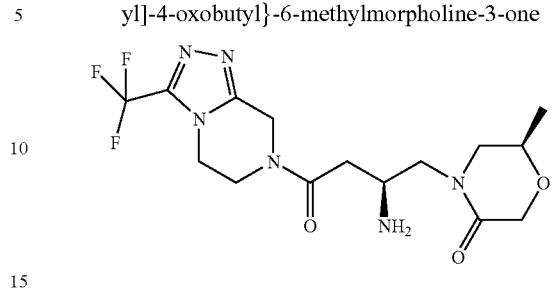

6.9 mg of the title compound was obtained in a yield of 59% at the same manner as in EXAMPLE 1, except that 14 mg (0.023 mmol) of t-butyl {(1S)-3-[2,4-bis(trifluoromethyl)-5,8-dihydropyrido[3,4-d]pyrimidin-7(6H)-yl]-1-{[(2S)-2-methyl-5-oxomorpholin-4-yl]methyl}-3-oxpropyl}carbamate obtained in PREPARATION 144 was used.

$^1$H NMR (CD$_3$OD) δ 4.89-4.80 (2H, m), 4.16-4.06 (3H, m), 3.92-3.85 (4H, m), 3.55-3.50 (2H, m), 3.34-3.30 (1H, m), 3.19 (1H, brs), 3.09 (1H, brs), 2.70-2.61 (1H, m), 2.59-2.53 (1H, m), 1.23-1.20 (3H, m)

Mass (m/e) 470 (M+1)

PREPARATION 145

Synthesis of t-butyl {(1S)-1-[(5,5-difluoro-2-oxopiperidin-1-yl)methyl]-3-[2-methyl-4-(trifluoromethyl)-5,8-dihydropyrido[3,4-d]pyrimidin-7(6H)-yl]-3-oxpropyl}carbamate 51.6 mg of the title compound was obtained in a yield of 59% at the same manner as in PREPARATION 45, except that 55.3 mg (0.164 mmol) of (3S)-3-[(t-butoxycarbonyl)amino]-4-(5,5-difluoro-2-oxopiperidin-1-yl)-butanoic acid obtained in PREPARATION 57 and 41.7 mg (0.164 mmol) of 2-methyl-4-(trifluoromethyl)-5,6,7,8-tetrahydropyrido[3,4-d]pyrimidine hydrochloric acid salt obtained in PREPARATION 126 were used.

$^1$H NMR (CDCl$_3$) δ 5.79-5.76 (1H, m), 4.84-4.78 (1H, m), 4.69-4.61 (1H, m), 4.18 (1H, brs), 3.88-3.80 (1H, m), 3.76-3.65 (3H, m), 3.60-3.52 (2H, m), 3.02-2.95 (3H, m), 2.82-2.73 (4H, m), 2.57-2.49 (3H, m), 2.27-2.20 (1H, m), 1.38-1.37 (9H, m)

Mass (m/e) 436 (M+1-Boc)

EXAMPLE 85

Synthesis of 1-{(2S)-2-amino-4-[2-methyl-4-(trifluoromethyl)-5,8-dihydropyrido[3,4-d]pyrimidin-7(6H)-yl]-4-oxobutyl}-5,5-difluoropiperidin-2-one

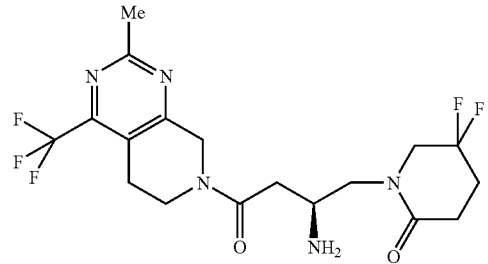

43 mg of the title compound was obtained in a yield of 78% at the same manner as in EXAMPLE 22, except that 51.6 mg (0.119 mmol) of t-butyl {(1S)-1-[(5,5-difluoro-2-oxopiperidin-1-yl)methyl]-3-[2-methyl-4-(trifluoromethyl)-5,8-dihydropyrido[3,4-d]pyrimidin-7(6H)-yl]-3-oxpropyl}carbamate obtained in PREPARATION 145 was used.

$^1$H NMR (CD$_3$OD) δ 4.83-4.77 (2H, m), 3.89-3.74 (4H, m), 3.68-3.60 (3H, m), 3.47-3.43 (1H, m), 3.30 (3H, s), 3.06 (1H, brs), 2.97 (1H, brs), 2.67-2.54 (2H, m), 2.37-2.30 (3H, m)

Mass (m/e) 436 (M+1)

PREPARATION 146

Synthesis of t-butyl {(1-S)-1-{[(2S)-2-methyl-5-oxomorpholin-4-yl]methyl}-3-[2-methyl-4-(trifluoromethyl)-5,8-dihydropyrido[3,4-d]pyrimidin-7(6H)-yl]-3-oxpropyl}carbamate 39.8 mg of the title compound was obtained in a yield of 39% at the same manner as in PREPARATION 45, except that 62.4 mg (0.197 mmol) of (3S)-3-[(t-butoxycarbonyl)amino]-4-[2(S)-2-methyl-5-oxomorpholin-4-yl]-butanoic acid obtained in PREPARATION 55 was reacted with 50 mg (0.197 mmol) of 2-methyl-4-(trifluoromethyl)-5,6,7,8-tetrahydropyrido[3,4-d]pyrimidine hydrochloric acid salt (product of PREPARATION 128).

$^1$H NMR (CDCl$_3$) δ 5.82-5.77 (1H, m), 4.90-4.78 (1H, m), 4.75-4.63 (1H, m), 4.29-4.09 (2H, m), 3.95-3.82 (2H, m), 3.80 (1H, brs), 3.76-3.62 (1H, m), 3.53-3.45 (1H, m), 3.41-3.29 (2H, m), 3.10-2.96 (2H, m), 2.89-2.80 (1H, m), 2.76 (3H, s), 2.60-2.49 (1H, m), 1.43-1.42 (9H, m), 1.28-1.24 (3H, m)

Mass (m/e) 470 (M+1-Boc)

EXAMPLE 86

Synthesis of (6S)-4-{(2S-2-amino-4-[2-methyl-4-(trifluoromethyl)-5,8-dihydropyrido[3,4-d]pyrimidin-7(6H)-yl]-4-oxobutyl}-6-methylmorpholine-3-one

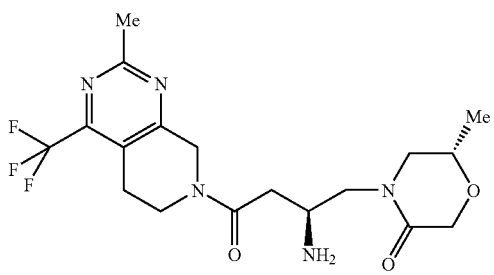

26.5 mg of the title compound was obtained in a yield of 76% at the same manner as in EXAMPLE 22, except that 39.8 mg (0.077 mmol) of t-butyl {(1S)-1-{[(2S)-2-methyl-5-oxomorpholin-4-yl]methyl}-3-[2-methyl-4-(trifluoromethyl)-5,8-dihydropyrido[3,4-d]pyrimidin-7(6H)-yl]-3-oxpropyl}carbamate obtained in PREPARATION 146 was used.

$^1$H NMR (CD$_3$OD) δ 4.83-4.77 (2H, m), 4.18-4.07 (3H, m), 3.95-3.88 (2H, m), 3.83-3.81 (1H, m), 3.58-3.52 (2H, m), 3.38-3.29 (1H, m), 3.07 (1H, brs), 2.97 (1H, brs), 2.81-2.76 (1H, m), 2.70-2.69 (3H, m), 2.67-2.60 (1H, m), 1.23 (3H, d, J=6.1 Hz)

Mass (m/e) 416 (M+1)

PREPARATION 147

Synthesis of t-butyl {(1S)-1-[(5,5-difluoro-2-oxopiperidin-1-yl)methyl]-3-oxo-3-[4-(trifluoromethyl)-5,8-dihydropyrido[3,4-d]pyrimidin-7(6H)-yl] propyl}carbamate 16.4 mg of the title compound was obtained in a yield of 47% at the same manner as in PREPARATION 45, except that 16 mg (0.067 mmol) of (3S)-3-[(t-butoxycarbonyl)amino]-4-(5,5-difluoro-2-oxopiperidin-1-yl)-butanoic acid obtained in PREPARATION 57 was reacted with 22.5 mg (0.067 mmol) of 4-trifluoromethyl-5,6,7,8-tetrahydropyrido[3,4-d]pyrimidine hydrochloric acid salt (product of PREPARATION 49).

$^1$H NMR (CDCl$_3$) δ 9.16-9.15 (1H, m), 5.81-5.79 (1H, m), 4.95-4.84 (1H, m), 4.81-4.70 (1H, m), 4.22-4.13 (1H, m), 3.92-3.89 (1H, m), 3.79-3.69 (3H, m), 3.65-3.52 (2H, m), 3.15-3.10 (1H, m), 3.06 (1H, brs), 2.86-2.79 (1H, m), 2.62-2.52 (3H, m), 2.36-2.22 (2H, m), 1.42-1.41 (9H, m)

Mass (m/e) 422 (M+1-BOC)

EXAMPLE 87

Synthesis of 1-{(2S)-2-amino-4-oxo-4-[4-(trifluoromethyl)-5,8-dihydropyrido[3,4-d]pyrimidin-7(6H)-yl]butyl}-5,5-difluoropiperidin-2-one

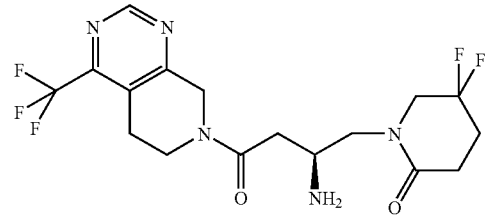

9.7 mg of the title compound was obtained in a yield of 67% at the same manner as in EXAMPLE 22, except that 16.4 mg (0.032 mmol) of t-butyl {(1S)-1-[(5,5-difluoro-2-oxopiperidin-1-yl)methyl]-3-oxo-3-[4-(trifluoromethyl)-5,8-dihydropyrido[3,4-d]pyrimidin-7(6H)-yl]propyl}carbamate obtained in PREPARATION 147 was used.

$^1$H NMR (CD$_3$OD) δ 9.03-9.02 (1H, m), 4.84-4.73 (2H, m), 3.84-3.66 (3H, m), 3.62-3.48 (3H, m), 3.43-3.35 (1H, m), 3.06-3.03 (1H, m), 2.95 (1H, brs), 2.75-2.57 (2H, m), 2.55-2.42 (2H, m), 2.31-2.20 (2H, m)

Mass (m/e) 422 (M+1)

PREPARATION 148

Synthesis of t-butyl {(1S)-1-{[(2S)-2-methyl-5-oxomorpholin-4-yl]methyl}-3-oxo-3-[4-(trifluoromethyl)-5,8-dihydropyrido[3,4-d]pyrimidin-7(6H)-yl] propyl}carbamate 16.4 mg of the title compound was obtained in a yield of 47% at the same manner as in PREPARATION 45, except that 21 mg (0.067 mmol) of (3S)-3-[(t-butoxycarbonyl)amino-4-[2(S)-2-methyl-5-oxomorpholin-4-yl]-butanoic acid obtained in PREPARATION 55 was reacted with 16 mg (0.067 mmol) of 4-trifluoromethyl-5,6,7,8-tetrahydropyrido[3,4-d]pyrimidine hydrochloric acid salt (product of PREPARATION 49).

$^1$H NMR (CDCl$_3$) δ 9.15-9.14 (1H, m), 5.83-5.78 (1H, m), 4.96-4.84 (1H, m), 4.82-4.70 (1H, m), 4.29-4.08 (3H, m), 3.93-3.83 (2H, m), 3.77 (1H, brs), 3.70-3.63 (1H, m), 3.40-3.31 (1H, m), 3.51-3.45 (1H, m), 3.40-3.31 (2H, m), 3.20-3.00 (2H, m), 2.61-2.50 (1H, m), 1.42-1.42 (9H, m), 1.28-1.26 (3H, m)

Mass (m/e) 402 (M+1-BOC)

EXAMPLE 88

Synthesis of (6S)-4-{(2S)-2-amino-4-oxo-4-[4-(trifluoromethyl)-5,8-dihydropyrido[3,4-d]pyrimidin-7(6H)-yl]butyl}-6-methylmorpholine-3-one

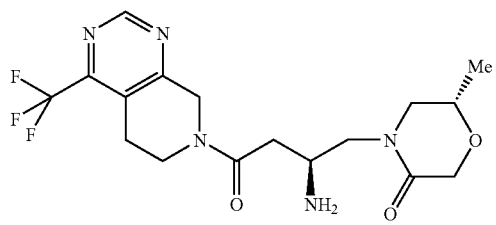

6.7 mg of the title compound was obtained in a yield of 73% at the same manner as in EXAMPLE 22, except that 10.5 mg (0.021 mmol) of t-butyl {(1S)-1-{[(2S)-2-methyl-5-oxomorpholin-4-yl]methyl}-3-oxo-3-[4-(trifluoromethyl)-5,8-dihydropyrido[3,4-d]pyrimidin-7(6H)-yl]propyl}carbamate obtained in PREPARATION 148 was used.

$^1$H NMR (CDCl$_3$) δ 9.11-9.10 (1H, m), 4.88-4.81 (2H, m), 4.17-4.08 (3H, m), 3.95-3.86 (2H, m), 3.85-3.81 (1H, m), 3.68-3.64 (1H, m), 3.53-3.50 (2H, m), 3.32-3.29 (1H, m), 3.12 (1H, brs), 3.02 (1H, brs), 2.80-2.75 (1H, m), 2.66-2.58 (1H, m), 1.23 (3H, d, J=6.1 Hz)

Mass (m/e) 402 (M+1)

PREPARATION 149

Synthesis of t-butyl {(1S)-1-[(5,5-difluoro-2-oxopiperidin-1-yl)methyl]-3-oxo-3-[3-(pentafluoroethyl)-5,6-dihydro[1,2,4]triazolo[4,3-a]pyrazin-7(8H)-yl]propyl}carbamate 63 mg of the title compound was obtained in a yield of 63% at the same manner as in PREPARATION 45, except that 43 mg (0.178 mmol) of (3S)-3-[(t-butoxycarbonyl)amino]-4-(5,5-difluoro-2-oxopiperidin-1-yl)butanoic acid obtained in PREPARATION 57 was reacted with 43 mg (0.178 mmol) of 3-(pentafluoroethyl)-5,6-dihydro[1,2,4]triazolo[4,3-a]pyrazine synthesized with reference to J.M.C 2005, 48, p 141-151.

$^1$H NMR (CDCl$_3$) δ 5.90-5.88 (1H, m), 5.13-4.77 (2H, m), 4.31-4.27 (2H, m), 4.20-4.09 (2H, m), 4.00-3.86 (1H, m), 3.73-3.63 (3H, m), 3.48-3.31 (1H, m), 2.88-2.72 (1H, m), 2.62-2.49 (2H, m), 2.43-2.39 (1H, m), 2.24-2.17 (2H, m), 1.42 (9H, s).

Mass (m/e) 461 (M+1-BOC)

EXAMPLE 89

Synthesis of 1-{(2S)-2-amino-4-oxo-4-[3-(pentafluoroethyl)-5,6-dihydro[1,2,4]triazolo[4,3-a]pyrazin-7(8H)-yl]butyl}-5,5-difluoropiperidin-2-one

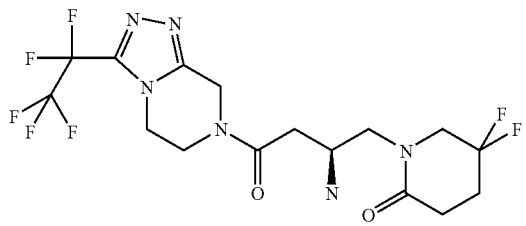

24.7 mg of the title compound was obtained in a yield of 44% at the same manner as in EXAMPLE 22, except that 63 mg (0.112 mmol) of t-butyl {(1S)-1-[(5,5-difluoro-2-oxopiperidin-1-yl)methyl]-3-oxo-3-[3-(pentafluoroethyl)-5,6-dihydro[1,2,4]triazolo[4,3-a]pyrazin-7(8H)-yl]propyl}carbamate obtained in PREPARATION 149 was used.

$^1$H NMR (CD$_3$OD) δ 5.12-5.00 (2H, m), 4.42-4.39 (1H, m), 4.30 (1H, brs), 4.21-4.02 (2H, m), 3.89-3.75 (4H, m), 3.62-3.54 (1H, m), 3.02-2.82 (2H, m), 2.65-2.56 (2H, m), 2.43-2.35 (2H, m)

Mass (m/e) 461 (M+1)

PREPARATION 150

Synthesis of t-butyl {(1S)-1-{[(2S)-2-methyl-5-oxomorpholin-4-yl]methyl}-3-oxo-3-[3-(pentafluoroethyl)-5,6-dihydro[1,2,4]triazolo[4,3-a]pyrazin-7(8H)-yl]propyl}carbamate 68 mg of the title compound was obtained in a yield of 71% at the same manner as in PREPARATION 45, except that 56 mg (0.178 mmol) of (3S)-3-[(t-butoxycarbonyl)amino]-4-[2(S)-2-methyl-5-oxomorpholin-4-yl]-butanoic acid obtained in PREPARATION 55 was reacted with 43 mg (0.178 mmol) of 3-(pentafluoroethyl)-5,6-dihydro[1,2,4]triazolo[4,3-a]pyrazine synthesized with reference to JMC 2005, 48, p 141-151.

$^1$H NMR (CDCl$_3$) δ 5.90-5.88 (1H, m), 5.13-4.77 (2H, m), 4.29-4.09 (5H, m), 4.05-3.95 (2H, m), 3.86-3.69 (2H, m), 3.40-3.23 (3H, m), 2.91-2.72 (1H, m), 2.60-2.50 (1H, m), 1.42 (9H, brs), 1.27-1.25 (3H, m)

Mass (m/e) 441 (M+1-BOC)

EXAMPLE 90

Synthesis of (6S)-4-{(2S)-2-amino-4-oxo-4-[3-(pentafluoroethyl)-5,6-dihydro[1,2,4]triazolo[4,3-a]pyrazin-7(8H)-yl]butyl}-6-methylmorpholine-3-one

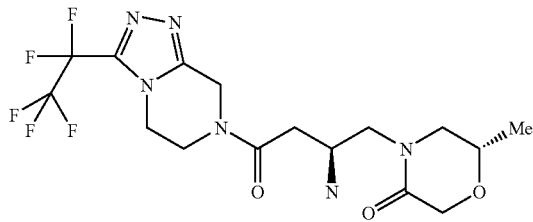

20.4 mg of the title compound was obtained in a yield of 30% at the same manner as in EXAMPLE 22, except that 68 mg (0.126 mmol) of t-butyl {(1S)-1-{[(2S)-2-methyl-5-oxomorpholin-4-yl]methyl}-3-oxo-3-[3-(pentafluoroethyl)-5,6-dihydro[1,2,4]triazolo[4,3-a]pyrazin-7(8H)-yl]propyl}carbamate obtained in PREPARATION 150 was used.

$^1$H NMR (CD$_3$OD) δ 5.11-5.00 (2H, m), 4.38 (1H, brs), 4.30 (1H, brs), 4.21-4.13 (3H, m), 4.10-4.05 (2H, m), 4.00-3.95 (1H, m), 3.80-3.75 (1H, m), 3.64-3.62 (2H, m), 3.36-3.33 (1H, m), 2.95-2.86 (1H, m), 2.82-2.76 (1H, m), 1.26 (3H, d, J=6.0 Hz)

Mass (m/e) 441 (M+1)

PREPARATION 151

Synthesis of t-butyl {(1S)-3-[2,4-bis(trifluoromethyl)-5,8-dihydropyrido[3,4-d]pyrimidin-7(6H)-yl]-1-[(2-methyl-5-oxothiomorpholin-4-yl)methyl]-3-oxpropyl}carbamate 24.5 mg of the title compound was obtained in a yield of 56% at the same manner as in PREPARATION 45, except that 25 mg (0.075 mmol) of (3S)-3-[(t-butoxycarbonyl)amino]-4-(2-methyl-5-oxothiomorpholin-4-yl)-butanoic acid obtained in PREPARATION 125 was reacted with 23 mg (0.075 mmol) of 2,4-bis(trifluoromethyl)-5,6,7,8-tetrahydropyrido[3,4-d]pyrimidine hydrochloric acid salt (product of PREPARATION 127).

$^1$H NMR (CDCl$_3$) δ 5.91-5.81 (1H, m), 5.08-4.78 (2H, m), 4.13-3.98 (1H, m), 3.85-3.77 (2H, m), 3.70-3.66 (2H, m), 3.50-3.38 (2H, m), 3.27-3.22 (3H, m), 3.15-3.07 (2H, m), 2.88-2.81 (1H, m), 2.55-2.47 (1H, m), 1.42-1.40 (9H, m), 1.31-1.23 (3H, m)

Mass (m/e) 486 (M+1-BOC)

EXAMPLE 91

Synthesis of 4-{(2S)-2-amino-4-[2,4-bis(trifluoromethyl)-5,8-dihydropyrido[3,4-d]pyrimidin-7(6H)-yl]-4-oxobutyl}-6-methylthiomorpholin-3-one

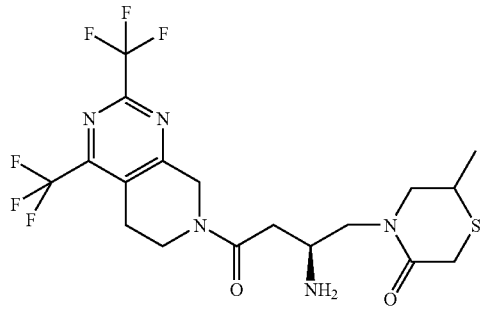

14.6 mg of the title compound was obtained in a yield of 67% at the same manner as in EXAMPLE 22, except that 24.5 mg (0.042 mmol) of t-butyl {(1S)-3-[2,4-bis(trifluoromethyl)-5,8-dihydropyrido[3,4-d]pyrimidin-7(6H)-yl]-1-[(2-methyl-5-oxothiomorpholin-4-yl)methyl]-3-oxpropyl}carbamate obtained in PREPARATION 151 was used.

$^1$H NMR (CD$_3$OD) δ 5.00-4.85 (2H, m), 3.96-3.86 (3H, m), 3.71-3.59 (2H, m), 3.50-3.30 (5H, m), 3.22-3.19 (1H, m), 3.09 (1H, brs), 2.66-2.62 (1H, m), 2.60-2.50 (1H, m), 1.28-1.27 (3H, m)

Mass (m/e) 486 (M+1)

PREPARATION 152

Synthesis of t-butyl {(1S)-3-[2-t-butyl-4-(trifluoromethyl)-5,8-dihydropyrido[3,4-d]pyrimidin-7(6H)-yl]1-1-[(5,5-difluoro-2-oxopiperidin-1-yl)methyl]-3-oxpropyl}carbamate 19 mg of the title compound was obtained in a yield of 66% at the same manner as in PREPARATION 45, except that 16.9 mg (0.050 mmol) of (3S)-3-[(t-butoxycarbonyl)amino]-4-(5,5-difluoro-2-oxopiperidin-1-yl)-butanoic acid PREPARATION 57 was reacted with 13.0 mg (0.050 mmol) of 2-t-butyl-4-(trifluoromethyl)-5,6,7,8-tetrahydropyrido[3,4-d]pyrimidine hydrochloric acid salt (product of PREPARATION 131).

$^1$H NMR (CDCl$_3$) δ 5.76 (1H, brs), 4.82 (1H, brs), 4.72-4.63 (1H, m), 4.20 (1H, brs), 3.87-3.85 (1H, m), 3.78-3.68 (3H, m), 3.62-3.53 (2H, m), 3.03-2.97 (1H, m), 2.84-2.80 (1H, m), 2.58-2.53 (4H, m), 2.29-2.20 (2H, m), 1.41-1.38 (18H, m)

Mass (m/e) 475 (M+1-BOC)

EXAMPLE 92

Synthesis of 1-{(2S)-2-amino-4-[2-t-butyl-4-(trifluoromethyl)-5,8-dihydropyrido[3,4-d]pyrimidin-7(6H)-yl]-4-oxobutyl}-5,5-difluoropiperidin-2-one

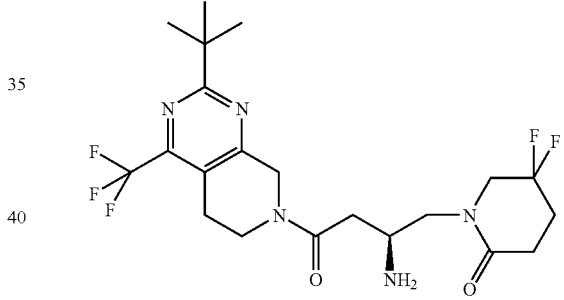

11.0 mg of the title compound was obtained in a yield of 92% at the same manner as in EXAMPLE 22, except that 19 mg (0.023 mmol) of t-butyl {(1S)-3-[2-t-butyl-4-(trifluoromethyl)-5,8-dihydropyrido[3,4-d]pyrimidin-7(6H)-yl]1-1-[(5,5-difluoro-2-oxopiperidin-1-yl)methyl]-3-oxpropyl}carbamate obtained in PREPARATION 152 was used.

$^1$H NMR (CD$_3$OD) δ 4.86-4.79 (2H, m), 3.90-3.74 (4H, m), 3.50-3.43 (1H, m), 3.29 (2H, brs), 3.06 (1H, brs), 2.96 (1H, brs), 2.67-2.51 (4H, m), 2.35-2.30 (2H, m), 1.38-1.37 (9H, m)

Mass (m/e) 478 (M+1)

PREPARATION 153

Synthesis of t-butyl [(1S)-3-[2-t-butyl-4-(trifluoromethyl)-5,8-dihydropyrido[3,4-d]pyrimidin-7(6H)-yl]-1-{[(2S)-2-methyl-5-oxomorpholin-4-yl]methyl}-3-oxpropyl]carbamate 18 mg of the title compound was obtained in a yield of 65% at the same manner as in PREPARATION 45, except that 16 mg (0.050 mmol) of (3S)-3-[(t-butoxycarbonyl)amino]-4-[2 (S)-2-methyl-5-oxomorpholin-4-yl]-butanoic acid obtained in PREPARATION 55 was reacted with 13 mg (0.050 mmol) of 2-t-butyl-4-(trifluoromethyl)-5,6,7,8-tetrahydropyrido[3,4-d]pyrimidine hydrochloric acid salt (product of PREPARATION 131).

$^1$H NMR (CDCl$_3$) δ 5.75-5.74 (1H, m), 4.90-4.79 (1H, m), 4.65-4.60 (1H, m), 4.24-4.10 (3H, m), 3.92-3.87 (2H, m), 3.77-3.74 (1H, m), 3.67-3.62 (1H, m), 3.55-3.49 (1H, m), 3.40-3.31 (2H, m), 3.04-2.98 (2H, m), 2.86-2.83 (1H, m), 2.58-2.55 (1H, m), 1.43-1.42 (9H, m), 1.39-1.38 (9H, s), 1.28-1.24 (3H, m)

Mass (m/e) 458 (M+1-BOC)

EXAMPLE 93

Synthesis of (6S)-4-{(2S-2-amino-4-[2-t-butyl-4-(trifluoromethyl)-5,8-dihydropyrido[3,4-d]pyrimidin-7(6H)-yl]-4-oxobutyl}-6-methylmorpholine-3-one

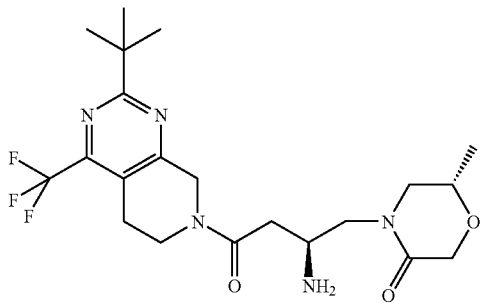

10.2 mg of the title compound was obtained in a yield of 94% at the same manner as in EXAMPLE 22, except that 18 mg (0.022 mmol) of t-butyl [(1S)-3-[2-t-butyl-4-(trifluoromethyl)-5,8-dihydropyrido[3,4-d]pyrimidin-7(6H)-yl]-1-{[(2S)-2-methyl-5-oxomorpholin-4-yl]methyl}-3-oxpropyl] carbamate obtained in PREPARATION 153 was used.

$^1$H NMR (CD$_3$OD) δ 4.86-4.75 (2H, m), 4.16-4.05 (2H, m), 3.94-3.89 (1H, m), 3.86-3.81 (1H, m), 3.55-3.50 (2H, m), 3.40-3.28 (4H, m), 3.07-3.05 (1H, m), 2.96 (1H, brs), 2.70-2.65 (1H, m), 2.57-2.52 (1H, m), 1.38-1.37 (9H, m), 1.22 (3H, d, J=6.2 Hz)

Mass (m/e) 458 (M+1)

PREPARATION 154

Synthesis of t-butyl {(1S)-1-[(2-methyl-5-oxothiomorpholin-4-yl)methyl]-3-oxo-3-[3-(trifluoromethyl)-5,6-dihydro[1,2,4]triazolo[4,3-a]pyrazin-7(8H)-yl]propyl}carbamate 21 mg of the title compound was obtained in a yield of 55% at the same manner as in PREPARATION 45, except that 25 mg (0.075 mmol) of (3S)-3-[(t-butoxycarbonyl)amino]-4-(2-methyl-5-oxothiomorpholin-4-yl)-butanoic acid obtained in PREPARATION 125 was reacted with 14.4 mg (0.075 mmol) of 3-(trifluoromethyl)-5,6-dihydro-8H-1,2,4-triazolo[4,3-a]pyrazine synthesized with reference to WO 03/004498.

$^1$H NMR (CDCl$_3$) δ 5.95-5.86 (1H, m), 5.12-4.80 (3H, m), 4.30-4.06 (3H, m), 3.99-3.90 (2H, m), 3.67-3.53 (2H, m), 3.42-3.35 (1H, m), 3.30-3.06 (3H, m), 2.90-2.74 (1H, m), 2.52-2.47 (1H, m), 1.40 (9H, s), 1.29-1.28 (3H, m)

Mass (m/e) 407 (M+1-BOC)

EXAMPLE 94

Synthesis of 4-{(2S)-2-amino-4-oxo-4-[3-(trifluoromethyl)-5,6-dihydro[1,2,4]triazolo[4,3-a]pyrazin-7 (8H)-yl]butyl}-6-methylthiomorpholin-3-one

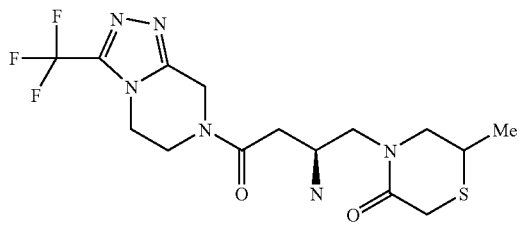

5.8 mg of the title compound was obtained in a yield of 34% at the same manner as in EXAMPLE 22, except that 21 mg (0.042 mmol) of t-butyl {(1S)-1-[(2-methyl-5-oxothiomorpholin-4-yl)methyl]-3-oxo-3-[3-(trifluoromethyl)-5,6-dihydro[1,2,4]triazolo[4,3-a]pyrazin-7(8H)-yl] propyl}carbamate obtained in PREPARATION 154 was used.

$^1$H NMR (CD$_3$OD) δ 5.08-4.98 (2H, m), 4.34 (1H, brs), 4.26 (1H, brs), 4.20-4.06 (2H, m), 3.74-3.69 (2H, m), 3.62 (1H, brs), 3.50-3.37 (4H, m), 3.32-3.23 (1H, m), 2.08-2.75 (1H, m), 2.68-2.62 (1H, m), 0.33-1.31 (3H, m)

Mass (m/e) 407 (M+1)

PREPARATION 155

Synthesis of t-butyl {(1S)-3-[2-ethyl-4-(trifluoromethyl)-5,8-dihydropyrido[3,4-d]pyrimidin-7(6H)-yl]-1-{[(5R)-5-methyl-2-oxopiperidin-1-yl]methyl}-3-oxpropyl}carbamate 63 mg of the title compound was obtained in a yield of 62% at the same manner as in PREPARATION 45, except that 66.3 mg (0.211 mmol) of (3S)-3-[(t-butoxycarbonyl)amino]-4-[(5R)-5-methyl-2-oxopiperidin-1-yl]butanoic acid obtained in PREPARATION 51 was reacted with 41 mg (0.192 mmol) of 2-ethyl-4-(trifluoromethyl)-5,6,7,8-tetrahydropyrido[3,4-d]pyrimidine hydrochloric acid salt (product of PREPARATION 128) was used.

$^1$H NMR (CDCl$_3$) δ 5.87 (1H, brs), 4.89-4.79 (1H, m), 4.76-4.65 (1H, m), 4.17 (1H, brs), 3.91-3.86 (1H, m), 3.78-3.75 (1H, m), 3.67-3.50 (2H, m), 3.89-3.35 (1H, m), 3.10-2.97 (6H, m), 2.88-2.81 (1H, m), 2.55-2.28 (3H, m), 1.95-1.88 (1H, m), 1.84-1.80 (1H, m), 1.42-1.40 (9H, m), 1.38-1.34 (3H, m), 1.01-0.99 (3H, m)

Mass (m/e) 438 (M+1-BOC)

EXAMPLE 95

Synthesis of (5R)-1-{(2S)-2-amino-4-[2-ethyl-4-(trifluoromethyl)-5,8-dihydropyrido[3,4-d]pyrimidin-7(6H)-yl]-4-oxobutyl}-5-methylpiperidin-2-one

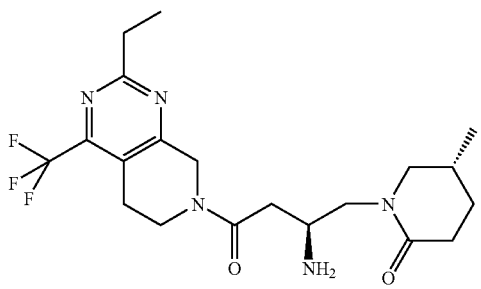

38.3 mg of the title compound was obtained in a yield of 69% at the same manner as in EXAMPLE 22, except that 63 mg (0.119 mmol) of t-butyl {(1S)-3-[2-ethyl-4-(trifluoromethyl)-5,8-dihydropyrido[3,4-d]pyrimidin-7(6H)-yl]-1-{[(5R)-5-methyl-2-oxopiperidin-1-yl]methyl}-3-oxpropyl}carbamate obtained in PREPARATION 155 was used.

$^1$H NMR (CD$_3$OD) δ 4.92-4.80 (2H, m), 3.94-3.91 (1H, m), 3.88-3.85 (1H, m), 3.78-3.76 (1H, m), 3.69-3.62 (1H, m), 3.58-3.53 (1H, m), 3.42-3.34 (2H, m), 3.15-3.09 (2H, m), 3.03-2.97 (2H, m), 2.92-2.85 (1H, m), 2.79-2.73 (1H, m), 2.48-2.34 (2H, m), 2.06-2.02 (1H, m), 1.89-1.84 (1H, m), 1.60-1.49 (1H, m), 1.41-1.35 (3H, m), 1.05 (3H, d, J=6.4 Hz)

Mass (m/e) 428 (M+1)

PREPARATION 156

Synthesis of t-butyl {(1S)-1-{[(5R)-5-methyl-2-oxopiperidin-1-yl]methyl}-3-oxo-3-[2-(pentafluoroethyl)-4-(trifluoromethyl)-5,8-dihydropyrido[3,4-d]pyrimidin-7(6H)-yl]propyl}carbamate 65 mg of the title compound was obtained in a yield of 84% at the same manner as in PREPARATION 45, except that 43 mg (0.137 mmol) of (3S)-3-[(t-butoxycarbonyl)amino]-4-[(5R)-5-methyl-2-oxopiperidin-1-yl]butyric acid obtained in PREPARATION 51 was reacted with 40 mg (0.125 mmol) 2-(pentafluoroethyl)-4-(trifluoromethyl)-5,6,7,8-tetrahydropyrido[3,4-d]pyrimidine hydrochloric acid salt (product of PREPARATION 129).

$^1$H NMR (CDCl$_3$) δ 5.98-5.91 (1H, m), 5.30-4.79 (2H, m), 4.14-4.02 (2H, m), 3.89-3.81 (2H, m), 3.69-3.47 (2H, m), 3.40-3.34 (1H, m), 3.24-3.01 (3H, m), 2.89-2.79 (1H, m), 2.57-2.43 (1H, m), 2.40-2.19 (2H, m), 1.94 (1H, brs), 1.84 (1H, brs), 1.42-1.40 (9H, m), 1.00 (3H, d, J=6.4 Hz)

Mass (m/e) 518 (M+1-BOC)

EXAMPLE 96

Synthesis of (5R)-1-{(2S)-2-amino-4-oxo-4-[2-(pentafluoroethyl)-4-(trifluoromethyl)-5,8-dihydropyrido[3,4-d]pyrimidin-7(6H)-yl]butyl}-5-methylpiperidin-2-one

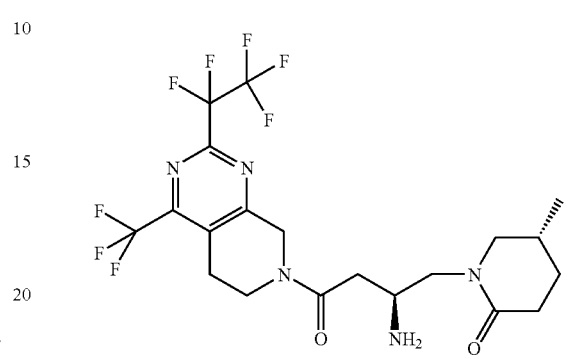

43.9 mg of the title compound was obtained in a yield of 82% at the same manner as in EXAMPLE 22, except that 65 mg (0.104 mmol) of t-butyl {(1S)-1-{[(5R)-5-methyl-2-oxopiperidin-1-yl]methyl}-3-oxo-3-[2-(pentafluoroethyl)-4-(trifluoromethyl)-5,8-dihydropyrido[3,4-d]pyrimidin-7(6H)-yl]propyl}carbamate obtained in PREPARATION 156 was used.

$^1$H NMR (CD$_3$OD) δ 4.99-4.95 (1H, m), 3.99-3.87 (3H, m), 3.69-3.68 (1H, m), 3.56-3.53 (2H, m), 3.41-3.38 (1H, m), 3.25 (1H, brs), 3.15-3.06 (2H, m), 2.84-2.77 (1H, m), 2.72-2.62 (1H, m), 2.45-2.34 (2H, m), 2.03 (1H, brs), 1.85 (1H, brs), 1.58-1.48 (1H, m), 1.05 (3H, d, J=6.4 Hz)

Mass (m/e) 518 (M+1)

PREPARATION 157

Synthesis of t-butyl {(1S)-1-{[(2S)-2-methyl-5-oxomorpholin-4-yl]methyl}-3-oxo-3-[2-(pentafluoroethyl)-4-(trifluoromethyl)-5,8-dihydropyrido[3,4-d]pyrimidin-7(6H)-yl]propyl}carbamate 58 mg of the title compound was obtained in a yield of 75% at the same manner as in PREPARATION 45, except that 43.3 mg (0.137 mmol) of (3S)-3-[(t-butoxycarbonyl)amino]-4-[2(S)-2-methyl-5-oxomorpholin-4-yl]-butanoic acid obtained in PREPARATION 55 was reacted with 40 mg (0.125 mmol) of 2-(pentafluoroethyl)-4-(trifluoromethyl)-5,6,7,8-tetrahydropyrido[3,4-d]pyrimidine hydrochloric acid salt (product of PREPARATION 129).

hu 1H NMR (CDCl$_3$) δ 5.87-5.84 (1H, m), 5.09-4.79 (2H, m), 4.23-3.98 (3H, m), 3.89-3.80 (2H, m), 3.72-3.65 (1H, m), 3.46-3.33 (4H, m), 3.22-3.13 (2H, m), 2.90-2.81 (1H, m), 2.61-2.50 (1H, m), 1.43-1.41 (9H, m), 1.26 (3H, d, J=6.0 Hz)

Mass (m/e) 520 (M+1-BOC)

EXAMPLE 97

Synthesis of (6S)-4-{(2S)-2-amino-4-oxo-4-[2-(pentafluoroethyl)-4-(trifluoromethyl)-5,8-dihydropyrido[3,4-d]pyrimidin-7(6H)-yl]butyl}-6-methylmorpholine-3-one

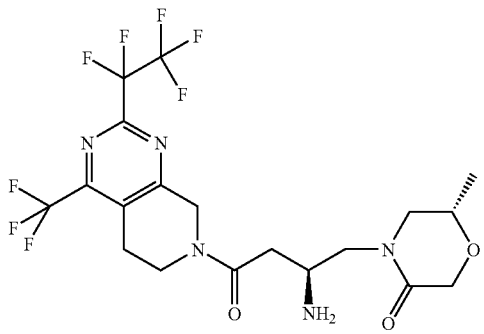

43.9 mg of the title compound was obtained in a yield of 90% at the same manner as in EXAMPLE 22, except that 58 mg (0.094 mmol) of t-butyl {(1S)-1-{[(2S)-2-methyl-5-oxo-morpholin-4-yl]methyl}-3-oxo-3-[2-(pentafluoroethyl)-4-(trifluoro)-5,8-dihydropyrido[3,4-d]pyrimidin-7(6H)-yl]propyl}carbamate obtained in PREPARATION 157 was used.

$^1$H NMR (CD$_3$OD) δ 4.99-4.95 (1H, m), 4.21-4.10 (2H, m), 4.05-3.90 (3H, m), 3.64-3.54 (2H, m), 3.50-3.39 (2H, m), 3.62-3.35 (2H, m), 3.24 (1H, brs), 3.14 (1H, brs), 2.79-2.73 (1H, m), 2.67-2.58 (1H, m), 1.26 (3H, d, J=6.0 Hz)

Mass (m/e) 520 (M+1)

PREPARATION 158

Synthesis of t-butyl {(1S)-1-[(5,5-difluoro-2-oxopiperidin-1-yl)methyl]-3-oxo-3-[2-(pentafluoroethyl)-4-(trifluoromethyl)-5,8-dihydropyrido[3,4-d]pyrimidin-7(6H)-yl]propyl}carbamate 16.4 mg of the title compound was obtained in a yield of 47% at the same manner as in PREPARATION 45, except that 46 mg (0.137 mmol) of (3S)-3-[(t-butoxycarbonyl)amino]-4-(5,5-difluoro-2-oxopiperidin-1-yl)-butanoic acid obtained in PREPARATION 57 was reacted with 40 mg (0.125 mmol) of 2-(pentafluoroethyl)-4-(trifluoromethyl)-5,6,7,8-tetrahydropyrido[3,4-d]pyrimidine hydrochloric acid salt (product of PREPARATION 129).

$^1$H NMR (CDCl$_3$) δ 5.85-5.78 (1H, m), 5.07-4.79 (2H, m), 4.17 (1H, brs), 4.04-3.61 (5H, m), 3.53-3.49 (1H, m), 3.19-3.13 (2H, m), 2.87-2.79 (1H, m), 2.62-2.48 (3H, m), 2.32-2.24 (2H, m), 1.42-1.41 (9H, m)

Mass (m/e) 540 (M+1-BOC)

EXAMPLE 98

Synthesis of 1-{(2S)-2-amino-4-oxo-4-[2-(pentafluoroethyl)-4-(trifluoromethyl)-5,8-dihydropyrido[3,4-d]pyrimidin-7(6H)-yl]butyl}-5,5-difluoropiperidin-2-one

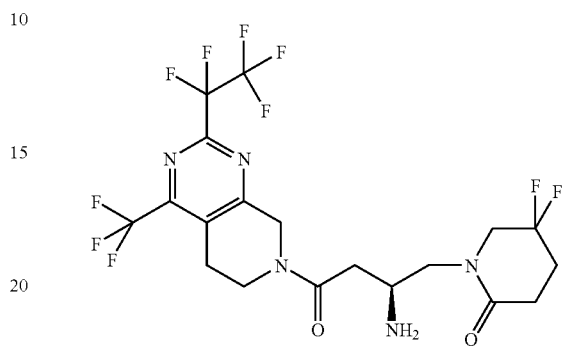

42.8 mg of the title compound was obtained in a yield of 83% at the same manner as in EXAMPLE 22, except that 64 mg (0.095 mmol) of t-butyl {(1S)-1-[(5,5-difluoro-2-oxopiperidin-1-yl)methyl]-3-oxo-3-[2-(pentafluoroethyl)-4-(trifluoromethyl)-5,8-dihydropyrido[3,4-d]pyrimidin-7(6H)-yl]propyl}carbamate obtained in PREPARATION 158 was used.

$^1$H NMR (CD$_3$OD) δ 4.98-4.95 (1H, m), 4.03-3.89 (2H, m), 3.85-3.77 (2H, m), 3.64-3.54 (2H, m), 3.52-3.46 (1H, m), 3.26-3.24 (1H, m), 3.14 (1H, brs), 2.80-2.72 (1H, m), 2.68-2.56 (4H, m), 2.04-2.03 (2H, m)

Mass (m/e) 540 (M+1)

PREPARATION 159

Synthesis of 2-propyl-4-(trifluoromethyl)-5,6,7,8-tetrahydropyrido[3,4-d]pyrimidine hydrochloric acid salt (1) Synthesis of Butane Imidamide 1.95 g of the title compound was obtained in a yield of 79% at the same manner as in PREPARATION 58-(1), except that 2.0 g (1.85 mmol) of butyronitrile was used.

NMR: $^1$H-NMR (CD$_3$OD) δ 2.45 (2H, t, J=6.5 Hz), 1.75 (2H, m), 1.05 (3H, t, J=7.2 Hz)

(2) Synthesis of t-butyl 2-propyl-4-(trifluoromethyl)-5,8-dihydropyrido[3,4-d]pyrimidin-7(6H)-carboxylate 144 mg of the title compound was obtained in a yield of 25% at the same manner as in PREPARATION 58-(2), except that 500 mg (1.69 mmol) of t-butyl 3-oxo-4-(trifluoroacetyl)piperidin-1-carboxylate obtained in the above step (1) and 146 mg (1.69 mmol) of butane imidamide was used.

$^1$H NMR (CDCl$_3$) δ 4.73 (2H, s), 3.76 (2H, t, J=8.0 Hz), 3.00 (4H, m), 1.89 (2H, m), 1.54 (9H, s), 1.06 (3H, t, J=8 Hz)

Mass (m/e) 346 (M+1)

(3) 2-propyl-4-(trifluoromethyl)-5,6,7,8-tetrahydro-pyrido[3,4-d]pyrimidine hydrochloric acid salt 72 mg of the title compound was obtained in a yield of 61% at the same manner as in PREPARATION 58-(3), except that 144 mg (0.42 mmol) of t-butyl 2-propyl-4-(trifluoromethyl)-5,8-dihydropyrido[3,4-d]pyrimidin-7(6H)-carboxylate obtained in the above step (2) was used.

$^1$H NMR (CD$_3$OD) δ 4.46 (2H, s), 3.59 (2H, t, J=6.0 Hz), 3.25 (2H, m), 2.94 (2H, t, J=7.2 Hz), 1.84 (2H, m), 0.97 (3H, t, J=7.2 Hz)

Mass (m/e) 246 (M+1)

PREPARATION 160

Synthesis of t-butyl {(1S)-1-{[(5R)-5-methyl-2-oxopiperidin-1-yl]methyl}-3-oxo-3-[2-propyl-4-(trifluoromethyl)-5,8-dihydropyrido[3,4-d]pyrimidin-7(6H)-yl]propyl}carbamate 70 mg of the title compound was obtained in a yield of 91% at the same manner as in PREPARATION 45, except that 44.0 mg (0.141 mmole) of (3S)-t-[(t-butoxycarbonyl)amino]-4-[(5R)-methyl-2-oxopiperidin-1-yl]butanoic acid obtained in PREPARATION 51 and 36.0 mg (0.128 mmole) of 2-propyl-4-(trifluoromethyl)-5,6,7,8-tetrahydropyrido[3,4-d]pyrimidine hydrochloric acid salt obtained in PREPARATION 159 were used.

$^1$H NMR (CDCl$_3$) δ 5.88 (1H, brs), 4.89-4.65 (2H, m), 4.18 (1H, brs), 3.89-3.86 (1H, m), 3.78-3.76 (1H, m), 3.62-51 (2H, m), 3.38-3.35 (1H, m), 3.11-2.80 (7H, m), 2.56-2.28 (3H, m), 1.94-1.82 (4H, m), 1.42-1.40 (9H, m), 1.01-0.98 (6H, m)

Mass (m/e) 542 (M+1)

EXAMPLE 99

Synthesis of (5R)-1-{(2S)-2-amino-4-oxo-4-[2-propyl-4-(trifluoromethyl)-5,8-dihydropyrido[3,4-d]pyrimidin-7(6H)-yl]butyl}-5-methylpiperidin-2-one

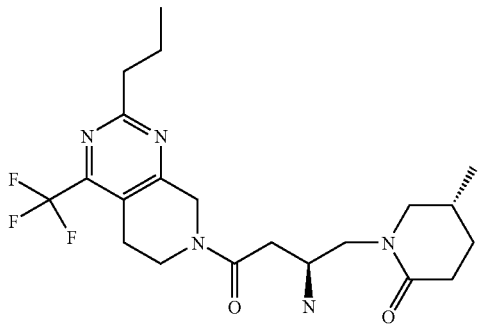

41.9 mg of the title compound was obtained in a yield of 68% at the same manner as in EXAMPLE 22, except that 70 mg (0.129 mmol) of t-butyl {(1S)-1-{[(5R)-5-methyl-2-oxopiperidin-1-yl]methyl}-3-oxo-3-[2-propyl-4-(trifluoromethyl)-5,8-dihydropyrido[3,4-d]pyrimidin-7(6H)-yl]propyl}carbamate obtained in PREPARATION 160 was used.

$^1$H NMR (CD$_3$OD) δ 4.86-4.79 (2H, m), 3.95-3.82 (2H, m), 3.67-3.64 (1H, m), 3.59-3.47 (2H, m), 3.41-3.37 (1H, m), 3.34-3.32 (1H, m), 3.11-3.10 (2H, m), 3.01-2.93 (2H, m), 2.79-2.73 (1H, m), 2.67-2.57 (1H, m), 2.47-2.31 (2H, m), 2.04-2.00 (1H, m), 1.92-1.82 (3H, m), 1.58-1.48 (1H, m), 1.06 (3H, d, J=6.4 Hz), 1.03-0.99 (3H, m)

Mass (m/e) 442 (M+1)

PREPARATION 161

Synthesis of t-butyl {(1S)-1-[(5,5-difluoro-2-oxopiperidin-1-yl)methyl]-3-oxo-3-[2-propyl-4-(trifluoromethyl)-5,8-dihydropyrido[3,4-d]pyrimidin-7(6H)-yl]propyl}carbamate 61 mg of the title compound was obtained in a yield of 77% at the same manner as in PREPARATION 45, except that 47.0 mg (0.141 mmol) of (3S)-3-[(t-butoxycarbonyl)amino]-4-(5,5-difluoro-2-oxopiperidin-1-yl)butanoic acid PREPARATION 57 and 36.0 mg (0.128 mmol) of 2-propyl-4-(trifluoromethyl)-5,6,7,8-tetrahydropyrido[3,4-d]pyrimidine hydrochloric acid salt obtained in PREPARATION 159 were used.

$^1$H NMR (CDCl$_3$) δ 5.78 (1H, brs), 4.83-4.68 (2H, m), 4.20 (1H, brs), 3.88-3.68 (4H, m), 3.60-3.56 (2H, m), 3.04-2.78 (5H, m), 2.61-2.55 (3H, m), 2.31-2.23 (2H, m), 1.87-1.82 (2H, m), 1.42-1.41 (9H, m), 1.02-0.98 (3H, m)

Mass (m/e) 564 (M+1)

EXAMPLE 100

Synthesis of 1-{(2S)-2-amino-4-oxo-4-[2-propyl-4-(trifluoromethyl)-5,8-dihydropyrido[3,4-d]pyrimidin-7(6H)-yl]butyl}-5,5-difluoropiperidin-2-one

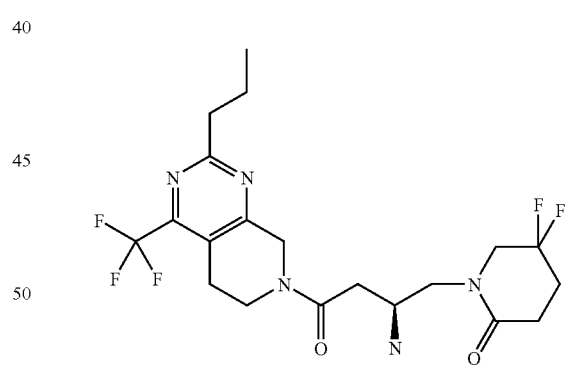

34.4 mg of the title compound was obtained in a yield of 64% at the same manner as in EXAMPLE 22, except that 47 mg (0.081 mmol) of t-butyl {(1S)-1-[(5,5-difluoro-2-oxopiperidin-1-yl)methyl]-3-oxo-3-[2-propyl-4-(trifluoromethyl)-5,8-dihydropyrido[3,4-d]pyrimidin-7(6H)-yl]propyl}carbamate obtained in PREPARATION 161 was used.

$^1$H NMR (CD$_3$OD) δ 4.90-4.79 (2H, m), 3.86-3.78 (4H, m), 3.57-3.46 (3H, m), 3.12-3.10 (1H, m), 3.00-2.93 (3H, m), 2.76-2.51 (4H, m), 2.41-2.31 (2H, m), 1.92-1.82 (2H, m), 1.03-0.95 (3H, m)

Mass (m/e) 464 (M+1)

PREPARATION 162

Synthesis of 2-(fluoromethyl)-4-(trifluoromethyl)-5,6,7,8-tetradropyrido[3,4-d]pyrimidine hydrochloric acid salt

(1) Synthesis of 2-fluoroethaneimidamide 1.77 g of the title compound was obtained in a yield of 93% at the same manner as in PREPARATION 58-(1), except that 1.5 g (0.025 mmol) of fluoroacetonitrile was used.

NMR: $^1$H-NMR (CD$_3$OD) δ 5.32 (2H, d, J=45.2 Hz)

(2) Synthesis of t-butyl 2-(fluoromethyl)-4-(trifluoromethyl)-5,8-dihydropyrido[3,4-d]pyrimidin-7(6H)-carboxylate 220 mg of the title compound was obtained in a yield of 19% at the same manner as in PREPARATION 58-(2), except that 1.0 g (3.39 mmol) of t-butyl 3-oxo-4-(trifluoroacetyl)piperidin-1-carboxylate and 335 mg (4.40 mmol) of 2-fluoroethaneimidamide obtained in the above step (1) were used.

$^1$H NMR (CDCl$_3$) δ 5.55 (2H, d, J=46.8 Hz), 4.78 (2H, s), 3.75 (2H, t, J=6.0 Hz), 3.00 (2H, brs), 1.50 (9H, s)

Mass (m/e) 336 (M+1)

(3) Synthesis of 2-(fluoromethyl)-4-(trifluoromethyl)-5,6,7,8-tetradropyrido[3,4-d]pyrimidine hydrochloric acid salt 170 mg of the title compound was obtained in a yield of 96% at the same manner as in PREPARATION 58-(3), except that 220 mg (0.66 mmol) of t-butyl 2-(fluoromethyl)-4-(trifluoromethyl)-5,8-dihydropyrido[3,4-d]pyrimidin-7(6H)-carboxylate obtained in the above step (2) was used.

$^1$H NMR (CD$_3$OD) δ 5.57 (2H, d, J=29.6 Hz), 4.76 (2H, s), 4.47 (2H, s), 3.26-3.20 (2H, m),

Mass (m/e) 236 (M+1)

PREPARATION 163

Synthesis of t-butyl [(1S)-3-[2-(fluoromethyl)-4-(trifluoromethyl-5,8-dihydropyrido[3,4-d]pyrimidin-7(6H)-yl]-1-{[(5R)-5-methyl-2-oxopiperidin-1-yl]methyl}-3-oxpropyl]carbamate 115 mg of the title compound was obtained in a yield of 60% at the same manner as in PREPARATION 45, except that 125 mg (0.398 mmole) of (3S)-3-[(t-butoxycarbonyl)amino]-4-[(5R)-5-methyl-2-oxopiperidin-1-yl]butanoic acid obtained in PREPARATION 51 and 85 mg (0.361 mmole) of 2-(fluoromethyl)-4-(trifluoromethyl)-5,6,7,8-tetrahydropyrido[3,4-d]pyrimidine hydrochloric acid salt obtained in PREPARATION 162 were used.

$^1$H NMR (CDCl$_3$) δ 5.90-5.88 (1H, m), 5.54 (2H, dd, J=46.5, 2.75 Hz), 4.97-4.72 (2H, m), 4.14 (1H, brs), 3.90 (1H, brs), 3.80-3.70 (1H, m), 3.55-3.52 (2H, m), 3.37-3.33 (1H, m), 3.10-2.98 (3H, m), 2.43-2.28 (4H, m), 1.45-1.38 (9H, m), 0.99 (3H, d, J=6.8 Hz)

Mass (m/e) 532 (M+1)

EXAMPLE 101

Synthesis of (5R)-1-{(2S)-2-amino-4-[2-(fluoromethyl)-4-(trifluoromethyl)-5,8-dihydropyrido[3,4-d]pyrimidin-7(6H)-yl]-4-oxobutyl}-5-methylpiperidin-2-one

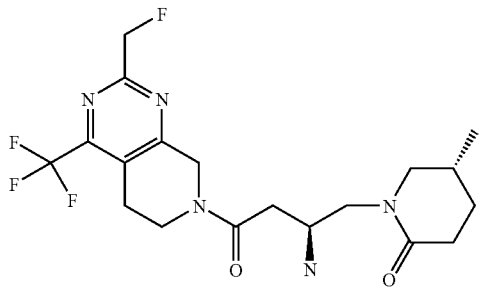

41.9 mg of the title compound was obtained in a yield of 68% at the same manner as in EXAMPLE 22, except that 70 mg (0.129 mmole) of t-butyl {(1S)-1-{[(5R)-5-methyl-2-oxopiperidin-1-yl]methyl}-3-oxo-3-[2-propyl-4-(trifluoromethyl)-5,8-dihydropyrido[3,4-d]pyrimidin-7(6H)-yl]propyl}carbamate obtained in PREPARATION 163 was used.

$^1$H NMR (CD$_3$OD) δ 4.86-4.79 (2H, m), 3.95-3.82 (2H, m), 3.67-3.64 (1H, m), 3.59-3.47 (2H, m), 3.41-3.37 (1H, m), 3.34-3.32 (1H, m), 3.11-3.10 (2H, m), 3.01-2.93 (2H, m), 2.79-2.73 (1H, m), 2.67-2.57 (1H, m), 2.47-2.31 (2H, m), 2.04-2.00 (1H, m), 1.92-1.82 (3H, m), 1.58-1.48 (1H, m), 1.06 (3H, d, J=6.4 Hz), 1.03-0.99 (3H, m)

Mass (m/e) 432 (M+1)

PREPARATION 164

Synthesis of t-butyl {(1S)-1-[(5,5-difluoro-2-oxopiperidin-1-yl)methyl]-3-[2-(fluoromethyl)-4-(trifluoromethyl)-5,8-dihydropyrido[3,4-d]pyrimidin-7(6H)-yl]-3-oxpropyl}carbamate 85 mg of the title compound was obtained in a yield of 43% at the same manner as in PREPARATION 45, except that 134 mg (0.398 mmole) of (3S)-3-[(t-butoxycarbonyl)amino]-4-(5,5-difluoro-2-oxopiperidin-1-yl)butanoic acid PREPARATION 57 and 85.0 mg (0.361 mmole) of 2-(fluoromethyl)-4-(trifluoromethyl)-5,6,7,8-tetrahydropyrido[3,4-d]pyrimidine hydrochloric acid salt obtained in PREPARATION 162 were used.

$^1$H NMR (CDCl$_3$) δ 5.80-5.78 (1H, brs), 5.47 (2H, d, J=24.4 Hz), 4.96-4.72 (2H, m), 4.18 (1H, brs), 3.91-3.89 (1H, m), 3.80-3.49 (5H, m), 3.11-3.00 (2H, m), 2.84-2.77 (1H, m), 2.59-2.48 (3H, m), 2.29-2.21 (2H, m), 1.42-1.40 (9H, m)

Mass (m/e) 554 (M+1)

EXAMPLE 102

Synthesis of 1-{(2S)-2-amino-4-[2-(fluoromethyl)-4-(trifluoromethyl)-5,8-dihydropyrido[3,4-d]pyrimidin-7(6H)-yl]-4-oxobutyl}-5,5-difluoropiperidin-2-one

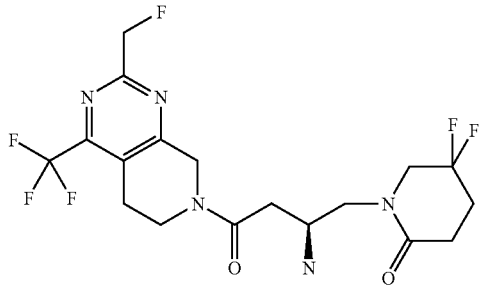

34.4 mg of the title compound was obtained in a yield of 64% at the same manner as in EXAMPLE 22, except that 47 mg (0.081 mmole) of t-butyl {(1S)-1-[(5,5-difluoro-2-oxopiperidin-1-yl)methyl]-3-[2-(fluoromethyl)-4-(trifluoromethyl)-5,8-dihydropyrido[3,4-d]pyrimidin-7(6H)-yl]-3-oxpropyl}carbamate obtained in PREPARATION 164 was used.

$^1$H NMR (CD$_3$OD) δ 4.90-4.79 (2H, m), 3.86-3.78 (4H, m), 3.57-3.46 (3H, m), 3.12-3.10 (1H, m), 3.00-2.93 (3H, m), 2.76-2.51 (4H, m), 2.41-2.31 (2H, m), 1.92-1.82 (2H, m), 1.03-0.95 (3H, m)

Mass (m/e) 464 (M+1)

PREPARATION 165

Synthesis of t-butyl (3S)-3-[(t-butoxycarbonyl)amino]-4-(4-methyl-2-oxo-2,5-dihydro-1H-pyrrol-1-yl)butanoate 410 mg of the title compound was obtained in a yield of 34% at the same manner as in PREPARATION 42, except that 3S-t-butoxycarbonylamino-4-oxo-butryic acid t-butylester (product of PREPARATION 41) and 590 mg (3.56 mmol) of 4-amino-3-methyl-2-butenoic acid methyl ester hydrochloric acid salt obtained in PREPARATION 6 were used.

$^1$H NMR (CDCl$_3$) δ 6.03 (1H, s), 5.34-5.31 (1H, m), 4.15-3.84 (3H, m), 3.71-3.62 (1H, m), 3.41-3.36 (1H, m), 2.54-2.38 (2H, m), 2.07-2.04 (3H, m), 1.45 (9H, s), 1.39 (9H, s)

Mass (m/e) 355 (M+1)

PREPARATION 166

Synthesis of (3S)-3-[(t-butoxycarbonyl)amino]-4-(4-methyl-2-oxo-2,5-dihydro-1H-pyrrol-1-yl)butanoic acid 310 mg of the title compound was obtained in a yield of 90% at the same manner as in PREPARATION 43, except that 410 mg (1.16 mmol) of t-butyl (3S)-3-[(t-butoxycarbonyl)amino]-4-(4-methyl-2-oxo-2,5-dihydro-1H-pyrrol-1-yl)butanoate obtained in PREPARATION 165 was used.

$^1$H NMR (CDCl$_3$) δ 9.03 (1H, brs), 6.12 (1H, s), 5.73 (1H, d, J=8.8 Hz), 4.16-4.11 (2H, m), 3.94-3.90 (1H, m), 3.78-3.72 (1H, m), 3.50-3.45 (1H, m), 2.66-2.54 (2H, m), 2.07 (3H, s), 1.39 (9H, s)

Mass (m/e) 299 (M+1)

PREPARATION 167

Synthesis of t-butyl (3S)-3-[(t-butoxycarbonyl)amino]-4-(4-methyl-2-oxopyrrolidin-1-yl)butanoate 1.03 g of the title compound was obtained in a yield of 64% at the same manner as in PREPARATION 42, except that 790 mg (4.71 mmol) of 4-amino-3-methyl-butyric acid methyl ester hydrochloric acid salt obtained in PREPARATION 2 was used.

Mass (m/e) 357 (M+1)

PREPARATION 168

Synthesis of (3S)-3-[(t-butoxycarbonyl)amino]-4-(4-methyl-2-oxopyrrolidin-1-yl)butanoic acid 670 mg of the title compound was obtained in a yield of 77% at the same manner as in PREPARATION 43, except that 1.03 g (2.89 mmol) of t-butyl (3S)-3-[(t-butoxycarbonyl)amino]-4-(4-methyl-2-oxopyrrolidin-1-yl)butanoate obtained in PREPARATION 167 was used.

$^1$H NMR (CDCl$_3$) δ 6.96 (1H, brs), 5.97-5.55 (1H, m), 4.16 (1H, brs), 3.78-3.40 (2H, m), 3.27-2.99 (1H, m), 2.66-2.47 (4H, m), 2.14-2.05 (1H, m), 1.44-1.42 (9H, s), 1.12 (3H, d, J=8.0 Hz)

Mass (m/e) 301 (M+1)

PREPARATION 169

Synthesis of t-butyl (3S)-3-[(t-butoxycarbonyl)amino]-4-[2-oxo-5-(trifluoromethyl)piperidin-1-yl]butanoate 49 mg of the title compound was obtained in a yield of 22% at the same manner as in PREPARATION 42, except that 132 mg (0.558 mmol) of 4-aminomethyl-5,5,5-trifluoro-pentanoic acid methyl ester hydrochloric acid salt obtained in PREPARATION 11 was used.

$^1$H NMR (CDCl$_3$) δ 5.56-5.25 (1H, m), 4.40 (1H, br s), 3.85-3.46 (1H, m), 3.42-3.36 (1H, m), 3.32-2.27 (1H, m), 2.62-2.36 (4H, m), 2.13-2.05 (2H, m), 1.92-1.79 (2H, m), 1.46 (9H, s), 1.42-1.41 (9H, m)

Mass (m/e) 425 (M+1)

PREPARATION 170

Synthesis of (3S)-3-[(t-butoxycarbonyl)amino]-4-[2-oxo-5-(trifluoromethyl)piperidin-1-yl]-butanoic acid 14 mg of the title compound was obtained in a yield of 13% at the same manner as in PREPARATION 43, except that 49 mg (0.115 mmol) of t-butyl (3S)-3-[(t-butoxycarbonyl)amino]-4-[2-oxo-5-(trifluoromethyl)piperidin-1-yl]butanoate PREPARATION 169 was used.

$^1$H NMR (CDCl$_3$) δ 4.25 (1H, br s), 3.68-3.48 (4H, m), 2.83 (2H, brs), 2.56-2.36 (2H, m), 2.16-2.10 (2H, m), 1.96-1.84 (2H, m), 1.47-1.44 (9H, s)

Mass (m/e) 369 (M+1)

PREPARATION 171

Synthesis of t-butyl (3S)-3-[(t-butoxycarbonyl)amino]-4-[2-oxo-4-(trifluoromethyl)pyrrolidin-1-yl]butanoate 134 mg of the title compound was obtained in a yield of 21% at the same manner as in PREPARATION 42, except that 390 mg (1.65 mmol) of 3-aminomethyl-4,4,4-trifluoro-butanoic acid ethyl ester hydrochloric acid salt obtained in PREPARATION 1 was used.

$^1$H NMR (CDCl$_3$) δ 5.10-5.09 (1H, brs), 4.12 (1H, br s), 3.67-3.50 (3H, m), 3.28-3.25 (1H, m), 3.10-3.04 (1H, m), 2.64-2.50 (2H, m), 2.44-2.40 (2H, m), 1.47 (9H, s), 1.40 (9H, s)

Mass (m/e) 411 (M+1)

PREPARATION 172

Synthesis of (3S)-3-[(t-butoxycarbonyl)amino]-4-[2-oxo-4-(trifluoromethyl)pyrrolidin-1-yl]-butanoic acid 89 mg of the title compound was obtained in a yield of 78% at the same manner as in PREPARATION 43, except that 134 mg (0.326 mmol) of t-butyl (3S)-3-[(t-butoxycarbonyl)amino]-4-[2-oxo-4-(trifluoromethyl)pyrrolidin-1-yl]butanoate PREPARATION 171 was used.

Mass (m/e) 355 (M+1)

PREPARATION 173

Synthesis of t-butyl (3S)-3-[(t-butoxycarbonyl)amino]-4-(4-methyl-2-oxooxopiperidin-1-yl)butanoate 750 mg of the title compound was obtained in a yield of 62% at the same manner as in PREPARATION 42, except that 620 mg (3.43 mmol) of 5-amino-3-methyl-pentanoic acid methyl ester hydrochloric acid salt obtained in PREPARATION 8 was used.

$^1$H NMR (CDCl$_3$) δ 5.35-5.30 (1H, m), 4.17 (1H, brs), 3.95-3.86 (1H, m), 3.78-3.64 (1H, m), 3.51-3.46 (1H, m), 3.30-3.26 (1H, m), 3.16-3.02 (1H, m), 2.54-2.46 (2H, m), 2.41-2.34 (1H, m), 2.01-1.84 (3H, m), 1.45 (9H, s), 1.41 (9H, s), 1.01 (3H, d, J=6.0 Hz)

Mass (m/e) 371 (M+1)

PREPARATION 174

Synthesis of (3S)-3-[(t-butoxycarbonyl)amino]-4-(4-methyl-2-oxopiperidin-1-yl)-butanoic acid 579 mg of the title compound was obtained in a yield of 92% at the same manner as in PREPARATION 43, except that 750 mg (2.02 mmol) of t-butyl (3S)-3-[(t-butoxycarbonyl)amino]-4-(4-methyl-2-oxooxopiperidin-1-yl)butanoate obtained in PREPARATION 173 was used.

$^1$H NMR (CDCl$_3$) δ 7.93 (1H, brs), 5.05-5.57 (1H, m), 4.20-4.19 (1H, m), 3.90-3.74 (1H, m), 3.57-3.51 (1H, m), 3.41-3.23 (2H, m), 2.66-2.52 (3H, m), 2.07-1.86 (3H, m), 1.33 (9H, s), 1.01 (3H, d, J=6.4 Hz)

Mass (m/e) 315 (M+1)

PREPARATION 175

Synthesis of t-butyl {(1S)-3-[2,4-bis(trifluoromethyl)-5,8-dihydropyrido[3,4-d]pyrimidin-7(6H)-yl]-1-[(4-methyl-2-oxo-2,5-dihydro-1H-pyrrol-1-yl)methyl]-3-oxpropyl}carbamate 45.0 mg of the title compound was obtained in a yield of 98% at the same manner as in PREPARATION 45, except that 25.0 mg (0.084 mmol) of (3S)-3-[(t-butoxycarbonyl)amino]-4-(4-methyl-2-oxo-2,5-dihydro-1H-pyrrol-1-yl)butanoic acid PREPARATION 166 and 25.8 mg (0.084 mmol) of 2,4-bis(trifluoromethyl)-5,6,7,8-tetrahydropyrido[3,4-d]pyrimidine hydrochloric acid salt obtained in PREPARATION 127 were used.

$^1$H NMR (CDCl$_3$) δ 6.12-5.99 (1H, m), 5.79 (1H, d, J=16.0 Hz), 5.09-4.84 (2H, m), 4.18-4.13 (1H, m), 4.07-3.91 (3H, m), 3.74-3.66 (1H, m), 3.58-3.53 (1H, m), 3.30-3.13 (3H, m), 2.95-2.83 (1H, m), 2.60-2.55 (1H, m), 2.09 (3H, d, J=1.2 Hz), 1.45-1.43 (9H, m)

Mass (m/e) 552 (M+1)

EXAMPLE 103

Synthesis of 1-{(2S)-2-amino-4-[2,4-bis(trifluoromethyl)-5,8-dihydropyrido[3,4-d]pyrimidin-7(6H)-yl]-4-oxobutyl}-4-methyl-1,5-dihydro-2H-pyrrol-2-one

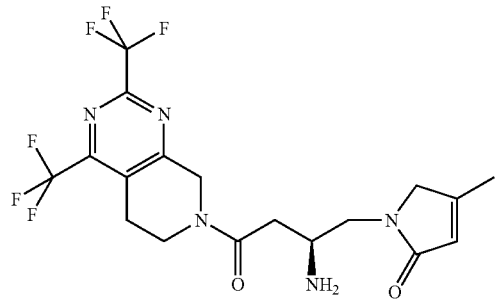

25.7 mg of the title compound was obtained in a yield of 65% at the same manner as in EXAMPLE 22, except that 45.0 mg (0.0816 mmol) of t-butyl {(1S)-3-[2,4-bis(trifluoromethyl)-5,8-dihydropyrido[3,4-d]pyrimidin-7(6H)-yl]-1-[(4-methyl-2-oxo-2,5-dihydro-1H-pyrrol-1-yl)methyl]-3-oxpropyl}carbamate obtained in PREPARATION 175 was used.

$^1$H NMR (CD$_3$OD) δ 5.86-5.84 (1H, m), 4.99-4.97 (2H, m), 4.14-4.13 (2H, m), 4.10-3.91 (3H, m), 3.78-3.70 (2H, m), 3.25 (1H, brs), 3.14 (1H, brs), 3.10-3.00 (1H, m), 2.88-2.82 (1H, m), 2.14 (3H, s)

Mass (m/e) 452 (M+1)

PREPARATION 176

Synthesis of t-butyl {(1S)-3-[2-(3-furyl)-4-(trifluoromethyl)-5,8-dihydropyrido[3,4-d]pyrimidin-7(6H)-yl]-1-[(4-methyl-2-oxo-2,5-dihydro-1H-pyrrol-1-yl)methyl]-3-oxpropyl}carbamate 44.9 mg of the title compound was obtained in a yield of 97% at the same manner as in PREPARATION 45, except that 25 mg (0.084 mmol) of (3S)-3-[(t-butoxycarbonyl)amino]-4-(4-methyl-2-oxo-2,5-dihydro-1H-pyrrol-1-yl)butanoic acid obtained in PREPARATION 166 and 25.6 mg (0.084 mmol) of 2-(3-furyl)-4-(trifluoromethyl)-5,6,7,8-tetrahydropyrido[3,4-d]pyrimidine hydrochloric acid salt obtained in PREPARATION 96 were used.

$^1$H NMR (CDCl$_3$) δ 8.27 (1H, s), 7.50-7.49 (1H, m), 7.06-7.05 (1H, m), 6.04-5.90 (1H, m), 5.80-5.79 (1H, m), 4.85 (1H, s), 4.83-4.70 (1H, m), 4.15-4.07 (1H, m), 4.02-3.95 (2H, m), 3.92-3.87 (1H, m), 3.84-3.81 (1H, m), 3.69-3.55 (2H, m), 3.08-3.06 (1H, m), 2.99 (1H, brs), 2.91-2.83 (1H, m), 2.57-2.52 (1H, m), 2.05-2.04 (3H, m), 1.41-1.40 (9H, m)

Mass (m/e) 550 (M+1)

EXAMPLE 104

Synthesis of 1-{(2S)-2-amino-4-[2-(3-furyl)-4-(trifluoromethyl)-5,8-dihydropyrido[3,4-d]pyrimidin-7(6H)-yl]-4-oxobutyl}-4-methyl-1,5-dihydro-2H-pyrrol-2-one

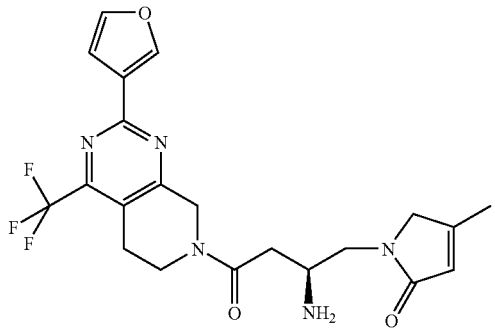

32.7 mg of the title compound was obtained in a yield of 82% at the same manner as in EXAMPLE 22, except that 44.9 mg (0.0817 mmol) of t-butyl {(1S)-3-[2-(3-furyl)-4-(trifluoromethyl)-5,8-dihydropyrido[3,4-d]pyrimidin-7(6H)-yl]-1-[(4-methyl-2-oxo-2,5-dihydro-1H-pyrrol-1-yl)methyl]-3-oxpropyl}carbamate obtained in PREPARATION 176 was used.

$^1$H NMR (CD$_3$OD) δ 8.35 (1H, s), 7.69-7.64 (1H, m), 7.08 (1H, s), 6.10 (1H, brs), 4.90-4.88 (2H, m), 4.23 (1H, brs), 3.95-3.81 (5H, m), 3.77-3.65 (1H, m), 3.19-3.03 (3H, m), 2.94-2.87 (1H, m), 2.15 (3H, m)

Mass (m/e) 450 (M+1)

PREPARATION 177

Synthesis of t-butyl {(1S)-3-[2,4-bis(trifluormethyl)-5,8-dihydropyrido[3,4-d]pyrimidin-7(6H)-yl]-1-[(4-methyl-2-oxopyrrolidin-1-yl)methyl]-3-oxpropyl}carbamate 13.0 mg of the title compound was obtained in a yield of 20% at the same manner as in PREPARATION 45, except that 35.0 mg (0.117 mmol) of (3S)-3-[(t-butoxycarbonyl)amino]-4-(4-methyl-2-oxopyrrolidin-1-yl)butanoic acid obtained in PREPARATION 168 and 33.0 mg (0.106 mmol) of 2,4-bis(trifluoromethyl)-5,6,7,8-tetrahydropyrido[3,4-d]pyrimidine hydrochloric acid salt obtained in PREPARATION 127 were used.

$^1$H NMR (CDCl$_3$) δ 5.78-5.75 (1H, m), 5.06-4.80 (2H, m), 4.15-4.09 (1H, m), 3.98-3.85 (2H, m), 3.65-3.55 (1H, m), 3.46-3.44 (2H, m), 3.19-3.06 (3H, m), 2.87-2.76 (1H, m), 2.59-2.45 (3H, m), 2.04-1.94 (1H, m), 1.42-1.40 (9H, m), 1.12-1.11 (3H, m)

Mass (m/e) 552 (M+1)

EXAMPLE 105

Synthesis of 1-{(2S)-2-amino-4-[2,4-bis(trifluoromethyl)-5,8-dihydropyrido[3,4-d]pyrimidin-7(6H)-yl]-4-oxobutyl}-4-methyloxopyrrolidin-2-one

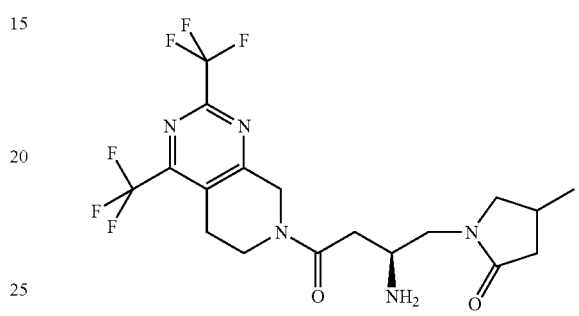

10.0 mg of the title compound was obtained in a yield of 87% at the same manner as in EXAMPLE 22, except that 13.0 mg (0.0235 mmol) of t-butyl {(1S)-3-[2,4-bis(trifluoromethyl)-5,8-dihydropyrido[3,4-d]pyrimidin-7(6H)-yl]-1-[(4-methyl-2-oxopyrrolidin-1-yl)methyl]-3-oxpropyl}carbamate obtained in PREPARATION 177 was used.

$^1$H NMR (CD$_3$OD) δ 5.05-4.97 (2H, m), 3.99 (1H, brs), 3.91-3.88 (2H, m), 3.77-3.73 (1H, m), 3.61-3.59 (1H, m), 3.48-3.45 (1H, m), 3.25 (1H, brs), 3.15 (2H, brs), 3.05-2.98 (1H, m), 2.89-2.79 (1H, m), 2.58-2.53 (2H, m), 2.12-2.07 (1H, m), 1.17-1.63 (3H, m)

Mass (m/e) 452 (M+1)

PREPARATION 178

Synthesis of t-butyl {(1S)-3-[2-(3-furyl)-4-(trifluoromethyl)-5,8-dihydropyrido[3,4-d]pyrimidin-7(6H)-yl]-1-[(4-methyl-2-oxopyrrolidin-1-yl)methyl]-3-oxpropyl}carbamate 26.0 mg of the title compound was obtained in a yield of 44% at the same manner as in PREPARATION 45, except that 35.0 mg (0.117 mmol) of (3S)-3-[(t-butoxycarbonyl)amino]-4-(4-methyl-2-oxopyrrolidin-1-yl)butanoic acid obtained in PREPARATION 168 and 32.4 mg (0.117 mmol) of 2-(3-furyl)-4-(trifluoromethyl)-5,6,7,8-tetrahydropyrido[3,4-d]pyrimidine hydrochloric acid salt obtained in PREPARATION 96 were used.

$^1$H NMR (CDCl$_3$) δ 8.27 (1H, s), 7.50 (1H, s), 7.06 (1H, s), 5.76-5.70 (1H, m), 4.86 (1H, s), 4.80-4.69 (1H, m), 4.15-4.09 (1H, m), 3.91-3.88 (1H, m), 3.80-3.79 (1H, m), 3.67-3.42 (3H, m), 3.09-3.00 (3H, m), 2.87-2.79 (1H, m), 2.58-2.35 (3H, m), 2.02-1.97 (1H, m), 1.42-1.41 (9H, m), 1.11 (3H, d, J=6.0 Hz)

Mass (m/e) 550 (M+1)

EXAMPLE 106

Synthesis of 1-{(2S)-2-amino-4-[2-(3-furyl)-4-(trifluoromethyl)-5,8-dihydropyrido[3,4-d]pyrimidin-7(6H)-yl]-4-oxobutyl}-4-methylpyrrolidin-2-one

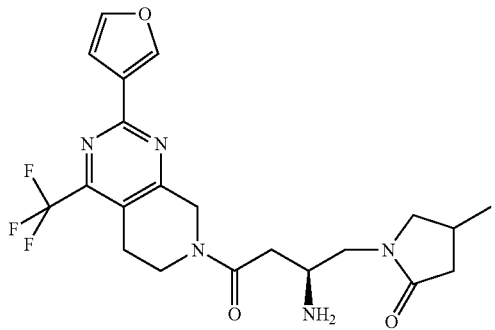

12.5 mg of the title compound was obtained in a yield of 54% at the same manner as in EXAMPLE 22, except that 26.0 mg (0.0471 mmol) of t-butyl {(1S)-3-[2-(3-furyl)-4-(trifluoromethyl)-5,8-dihydropyrido[3,4-d]pyrimidin-7(6H)-yl]-1-[(4-methyl-2-oxopyrrolidin-1-yl)methyl]-3-oxpropyl}carbamate obtained in PREPARATION 178 was used.

$^1$H NMR (CD$_3$OD) δ 8.36 (1H, s), 7.65 (1H, s), 7.09 (1H, s), 4.91-4.84 (2H, m), 3.97 (1H, brs), 3.87 (2H, brs), 3.71-3.58 (3H, m), 3.14 (2H, brs), 3.04-2.99 (2H, m), 2.86-2.79 (1H, m), 2.60-2.51 (1H, m), 2.10-2.05 (2H, m), 1.22-1.16 (3H, m)

Mass (m/e) 450 (M+1)

PREPARATION 179

Synthesis of t-butyl [(1S)-3-[2,4-bis(trifluoromethyl)-5,8-dihydropyrido[3,4-d]pyrimidin-7(6H)-yl]-3-oxo-1-{[2-oxo-5-(trifluoromethyl)piperidin-1-yl]methyl}propyl]carbamate 18.0 mg of the title compound was obtained in a yield of 76% at the same manner as in PREPARATION 45, except that 14.0 mg (0.038 mmol) of (3S)-3-[(t-butoxycarbonyl)amino]-4-[2-oxo-5-(trifluoromethyl)piperidin-1-yl]butanoic acid PREPARATION 170 and 12.3 mg (0.038 mmol) of 2,4-bis(trifluoromethyl)-5,6,7,8-tetrahydropyrido[3,4-d]pyrimidine hydrochloric acid salt obtained in PREPARATION 127 were used.

$^1$H NMR (CDCl$_3$) δ 5.86-5.76 (1H, m), 5.04-4.91 (2H, m), 4.17 (1H, brs), 4.15-3.78 (2H, m), 3.68-3.44 (4H, m), 3.22-3.10 (2H, m), 2.87-2.80 (1H, m), 2.60-2.45 (3H, m), 2.36-2.30 (1H, m), 2.07 (1H, brs), 1.88-1.84 (1H, m), 1.40-1.39 (9H, m)

Mass (m/e) 622 (M+1)

EXAMPLE 107

Synthesis of 1-{(2S)-2-amino-4-[2,4-bis(trifluoromethyl)-5,8-dihydropyrido[3,4-d]pyrimidin-7(6H)-yl]-4-oxobutyl}-5-(trifluoromethyl)piperidin-2-one

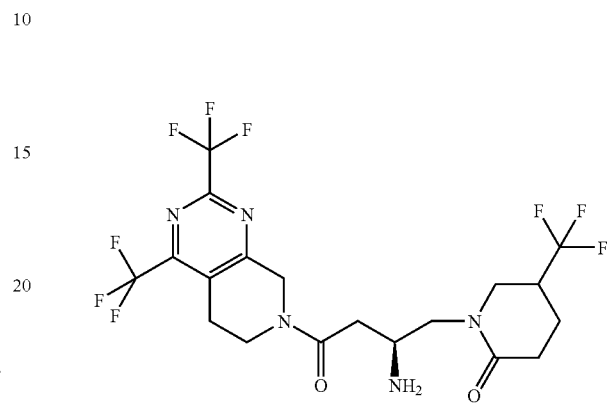

13.3 mg of the title compound was obtained in a yield of 83% at the same manner as in EXAMPLE 22, except that 18.0 mg (0.0289 mmol) of t-butyl [(1S)-3-[2,4-bis(trifluoromethyl)-5,8-dihydropyrido[3,4-d]pyrimidin-7(6H)-yl]-3-oxo-1-{[2-oxo-5-(trifluoromethyl)piperidin-1-yl]methyl}propyl]carbamate obtained in PREPARATION 178 was used.

$^1$H NMR (CD$_3$OD) δ 4.94-4.79 (2H, m), 3.89-3.86 (1H, m), 3.82-3.72 (2H, m), 3.66-3.52 (5H, m), 3.16-3.11 (1H, m), 3.04 (1H, brs), 2.94-2.73 (2H, m), 2.43-2.41 (2H, m), 2.08-2.02 (1H, m), 1.89-1.82 (1H, m)

Mass (m/e) 522 (M+1)

PREPARATION 180

Synthesis of t-butyl {(1S)-3-[2,4-bis(trifluoromethyl)-5,8-dihydropyrido[3,4-d]pyrimidin-7(6H)-yl]-3-oxo-1-{[2-oxo-4-(trifluoromethyl)pyrrolidin-1-yl]methyl}propyl}carbamate 21.0 mg of the title compound was obtained in a yield of 41% at the same manner as in PREPARATION 45, except that 25.0 mg (0.061 mmol) of (3S)-3-[(t-butoxycarbonyl)amino]-4-[2-oxo-4-(trifluoromethyl)pyrrolidin-1-yl]butanoic acid obtained in PREPARATION 172 and 31.5 mg (0.061 mmol) of 2,4-bis(trifluoromethyl)-5,6,7,8-tetrahydropyrido[3,4-d]pyrimidine hydrochloric acid salt obtained in PREPARATION 127 were used.

$^1$H NMR (CDCl$_3$) δ 5.59 (1H, brs), 5.04-4.80 (2H, m), 4.17-4.11 (1H, m), 4.02-3.82 (2H, m), 3.75-3.66 (2H, m), 3.63-3.58 (2H, m), 3.20-3.04 (3H, m), 2.86-2.75 (1H, m), 2.64-2.39 (3H, m), 1.42-1.40 (9H, m)

Mass (m/e) 608 (M+1)

EXAMPLE 108

Synthesis of 1-{(2S)-2-amino-4-[2,4-bis(trifluoromethyl)-5,8-dihydropyrido[3,4-d]pyrimidin-7(6H)-yl]-4-oxobutyl}-4-(trifluoromethyl)pyrrolidin-2-one

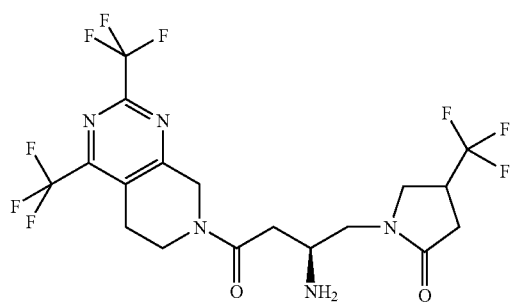

18.2 mg of the title compound was obtained in a yield of 96% at the same manner as in EXAMPLE 22, except that 21.0 mg (0.0346 mmol) of t-butyl {(1S)-3-[2,4-bis(trifluoromethyl)-5,8-dihydropyrido[3,4-d]pyrimidin-7(6H)-yl]-3-oxo-1-{[2-oxo-4-(trifluoromethyl)pyrrolidin-1-yl]methyl}propyl}carbamate obtained in PREPARATION 180 was used.

$^1$H NMR (CD$_3$OD) δ 5.01-4.91 (2H, m), 3.98-3.76 (4H, m), 3.72-3.52 (4H, m), 3.22 (1H, brs), 3.11 (1H, m), 3.03-2.94 (1H, m), 2.89-2.80 (1H, m), 2.73-2.65 (1H, m), 2.57-2.52 (1H, m)

Mass (m/e) 508 (M+1)

EXAMPLE 109

Synthesis of 1-{(2S)-2-amino-4-[2-(3-furyl)-4-(trifluoromethyl)-5,8-dihydropyrido[3,4-d]pyrimidin-7(6H)-yl]-4-oxobutyl}-4-(trifluoromethyl)pyrrolidin-2-one

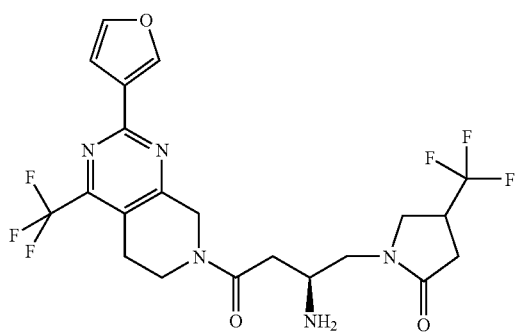

24.7 mg of the title compound was obtained in a yield of 92% at the same manner as in EXAMPLE 22, except that 30.0 mg (0.050 mmol) of t-butyl [(1S)-3-[2-(3-furyl)-4-(trifluoromethyl)-5,8-dihydropyrido[3,4-d]pyrimidin-7(6H)-yl]-3-oxo-1-{[2-oxo-4-(trifluoromethyl)pyrrolidin-1-yl]methyl}propyl]carbamate obtained in PREPARATION 181 was used.

$^1$H NMR (CD$_3$OD) δ 8.36 (1H, s), 7.65 (1H, s), 7.09 (1H, s), 4.92-4.90 (2H, m), 3.97-3.80 (4H, m), 3.70-3.55 (4H, m), 3.15-3.10 (1H, m), 3.05-3.95 (2H, m), 2.85-2.72 (2H, m), 2.65-2.55 (1H, m)

Mass (m/e) 506 (M+1)

PREPARATION 181

Synthesis of t-butyl [(1S)-3-[2-(3-furyl)-4-(trifluoromethyl)-5,8-dihydropyrido[3,4-d]pyrimidin-7(6H)-yl]-3-oxo-1-{[2-oxo-4-(trifluoromethyl)pyrrolidin-1-yl]methyl}propyl]carbamate 30.0 mg of the title compound was obtained in a yield of 82% at the same manner as in PREPARATION 45, except that 25.0 mg (0.061 mmol) of (3S)-3-[(t-butoxycarbonyl)amino]-4-[2-oxo-4-(trifluoromethyl)pyrrolidin-1-yl]butanoic acid obtained in PREPARATION 172 and 22.0 mg (0.061 mmol) of 2-(3-furyl)-4-(trifluoromethyl)-5,6,7,8-tetrahydropyrido[3,4-d]pyrimidine hydrochloric acid salt obtained in PREPARATION 96 were used.

$^1$H NMR (CDCl$_3$) δ 8.26 (1H, s), 7.49 (1H, d, J=1.2 Hz), 7.04 (1H, d, J=6.1 Hz), 5.61-5.55 (1H, m), 4.84 (2H, s), 4.76-4.68 (2H, m), 4.18 (1H, brs), 3.98 (1H, brs), 3.74-3.46 (4H, m), 3.10-2.98 (3H, m), 2.83-2.77 (1H, m), 2.63-2.50 (3H, m), 1.41-1.39 (9H, m)

Mass (m/e) 606 (M+1)

PREPARATION 182

Synthesis of t-butyl {(1S)-3-[2,4-bis(trifluoromethyl)-5,8-dihydropyrido[3,4-d]pyrimidin-7(6H)-yl]-1-[(4-methyl-2-oxopiperidin-1-yl)$_m$ethyl]-3-oxpropyl}carbamate 25 mg of the title compound was obtained in a yield of 46% at the same manner as in PREPARATION 45, except that 30.0 mg (0.096 mmol) of (3S)-3-[(t-butoxycarbonyl)amino]-4-(4-methyl-2-oxopiperidin-1-yl)butanoic acid obtained in PREPARATION 174 and 29.4 mg (0.096 mmol) of 2,4-bis(trifluoromethyl)-5,6,7,8-tetrahydropyrido[3,4-d]pyrimidine hydrochloric acid salt obtained in PREPARATION 127 were used.

$^1$H NMR (CDCl$_3$) δ 6.00-5.94 (1H, m), 5.12-4.81 (2H, m), 4.19-4.05 (2H, m), 3.88 (2H, brs), 3.74-3.66 (1H, m), 3.50-3.40 (3H, m), 3.30-3.15 (2H, m), 2.93-2.82 (1H, m), 2.58-2.37 (2H, m), 2.00-1.88 (3H, m), 1.46-1.44 (9H, m), 1.04-1.03 (3H, m)

Mass (m/e) 568 (M+1)

EXAMPLE 110

Synthesis of 1-{(2S)-2-amino-4-[2,4-bis(trifluoromethyl)-5,8-dihydropyrido[3,4-d]pyrimidin-7(6H)-yl]-4-oxobutyl}-4-methyloxopiperidin-2-one

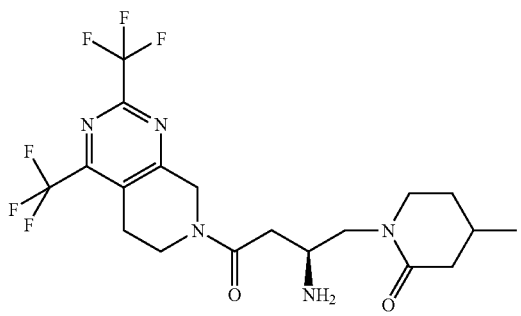

21 mg of the title compound was obtained in a yield of 95% at the same manner as in EXAMPLE 22, except that 25 mg (0.044 mmol) of t-butyl {(1S)-3-[2,4-bis(trifluoromethyl)-5,8-dihydropyrido[3,4-d]pyrimidin-7(6H)-yl]-1-[(4-methyl-2-oxopiperidin-1-yl)methyl]-3-oxpropyl}carbamate obtained in PREPARATION 182 was used.

$^1$H NMR (CD$_3$OD) δ 5.06-4.94 (2H, m), 4.00-3.86 (3H, m), 3.82-3.74 (1H, m), 3.61-3.59 (1H, m), 3.50-3.45 (2H, m), 3.26 (1H, brs), 3.15 (1H, brs), 3.05-2.98 (1H, m), 2.92-2.85 (1H, m), 2.47-2.44 (1H, m), 2.07-1.92 (3H, m), 1.57 (1H, brs), 1.05 (3H, d, J=4.8 Hz)

Mass (m/e) 468 (M+1)

PREPARATION 183

Synthesis of t-butyl {(1S)-3-[2-(3-furyl)-4-(trifluoromethyl)-5,8-dihydropyrido[3,4-d]pyrimidin-7(6H)-yl]-1-[(4-methyl-2-oxopiperidin-1-yl)methyl]-3-oxpropyl}carbamate 43 mg of the title compound was obtained in a yield of 80% at the same manner as in PREPARATION 45, except that 30.0 mg (0.096 mmol) of (3S)-3-[(t-butoxycarbonyl)amino]-4-(4-methyl-2-oxopyrrolidin-1-yl)butanoic acid obtained in PREPARATION 174 and 29.2 mg (0.096 mmol) of 2-(3-furyl)-4-(trifluoromethyl)-5,6,7,8-tetrahydropyrido[3,4-d]pyrimidine hydrochloric acid salt obtained in PREPARATION 96 were used.

$^1$H NMR (CDCl$_3$) δ 8.30 (1H, s), 7.54-7.53 (1H, m), 7.09 (1H, s), 5.92-5.90 (1H, m), 4.89 (1H, s), 4.80-4.76 (1H, m), 4.23 (1H, brs), 3.94-3.79 (3H, m), 3.68-3.39 (4H, m), 3.11-3.03 (2H, m), 2.97-2.87 (1H, m), 2.57-2.47 (2H, m), 2.03-1.87 (3H, m), 1.46-1.44 (9H, m), 1.03 (3H, d, J=5.6 Hz)

Mass (m/e) 566 (M+1)

EXAMPLE 111

Synthesis of 1-{(2S)-2-amino-4-[2-(3-furyl)-4-(trifluoromethyl)-5,8-dihydropyrido[3,4-d]pyrimidin-7(6H)-yl]-4-oxobutyl}-4-methylpiperidin-2-one

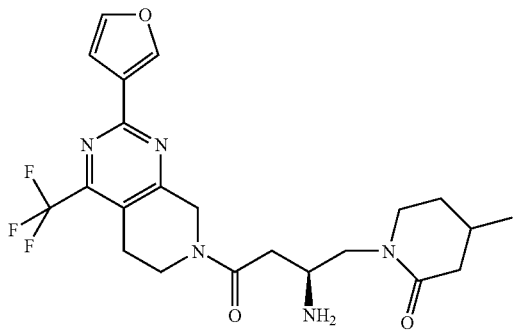

37 mg of the title compound was obtained in a yield of 97% at the same manner as in EXAMPLE 22, except that 43 mg (0.076 mmol) of t-butyl {(1S)-3-[2-(3-furyl)-4-(trifluoromethyl)-5,8-dihydropyrido[3,4-d]pyrimidin-7(6H)-yl]-1-[(4-methyl-2-oxopiperidin-1-yl)methyl]-3-oxpropyl}carbamate obtained in PREPARATION 183 was used.

$^1$H NMR (CD$_3$OD) δ 8.24 (1H, d, J=0.8 Hz), 7.57-7.52 (1H, m), 6.96 (1H, d, J=1.2 Hz), 4.79-4.73 (2H, m), 3.90-3.82 (4H, m), 3.77-3.71 (1H, m), 3.51-3.47 (1H, m), 3.43-3.31 (2H, m), 3.03 (1H, brs), 2.97-2.90 (1H, m), 2.84-2.75 (1H, m), 2.40-2.34 (1H, m), 2.01-1.80 (3H, m), 1.46 (1H, brs), 0.93 (3H, d, J=4.0 Hz)

Mass (m/e) 466 (M+1)

PREPARATION 184

Synthesis of 2-cyclobutyl-4-(trifluoromethyl)-5,6,7,8-tetrahydropyrido[3,4-d]pyrimidin hydrochloric acid salt (1) Synthesis of cyclobutanecarboxymidamide 1.28 g of the title compound was obtained in a yield of 87% at the same manner as in PREPARATION 58-(1), except that 1.22 g (15 mmol) of cyclobutanecarbonitrile was used.

NMR: $^1$H-NMR (CD$_3$OD) δ 3.50 (1H, m), 2.35 (4H, m), 2.1 (1H, m), 1.9 (1H, m)

(2) Synthesis of t-butyl-2-cyclobutyl-4-(trifluoromethyl)-5,8-dihydropyrido[3,4-d]pyrimidin-7(6H)-carboxylate 200 mg of the title compound was obtained in a yield of 33% at the same manner as in PREPARATION 58-(2), except that 500 mg (1.69 mmol) of t-butyl 3-oxo-4-(trifluoroacetyl)piperidin-1-carboxylate and 166 mg (1.69 mmol) of cyclobutanecarboxymidamide obtained in the above step (1) were used.

$^1$H NMR (CDCl$_3$) δ 4.69 (2H, s), 3.80 (1H, m), 3.70 (2H, t, J=5.5 Hz), 2.97 (2H, br s), 2.45 (2H, m), 2.37 (2H, m), 2.08 (1H, m), 1.96 (1H, m), 1.49 (9H, s)

Mass (m/e) 358 (M+1)

(3) Synthesis of 2-cyclobutyl-4-(trifluoromethyl)-5,6,7,8-tetrahydropyrido[3,4-d]pyrimidin hydrochloric acid salt 100 mg of the title compound was obtained in a yield of 69% at the same manner as in PREPARATION 58-(3), except that 200 mg (0.56 mmol) of t-butyl-2-cyclobutyl-4-(trifluoromethyl)-5,8-dihydropyrido[3,4-d]pyrimidin-7(6H)-carboxylate obtained in the above step (2) was used.

$^1$H NMR (CD$_3$OD) δ 4.47 (2H, s), 3.85 (1H, m), 3.59 (2H, t, J=6.5 Hz), 3.29 (2H, br s), 2.4 (4H, m), 2.14 (1H, m), 1.95 (1H, m)

Mass (m/e) 258 (M+1)

PREPARATION 185

Synthesis of t-butyl {(1S)-3-[2-cyclobutyl-4-(trifluoromethyl)-5,8-dihydropyrido[3,4-d]pyrimidin-7(6H)-yl]-1-[{(5R)-5-methyl-2-oxopiperidin-1-yl]methyl}-3-oxopropyl}carbamate 65.0 mg of the title compound was obtained in a yield of 65% at the same manner as in PREPARATION 45, except that 57 mg (0.181 mmole) of (3S)-3-[(t-butoxycarbonyl)amino]-4-[(5R)-5-methyl-2-oxopiperidin-1-yl]butanoic acid obtained in PREPARATION 51 and 40.0 mg (0.164 mmole) of 2-cyclobutyl-4-(trifluoromethyl)-5,6,7,8-tetrahydropyrido[3,4-d]pyrimidine hydrochloric acid salt obtained in PREPARATION 184 were used.

$^1$H NMR (CDCl$_3$) δ 5.87-5.83 (1H, m), 4.88-4.80 (1H, m), 4.75-4.64 (1H, m), 4.18-4.15 (1H, m), 3.90-3.74 (3H, m), 3.58-3.47 (2H, m), 3.36-3.33 (1H, m), 3.08-2.96 (3H, m), 2.86-2.80 (1H, m), 2.50-2.30 (8H, m), 2.10-2.03 (1H, m), 2.00-1.90 (2H, m), 1.81-1.78 (1H, m), 1.43-1.39 (9H, m), 0.99-0.98 (3H, m)

Mass (m/e) 554 (M+1)

EXAMPLE 112

Synthesis of (5R)-1-{(2S)-2-amino-4-[2-cyclobutyl-4-(trifluoromethyl)-5,8-dihydropyrido[3,4-d]pyrimidin-7(6H)-yl]-4-oxobutyl}-5-methylpiperidin-2-one

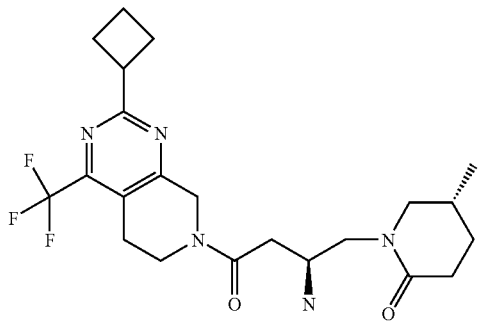

42.4 mg of the title compound was obtained in a yield of 80% at the same manner as in EXAMPLE 22, except that 65.0 mg (0.117 mmole) of t-butyl {(1S)-3-[2-cyclobutyl-4-(trifluoromethyl)-5,8-dihydropyrido[3,4-d]pyrimidin-7(6H)-yl]-1-{[(5R)-5-methyl-2-oxopiperidin-1-yl]methyl}-3-oxopropyl}carbamate obtained in PREPARATION 185 was used.

$^1$H NMR (CD$_3$OD) δ 4.92-4.80 (2H, m), 3.91-3.83 (3H, m), 3.64-3.62 (1H, m), 3.55-3.41 (3H, m), 3.11-3.00 (3H, m), 2.78-2.73 (1H, m), 2.65-2.56 (1H, m), 2.52-2.31 (6H, m), 2.19-2.10 (1H, m), 2.03-1.94 (2H, m), 1.87-1.84 (1H, m), 1.58-1.47 (1H, m), 1.04 (3H, d, J=6.8 Hz)

Mass (m/e) 454 (M+1)

PREPARATION 186

Synthesis of t-butyl {(1S)-3-[2-cyclobutyl-4-(trifluoromethyl)-5,8-dihydropyrido[3,4-d]pyrimidin-7(6H)-yl]-1-[(5,5-difluoro-2-oxopiperidin-1-yl)methyl]-3-oxopropyl}carbamate 67.0 mg of the title compound was obtained in a yield of 64% at the same manner as in PREPARATION 45, except that 61 mg (0.181 mmole) of (3S)-3-[(t-butoxycarbonyl)amino]-4-(5,5-difluoro-2-oxopiperidin-1-yl)butanoic acid PREPARATION 57 and 40.0 mg (0.164 mmole) of 2-cyclobutyl-4-(trifluoromethyl)-5,6,7,8-tetrahydropyrido[3,4-d]pyrimidine hydrochloric acid salt obtained in PREPARATION 194 were used.

$^1$H NMR (CDCl$_3$) δ 5.77 (1H, brs), 4.88-4.80 (1H, m), 4.73-4.65 (1H, m), 4.22-4.18 (1H, m), 3.88-3.68 (5H, m), 3.59-3.48 (2H, m), 3.04-2.98 (2H, m), 2.84-2.79 (1H, m), 2.58-2.50 (3H, m), 2.48-2.34 (4H, m), 2.30-2.20 (2H, m), 2.10-2.03 (1H, m), 1.98-1.92 (1H, m), 1.41-1.40 (9H, m)

Mass (m/e) 576 (M+1-Boc)

EXAMPLE 113

Synthesis of 1-{(2S)-2-amino-4-[2-cyclobutyl-4-(trifluoromethyl)-5,8-dihydropyrido[3,4-d]pyrimidin-7(6H)-yl]-4-oxobutyl}-5,5-difluoropiperidin-2-one

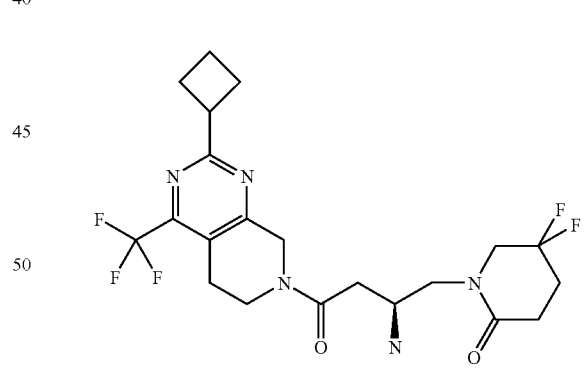

43.9 mg of the title compound was obtained in a yield of 79% at the same manner as in EXAMPLE 22, except that 67 mg (0.116 mmole) of t-butyl {(1S)-3-[2-cyclobutyl-4-(trifluoromethyl)-5,8-dihydropyrido[3,4-d]pyrimidin-7(6H)-yl]-1-[(5,5-difluoro-2-oxopiperidin-1-yl)methyl]-3-oxopropyl}carbamate obtained in PREPARATION 186 was used.

$^1$H NMR (CD$_3$OD) δ 4.91-4.79 (2H, m), 3.87-3.80 (5H, m), 3.53-3.48 (3H, m), 3.10-3.00 (2H, m), 2.73-2.32 (9H, m), 2.14-2.11 (1H, m), 1.99-1.96 (2H, m)

Mass (m/e) 476 (M+1)

EXPERIMENT

Measurement of DPP-IV Activity-Inhibiting Ability

Dipeptidyl Peptidase-IV (DPP-IV), known as serine protease, was obtained by a modification of the known method (Tanaka T. et al, Proc. Natl. Acad. Sci. USA, (1994) 91, 3082-3086), which comprises cloning, purification by use of Baculo-Virus and activation steps. DPP-IV was used to test the pharmaceutical efficacy of candidate inhibitors as follows. The cloned DP-IV was expressed in Baculo-Virus, which was purified by nickel column and then subjected to dialysis. The inhibitors synthesized in Examples were tested to determine the binding activity there of using a fluorescent substrate, Ac-Gly-Pro-AFC. Enzyme reactions were conducted for various concentrations of inhibitors, using 100 M Ac-Gly-Pro-AFC at 25° C. in a buffer solution containing 50 mmol HEPES (pH 7.4), with the concentration of DP-IV being 7.1 nM. The inhibitor's $IC_{50}$ value was determined by measuring the amount of fluorescence emitted in a fluorescent spectrometer after allowing enzyme reaction for 1 hour, and then calculating the concentration of inhibitors exhibiting 50% inhibition of the total enzyme reaction. As the fluorescent spectrometer, Spectra MAX GeminiXS fluorescent spectrometer from Molecular Device Co. was used and the excitation frequency and emission frequency were set to 400 nm and 505 nm, respectively. The result is summarized in TABLE 1 below.

TABLE 1

| Example No. | $IC_{50}$ (nM) |
|---|---|
| Ex. 1 | >10,000 |
| Ex. 2 | 950 |
| Ex. 3 | 122 |
| Ex. 4 | 127 |
| Ex. 5 | >10,000 |
| Ex. 6 | 989 |
| Ex. 7 | >10,000 |
| Ex. 8 | 4,150 |
| Ex. 9 | 201 |
| Ex. 10 | 141 |
| Ex. 11 | 75 |
| Ex. 12 | 35 |
| Ex. 13 | 378 |
| Ex. 14 | 217 |
| Ex. 15 | 2,497 |
| Ex. 16 | 66 |
| Ex. 17 | 2,017 |
| Ex. 18 | 816 |
| Ex. 19 | 712 |
| Ex. 20 | 268 |
| Ex. 21 | 24 |
| Ex. 22 | 49 |
| Ex. 23 | 130 |
| Ex. 24 | 66 |
| Ex. 25 | 9 |
| Ex. 26 | 5 |
| Ex. 27 | 28 |
| Ex. 28 | 1,162 |
| Ex. 29 | 175 |
| Ex. 30 | 21 |
| Ex. 31 | 25 |
| Ex. 32 | 199 |
| Ex. 33 | 170 |
| Ex. 34 | 34 |
| Ex. 35 | 51 |
| Ex. 36 | 33 |
| Ex. 37 | 36 |
| Ex. 38 | 20 |
| Ex. 39 | 51 |
| Ex. 40 | 30 |
| Ex. 41 | 14 |
| Ex. 42 | 14 |
| Ex. 43 | 9 |
| Ex. 44 | 13 |
| Ex. 45 | 22 |
| Ex. 46 | 22 |
| Ex. 47 | 279 |
| Ex. 48 | 357 |
| Ex. 49 | 236 |
| Ex. 50 | 422 |
| Ex. 51 | 114 |
| Ex. 52 | 18 |
| Ex. 53 | 26 |
| Ex. 54 | 30 |
| Ex. 55 | 20 |
| Ex. 56 | 11 |
| Ex. 57 | 48 |
| Ex. 58 | 14 |
| Ex. 59 | 36 |
| Ex. 60 | 61 |
| Ex. 61 | 55 |
| Ex. 62 | 32 |
| Ex. 63 | 35 |
| Ex. 64 | 5 |
| Ex. 65 | 12 |
| Ex. 66 | 16 |
| Ex. 67 | 10 |
| Ex. 68 | 72 |
| Ex. 69 | 55 |
| Ex. 70 | 8 |
| Ex. 71 | 5 |
| Ex. 72 | 23 |
| Ex. 73 | 27 |
| Ex. 74 | 26 |
| Ex. 75 | 16 |
| Ex. 76 | 30 |
| Ex. 77 | 94 |
| Ex. 78 | 163 |
| Ex. 79 | 385 |
| Ex. 80 | 8,850 |
| Ex. 81 | 10 |
| Ex. 82 | 16 |
| Ex. 83 | 18 |
| Ex. 84 | 38 |
| Ex. 85 | 16 |
| Ex. 86 | 30 |
| Ex. 87 | 29 |
| Ex. 88 | 48 |
| Ex. 89 | 214 |
| Ex. 90 | 356 |
| Ex. 91 | 85 |
| Ex. 92 | 48 |
| Ex. 93 | 55 |
| Ex. 94 | 238 |
| Ex. 95 | 13 |
| Ex. 96 | 7 |
| Ex. 97 | 57 |
| Ex. 98 | 68 |
| Ex. 99 | 19 |
| Ex. 100 | 18 |
| Ex. 101 | 21 |
| Ex. 102 | 29 |
| Ex. 103 | 74 |
| Ex. 104 | 110 |
| Ex. 105 | 59 |
| Ex. 106 | 45 |
| Ex. 107 | 636 |
| Ex. 108 | 54 |
| Ex. 109 | 55 |
| Ex. 110 | 56 |
| Ex. 111 | 70 |
| Ex. 112 | 10 |
| Ex. 113 | 13 |

INDUSTRIAL APPLICABILITY

As described above, the novel compounds according to the present invention inhibited DPP-IV activity, resulting in high insulin levels and decreased blood glucose levels. Accordingly, these compounds can be used as formulations to treat or prevent DPP-IV related diseases, for example, diabetes mellitus (particularly, type II), obesity and the like.

Other embodiments and uses of the invention will be apparent to those skilled in the art from consideration of the specification and practice of the invention disclosed herein. It is intended that the specification and examples be considered as exemplary only, with the scope of particular embodiments of the invention indicated by the following claims.

What is claimed is:

1. A compound of the following formula (1) or pharmaceutically acceptable salt thereof:

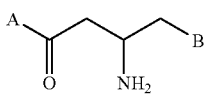
(1)

wherein
A is a substituent of the following formula (5):

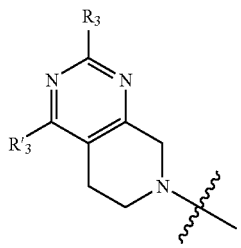
(5)

wherein $R_3$ is hydrogen, or substituted or unsubstituted $C_1$-$C_4$ alkyl, cycloalkyl, aryl or heteroaryl; and $R'_3$ is hydrogen, or $CF_3$;

B is selected from the group consisting of substituents of the following formulas (8) to (11):

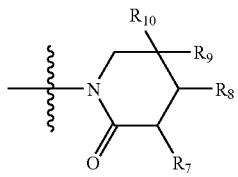
(8)

wherein $R_7$, $R_8$, $R_9$ and $R_{10}$ are each independently hydrogen, halogen, or substituted or unsubstituted $C_1$-$C_4$ alkyl;

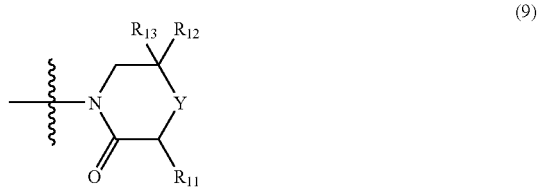
(9)

wherein $R_{11}$, $R_{12}$ and $R_{13}$ are each independently hydrogen, halogen, or substituted or unsubstituted $C_1$-$C_4$ alkyl; and Y is oxygen, sulfur or $SO_2$;

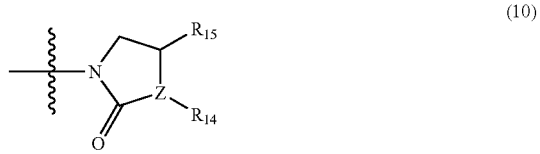
(10)

wherein $R_{14}$ and $R_{15}$ are each independently hydrogen, halogen, or substituted or unsubstituted $C_1$-$C_4$ alkyl; and Z is —CH— or oxygen, where Z is oxygen, $R_{14}$ is nothing; and

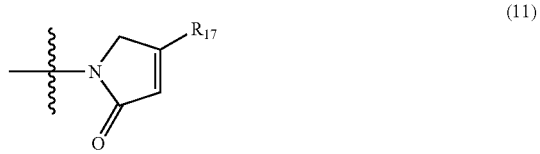
(11)

wherein $R_{17}$ is substituted or unsubstituted $C_1$-$C_4$ alkyl, wherein the substituted $C_1$-$C_4$ alkyl is substituted with halogen.

2. The compound according to claim 1, or pharmaceutically acceptable salt thereof, wherein the halogen is fluoride.

3. The compound according to claim 1, or pharmaceutically acceptable salt thereof, wherein $R_3$ is selected from the group consisting of:
hydrogen;
substituted or unsubstituted $C_1$-$C_4$ alkyl;
formula —$CH_2$-$R_{18}$, wherein $R_{18}$ is $C_1$-$C_4$ alkoxyalkyl, or $C_3$-$C_7$ cycloalkyl unsubstituted or substituted with halogen or hydroxy, or phenyl unsubstituted or substituted with halogen or hydroxy, or heteroaryl;
substituted or unsubstituted $C_3$-$C_7$ cycloalkyl;
formula

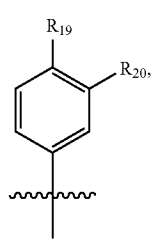

wherein $R_{19}$ and $R_{20}$ are each independently hydrogen, halogen, or substituted or unsubstituted $C_1$-$C_4$ alkyl; and 5-membered or 6-membered heteroaryl unsubstituted or substituted with halogen or hydroxy,
wherein the substituted $C_3$-$C_7$ cycloalkyl and $C_1$-$C_4$ alkyl are the cycloalkyl and alkyl substituted with halogen or hydroxy.

4. The compound according to claim 1, or pharmaceutically acceptable salt thereof, wherein the heteroaryl is a 2-furan, 3-furan, 2-thiophene, 3-thiophene, 2-pyridine, 3-pyridine, 4-pyridine, 2-pyrrole or 3-pyrrole, unsubstituted or substituted with a halogen or hydroxy.

5. The compound according to claim 1, or pharmaceutically acceptable salt thereof, wherein the compound is a stereoisomer as represented in the following formula (1a):

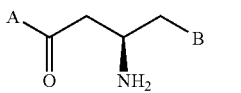

(1a)

wherein A and B are the same as in formula (1).

6. The compound according to claim 1, or pharmaceutically acceptable salt thereof, wherein the compound is selected from the group consisting of:
1-[2S-amino-4-oxo-4-(4-trifluoromethyl-5,8-dihydro-6H-pyrido[3,4-d]pyrimidin-7-yl)-butyl]-5R-methyl-1-piperidin-2-one;
(5R)-1-{(2S)-2-amino-4-oxo-4-[2-phenyl-4-(trifluoromethyl)-5,8-dihydropyrido[3,4-d]pyrimidin-7(6H)-yl]butyl}-5-methylpiperidin-2-one;
(6S)-4-{(2S)-2-amino-4-oxo-4-[2-phenyl-4-(trifluoromethyl)-5,8-dihydropyrido[3,4-d]pyrimidin-7(6H)-yl]butyl}-6-methylmorpholin-3-one;
1-{(2S)-2-amino-4-oxo-4-[2-phenyl-4-(trifluoromethyl)-5,8-dihydropyrido[3,4-d]pyrimidin-7(6H)-yl]butyl}-5,5-difluoropiperidin-2-one;
1-{(2S)-2-amino-4-[2-cyclopropyl-4-(trifluoromethyl)-5,8-dihydropyrido[3,4-d]pyrimidin-7(6H)-yl]-4-oxobutyl}-5,5-difluoropiperidin-2-one;
1-{(2S)-2-amino-4-[2-cyclopropyl-4-(trifluoromethyl)-5,8-dihydropyrido[3,4-d]pyrimidin-7(6H)-yl]-4-oxobutyl}-5-methylpiperidin-2-one;
(6S)-4-{(2S)-2-amino-4-[2-cyclopropyl-4-(trifluoromethyl)-5,8-dihydropyrido[3,4-d]pyrimidin-7(6H)-yl]-4-oxobutyl}-6-methylmorpholin-3-one;
1-{(2S)-2-amino-4-[2-(4-fluorophenyl)-4-(trifluoromethyl)-5,8-dihydropyrido[3,4-d]pyrimidin-7(6H)-yl]-4-oxobutyl}-5,5-difluoropiperidin-2-one;
(6S)-4-{(2S)-2-amino-4-[2-(4-fluorophenyl)-4-(trifluoromethyl)-5,8- dihydropyrido[3,4-d]pyrimidin-7(6H)-yl]-4-oxobutyl}-6-methylmorpholin-2-one;
1-{(2S)-2-amino-4-[2-(3-fluorophenyl)-4-(trifluoromethyl)-5,8-dihydropyrido[3,4- d]pyrimidin-7(6H)-yl]-4-oxobutyl}-5,5-difluoropiperidin-2-one;
(6S)-4-{(2S)-2-amino-4-[2-(3-fluorophenyl)-4-(trifluoromethyl)-5,8-dihydropyrido[3,4-d]pyrimidin-7(6H)-yl]-4-oxobutyl}-6-methylmorpholin-3-one;
(5R)-1-{(2S)-2-amino-4-[2-(4-fluorophenyl)-4-(trifluoromethyl)-5,8-dihydropyrido[3,4-d]pyrimidin-7(6H)-yl]-4-oxobutyl}-5-methylpiperidin-2-one;
1-{(2S)-2-amino-4-[2-(3,4-difluorophenyl)-4-(trifluoromethyl)-5,8-dihydropyrido[3,4-d]pyrimidin-7(6H)-yl]-4-oxobutyl}-5,5-difluoropiperidin-2-one;
(6S)-4-{(2S)-2-amino-4-[2-(3,4-difluorophenyl)-4-(trifluoromethyl)-5,8-dihydropyrido[3,4-d]pyrimidin-7(6H)-yl]-4-oxobutyl}-6-methylmorpholin-3-one;
(5R)-1-{(2S)-2-amino-4-[2-(3,4-difluorophenyl)-4-(trifluoromethyl)-5,8-dihydropyrido[3,4-d]pyrimidin-7(6H)-yl]-4-oxobutyl}-5-methylpiperidin-2-one;
(5R)-1-{(2S)-2-amino-4-[2-cyclopentyl-4-(trifluoromethyl)-5,8-dihydropyrido[3,4-d]pyrimidin-7(6H)-yl]-4-oxobutyl}-5-methylpiperidin-2-one;
(6S)-4-{(2S)-2-amino-4-[2-cyclopentyl-4-(trifluoromethyl)-5,8-dihydropyrido[3,4-d]pyrimidin-7(6H)-yl]-4-oxobutyl}-6-methylmorpholin-3-one;
1-{(2S)-2-amino-4-[2-cyclopentyl-4-(trifluoromethyl)-5,8-dihydropyrido[3,4-d]pyrimidin-7(6H)-yl]-4-oxobutyl}-5,5-difluoropiperidin-2-one;
(5R)-1-{(2S)-2-amino-4-[2-(2-methoxyethyl)-4-(trifluoromethyl)-5,8-dihydropyrido[3,4-d]pyrimidin-7(6H)-yl]-4-oxobutyl}-5-methylpiperidin-2-one;
1-{(2S)-2-amino-4-[2-(2-methoxyethyl)-4-(trifluoromethyl)-5,8-dihydropyrido[3,4-d]pyrimidin-7(6H)-yl]-4-oxobutyl}-5,5-difluoropiperidin-2-one;
(5R)-1-{(2S)-2-amino-4-[2-(cyclopropylmethyl)-4-(trifluoromethyl)-5,8-dihydropyrido[3,4-d]pyrimidin-7(6H)-yl]-4-oxobutyl}-5-methylpiperidin-2-one;
1-{(2S)-2-amino-4-[2-(cyclopropylmethyl)-4-(trifluoromethyl)-5,8-dihydropyrido[3,4-d]pyrimidin-7(6H)-yl]-4-oxobutyl}-5,5-difluoropiperidin-2-one;
(5R)-1-{(2S)-2-amino-4-oxo-4-[2-pyridin-4-yl-4-(trifluoromethyl)-5,8-dihydropyrido[3,4-d]pyrimidin-7(6H)-yl]butyl}-5-methylpiperidin-2-one;
1-{(2S)-2-amino-4-oxo-4-[2-pyridin-4-yl-4-(trifluoromethyl)-5,8-dihydropyrido[3,4-d]pyrimidin-7(6H)-yl]butyl}-5,5-difluoropiperidin-2-one;
(5R)-1-{(2S)-2-amino-4-[2-(4-fluorobenzyl)-4-(trifluoromethyl)-5,8- dihydropyrido[3,4-d]pyrimidin-7(6H)-yl]-4-oxobutyl}-5-methylpiperidin-2-one;
1-{(2S)-2-amino-4-[2-(4-fluorobenzyl)-4-(trifluoromethyl)-5,8-dihydropyrido[3,4-d]pyrimidin-7(6H)-yl]-4-oxobutyl}-5,5-difluoropiperidin-2-one;
(5R)-1-{(2S)-2-amino-4-oxo-4-[2-(3-thienyl)-4-(trifluoromethyl)-5,8-dihydropyrido[3,4-d]pyrimidin-7(6H)-yl]butyl}-5-methylpiperidin-2-one;
1-{(2S)-2-amino-4-oxo-4-[2-(3-thienyl)-4-(trifluoromethyl)-5,8-dihydropyrido[3,4-d]pyrimidin-7(6H)-yl]butyl}-5,5-difluoropiperidin-2-one;
(5R)-1-{(2S)-2-amino-4-oxo-4-[2-(2-thienyl)-4-(trifluoromethyl)-5,8- dihydropyrido[3,4-d]pyrimidin-7(6H)-yl]butyl}-5-methylpiperidin-2-one;
1-{(2S)-2-amino-4-oxo-4-[2-(2-thienyl)-4-(trifluoromethyl)-5,8-dihydropyrido[3,4-d]pyrimidin-7(6H)-yl]butyl}-5,5-difluoropiperidin-2-one;
(5R)-1-{(2S)-2-amino-4-[2-(2-furyl)-4-(trifluoromethyl)-5,8-dihydropyrido[3,4-d]pyrimidin-7(6H)-yl]-4-oxobutyl}-5-methylpiperidin-2-one;
1-{(2S)-2-amino-4-[2-(2-furyl)-4-(trifluoromethyl)-5,8-dihydropyrido[3,4-d]pyrimidin-7(6H)-yl]-4-oxobutyl}-5,5-difluoropiperidin-2-one;
(5R)-1-{(2S)-2-amino-4-[2-(3-furyl)-4-(trifluoromethyl)-5,8-dihydropyrido[3,4-d]pyrimidin-7(6H)-yl]-4-oxobutyl}-5-methylpiperidin-2-one;
1-{(2S)-2-amino-4-[2-(3-furyl)-4-(trifluoromethyl)-5,8-dihydropyrido[3,4-d]pyrimidin-7(6H)-yl]-4-oxobutyl}-5,5-difluoropiperidin-2-one;
(5R)-1-{(2S)-2-amino-4-oxo-4-[2-(1H-pyrrol-2-yl)-4-(trifluoromethyl)-5,8-dihydropyrido[3,4-d]pyrimidin-7(6H)-yl]butyl}-5-methylpiperidin-2-one;
1-{(2S)-2-amino-4-oxo-4-[2-(1H-pyrrol-2-yl)-4-(trifluoromethyl)-5,8-dihydropyrido[3,4-d]pyrimidin-7(6H)-yl]butyl}-5,5-difluoropiperidin-2-one;

(5R)-1-{(2S)-2-amino-4-oxo-4-[2-pyridin-3-yl-4-(trifluoromethyl)-5,8-dihydropyrido[3,4-d]pyrimidin-7(6H)-yl]butyl}-5-methylpiperidin-2-one;

1-{(2S)-2-amino-4-oxo-4-[2-pyridin-3-yl-4-(trifluoromethyl)-5,8-dihydropyrido[3,4-d]pyrimidin-7(6H)-yl]butyl}-5,5-difluoropiperidin-2-one;

1-{(2S)-2-amino-4-[2-ethyl-4-(trifluoromethyl)-5,8-dihydropyrido[3,4-d]pyrimidin-7(6H)-yl]-4-oxobutyl}-5,5-difluoropiperidin-2-one;

(6S)-4-{(2S)-2-amino-4-[2-ethyl-4-(trifluoromethyl)-5,8-dihydropyrido[3,4-d]pyrimidin-7(6H)-yl]-4-oxobutyl}-6-methylmorpholin-3-one;

1-{(2S)-2-amino-4-[2-isopropyl-4-(trifluoromethyl)-5,8-dihydropyrido[3,4-d]pyrimidin-7(6H)-yl]-4-oxobutyl}-5,5-difluoropiperidin-2-one;

1-{(2S)-2-amino-4-[2-isopropyl-4-(trifluoromethyl)-5,8-dihydropyrido[3,4-d]pyrimidin-7(6H)-yl]-4-oxobutyl}-5-methylpiperidin-2-one;

(6S)-4-{(2S)-2-amino-4-[2-isopropyl-4-(trifluoromethyl)-5,8-dihydropyrido[3,4-d]pyrimidin-7(6H)-yl]-4-oxobutyl}-6-methylmorpholin-3-one;

(5S)-1-{(2S)-2-amino-4-[2,4-bis(trifluoromethyl)-5,8-dihydropyrido[3,4-d]pyrimidin-7(6H)-yl]-4-oxobutyl}-5-methylpiperidin-2-one;

(5R)-1-{(2S)-2-amino-4-[2-methyl-4-(trifluoromethyl)-5,8-dihydropyrido[3,4-d]pyrimidin-7(6H)-yl]-4-oxobutyl}-5-methylpiperidin-2-one;

(5R)-1-{(2S)-2-amino-4-[2,4-bis(trifluoromethyl)-5,8-dihydropyrido[3,4-d]pyrimidin-7(6H)-yl]-4-oxobutyl}-5-methylpiperidin-2-one;

1-{(2S)-2-amino-4-[2,4-bis(trifluoromethyl)-5,8-dihydropyrido[3,4-d]pyrimidin-7(6H)-yl]-4-oxobutyl}-5,5-difluoropiperidin-2-one;

1-{(2S)-2-amino-4-[2-methyl-4-(trifluoromethyl)-5,8-dihydropyrido[3,4-d]pyrimidin-7(6H)-yl]-4-oxobutyl}-5,5-difluoropiperidin-2-one;

(6S)-4-{(2S)-2-amino-4-[2-methyl-4-(trifluoromethyl)-5,8-dihydropyrido[3,4-d]pyrimidin-7(6H)-yl]-4-oxobutyl}-6-methylmorpholin-3-one;

1-{(2S)-2-amino-4-oxo-4-[4-(trifluoromethyl)-5,8-dihydropyrido[3,4-d]pyrimidin-7(6H)-yl]butyl}-5,5-difluoropiperidin-2-one;

(6S)-4-{(2S)-2-amino-4-oxo-4-[4-(trifluoromethyl)-5,8-dihydropyrido[3,4-d]pyrimidin-7(6H)-yl]butyl}-6-methylmorpholin-3-one;

4-{(2S)-2-amino-4-[2,4-bis(trifluoromethyl)-5,8-dihydropyrido[3,4-d]pyrimidin-7(6H)-yl]-4-oxobutyl}-6-methylthiomorpholin-3-one;

(5R)-1-{(2S)-2-amino-4-[2-ethyl-4-(trifluoromethyl)-5,8-dihydropyrido[3,4-d]pyrimidin-7(6H)-yl]-4-oxobutyl}-5-methylpiperidin-2-one;

(5R)-1-{(2S)-2-amino-4-oxo-4-[2-(pentafluoroethyl)-4-(trifluoromethyl)-5,8-dihydropyrido[3,4-d]pyrimidin-7(6H)-yl]butyl}-5-methylpiperidin-2-one;

(6S)-4-{(2S)-2-amino-4-oxo-4-[2-(pentafluoroethyl)-4-(trifluoromethyl)-5,8-dihydropyrido[3,4-d]pyrimidin-7(6H)-yl]butyl}-6-methylmorpholin-3-one;

1-{(2S)-2-amino-4-oxo-4-[2-(pentafluoroethyl)-4-(trifluoromethyl)-5,8-dihydropyrido[3,4-d]pyrimidin-7(6H)-yl]butyl}-5,5-difluoropiperidin-2-one;

(5R)-1-{(2S)-2-amino-4-oxo-4-[2-propyl-4-(trifluoromethyl)-5,8-dihydropyrido[3,4-d]pyrimidin-7(6H)-yl]butyl}-5-methylpiperidin-2-one;

1-{(2S)-2-amino-4-oxo-4-[2-propyl-4-(trifluoromethyl)-5,8-dihydropyrido[3,4-d]pyrimidin-7(6H)-yl]butyl}-5,5-difluoropiperidin-2-one;

(5R)-1-{(2S)-2-amino-4-[2-(fluoromethyl)-4-(trifluoromethyl)-5,8-dihydropyrido[3,4-d]pyrimidin-7(6H)-yl]-4-oxobutyl}-5-methylpiperidin-2-one;

1-{(2S)-2-amino-4-[2-(fluoromethyl)-4-(trifluoromethyl)-5,8-dihydropyrido[3,4-d]pyrimidin-7(6H)-yl]-4-oxobutyl}-5,5-difluoropiperidin-2-one;

1-{(2S)-2-amino-4-[2,4-bis(trifluoromethyl)-5,8-dihydropyrido[3,4-d]pyrimidin-7(6H)-yl]-4-oxobutyl}-4-methyl-1,5-dihydro-2H-pyrrol-2-one;

1-{(2S)-2-amino-4-[2-(3-furyl)-4-(trifluoromethyl)-5,8-dihydropyrido[3,4-d]pyrimidin-7(6H)-yl]-4-oxobutyl}-4-methyl-1,5-dihydro-2H-pyrrol-2-one;

1-{(2S)-2-amino-4-[2,4-bis(trifluoromethyl)-5,8-dihydropyrido[3,4-d]pyrimidin-7(6H)-yl]-4-oxobutyl}-4-methyloxopyrolidin-2-one;

1-{(2S)-2-amino-4-[2-(3-furyl)-4-(trifluoromethyl)-5,8-dihydropyrido[3,4-d]pyrimidin-7(6H)-yl]-4-oxobutyl}-4-methylpyrolidin-2-one;

1-{(2S)-2-amino-4-[2,4-bis(trifluoromethyl)-5,8-dihydropyrido[3,4-d]pyrimidin-7(6H)-yl]-4-oxobutyl}-5-(trifluoromethyl)piperidin-2-one;

1-{(2S)-2-amino-4-[2,4-bis(trifluoromethyl)-5,8-dihydropyrido[3,4-d]pyrimidin-7(6H)-yl]-4-oxobutyl}-4-(trifluoromethyl)pyrolidin-2-one;

1-{(2S)-2-amino-4-[2-(3-furyl)-4-(trifluoromethyl)-5,8-dihydropyrido[3,4-d]pyrimidin-7(6H)-yl]-4-oxobutyl}-4-(trifluoromethyl)pyrolidin-2-one;

1-{(2S)-2-amino-4-[2,4-bis(trifluoromethyl)-5,8-dihydropyrido[3,4-d]pyrimidin-7(6H)-yl]-4-oxobutyl}-4-methyloxopiperidin-2-one;

1-{(2S)-2-amino-4-[2-(3-furyl)-4-(trifluoromethyl)-5,8-dihydropyrido[3,4-d]pyrimidin-7(6H)-yl]-4-oxobutyl}-4-methylpiperidin-2-one;

(5R)-1-{(2S)-2-amino-4-[2-cyclobutyl-4-(trifluoromethyl)-5,8-dihydropyrido[3,4-d]pyrimidin-7(6H)-yl]-4-oxobutyl}-5-methylpiperidin-2-one; and 1-{(2S)-2-amino-4-[2-cyclobutyl-4-(trifluoromethyl)-5,8-dihydropyrido[3,4-d]pyrimidin-7(6H)-yl]-4-oxobutyl}-5,5-difluoropiperidin-2-one .

7. A pharmaceutical composition for inhibiting Dipeptidyl Peptidase-IV(DPP-IV) comprising the compound according to claim 1 or a pharmaceutically acceptable salt thereof and a pharmaceutically acceptable carrier.

8. The pharmaceutical composition according to claim 7, wherein the composition is used for treating diabetes mellitus or obesity.

9. The compound according to claim 1, or pharmaceutically acceptable salt thereof, wherein the compound or pharmaceutically acceptable salt is selected from the group consisting of (5R)-1-{(2S)-2-amino-4-[2-methyl-4-(trifluoromethyl)-5,8-dihydropyrido[3,4-d]pyrimidin-7(6H)-yl]-4-oxobutyl}-5-methylpiperidin-2-one, and salts thereof with maleic acid, phosphoric acid, tartaric acid, hydrochloric acid, methanesulfonic acid or citric acid.

10. The compound according to claim 1, or pharmaceutically acceptable salt thereof, wherein the compound or pharmaceutically acceptable salt is selected from the group consisting of (5R)-1-{(2S)-2-amino-4-[2,4-bis(trifluoromethyl)-5,8-dihydropyrido[3,4-d]pyrimidin-7(6H)-yl]-4-oxobutyl}-5-methylpiperidin-2-one, and salts thereof with maleic acid, phosphoric acid, tartaric acid, hydrochloric acid, methanesulfonic acid or citric acid.

11. The compound according to claim 1, or pharmaceutically acceptable salt thereof, wherein the compound or pharmaceutically acceptable salt is selected from the group consisting of 1-{(2S)-2-amino-4-[2,4-bis(trifluoromethyl)-5,8-dihydropyrido[3,4-d]pyrimidin-7(6H)-yl]-4-oxobutyl}-5,5- difluoropiperidin-2-one, and salts thereof with maleic acid, phosphoric acid, tartaric acid, hydrochloric acid, methanesulfonic acid or citric acid.

12. The compound according to claim 1, or pharmaceutically acceptable salt thereof, wherein the compound or pharmaceutically acceptable salt is selected from the group consisting of 1-{(2S)-2-amino-4-[2-methyl-4-(trifluoromethyl)-5,8-dihydropyrido[3,4-d]pyrimidin-7(6H)-yl]-4-oxobutyl}-5,5-difluoropiperidin-2-one, and salts thereof with maleic acid, phosphoric acid, tartaric acid, hydrochloric acid, methanesulfonic acid or citric acid.

13. The compound according to claim 1, or pharmaceutically acceptable salt thereof, wherein the compound or pharmaceutically acceptable salt is selected from the group consisting of (6S)-4-{(2S)-2-amino-4-[2-methyl-4-(trifluoromethyl)-5,8-dihydropyrido[3,4-d]pyrimidin-7(6H)-yl]-4-oxobutyl}-6-methylmorpholin-3-one, and salts thereof with maleic acid, phosphoric acid, tartaric acid, hydrochloric acid, methanesulfonic acid or citric acid.

14. The compound according to claim 1, or pharmaceutically acceptable salt thereof, wherein the compound or pharmaceutically acceptable salt is selected from the group consisting of (6S)-4-{(2S)-2-amino-4-[2-(4-fluorophenyl)-4-(trifluoromethyl)-5,8-dihydropyrido[3,4-d]pyrimidin-7(6H)-yl]-4-oxobutyl}-6-methylmorpholin-2-one, and salts thereof with maleic acid, phosphoric acid, tartaric acid, hydrochloric acid, methanesulfonic acid or citric acid.

15. The compound according to claim 1, or pharmaceutically acceptable salt thereof, wherein the compound or pharmaceutically acceptable salt is selected from the group consisting of 1-{(2S)-2-amino-4-[2-t-butyl-4-(trifluoromethyl)-5,8-dihydropyrido[3,4-d]pyrimidin-7(6H)-yl]-4-oxobutyl}-5,5-difluoropiperidin-2-one, and salts thereof with maleic acid, phosphoric acid, tartaric acid, hydrochloric acid, methanesulfonic acid or citric acid.

16. The compound according to claim 1, or pharmaceutically acceptable salt thereof, wherein the compound or pharmaceutically acceptable salt is selected from the group consisting of (6S)-4-{(2S)-2-amino-4-[2-t-butyl-4-(trifluoromethyl)-5,8-dihydropyrido[3,4-d]pyrimidin-7(6H)-yl]-4-oxobutyl}-6-methylmorpholin-3-one, and salts thereof with maleic acid, phosphoric acid, tartaric acid, hydrochloric acid, methanesulfonic acid or citric acid.

17. The compound according to claim 1, or pharmaceutically acceptable salt thereof, wherein the compound or pharmaceutically acceptable salt is selected from the group consisting of (6S)-4-{(2S)-2-amino-4-[2-cyclopropyl-4-(trifluoromethyl)-5,8-dihydropyrido[3,4-d]pyrimidin-7(6H)-yl]-4-oxobutyl}-6-methylmorpholin-3-one, and salts thereof with maleic acid, phosphoric acid, tartaric acid, hydrochloric acid, methanesulfonic acid or citric acid.

18. The compound according to claim 1, or pharmaceutically acceptable salt thereof, wherein the compound or pharmaceutically acceptable salt is selected from the group consisting of (5R)-1-{(2S)-2-amino-4-oxo-4-[2-(pentafluoroethyl)-4-(trifluoromethyl)-5,8-dihydropyrido[3,4-d]pyrimidin-7(6H)-yl]butyl}-5-methylpiperidin-2-one, and salts thereof with maleic acid, phosphoric acid, tartaric acid, hydrochloric acid, methanesulfonic acid or citric acid.

19. The compound according to claim 1, or pharmaceutically acceptable salt thereof, wherein the compound or pharmaceutically acceptable salt is selected from the group consisting of (6S)-4-{(2S)-2-amino-4-oxo-4-[2-(pentafluoroethyl)-4-(trifluoromethyl)-5,8-dihydropyrido[3,4-d]pyrimidin-7(6H)-yl]butyl}-6-methylmorpholin-3-one, and salts thereof with maleic acid, phosphoric acid, tartaric acid, hydrochloric acid, methanesulfonic acid or citric acid.

20. The compound according to claim 1, or pharmaceutically acceptable salt thereof, wherein the compound or pharmaceutically acceptable salt is selected from the group consisting of 1-{(2S)-2-amino-4-oxo-4-[2-(pentafluoroethyl)-4-(trifluoromethyl)-5,8-dihydropyrido[3,4-d]pyrimidin-7(6H)-yl]butyl}-5,5-difluoropiperidin-2-one, and salts thereof with maleic acid, phosphoric acid, tartaric acid, hydrochloric acid, methanesulfonic acid or citric acid.

21. The compound according to claim 1, or pharmaceutically acceptable salt thereof, wherein the compound or pharmaceutically acceptable salt is selected from the group consisting of (5R)-1-{(2S)-2-amino-4-[2-(fluoromethyl)-4-(trifluoromethyl)-5,8-dihydropyrido[3,4-d]pyrimidin-7(6H)-yl]-4-oxobutyl}-5-methylpiperidin-2-one, and salts thereof with maleic acid, phosphoric acid, tartaric acid, hydrochloric acid, methanesulfonic acid or citric acid.

22. The compound according to claim 1, or pharmaceutically acceptable salt thereof, wherein the compound or pharmaceutically acceptable salt is selected from the group consisting of 1-{(2S)-2-amino-4-[2-(fluoromethyl)-4-(trifluoromethyl)-5,8-dihydropyrido[3,4-d]pyrimidin-7(6H)-yl]-4-oxobutyl}-5,5-difluoropiperidin-2-one, and salts thereof with maleic acid, phosphoric acid, tartaric acid, hydrochloric acid, methanesulfonic acid or citric acid.

* * * * *